(12) United States Patent
Guzi et al.

(10) Patent No.: US 8,603,998 B2
(45) Date of Patent: Dec. 10, 2013

(54) MODULATORS OF CELL CYCLE CHECKPOINTS AND THEIR USE IN COMBINATION WITH CHECKPOINT KINASE INHIBITORS

(75) Inventors: Timothy J. Guzi, Sudbury, MA (US); David A. Parry, Mountain View, CA (US); Marc A. Labroli, Moorestown, NJ (US); Michael D. Dwyer, Scotch Plains, NJ (US); Kamil Paruch, Tisnov (CZ)

(73) Assignee: Merck Sharp & Dohme Corp., Rahway, NJ (US)

( * ) Notice: Subject to any disclaimer, the term of this patent is extended or adjusted under 35 U.S.C. 154(b) by 498 days.

(21) Appl. No.: 12/744,021

(22) PCT Filed: Nov. 5, 2008

(86) PCT No.: PCT/US2008/082429
§ 371 (c)(1),
(2), (4) Date: Mar. 14, 2011

(87) PCT Pub. No.: WO2009/061781
PCT Pub. Date: May 14, 2009

(65) Prior Publication Data
US 2011/0183933 A1    Jul. 28, 2011

Related U.S. Application Data

(60) Provisional application No. 60/986,089, filed on Nov. 7, 2007.

(51) Int. Cl.
*A61K 31/70* (2006.01)
*C07H 19/00* (2006.01)
*A61K 31/535* (2006.01)
*C07D 487/00* (2006.01)

(52) U.S. Cl.
USPC ...... 514/49; 536/28.5; 536/28.52; 514/234.2; 544/281

(58) Field of Classification Search
None
See application file for complete search history.

(56) References Cited

U.S. PATENT DOCUMENTS

| 6,749,988 B2 | 6/2004 | Hatakeyama et al. | |
| 7,521,557 B2 | 4/2009 | Devasthale et al. | |
| 7,776,865 B2 * | 8/2010 | Paruch et al. | 514/259.3 |
| 8,211,854 B2 * | 7/2012 | Guzi et al. | 514/259.3 |
| 2007/0117804 A1 * | 5/2007 | Zhao et al. | 514/249 |
| 2007/0275963 A1 * | 11/2007 | Guzi et al. | 514/234.2 |

FOREIGN PATENT DOCUMENTS

| EP | 0184365 B1 | 6/1986 |
| JP | 1976068578 A | 6/1976 |
| WO | 2009061781 A1 | 5/2009 |
| WO | 2011028638 A1 | 3/2011 |

OTHER PUBLICATIONS

Enouf, J et al., Cancer Research, vol. 39, pp. 4497-4502, (1979), "Relationship between inhibition of protein methylase I and inhibition of rous sarcoma virus-induced cell transformation".
Brodbeck, U et al., Journal of Organic Chemistry, vol. 35, No. 10, pp. 3552-3558 (1970), "Carbodiimide-sulfoxide reactions. IX. Synthesis of 2'- or 3'-keto derivatives of cytidine".
Nakagawa, I et al., Tetrahedron Letters, No. 17, pp. 1409-1412 (1975), "A convenient method for the synthesis of 5'-S-alkylthio-5'-deoxyribonucleosides".
Remin, M et al., Journal of the American Chemical Society, vol. 95, No. 24, pp. 8146-8156 (1973), "Conformational analysis of cytidine, 1-beta-D-(arabinofuranosyl)cytosine and their 0'-methyl derivatives by proton magnetic resonance spectroscopy".
Coat, JP et al., Carbohydrate Research, vol. 12, pp. 335-346 (1970), "Preparation et couplage sur des polypeptides de 5'-O-carboxymethyl-ribonucleosides".
Kusmierek, JT et al., Biochemistry, vol. 12, No. 2, pp. 194-200 (1973) "Preparation of 0'-alkyl derivatives of cytosine and uracil nucleosides".
Pechenov, AE et al., Russian Journal of Bioorganic Chemistry, vol. 26, No. 5, pp. 327-333 (2000), "The S,X-acetals in nucleoside chemistry. I. The Synthesis of 2'- and 5'-O-methylthiomethylribonucleosides".

* cited by examiner

*Primary Examiner* — Lawrence E Crane
(74) *Attorney, Agent, or Firm* — Joan E. Switzer; David A. Muthard

(57) ABSTRACT

In its many embodiments, the present invention provides a novel class of pyrimidine analogs of formula (V) as targeted mechanism-based modulators of cell cycle checkpoints. Cancers and/or malignancies can be treated by administration of a cell cycle checkpoint modulator of the invention. Also discussed are suitable combinations of the cell cycle checkpoint modulator with a checkpoint kinase inhibitor to produce synergistic apoptosis in cancer cells. The invention includes methods of treating cancers by administering the combination of the cell cycle checkpoint modulator and the checkpoint kinase inhibitor, pharmaceutical compositions comprising the activator as well as the combination and pharmaceutical kits.

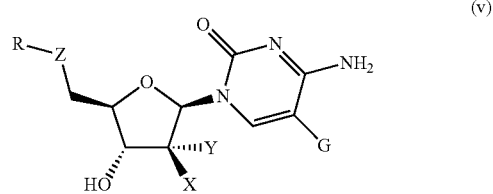

(V)

7 Claims, No Drawings

MODULATORS OF CELL CYCLE CHECKPOINTS AND THEIR USE IN COMBINATION WITH CHECKPOINT KINASE INHIBITORS

Cross Reference to Related Application

This application is entered into national stage examination under 37 U.S.C. 371 and stems from international patent application No. PCT/US2008/082429 filed on Nov. 5, 2008.

FIELD OF THE INVENTION

The invention relates to certain pyrimidine analogs useful as targeted mechanism-based modulators of the cell cycle checkpoints, particularly checkpoint kinase 1 ("Chk1"), pharmaceutical compositions containing the compounds, and methods of treatment using the compounds and compositions to treat diseases such as, for example, cancer, inflammation, arthritis, viral diseases, neurodegenerative diseases such as Alzheimer's disease, cardiovascular diseases, and fungal diseases. It also relates to methods of treating cancers by administering the combination of the cell cycle checkpoint modulator(s) and at least one checkpoint kinase inhibitor, pharmaceutical compositions comprising the combination of drugs used in these methods, as well as pharmaceutical kits.

BACKGROUND OF THE INVENTION

Cancer kills hundreds of thousands of people every year in the United States alone, and many more cases of cancer are diagnosed each year. Despite advances in the treatment of certain forms of cancer (including surgery, radiotherapy, and chemotherapy), many types of cancer are essentially incurable. Even when an effective treatment is available for a certain cancer, the side effects of such treatment are often severe and can result in a significant decrease in quality of life.

While there are many forms of cancer, all cancers are characterized by inappropriate cell proliferation. Multiple checkpoints are built into the machinery of the cell proliferation cycle where cells make a commitment to commence and accurately regulate DNA synthesis to repair DNA damage or to undergo cell death. Unlike normal cells, cancer cells have lost checkpoint control and have an uncontrolled proliferation drive. The approximately $10^{16}$ cell multiplications in the human lifetime, together with inevitable errors in DNA replication and exposure to ultraviolet rays and mutagens, underscores the requirement for checkpoint functions. Major checkpoints occur at G1/S phase and at the G2/M phase transitions where cells make a commitment to repair DNA or undergo apoptosis. Cells are generally thought to undergo apoptosis when DNA damage is irreparable (Li, C J et al. (1999) Proc. Natl. Acad. Sci. USA 96:13369-13374).

Checkpoint kinases (e.g., Chk1, Chk2, and the like) play an important role as a checkpoint in cell cycle progression. Checkpoints prevent cell cycle progression at inappropriate times, such as in response to DNA damage, and maintain the metabolic balance of cells while the cell is arrested, and in some instances can induce apoptosis (programmed cell death) when the requirements of the checkpoint have not been met. Checkpoint control can occur in the G1 phase (prior to DNA synthesis) during S-phase (the replication checkpoint) and in G2, prior to entry into mitosis.

Another important cellular checkpoint is the DNA replication checkpoint, also mediated by CHK1, an essential serine/threonine kinase, which is active during DNA synthesis and functions to coordinate the progression of the cell cycle. Amongst other important functions, the replication checkpoint ensures appropriate control of DNA polymerase progression, order of replication origin firing and suppression of mitosis. In the presence of a replication stress, sufficient to stall replication fork progression, the replication checkpoint becomes critical for maintaining viability, acting to stabilize and preserve the replication fork complexes. Collapse of an active replication fork leads to rapid generation of double strand DNA breaks and cell death. Replication fork collapse is an irretrievable and catastrophic event for a cell.

A primary mechanism of action assigned to DNA antimetabolite drugs, such as cytarabine and gemcitabine, is to suppress DNA synthesis. This is invariably associated with stalled replication forks, activation of the replication checkpoint, and CHK1. CHK1 activity is essential for suppression of DNA damage during exposure to antimetabolites. Cells lacking CHK1 were unable to resume DNA synthesis and subsequently underwent apoptosis. See, e.g., Cho et al, Cell Cycle, 4:1, 131-139 (2005), Syljuäsen R G et al, Mol. Cell. Biol., 25(9):3553-62 (2005).

Generically speaking, therapeutic agents that modulate cell cycle checkpoints generally are referred to herein as "checkpoint modulators." Therapeutic agents that activate cell cycle checkpoint kinases generally are referred to herein as "checkpoint kinase activators." Therapeutic agents that activate the checkpoint kinase designated "Chk1" (pronounced "check one") are referred to herein as "Chk1 activators." Therapeutic agents that activate the checkpoint kinase designated "Chk2" are referred to herein as "Chk2 activators." Inhibitors of such checkpoint kinases, generally and specifically, are referred to herein as "checkpoint kinase inhibitors", "Chk1 inhibitors" and "Chk2 inhibitors" and the like, Inhibition of various DNA damage and replication check points therefore is expected to assist in preventing cells from repairing therapeutically induced DNA damage or suppressing replication fork collapse (and other downstream consequences of replication checkpoint activation) and to thus sensitize targeted cells to such therapeutic agents. Such sensitization is in turn expected to increase the therapeutic index of these therapies.

Selective manipulation of checkpoint control in cancer cells could afford broad utilization in cancer chemotherapeutic and radiotherapy regimens and may, in addition, offer a common hallmark of human cancer "genomic instability" to be exploited as the selective basis for the destruction of cancer cells. A number of factors place Chk1 as a pivotal target in DNA-damage and replication checkpoint control. The elucidation of inhibitors of this and functionally related kinases such as CDS1/Chk2, a kinase recently discovered to cooperate with Chk1 in regulating S phase progression (see Zeng et al., Nature, 395, 507-510 (1998); Matsuoka, Science, 282, 1893-1897 (1998)), could provide valuable new therapeutic entities for the treatment of cancer.

Identification of therapeutic agents modulating the checkpoint control may improve cancer treatment. Indeed, recent reports suggest that activation of cell cycle checkpoints may represent an important new paradigm in the treatment of cancer (see, e.g., Y. Li et al., Proc. Natl. Acad. Sci. USA (2003), 100(5), 2674-8). The cell cycle checkpoint activator, β-lapachone, which acts at the G1/S phase transition, has been found to exhibit significant anti-tumor activity against a range of tumor types both in vitro and in animal studies while exhibiting a favorable side effect profile, leading to the initiation of human clinical trials. In addition, it has been reported that β-lapchone induces necrosis in human breast cancer cells, and apoptosis in ovary, colon, and pancreatic cancer cells through induction of caspase (Li, Y Z et al., *Molecular Medicine* (1999) 5:232-239):

It has also been reported that β-lapchone, when combined with Taxol® (paclitaxel; Bristol-Myers Squibb Co:: New York, N.Y.) at moderate doses, has effective anti-tumor activity in human ovarian, prostate and breast cancer xenograft models in nude mice. No signs of toxicity to the mice were observed, and no weight loss was recorded during the subsequent two months following treatment during which the tumors did not reappear (See Li, C J et al. *Proc. Natl. Acad. Sci. USA* (1999) 96:13369-13374). Taxol is believed to act at the G2/M phase transition of the cell cycle.

Inhibitors of checkpoint kinases are known. For example, commonly assigned US 2007/0083044 and US 2007/0082900, both published Apr. 12, 2007 describes several pyrazolopyrimidines as protein kinase inhibitors, including checkpoint kinase inhibitors and methods of using them. Also, commonly assigned US 2007/0117804 published May 24, 2007 describes several imidazopyrazines as protein kinase inhibitors, including checkpoint kinase inhibitors and methods of using them. Furthermore, S. Ashwell et al, *Expert Opin. Investig. Drugs* (2008) 17(9): 1331-1340 describe several checkpoint kinase inhibitors, particularly those in development.

Many conventional chemotherapy agents cause damage to cancerous and non-cancerous cells alike. While this broad-spectrum activity allows the chemotherapy to kill many different types of cancers, it often also results in damage to normal cells. The therapeutic index of such compounds (a measure of the ability of the therapy to discriminate between normal and cancerous cells) can be quite low; frequently, a dose of a chemotherapy drug that is effective to kill cancer cells will also kill normal cells, especially those normal cells (such as epithelial cells) which undergo frequent cell division. When normal cells are affected by the therapy, side effects such as hair loss, suppression of hematopoesis, and nausea can occur.

Recent advances in cancer chemotherapeutics have resulted in the development of new "targeted" anti-cancer agents, designed to affect biological targets that are primarily associated with cancerous cells, rather than normal cells. Examples of such agents include imatinib (sold by Novartis under the trade name Gleevec® in the United States), gefitinib (developed by Astra Zeneca under the trade name Iresse), and erlotinib (sold under the name of Tarceva® by Genentech, OSI, and Roche). While such agents can be quite effective against the intended cellular target, and can have lower rates of side effects than conventional chemotherapies, targeted therapies are, by design, effective only against cells expressing the biological target. Cancer cells which do not express this specific target, or which express a mutated form of the target, may be less affected by a targeted agent. These agents are therefore of limited utility. Researchers have always looked for improved agents.

For example, Gemcitabine (Formula I; 2',2'-difluoro-2'-deoxycytidine; dFdC) is a pyrimidine analog that has shown activity in various solid tumors,

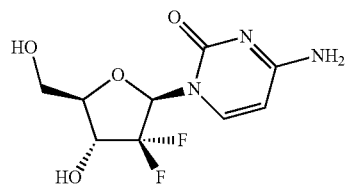

including non-small cell lung cancer (NSCLC), small cell lung cancer, head and neck squamous cell cancer, germ cell tumors, lymphomas (cutaneous T-cell and Hodgkins' disease), mesothelioma, and tumors of the bladder, breast, ovary, cervix, pancreas, and biliary tract, as well as some hematologic malignancies. The compound was first reported by Lilly Research Laboratories, Eli Lilly and Co.; Indianapolis, Ind. Hertel et al., *Cancer Res.* 50, 4417-4422 (1990); U.S. Pat. Nos. 4,808,614 and 5,464,826) and sold by Lilly under the trade name, Gemzar®. Gemcitabine is a deoxycytidine analog with structural similarities to cytarabine (Ara-C®).

Gemcitabine is metabolized intracellularly by nucleoside kinases to the active diphosphate (Formula II; dFdCDP) and triphosphate (Formula III; dFdCTP) nucleotide metabolites.

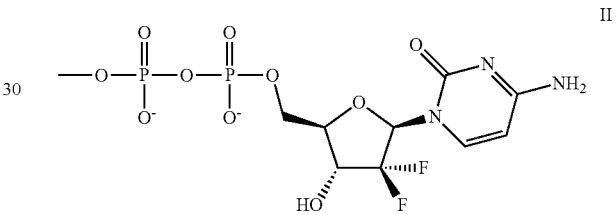

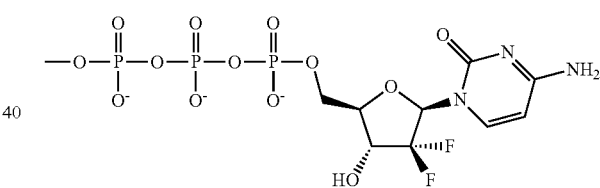

The cytotoxic effect of gemcitabine is generally attributed to the actions of diphosphate and the triphosphate nucleotides, which lead to inhibition of DNA synthesis. Gemcitabine diphosphate (dFdCDP) inhibits ribonucleotide reductase (RNR), which is essential for DNA synthesis and is responsible for catalyzing the reactions that generate the deoxynucleotide triphosphates for DNA synthesis. Inhibition of RNR by the diphosphate nucleotide causes a reduction in the concentration of the deoxynucleotides, including deoxycytidine triphosphate (dCTP). Gemcitabine triphosphate (dFdCTP) competes with dCTP for incorporation into DNA. The reduction in the intracellular concentration of dCTP (by the action of the diphosphate) further enhances the incorporation of gemcitabine triphosphate into DNA, a process referred to as self-potentiation. After the gemcitabine nucleotide is incorporated into DNA, only one additional nucleotide is added to the growing DNA strand. Further DNA synthesis is inhibited, as DNA polymerase epsilon is unable to remove the gemcitabine nucleotide and repair the growing DNA strand, resulting in what is known as masked chain termination. Gemcitabine induces an S-phase arrest in the cell cycle, and triggers apoptosis in both human leukemic cells and solid tumors. Tolls et al., *Eur. J. Cancer,* 35, 797-808

(1999). In addition to its cytotoxic effect, gemcitabine is a potent radiosensitizer, Gemcitabine has been investigated as a radiosensitizer for rodent and human tumor cells, including those found in pancreatic, non-small cell lung, head and neck, colorectal, breast, and cervical cancer. Pauwels et al., *Oncologist* 10(1), 34-51 (2005).

Another known RNR inhibitor is hydroxyurea (HU) or hydroxycarbamide, (Formula IV; brand names include Hydrea® from Bristol-Myers Squibb):

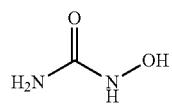

IV is an antineoplastic drug used in hematological malignancies. Its mechanism of action is believed to be based on its inhibition of the enzyme ribonucleotide reductase by scavenging tyrosyl tree radicals.

Combinations of a CHK-1 activator with a CHK-1 inhibitor are disclosed in the past. See, for example, S. Cho et al, *Cell Cycle*, Vol. 4(1), 131-139 (January 2005) and R. Syljuasen et al, *Molecular and Cellular Biology*, Vol. 25(9), 3553-3562 (2005).

Despite the progress made to date in discovering new antitumor treatments, new treatments for cancer are needed.

In an aspect, this invention provides novel compounds and pharmaceutical compositions for the treatment of cancer and precancerous conditions.

In another aspect, this invention provides methods for treating precancerous conditions or cancer using compounds according to the present invention.

In another aspect, this invention provides methods for treating precancerous conditions or cancer using compounds which modulate cell cycle checkpoints in combination with agents which inhibit checkpoint kinase.

In another aspect, this invention provides methods for treating precancerous conditions or cancer using compounds which activate checkpoint kinases in combination with agents which inhibit checkpoint kinase.

Any one of these and/or other objects of the invention may be readily gleaned from a review of the description of the invention which follows.

SUMMARY OF THE INVENTION

In one aspect, the present invention provides compounds, as well as pharmaceutically acceptable salts, solvates, esters and prodrugs thereof, said compounds being represented by Formula V:

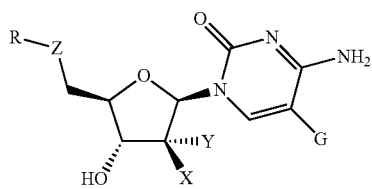

V wherein:
G is H or halo;
X is selected from the group consisting of H, F, $OR^2$ and alkyl;
Y is selected from the group consisting of H, F, $OR^2$ and alkyl;
Z is selected from the group consisting of O, $NR^2$, S, $CR^2R^3$ and $SO_2$;
R is selected from the group consisting of -alkyl, -alkenyl, -cycloalkyl, -aryl, -alkylaryl, -heteroaryl, -alkylheteroaryl, heterocyclyl, -alkylheterocyclyl, -alkyl-$C(O)R^2$ and -alkyl-$C(O)NR^2R^3$, wherein each of said alkyl, aryl, heteroaryl and heterocyclyl can be unsubstituted or optionally independently substituted with one or more groups which can be the same or different, each substituent being independently selected from the group consisting of halo, cyano, alkyl, alkenyl, alkynyl, hydroxyl, alkoxy, aryloxy, alkylthio, arylthio, aryl, heteroaryl, heterocyclyl, heterocycienyl, cycioalkyi, cycloalkenyl, $—OR^2$, $—NR^2R^3$, $—C(O)R^2$, $—C(O)OR^2$ and $C(O)NR^2R^3$;
$R^2$ is selected from the group consisting of H, -alkyl, -aryl and -heteroaryl, wherein each of said alkyl, aryl and heteroaryl can be unsubstituted or optionally independently substituted with one or more groups which can be the same or different and are independently selected from the group consisting of halo, cyano, alkyl, alkenyl, alkynyl, hydroxyl, alkoxy, aryloxy, alkylthio, arylthio, aryl, heteroaryl, heterocyclyl, heterocyclenyl, cycloalkyl, cycloalkenyl, $—OR^2$, $—NR^2R^3$, $C(O)R^2$ and $C(O)NR^2R^3$; and
$R^3$ is selected from the group consisting of -alkyl, -aryl and -heteroaryl, wherein each of said alkyl, aryl and heteroaryl can be unsubstituted or optionally independently substituted with one or more groups which can be the same or different and are independently selected from the group consisting of halo, cyano, alkyl, alkenyl, alkynyl, hydroxyl, alkoxy, aryloxy, alkylthio, arylthio, aryl, heteroaryl, heterocyclyl, heterocyclenyl, cycloalkyl, cycloalkenyl, $—OR^2$, $—NR^2R^3$, $C(O)R^2$ and $C(O)NR^2R^3$, or
$R^2$ and $R^3$ in $NR^2R^3$ or $—C(O)NR^2R^3$ can be connected to the N of said $NR^2R^3$ to form a 5-8 membered heterocyclyl ring containing 1-3 heteroatoms including said N.

In another aspect, this invention provides compositions comprising at least one compound of Formula V.

In another aspect, this invention provides pharmaceutical compositions comprising at least one compound of Formula V and at least one pharmaceutically acceptable carrier.

In another aspect, this invention provides a method of modulating cell cycle checkpoints using therapeutically effective amounts of at least one compound of Formula V.

In another aspect, this invention provides a method of activating checkpoint kinases using therapeutically effective amounts of at least one compound of Formula V.

In another aspect, this invention provides compositions comprising at least one compound of Formula V and at least one checkpoint kinase inhibitor.

In another aspect, this invention provides compositions comprising at least one compound of Formula V and at least one checkpoint kinase 1 inhibitor.

In another aspect, this invention provides a method of inhibiting RNR using therapeutically effective amounts of at least one compound of Formula V.

In another aspect, this invention provides a method of inhibiting DNA synthesis using therapeutically effective amounts of at least one compound of Formula V.

In another aspect, this invention provides a method of inhibiting RNR using therapeutically effective amounts of a composition comprising at least one compound of Formula V and at least one checkpoint kinase 1 inhibitor.

In another aspect, this invention provides a method of inhibiting DNA synthesis using therapeutically effective amounts of a composition comprising at least one compound of Formula V and at least one checkpoint kinase 1 inhibitor.

BRIEF DESCRIPTION OF THE DRAWINGS

The present invention is further described by way of the enclosed drawings.

DESCRIPTION OF THE INVENTION

In an embodiment, the present invention discloses compounds of Formula V, or pharmaceutically acceptable salts, solvates, esters or prodrugs thereof.

In another embodiment, G is H.
In another embodiment, G is halo.
In another embodiment, G is Br.
In another embodiment, X is H.
In another embodiment, X is F.
In another embodiment, X is —$OR^2$.
In another embodiment, X is alkyl.
In another embodiment, X is alkoxy-.
In another embodiment, X is aryloxy-.
In another embodiment. X is heteroaryloxy-,
In another embodiment, Y is H.
In another embodiment, Y is F.
In another embodiment, Y is —$OR^2$.
In another embodiment, Y is alkyl.
In another embodiment, Y is alkoxy-.
In another embodiment, Y is aryloxy-.
In another embodiment, Y is heteroaryloxy-.
In another embodiment, Z is —O—.
In another embodiment, Z is —NH—.
In another embodiment, Z is —N($R^2$)—.
In another embodiment, Z is —S—.
In another embodiment, Z is —C($R^2R^3$)—.
In another embodiment, Z is —$SO_2$—.
In another embodiment, R is alkyl.
In another embodiment, R is aryl.
In another embodiment, R is heteroaryl.
In another embodiment, R is -alkylaryl.
In another embodiment, R is -alkylheteroaryl.
In another embodiment, R is heterocyclyl.
In another embodiment, R is -alkylheterocyclyl.
In another embodiment, R is -alkyl-C(O)$R^2$.
In another embodiment, R is -alkyl-$NR^2R^3$.
In another embodiment, R is -alkyl-$NR^2R^3$, where both $R^2$ and $R^3$ are alkyl groups.
IN another embodiment, R is diethylaminoalkyl-.
In another embodiment, R is —$NR^2R^3$, where $R^2$ and $R^3$ in the —$NR^2R^3$ are connected to the N of said $NR^2R^3$ to form a 5-8 membered heterocyclyl ring containing 1-3 heteroatoms including said N.
In another embodiment, R is -alkyl-C(O)$NR^2R^3$.
In another embodiment, R is -alkyl-C(O)$NR^2R^3$, where both $R^2$ and $R^3$ are alkyl groups.
In another embodiment, R is —C(O)$NR^2R^3$, where $R^2$ and $R^3$ in the —C(O)$NR^2R^3$ are connected to the N of said $NR^2R^3$ to form a 5-8 membered heterocyclyl ring containing 1-3 heteroatoms including said N.
In another embodiment, R is -alkyl(pyrrolidinone).
In another embodiment, R is -alkyl(pyrrolidin-2-one).
In another embodiment, R is -alkyl-$OR^2$.
In another embodiment, R is hydroxyalkyl.
In another embodiment, R is heteroaryl.
In another embodiment, R is alkoxyalkyl-.
In another embodiment, $R^2$ is H.
In another embodiment, $R^2$ is alkyl.
In another embodiment, $R^2$ is aryl.
In another embodiment, $R^2$ is heteroaryl.
In another embodiment, $R^3$ is alkyl.
In another embodiment, $R^3$ is aryl.
In another embodiment, $R^3$ is heteroaryl.
In another embodiment, Z is $NR^2$ and R is alkoxyalkyl-. in another embodiment, Z is NH and R is alkoxyalkyl-.
In another embodiment, Z is $NR^2$ and R is alkylthioalkyl-.
In another embodiment, Z is NH and R is alkylthioalkyl-.
In another embodiment, Z is $NR^2$ and R is amidoalkyl.
In another embodiment, Z is NH and R is amidoalkyl.
In another embodiment, Z is $NR^2$ and R is heteroaryl.
In another embodiment, Z is NH and R is heteroaryl.
In another embodiment, Z is $NR^2$ and R is heterocyclylalkyl.
In another embodiment, Z is NH and R is heterocyclylalkyl.
In another embodiment, Z is $NR^2$ and R is tetrahydrofuranylalkyl.
In another embodiment, Z is NH and R is tetrahydrofuranylalkyl.
In another embodiment, G, X, Y, Z and R, $R^2$ and $R^3$ are independently selected, wherein G=H, Z is $NR^2$ and R is alkoxyalkyl-.
In another embodiment, G, X, Y, Z and R, $R^2$ and $R^3$ are independently selected, wherein G=H, X=Y=F, Z is NH and R is alkoxyalkyl-.
In another embodiment, G, X, Y, Z and R, $R^2$ and $R^3$ are independently selected, wherein G=H, X=Y=F, Z is $NR^2$ and R is alkylthioalkyl-.
In another embodiment, G, X, Y, Z and R, $R^2$ and $R^3$ are independently selected, wherein G=H, X=Y=F, Z is NH and R is alkylthioalkyl-.
In another embodiment, G, X, Y, Z and R, $R^2$ and $R^3$ are independently selected, wherein G=H, X=Y=F, Z is $NR^2$ and R is amidoalkyl-.
In another embodiment, G, X, Y, Z and R, $R^2$ and $R^3$ are independently selected, wherein G=H, X=Y=F, Z is NH and R is aminoalkyl-.
In another embodiment, G, X, Y, Z and R, $R^2$ and $R^3$ are independently selected, wherein G=H, X=Y=F, Z is $NR^2$ and R is heterocyclylalkyl-.
In another embodiment, G, X, Y, Z and R, $R^2$ and $R^3$ are independently selected, wherein G=H, X=Y=F, Z is NH and R is heterocyclylalkyl-.
In another embodiment, G, X, Y, Z and R, $R^2$ and $R^3$ are independently selected, wherein G=H, X=Y=F, Z is $NR^2$ and R is tetrahydrofuranylalkyl-.
In another embodiment, G, X, Y, Z and R, $R^2$ and $R^3$ are independently selected, wherein G=H, X=Y=F, Z is NH and R is tetrahydrofuranylalkyl-.
In another embodiment, G, X, Y, Z and R, $R^2$ and $R^3$ are independently selected, wherein G=H, X=Y=F, Z is $NR^2$ and R is methoxymethyl-.
In another embodiment, G, X, Y, Z and R, $R^2$ and $R^3$ are independently selected, wherein G=H, X=Y=F, Z is NH and R is methoxyethyl-.
In another embodiment, G, X, Y, Z and R, $R^2$ and $R^3$ are independently selected, wherein G=H, X=Y=F, Z is $NR^2$ and R is methylthioethyl-.
In another embodiment, G, X, Y, Z and R, $R^2$ and $R^3$ are independently selected, wherein G=H, X=Y=F, Z is NH and R is methylthioethyl-.
In another embodiment, G, X, Y, Z and R, $R^2$ and $R^3$ are independently selected, wherein G=H, Z is $NR^2$ and R is —$CH_2$—C(O)$NH_2$.

In another embodiment, G, X, Y, Z and R, R² and R³ are independently selected, wherein G=H, X=Y=F, Z is NH and R is —CH₂—C(O)NH₂.

In another embodiment, G, X, Y, Z and R, R² and R³ are independently selected, wherein G=H, X=Y=F, Z is NR² and R is tetrahydrofuran-2-ylmethyl-.

In another embodiment, G, X, Y, Z and R, R² and R³ are independently selected, wherein G=H, X=Y=F, Z is NH and R is tetrahydrofuran-2-ylmethyl-.

In another embodiment, G, X, Y, Z and R, R² and R³ are independently selected, wherein G=H, X=Y=F, Z is NH and R is hydroxyethyl-.

In another embodiment, G=X, Y, Z and R, R² and R³ are independently selected, wherein G=H, X=Y=F, Z is NH and R is dimethylaminoethyl-.

In another embodiment, G, X, Y, Z and R, R² and R³ are independently selected, wherein G=H, X=Y=F, Z is NH and R is (pyrrolidinone-2-yl)propyl-.

In another embodiment, G, X, Y, Z and R, R² and R³ are independently selected, wherein G=H, X=Y=F, Z is NR² and R is:

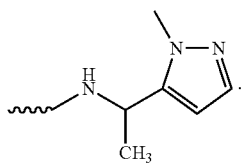

In another embodiment, G, X, Y, Z and R, R² and R³ are independently selected, wherein G=H, X=Y=F, Z is NH and R is:

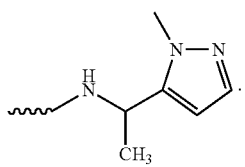

In another embodiment, G, X, Y, Z and R, R² and R³ are independently selected, wherein G=H, Z is NH and R is n-butyl.

In another embodiment, 0, X, Y, Z and R, R² and R³ are independently selected, wherein G<halo, Z is NH and R is n-butyl.

In another embodiment, G, X, Y, Z and R, R² and R³ are independently selected, wherein G=Br, Z is NH and R is n-butyl.

As noted above, in the several alternative embodiments described above for the compound of Formula V, the moieties G, X, Y, Z, R, R², R³ and R⁴ are independently selected.

Non-limiting examples of the compound of Formula V are shown below:

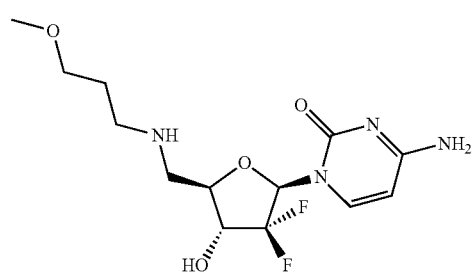

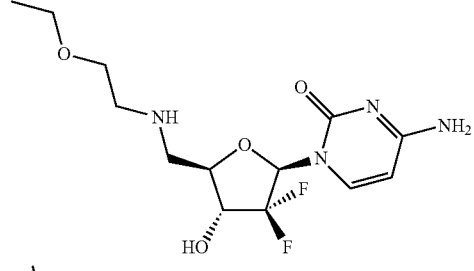

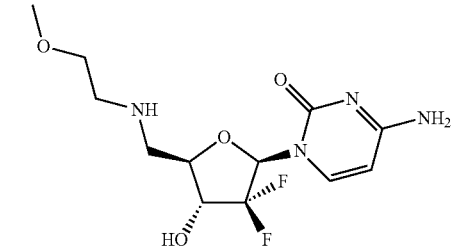

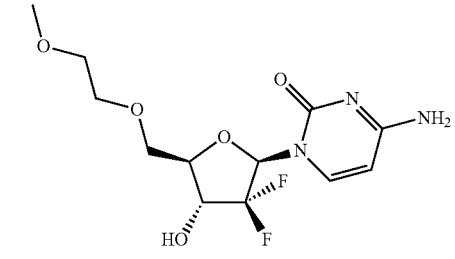

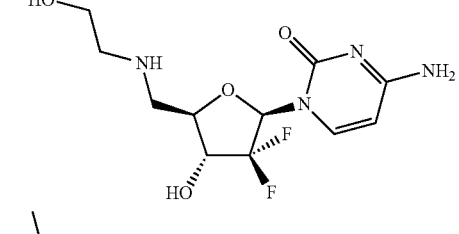

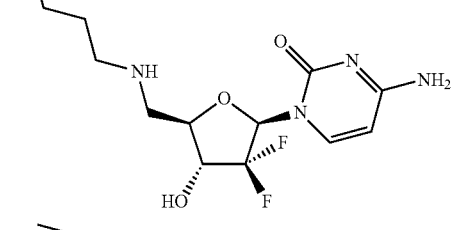

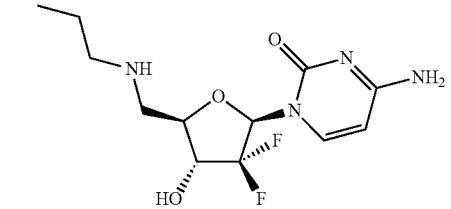

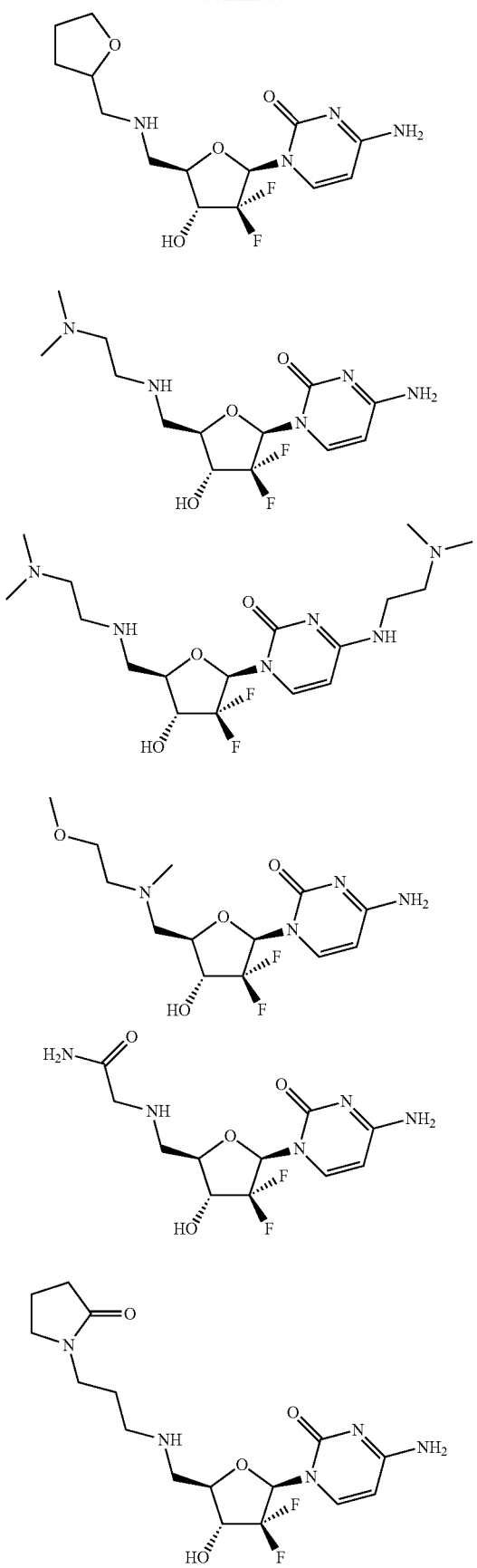
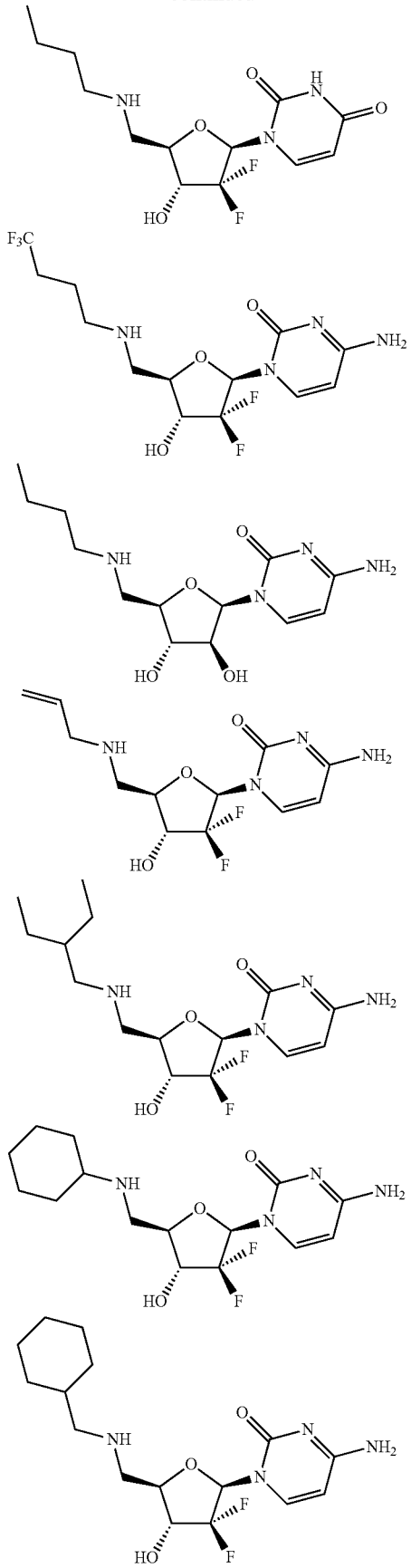

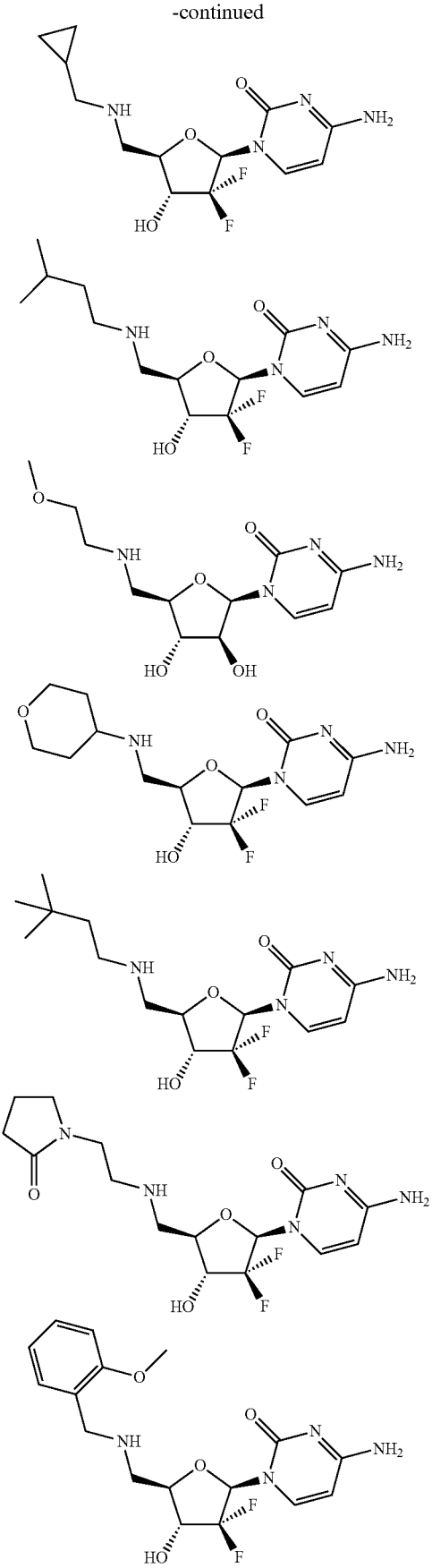
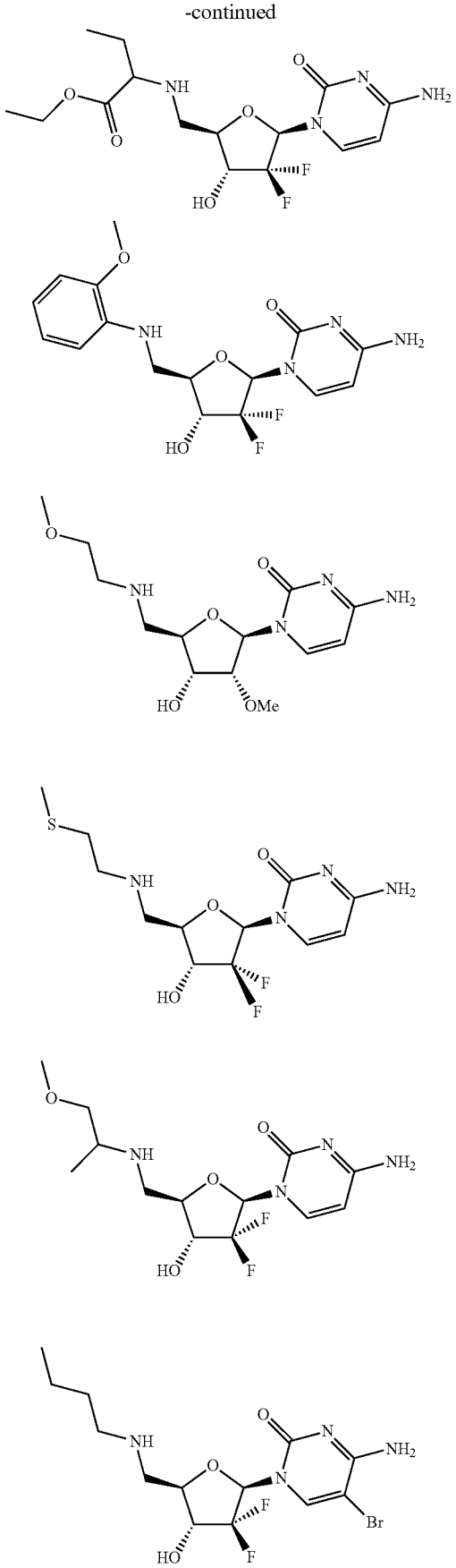

15

-continued

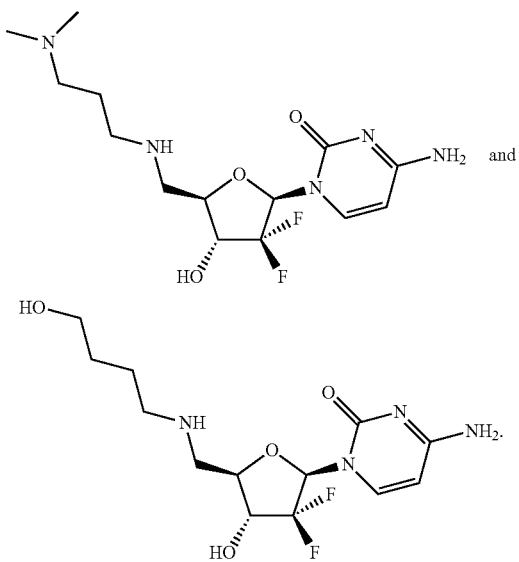

Additional compounds of the invention are shown below:

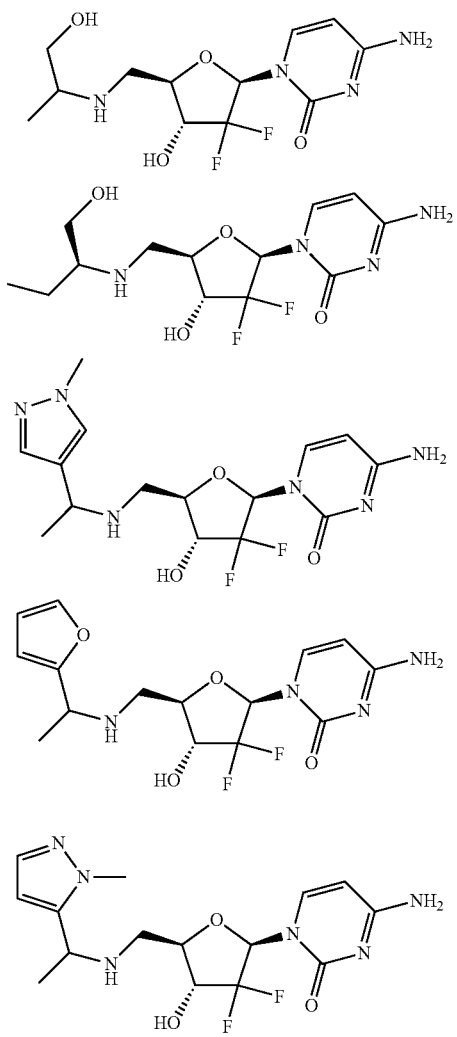

16

-continued

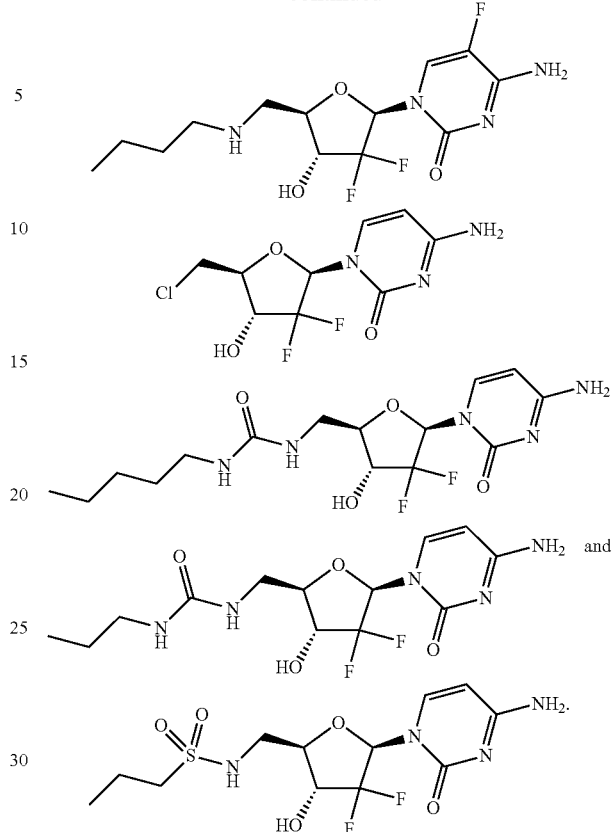

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. Lower alkyl means a group having about 1 to about 6 carbon atoms in the chain which may be straight or branched. Alkyl may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, oxime (e.g., =N—OH), —NH(alkyl), —NH(cycloalkyl), —N(alkyl)$_2$, —O—C(O)-aryl, —O—C(O)-cycloalkyl, carboxy and –C(O)O-alkyl. Non-limiting examples of suitable alkyl groups include methyl, ethyl, n-propyl, isopropyl and t-butyl, "Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. Lower alkenyl means about 2 to about 6 carbon atoms in the chain which may be straight or branched. Alkenyl may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. Lower alkynyl means about 2 to about 6 carbon atoms in the chain which may be straight or branched. Non-limiting examples of suitable alkynyl groups include ethynyl, propynyl, 2-butynyl and 3-methylbutynyl. Alkynyl may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryl is comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —O—C(O)-aryl, —O—C(O)-cycloalkyl, —C(=N—CN)—NH$_2$, —C(=NH)—NH$_2$, —C(=NH)—NH(alkyl), oxime (e.g., N—OH), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

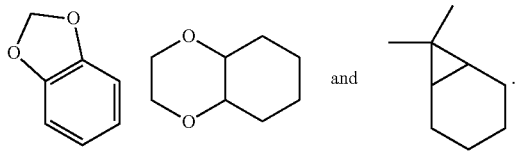

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also mean a single moiety (e.g., carbonyl) which simultaneously replaces two available hydrogens on the same carbon atom on a ring system. Example of such moiety is pyrrolidone:

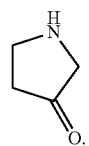

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like, "Heterocyclenyl" may also mean a single moiety (e.g., carbonyl) which simultaneously replaces two available hydrogens on the same carbon atom on a ring system. Example of such moiety is pyrrolidinone:

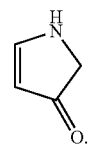

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

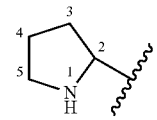

there is no —OH attached directly to carbons marked 2 and 5.

It should also be noted that tautomeric forms such as, for example, the moieties:

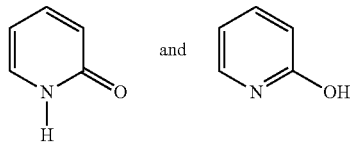 [SMILES: O=c1cccc[nH]1 ; Oc1ccccn1]

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkoxyalkyl-" means an alkyl-O-alkyl- group in which the alkyl group is as previously described. Non-limiting examples of suitable alkoxyalkyl groups include methoxymethyl, ethoxymethyl, n-propoxyethyl, isopropoxyethyl and n-butoxymethyl. The bond to the parent moiety is through the alkyl-.

"Aryloxy" means an aryl-O— group in which the aryl group is as previously described. Non-limiting examples of suitable aryloxy groups include phenoxy and naphthoxy. The bond to the parent moiety is through the ether oxygen.

"Aryloxyalkyl-" means an aryl-O-alkyl- group in which the aryl and aryl groups are as previously described. Non-limiting examples of suitable aryloxyalkyl groups include phenoxymethyl and naphthoxymethyl. The bond to the parent moiety is through the alkyl.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Alkylthioalkyl-" means an alkyl-S-alkyl- group in which the alkyl group is as previously described. Non-limiting examples of suitable alkylthioalkyl groups include methylthioethyl and ethylthiomethyl. The bond to the parent moiety is through the alkyl-.

"Arylthio" means an aryl-S— group in which the aryl group is as previously described. Non-limiting examples of suitable arylthio groups include phenylthio and naphthylthio. The bond to the parent moiety is through the sulfur.

"Arylthioalkyl-" means an aryl-S-alkyl- group in which the aryl group is as previously described. Non-limiting examples of suitable arylthioalkyl groups include phenylthioethyl and phenylthiomethyl. The bond to the parent moiety is through the alkyl-.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-$S(O_2)$— group. Preferred groups are those in which the alkyl group is lower alkyl. The bond to the parent moiety is through the sulfonyl.

"Arylsulfonyl" means an aryl-$S(O_2)$— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula V, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g. a drug precursor) that is transformed in vivo to yield a compound of Formula V or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula V or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$ alkyl, and the like.

Similarly, if a compound of Formula V contains an alcohol functional group, a prodrug can be formed by the replacement of the hydrogen atom of the alcohol group with a group such as, for example, $(C_1-C_6)$alkanoyloxymethyl, 1-($(C_1-C_6)$alkanoyloxy)ethyl, 1-methyl-1-($(C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)$alkyl$)_2$ or glycosyl (the radical resulting from the removal of a hydroxyl group of the hemiacetal form of a carbohydrate), and the like.

If a compound of Formula V incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl, —$C(OH)C(O)OY^1$ wherein $Y^1$ is H, $(C_1-C_6)$alkyl or benzyl, —$C(OY^2)Y^3$ wherein $Y^2$ is $(C_1-C_4)$ alkyl and $Y^3$ is $(C_1-C_6)$alkyl, carboxy$(C_1-C_6)$alkyl, amino $(C_1-C_4)$alkyl or mono-N—or di-N,N—$(C_1-C_6)$alkylaminoalkyl, —$C(Y^4)Y^5$ wherein $Y^4$ is H or methyl and $Y^5$ is mono-N—or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham at al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The term "effective" is used herein, unless otherwise indicated, to describe an amount of a compound or composition which, in context, is used to produce or effect an intended result, whether that result relates to the treatment of a tumor including a carcinogenic tumor or other cancer or the treatment of a precancerous lesion or other cell(s) which express abnormal or foreign proteins or immunogens on a cell surface. With respect to an anti-cancer effect, that effect may be one or more of inhibiting further growth of tumor or cancer cells, reducing the likelihood or eliminating metastasis or producing cell death in the tumor or cancer cells, resulting in a shrinkage of the tumor or a reduction in the number of cancer cells or preventing the regrowth of a tumor or cancer after the patient's tumor or cancer is in remission.

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Representative cancers include, for example, stomach, colon, rectal, liver, pancreatic, lung, breast, cervix uteri, corpus uteri, ovary, prostate, testis, bladder, renal, brain/CNS, head and neck, throat, Hodgkin's disease, non-Hodgkin's lymphoma, multiple myeloma, leukemia, melanoma, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer and lymphoma, among others, which may be treated by one or more compounds according to the present invention.

The term "tumor" is used to describe a malignant or benign growth or tumefacent.

The term "precancerous" refers to a state in which cells are growing in an uncontrolled manner and where that growth has yet to develop into a cancerous growth. The compounds of Formula V can form salts which are also within the scope of this invention. Reference to a compound of Formula V herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula V contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula V may be formed, for example, by reacting a compound of Formula V with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1), 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Formula V, and salts, solvates, esters and prodrugs thereof, may exist in their tautomeric form (for example, as an amide or imino ether). All such tautomeric forms are contemplated herein as part of the present invention.

The compounds of Formula V may contain asymmetric or chiral centers, and, therefore, exist in different stereoisomeric forms. It is intended that all stereoisomeric forms of the compounds of Formula V as well as mixtures thereof, including racemic mixtures, form part of the present invention. In addition, the present invention embraces all geometric and positional isomers. For example, if a compound of Formula V incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula V may be atropisomers (e.g., substituted biaryls) and are considered as part of this invention. Enantiomers can also be separated by use of chiral HPLC column.

It is also possible that the compounds of Formula V may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula V incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula V (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labelled compounds of Formula V can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula V, and of the salts, solvates, esters and prodrugs of the compounds of Formula V, are intended to be included in the present invention.

The compounds according to the invention have pharmacological properties; in particular, the compounds of Formula V can be useful as targeted mechanism-based modulators of checkpoints. The compounds of Formula V can be useful as targeted mechanism-based activators of checkpoint kinases such as, for example, checkpoint kinase1 ("Chk1"), checkpoint kinase2 ("Chk2") and the like. They are especially targeted mechanism-based activators of Chk1.

The compounds according to the invention have the desired profile of an RNR inhibitor such as, for example, mechanism-based activation of CHK-1, synergy with CHK-1 inhibitor and the like.

As checkpoint modulators, the compounds of the invention have pharmacological use. Thus, this invention includes methods of modulating cell cycle checkpoints in a patient in a mechanism-based pathway by administering therapeutically effective amounts of at least one compound of Formula V to said patient.

As checkpoint activators, the compounds of the invention have pharmacological use. Thus, this invention includes methods of activating checkpoint kinases (e.g., Chk1, Chk2, and the like) in a patient in a mechanism-based pathway by administering therapeutically effective amounts of at least one compound of Formula V to said patient.

The invention also includes methods of treating a cancer in a patient by administering at least one compound of Formula V to said patient.

The invention also includes methods of treating a cancer in a patient by administering at least one compound of Formula V to activate Checkpoint kinases, e.g., Chk1, in said patient.

The invention includes compositions, e.g., pharmaceutical compositions comprising at least one compound of Formula V. For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Other carriers include Poloxamer, Povidone K17, Povidone K12, Tween 80, ethanol, Cremophor/ethanol, polyethylene glycol (PEG) 400, propylene glycol, Trappsol, alpha-cyclodextrin or analogs thereof, beta-cyclodextrin or analogs thereof, or gamma-cyclodextrin or analogs thereof. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

The therapeutic agents of the present invention are preferably formulated in pharmaceutical compositions and then, in accordance with the methods of the invention, administered to a subject, such as a human subject, in a variety of forms adapted to the chosen route of administration. For example, the therapeutic agents may be formulated for intravenous administration. The formulations may, however, include those suitable for oral, rectal, vaginal, topical, nasal, ophthalmic, or other parenteral administration (including subcutaneous, intramuscular, intrathecal, intraperitoneal and intratumoral, in addition to intravenous) administration.

Formulations suitable for parenteral administration conveniently include a sterile aqueous preparation of the active agent, or dispersions of sterile powders of the active agent, which are preferably isotonic with the blood of the recipient.

Parenteral administration of the therapeutic agents (e.g., through an I.V. drip) is an additional form of administration. Isotonic agents that can be included in the liquid preparation include sugars, buffers, and sodium chloride. Solutions of the active agents can be prepared in water, optionally mixed with a nontoxic surfactant. Dispersions of the active agent can be prepared in water, ethanol, a polyol (such as glycerol, propylene glycol, liquid polyethylene glycols, and the like), vegetable oils, glycerol esters, and mixtures thereof. The ultimate dosage form is sterile, fluid, and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the active agent, preferably by filter sterilization. Preferred methods for preparing powders include vacuum drying and freeze drying of the sterile injectable solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the active agents over a prolonged period can be achieved by including agents for delaying, for example, aluminum monostearate and gelatin.

Formulations of the present invention suitable for oral administration may be presented as discrete units such as tablets, troches, capsules, lozenges, wafers, or cachets, each containing a predetermined amount of the active agent as a powder or granules, as liposomes containing the first and/or second therapeutic agents, or as a solution or suspension in an aqueous liquor or non-aqueous liquid such as a syrup, an elixir, an emulsion, or a draught. Such compositions and preparations may contain at least about 0.1 wt-% of the active agent. The amounts of the therapeutic agents should be such that the dosage level will be effective to produce the desired result in the subject.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

Preferably the compound is administered orally, intraperitoneally, or intravenously or intrathecally or some suitable combination(s) thereof.

Methods of administering small molecule therapeutic agents such gemcitabine are well-known in the art. Dosage calculation for antitumor agents are exemplified, for example, by Gurney H., *J. Clin. Oncol.*, 14, 2590-2611. Methods for extrapolation of effective dosages in mice, and other animals, to humans are also known in the art; for example, see U.S. Pat. No. 4,938,949. Dosage calculations for individual therapeutic agents may also be readily determined from the literature by those skilled in the art. For example, dosing and clinical studies of gemcitabine, and numerous other drugs may be found at the U.S. Food and Drug Administration Center for Drug Evaluation and Research website, and from literature that accompanies commercially available therapeutic agents, such as product literature for GEMZAR® (Eli Lilly and Company), the commercially available injectable form of gemcitabine HCL (PV 4046 AMP; Eli Lilly and Company, 2005).

The therapeutic agents described in the present disclosure can be administered to a subject alone or together (coadministered, optionally, but not necessarily, in a single formulation) with other active agents as described herein, and are preferably administered with a pharmaceutically acceptable buffer. The therapeutic agents can be combined with a variety of physiological acceptable carriers, additives for delivery to a subject, including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the peptide, can be used. Other suitable carriers include, but are not limited to, alcohol, phosphate buffered saline, and other balanced salt solutions.

The formulations may be conveniently presented in unit dosage form and may be prepared by any of the methods well known in the art of pharmacy. Preferably, such methods include the step of bringing the therapeutic agent (i.e., the active agent) into association with a carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering the therapeutic agents to a subject in an amount effective to produce the desired effect. The therapeutic agents can be administered as a single dose or in multiple doses. Useful dosages of the active agents can be determined by comparing their in vitro activity and the in vivo activity in animal models.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of Formula V, or a pharmaceutically acceptable salt, solvate, ester or prodrug of said compound and a pharmaceutically acceptable carrier, vehicle or diluent.

In the embodiment in which a first therapeutic agent is administered to increasing receptor expression and a second therapeutic agent is administered that targets the receptors, the first and second therapeutic agents may be administered together or separately in a single dose or in multiple doses. Administration of the second therapeutic agent after administration of the first therapeutic agent provides the advantage of providing time for the first therapeutic agent to enrich receptor expression in the cancer cells, thereby facilitating targeting of the second therapeutic agent to the cancer. The second therapeutic agent may be administered as much as two weeks after the administration of the first therapeutic agent or as little as two days afterward or even sooner, such as 24 hours after administration of the first therapeutic agent. In a preferred embodiment, the second therapeutic is administered about 3 to 6 days following the administration of the first therapeutic agent.

Moreover, treatment of a subject afflicted with a cancer or precancerous condition by administering a first and second therapeutic may result in an additive effect. More preferably, treatment by administering a first and second therapeutic agent results in a synergistic therapeutic effect. A synergistic effect, as defined herein, occurs when treatment by a first therapeutic agent in conjunction with a second therapeutic agent results in a reduction in tumor load or growth delay that is greater than the reduction in tumor load or growth delay that is observed when the effects of separate treatment by the first therapeutic agent and the second therapeutic agent of the invention are added together, where the dosages and treatment schedules are otherwise the same when used individually or in combination. The comparison of the combined treatment with the effects of separate treatment, added together, result in a ratio that will be greater than 1 (i.e., greater than 100%) if a synergistic effect is present. Preferably, a synergistic effect with a ratio of at least 2 (i.e., at least 200%) is provided by the method of the invention, and more preferably the synergistic effect has a ratio of at least 3 (i.e., at least 300%).

Yet another aspect of the invention is a composition, e.g., a pharmaceutical composition, comprising at least one compound of Formula V, or a pharmaceutically acceptable salt, solvate, ester or prodrug thereof, in combination with at least one Checkpoint kinase inhibitor, such as, Chk1 inhibitor, Chk2 inhibitor and the like, or a pharmaceutically acceptable salt, solvate, ester or prodrug thereof. Preferably, the pharmaceutical composition comprises at least one compound of Formula V, or a pharmaceutically acceptable salt, solvate, ester or prodrug thereof, in combination with at least one Chk1 inhibitor, or a pharmaceutically acceptable salt, solvate, ester or prodrug thereof. Suitable Chk1 inhibitors for such combinations are disclosed in the afore-mentioned US 2007/0083044, US 2007/0082900, US 2007/0105864 and US 2007/0117804, the disclosures of which are incorporated herein by reference thereto. Other suitable Checkpoint kinase inhibitors include, for example, UCN-01 (KW-24101; 7-Hydroxystaurosporine; from Kyowa Hakko Kogyo Co., Ltd., Tokyo, Japan and Keryx Biopharmaceuticals, Inc., New York, N.Y.), Lilly/ICOS IC83/LY2603618 (from Eli Lilly, Indianapolis, Ind.), XL-844 (EXEL-9844 from Exelixis), AZD7762 (from Astra Zeneca), PF-394691 (from Pfizer), PF-473336 (from Pfizer) and the like.

Non-limiting examples of preferred Chk1 inhibitors, suitable as combination agents according to one aspect of this invention, are pyrazolopyrimidine compounds or imidazopyrazine compounds, or a pharmaceutically acceptable salt, solvate, ester or prodrug thereof. Non-limiting examples of suitable pyrazolopyrimidines are disclosed in US 2007/0072881, U.S. Pat. No. 7,161,003, U.S. Pat. No. 7,119,200, U.S. Pat. No. 7,196,078, U.S. Pat. No. 7,067,661, U.S. Pat. No. 7,205,308, US 2007/0072880, U.S. Pat. No. 7,078,525, U.S. Pat. No. 7,196,092. US 2007/0072882, U.S. Pat. No. 7,084,271, and U.S. Pat. No. 7,074,924, the disclosures of which are incorporated herein by reference thereto. Non-limiting examples of suitable imidazopyrazines are disclosed in U.S. Pat. No. 6,919,341, US 2006/0106023, US 2007/0105864, US 2007/0117804, U.S. Pat. No. 7,186,740, U.S. application Ser. No. 11/758,243 (filed Jun. 5, 2007), U.S. provisional Patent application Ser. No. 60/858,244 (filed Nov. 8, 2006) and U.S. provisional patent application Ser. No. 60/943,999 (filed Jun. 14, 2007), the disclosures of which are incorporated herein by reference thereto.

Non-limiting examples of preferred pyrazolopyrimidine compounds, suitable as combination agents according to one aspect of this invention, are the following compounds:

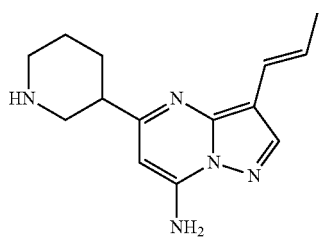

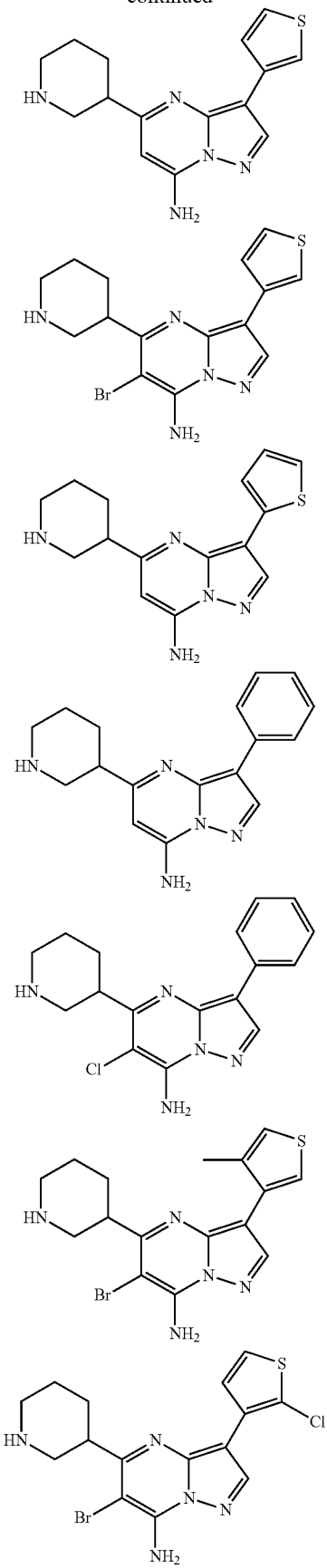

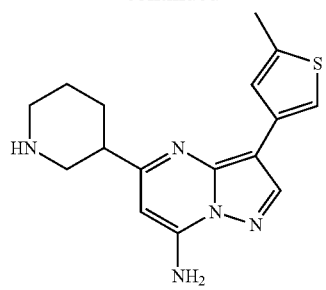
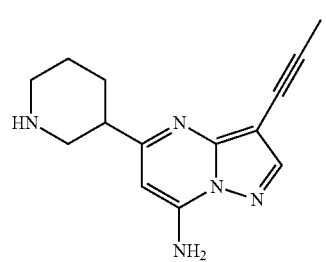
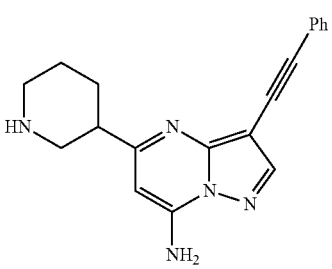
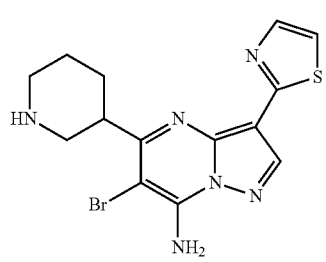
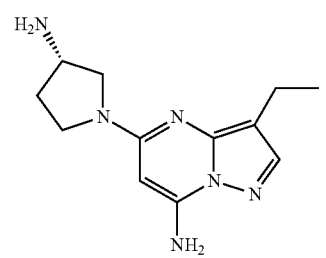
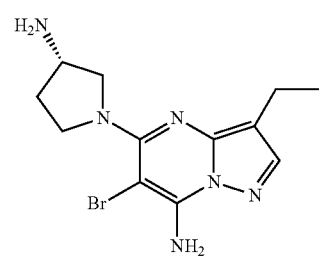
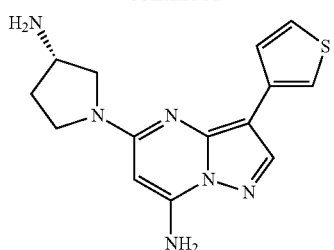
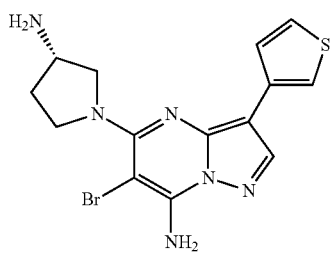
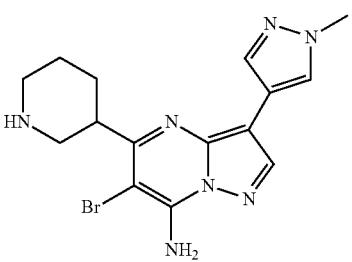
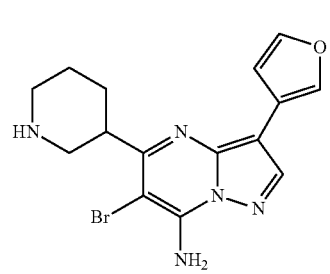
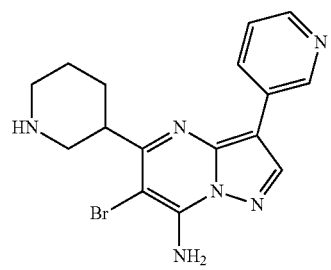
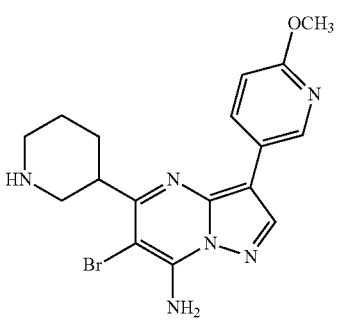

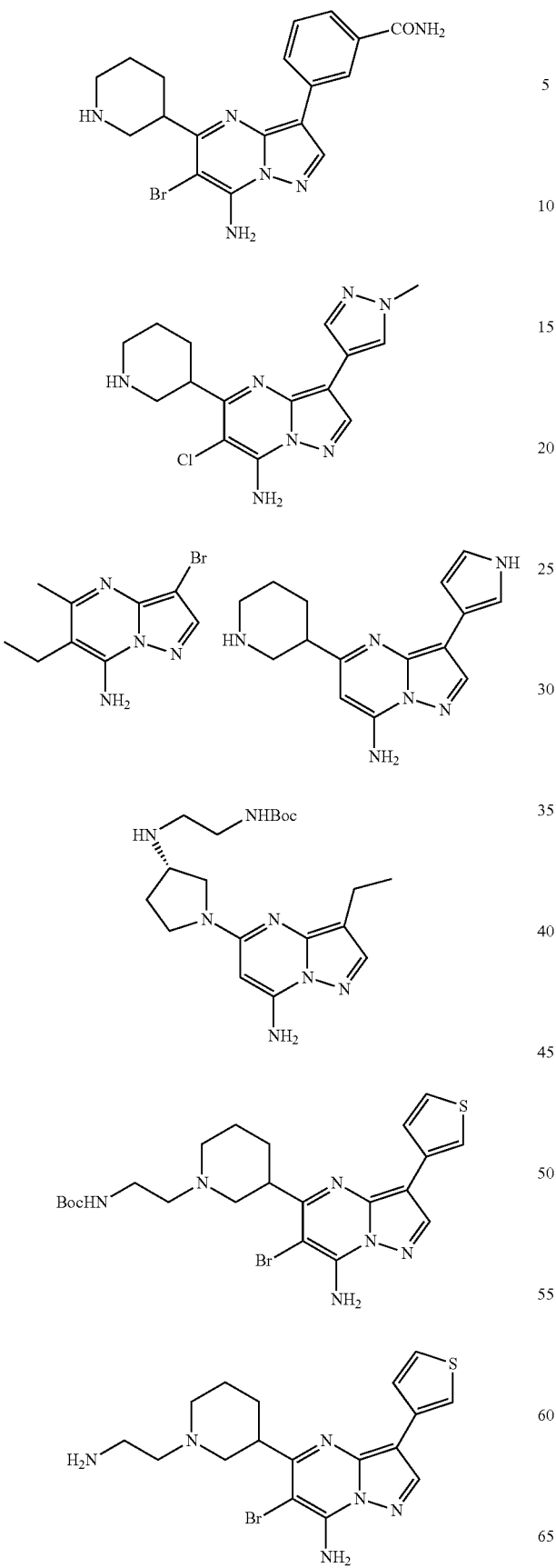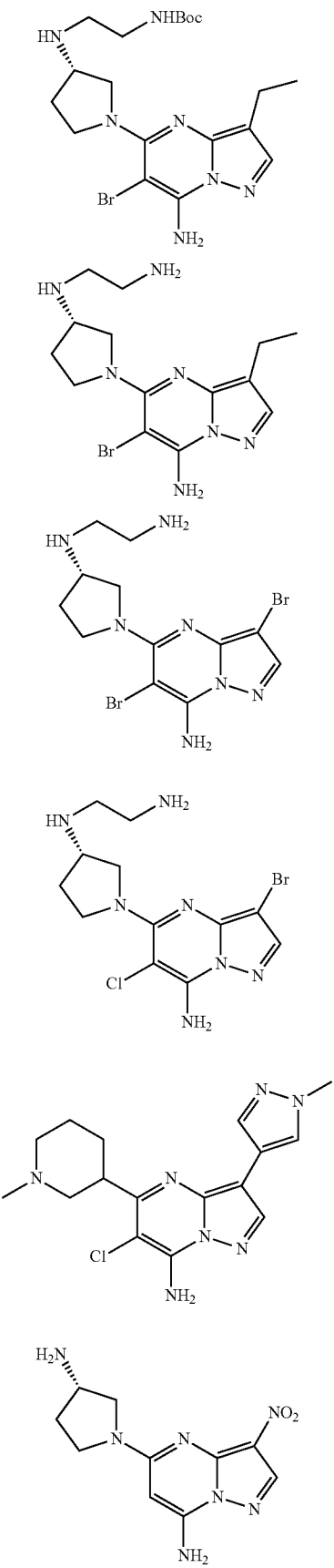

37
-continued
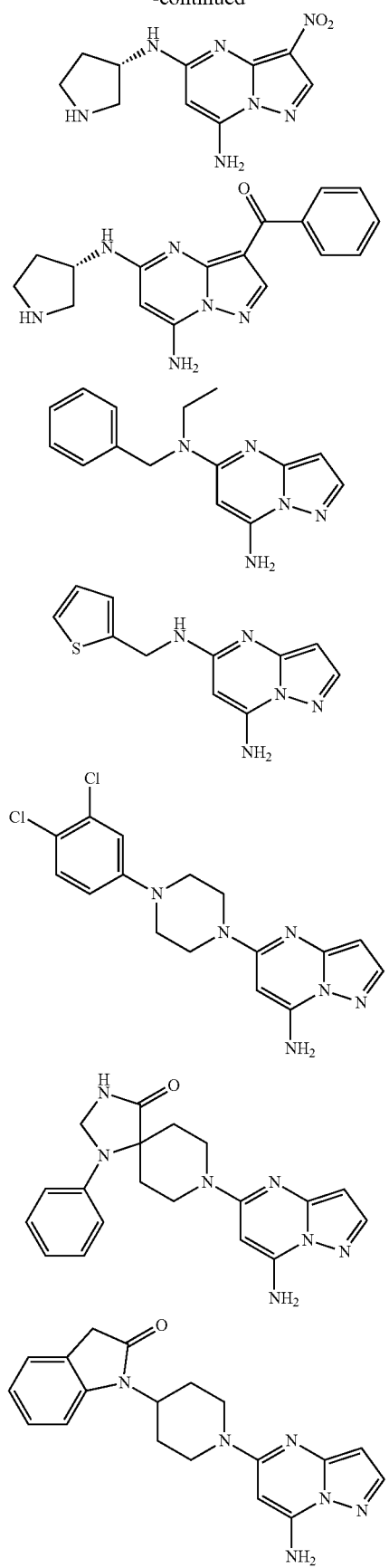
38
-continued
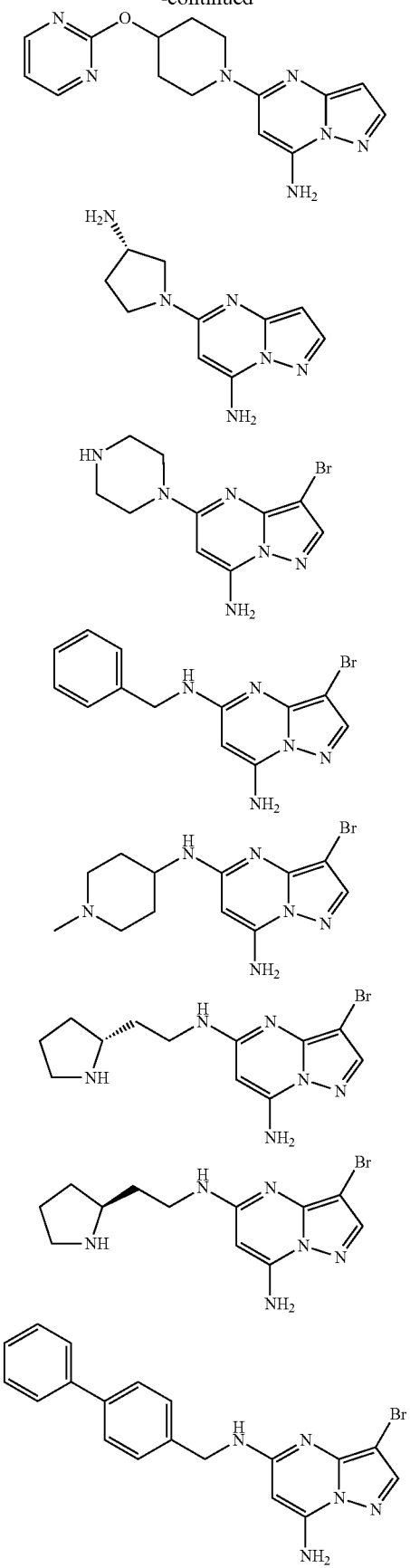

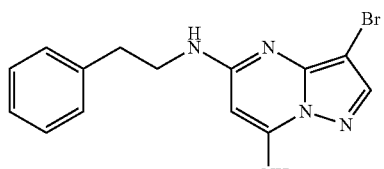
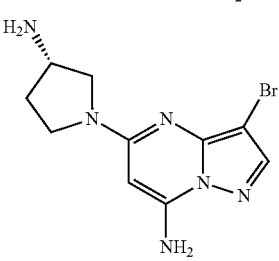
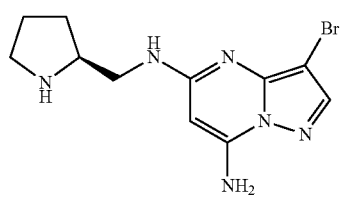
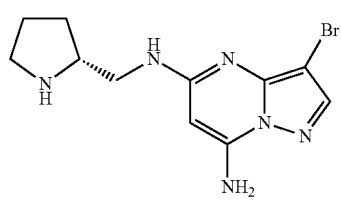
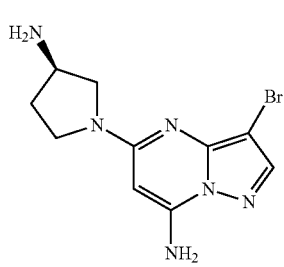
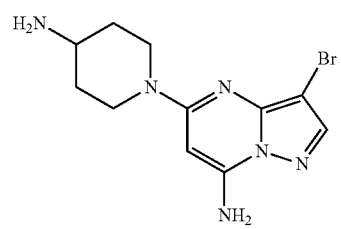
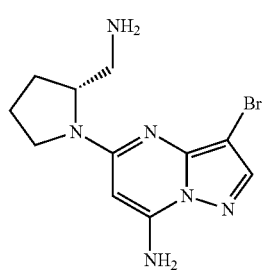
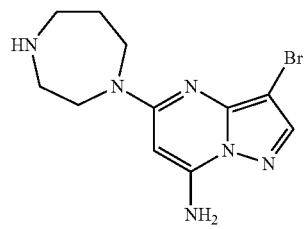
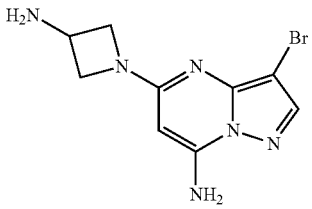
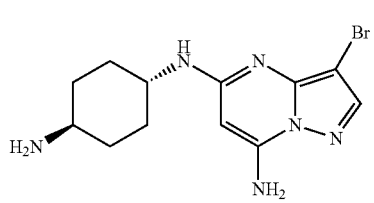
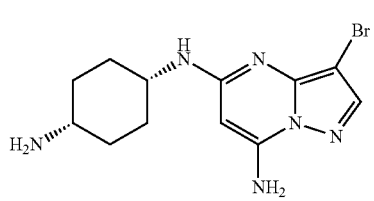
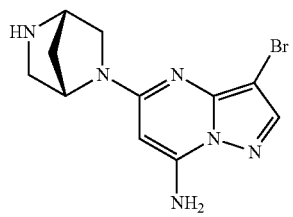
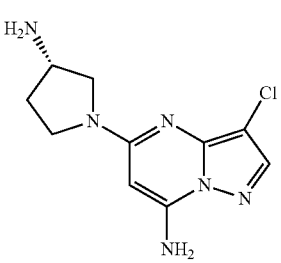
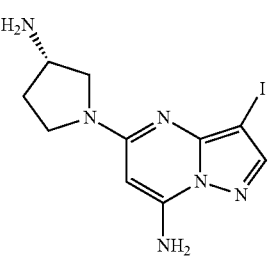

-continued
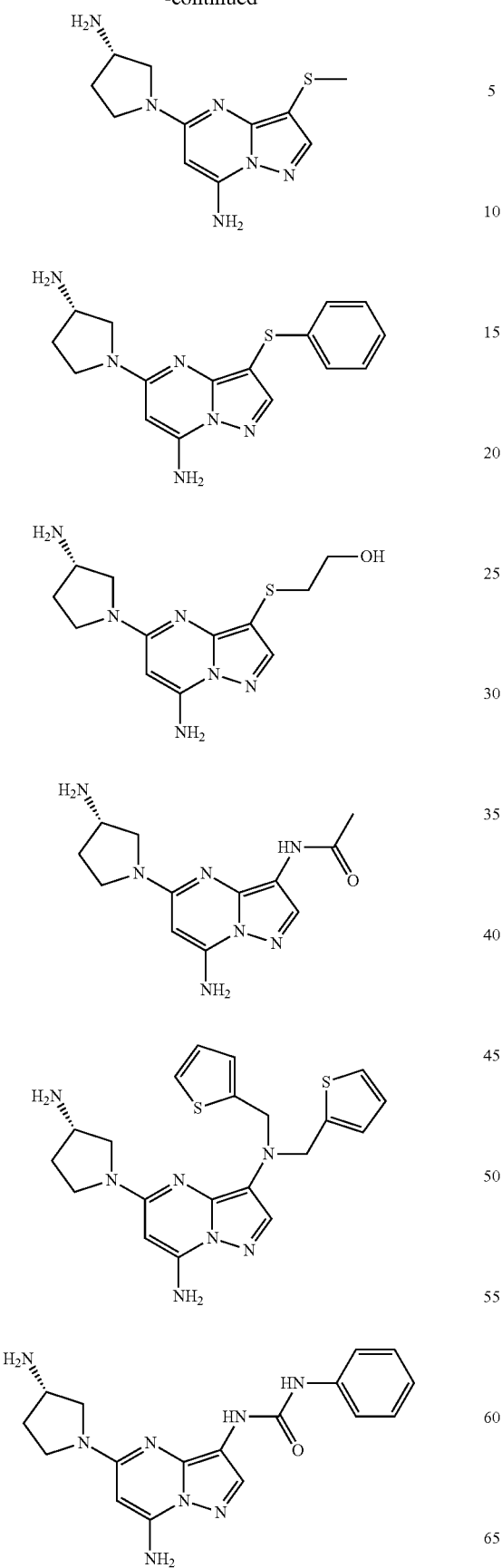
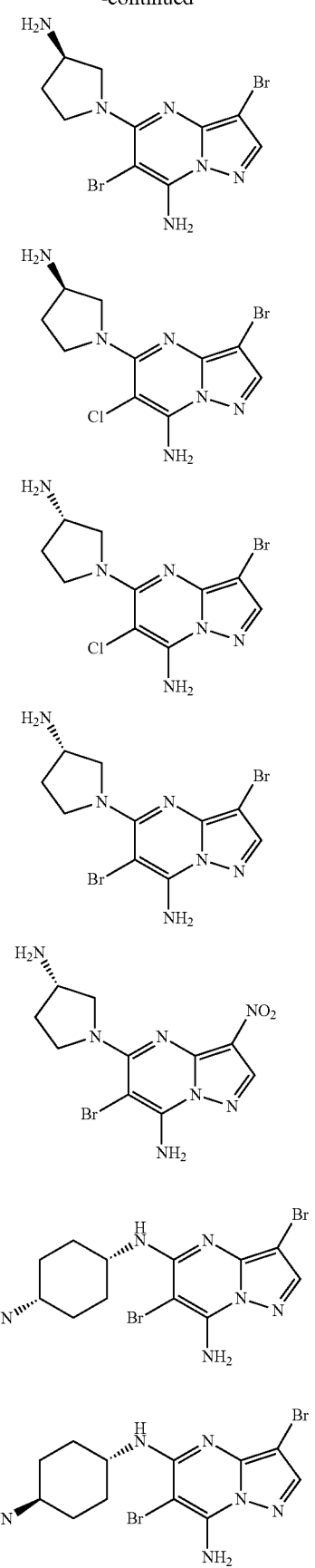

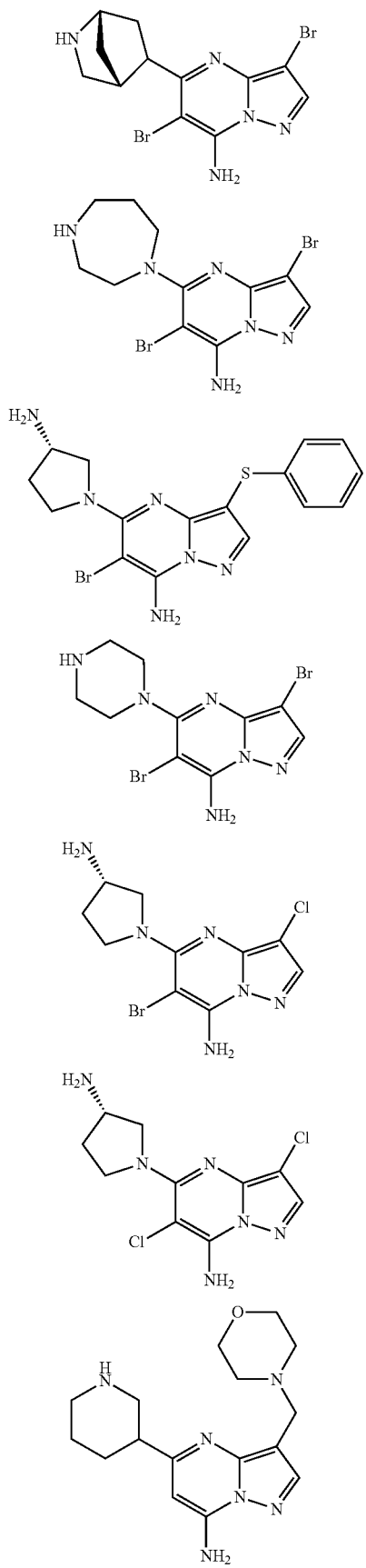
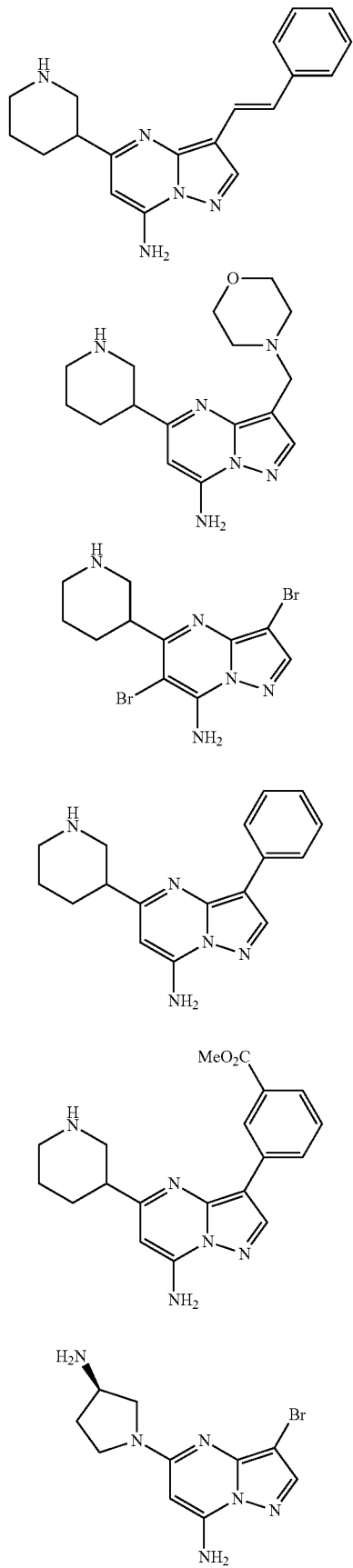

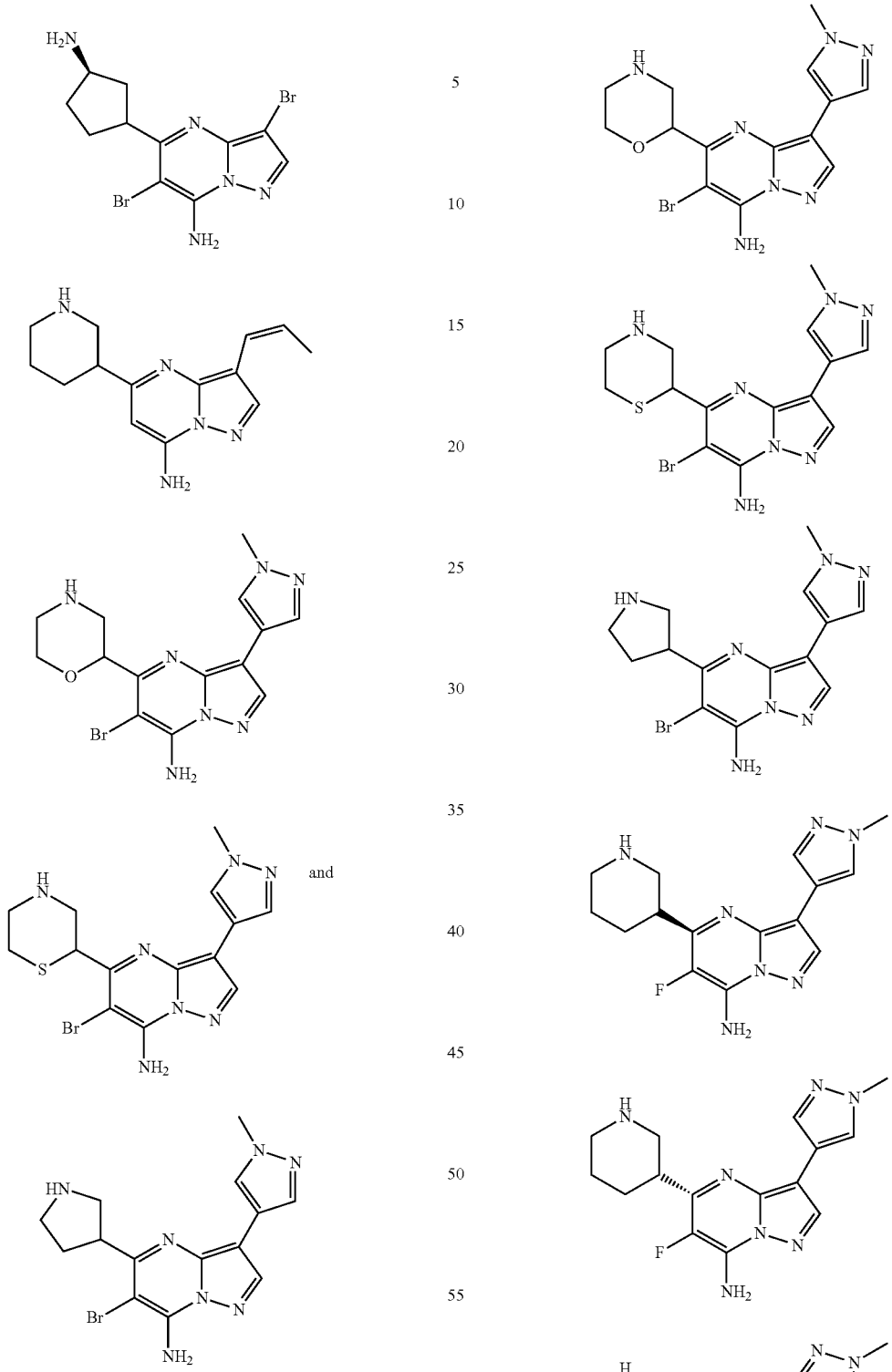
or a pharmaceutically acceptable salt, ester or prodrug thereof.
Non-limiting examples of more preferred pyrazolo[1,5-a]pyrimidine compounds, suitable as combination agents according to one aspect of this invention, are the following compounds, or a pharmaceutically acceptable salt, ester or prodrug thereof:

-continued
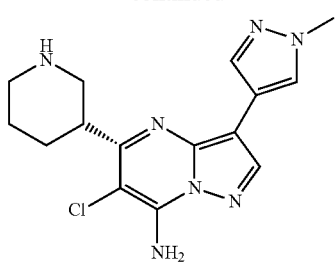
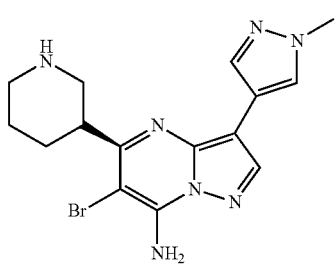
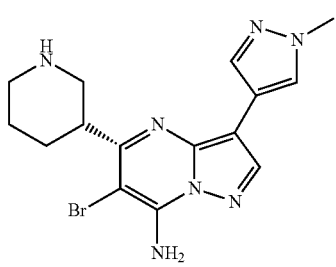
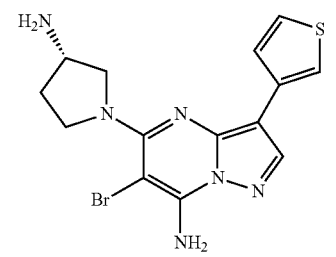
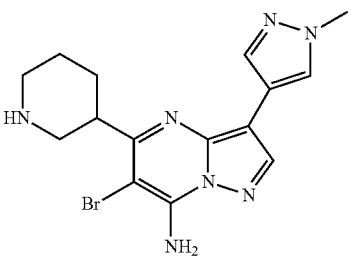
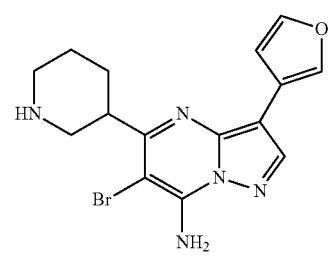
-continued
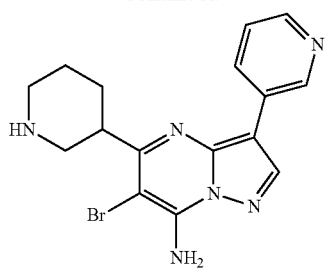
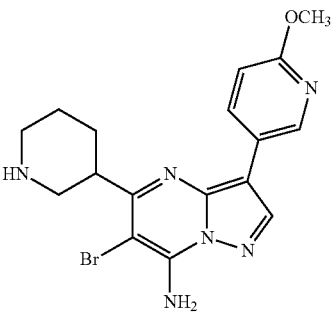
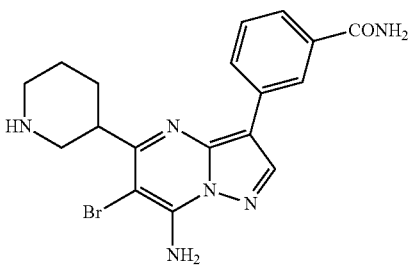
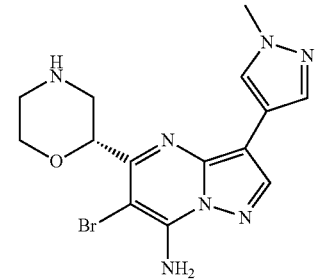
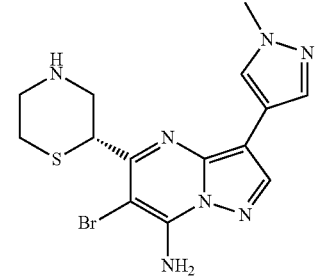
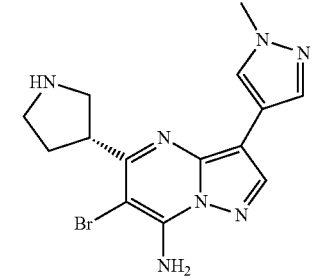

-continued
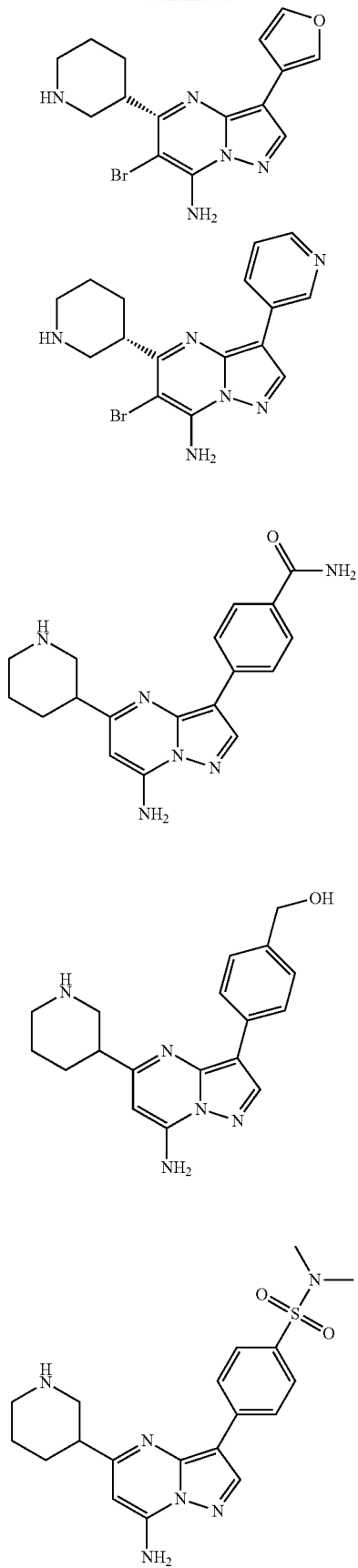
-continued
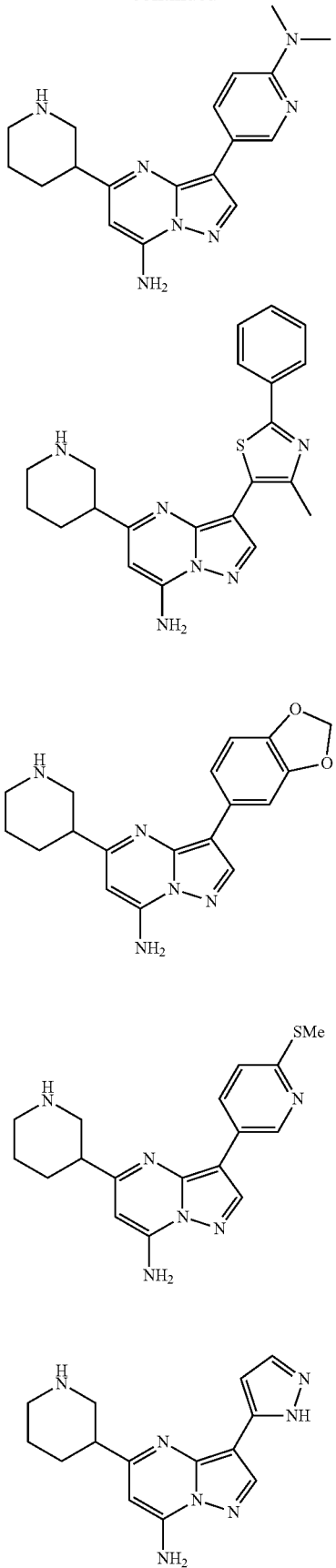

51
-continued
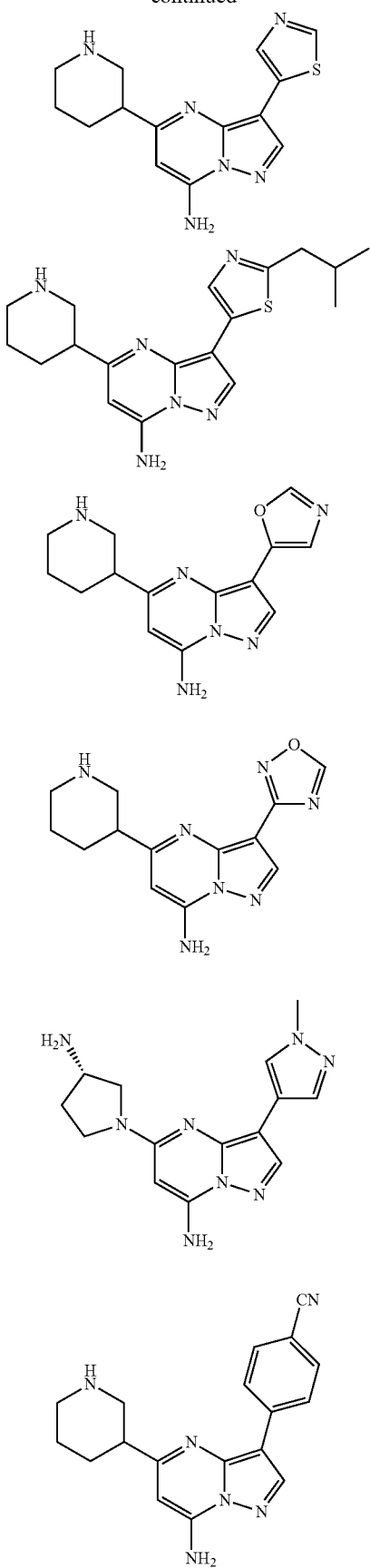
52
-continued
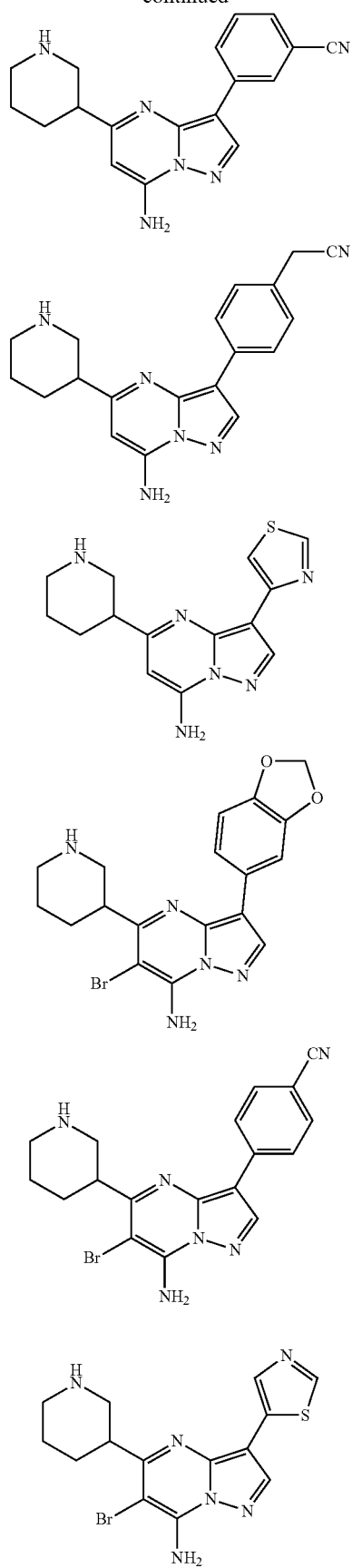

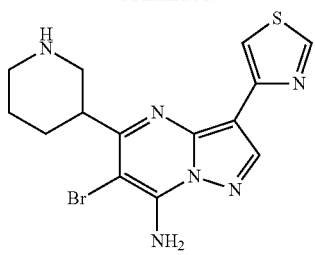
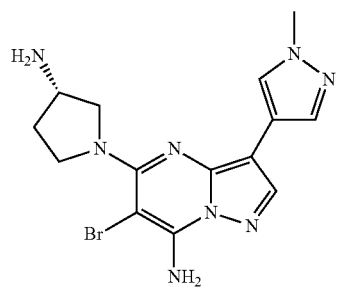
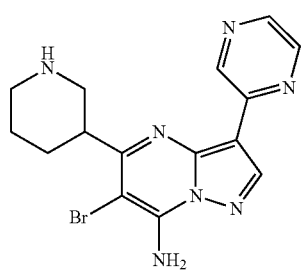
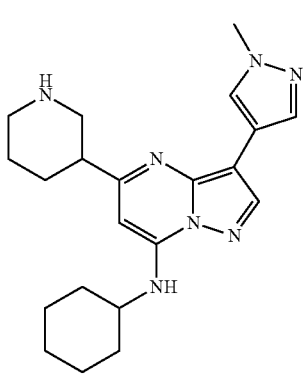
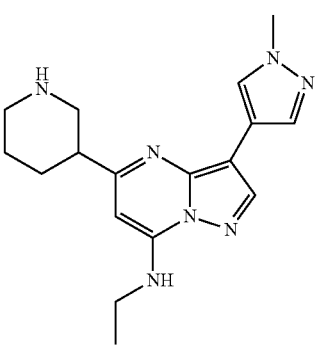
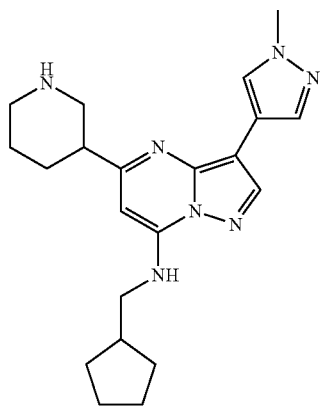
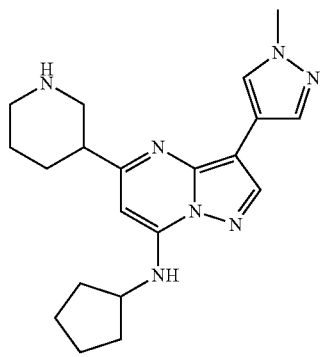
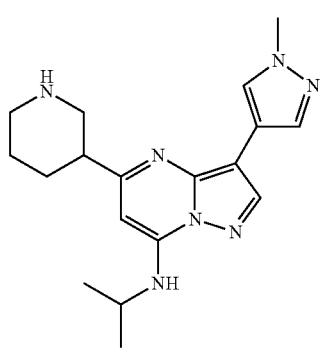
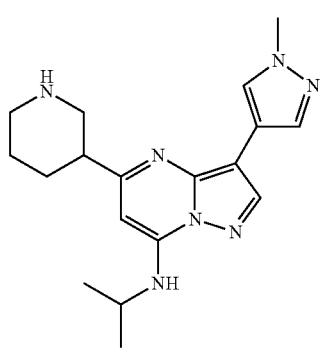

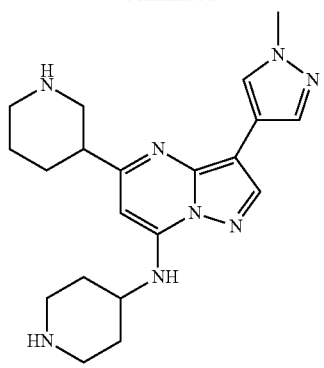
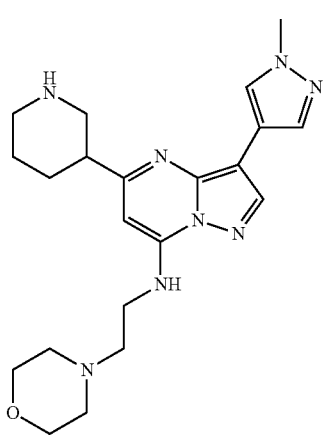
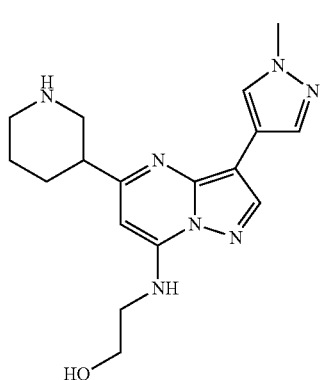
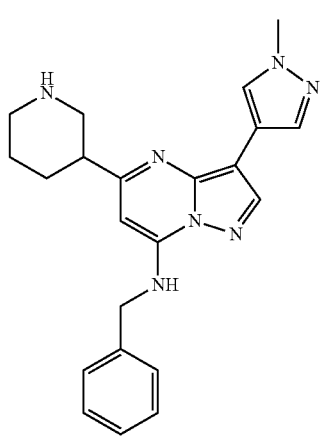
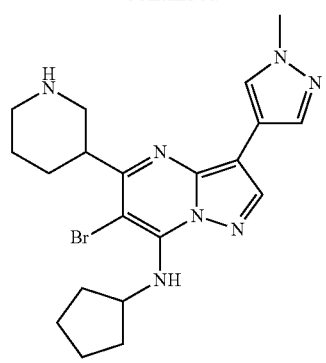
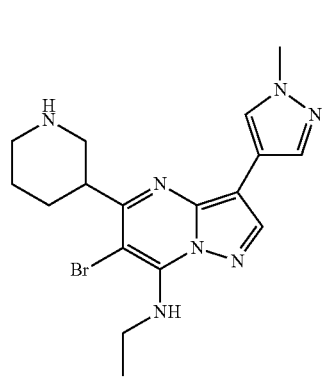
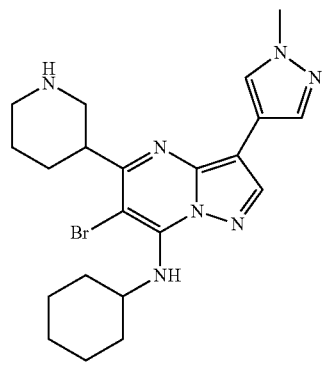
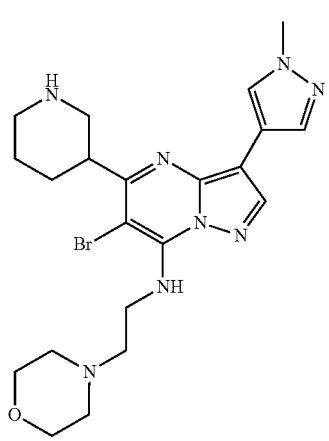

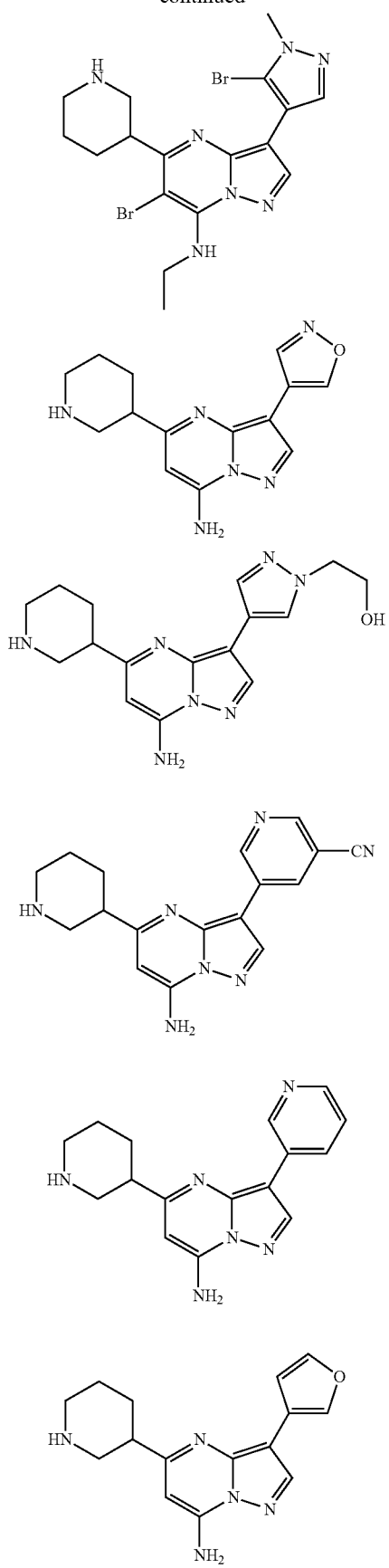
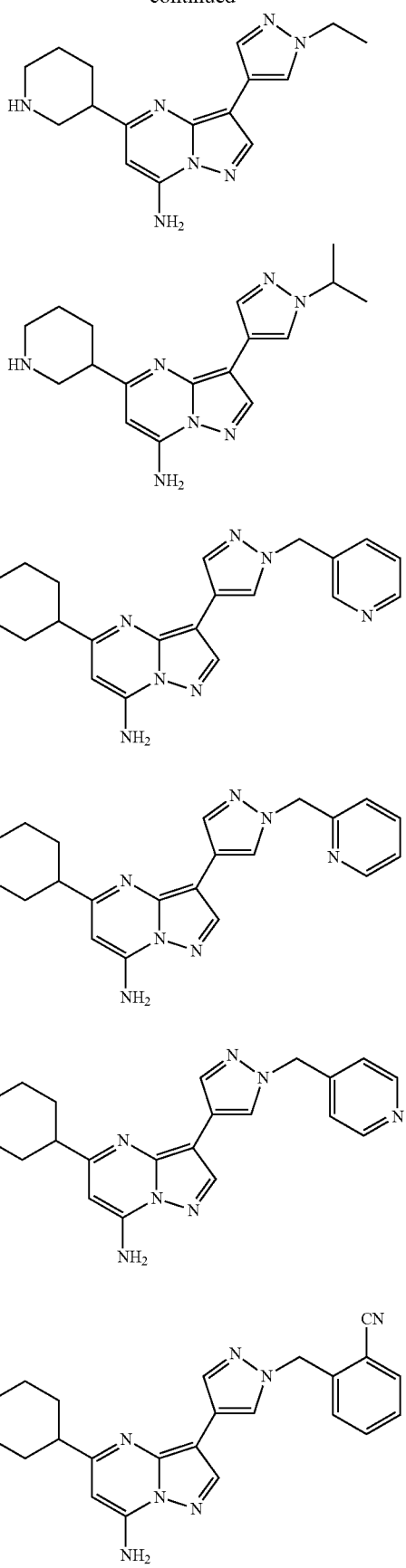

59
-continued
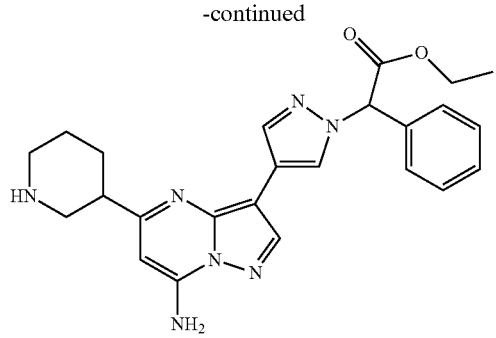
60
-continued
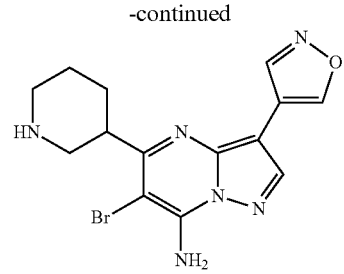
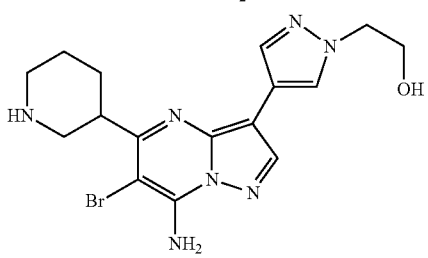
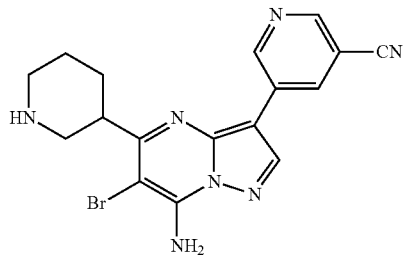
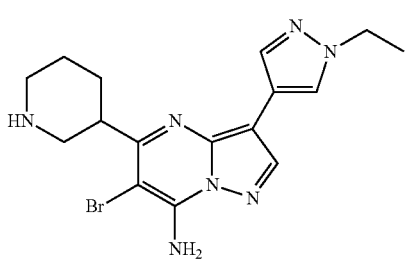
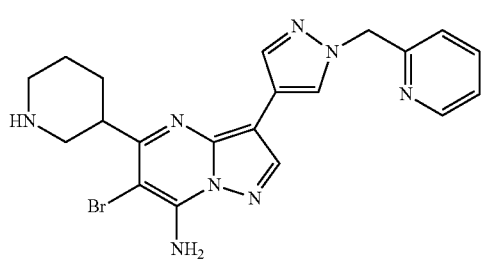
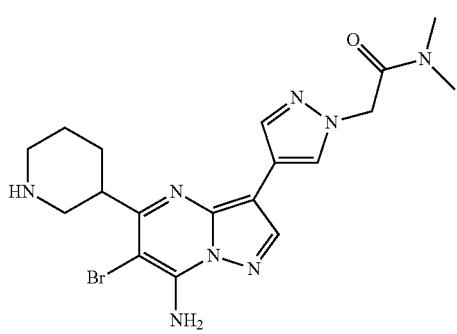

61
-continued
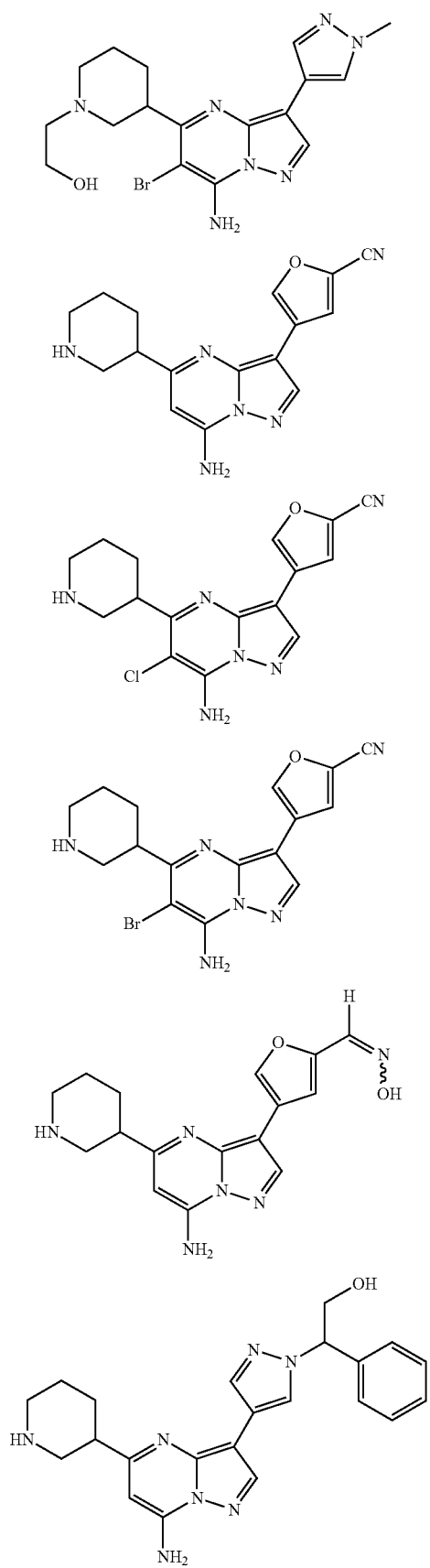
62
-continued
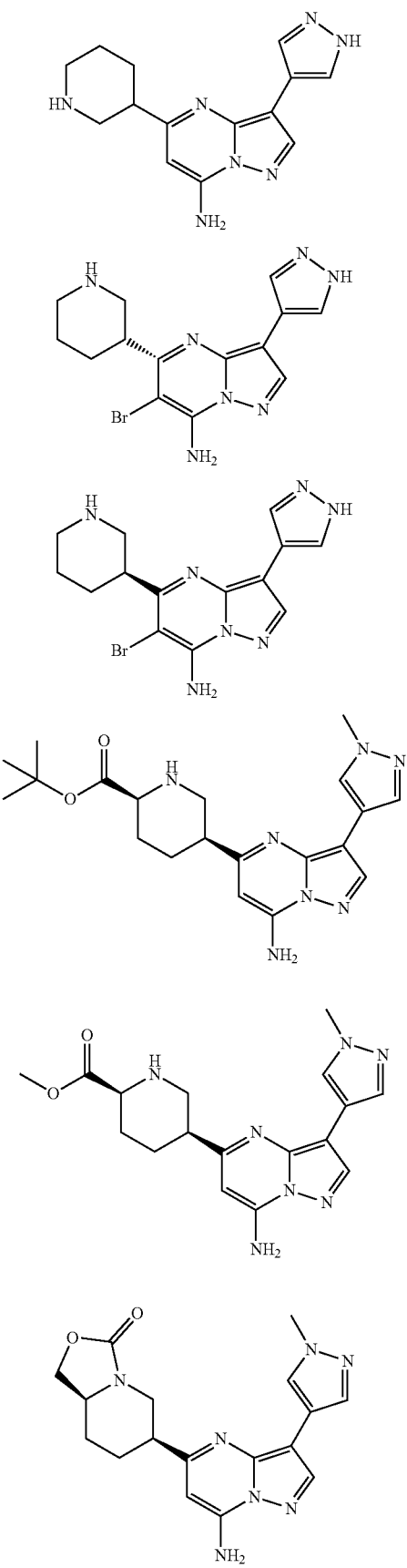

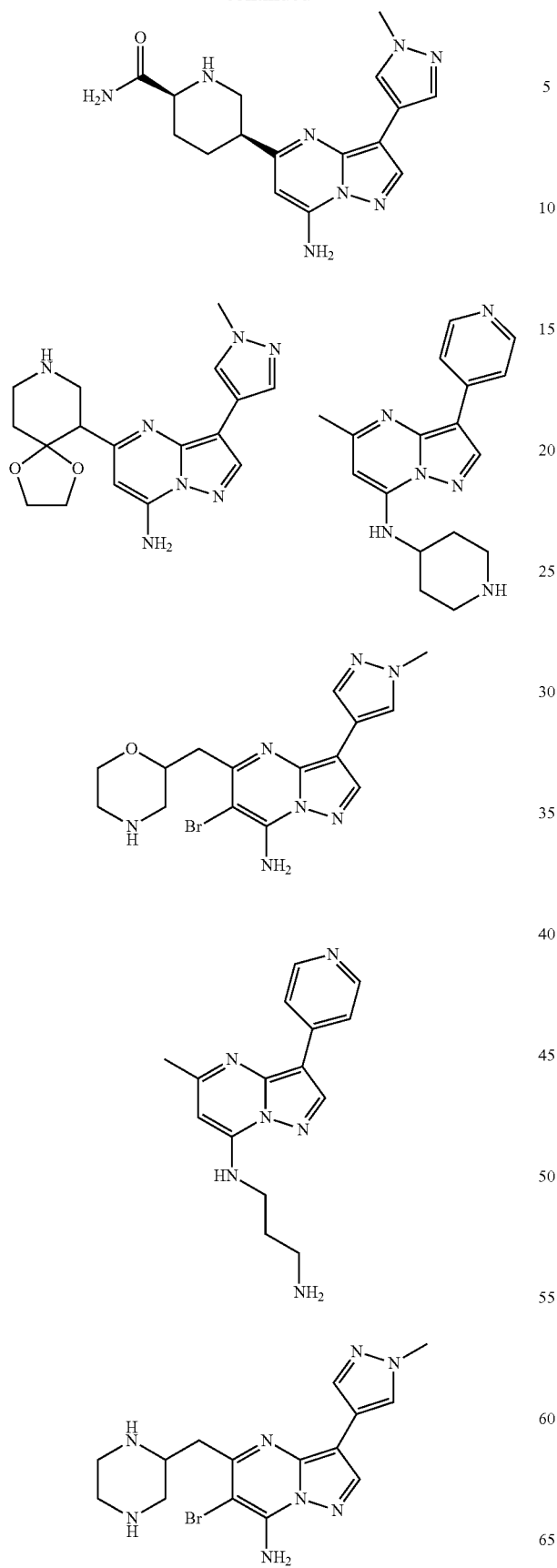
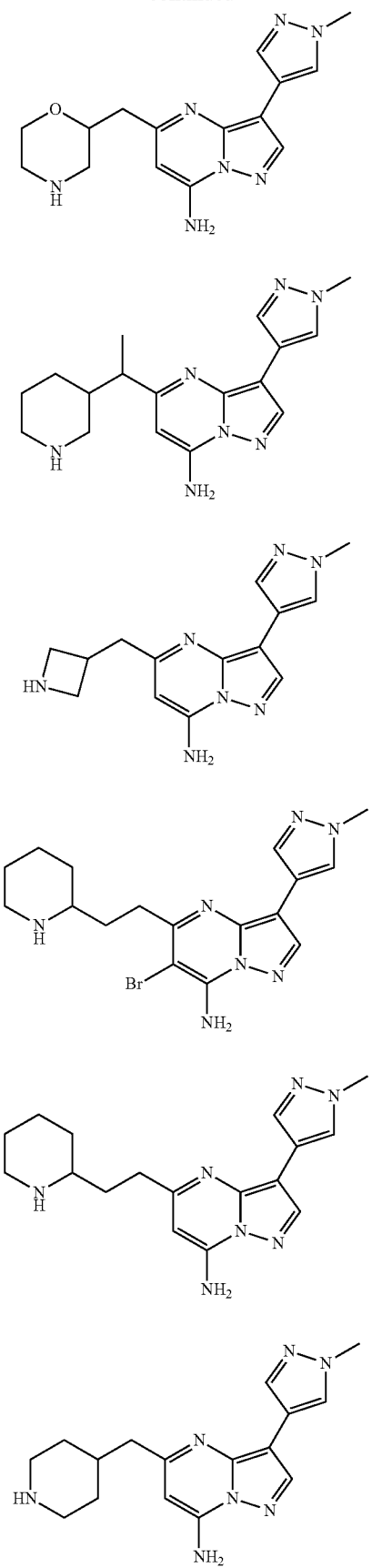

65
-continued
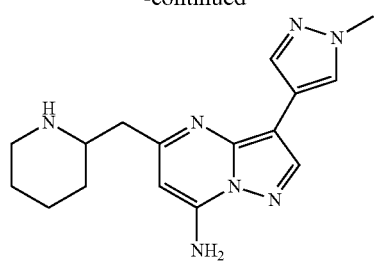
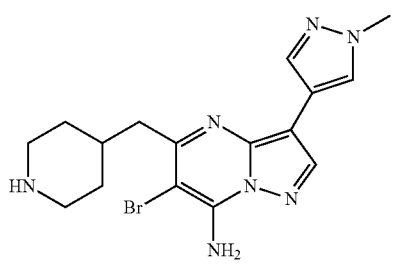
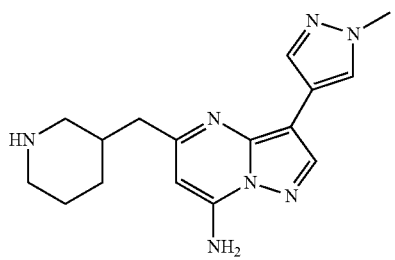
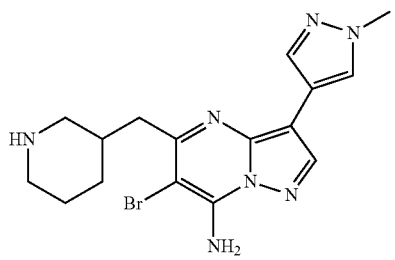
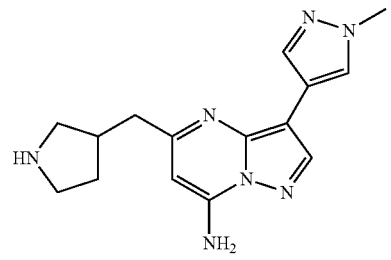
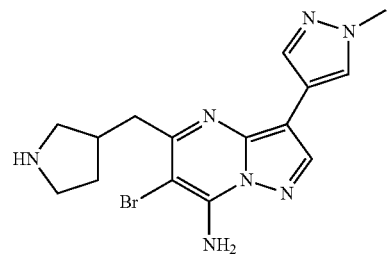
66
-continued
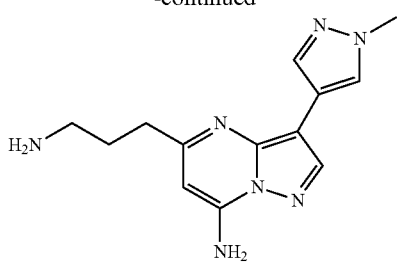
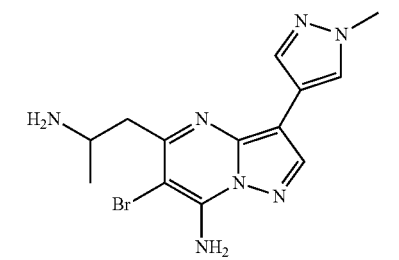
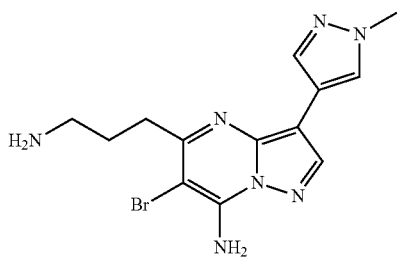
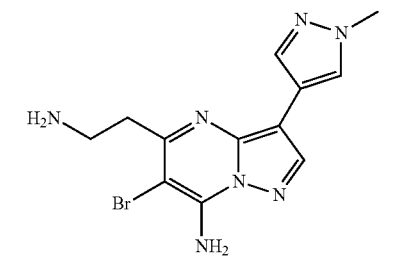

-continued
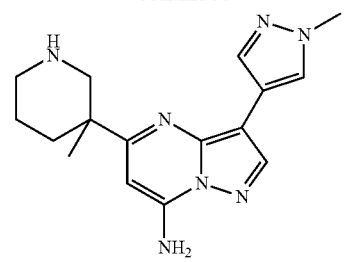
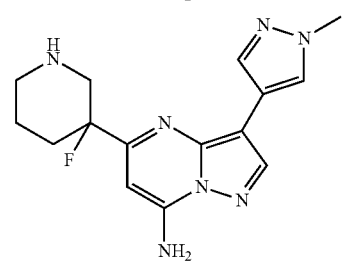
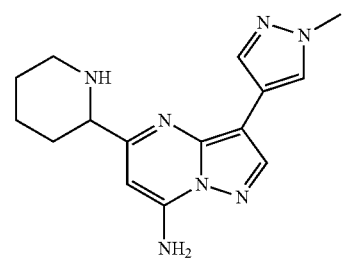
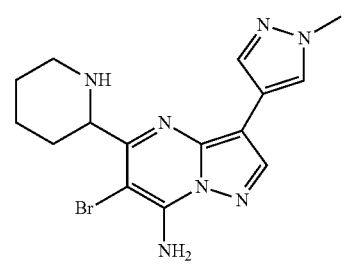
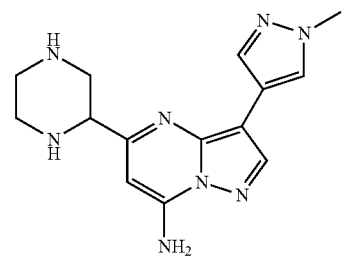
isomer 2
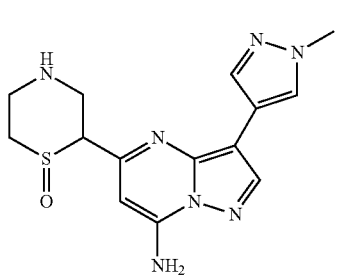
-continued
isomer 1
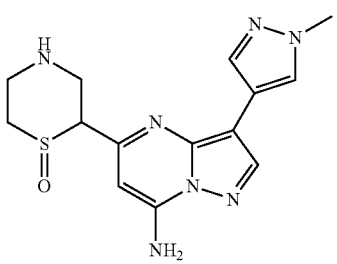
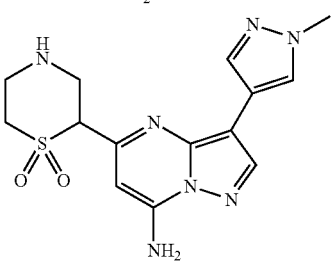
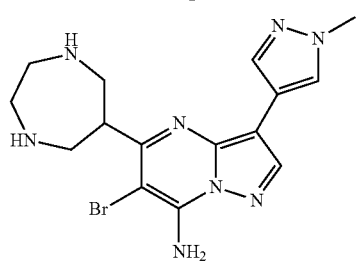
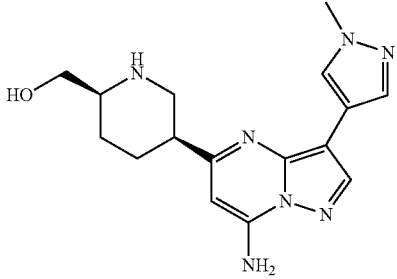
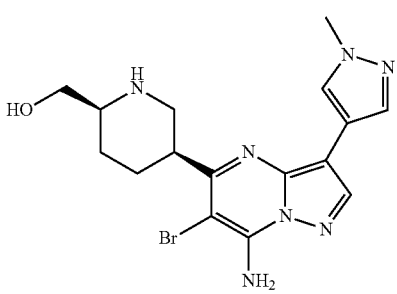
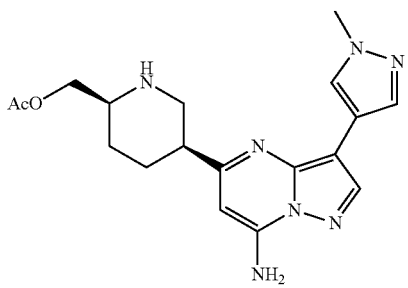

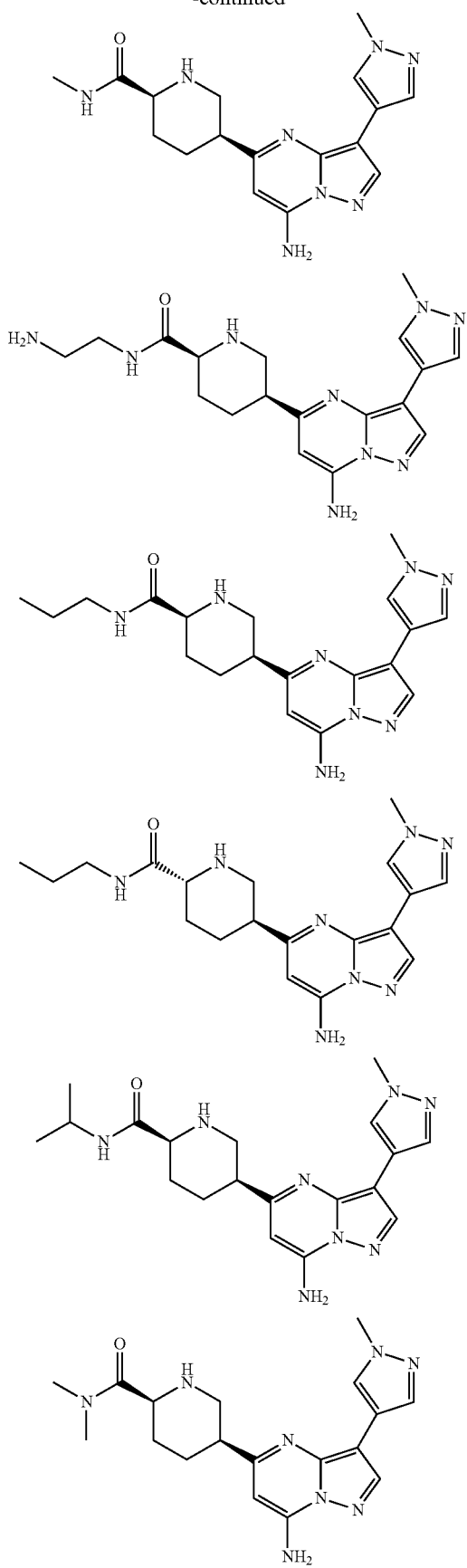
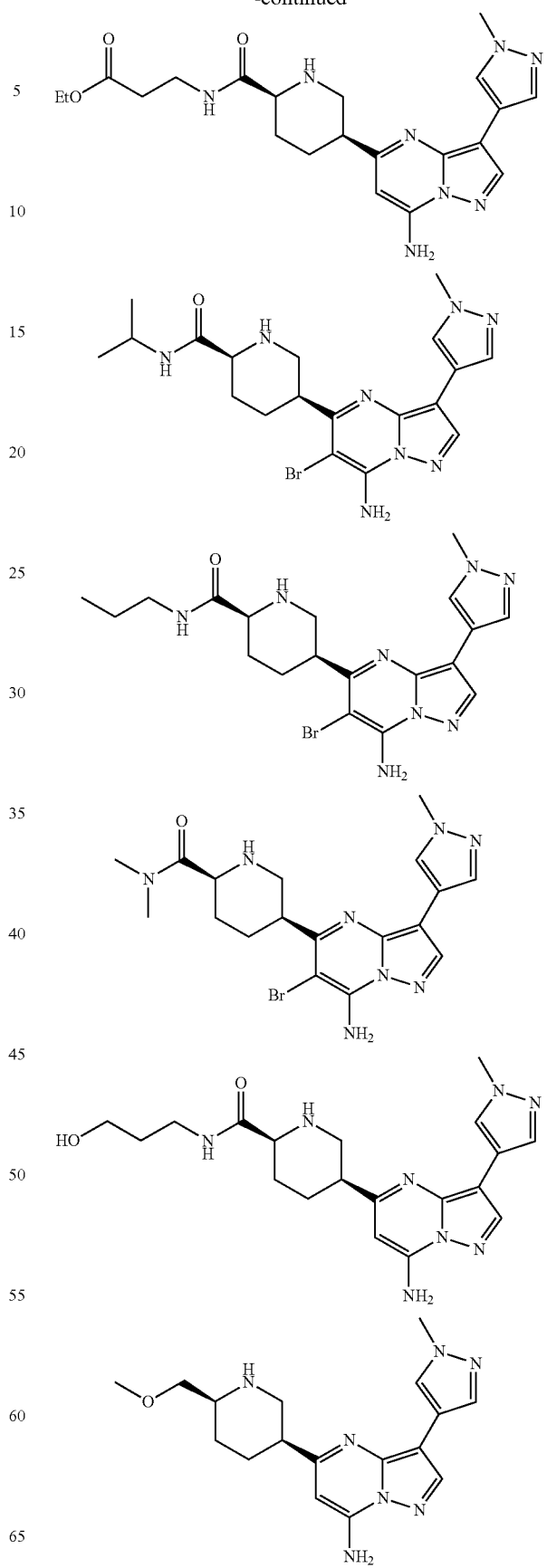

71
-continued
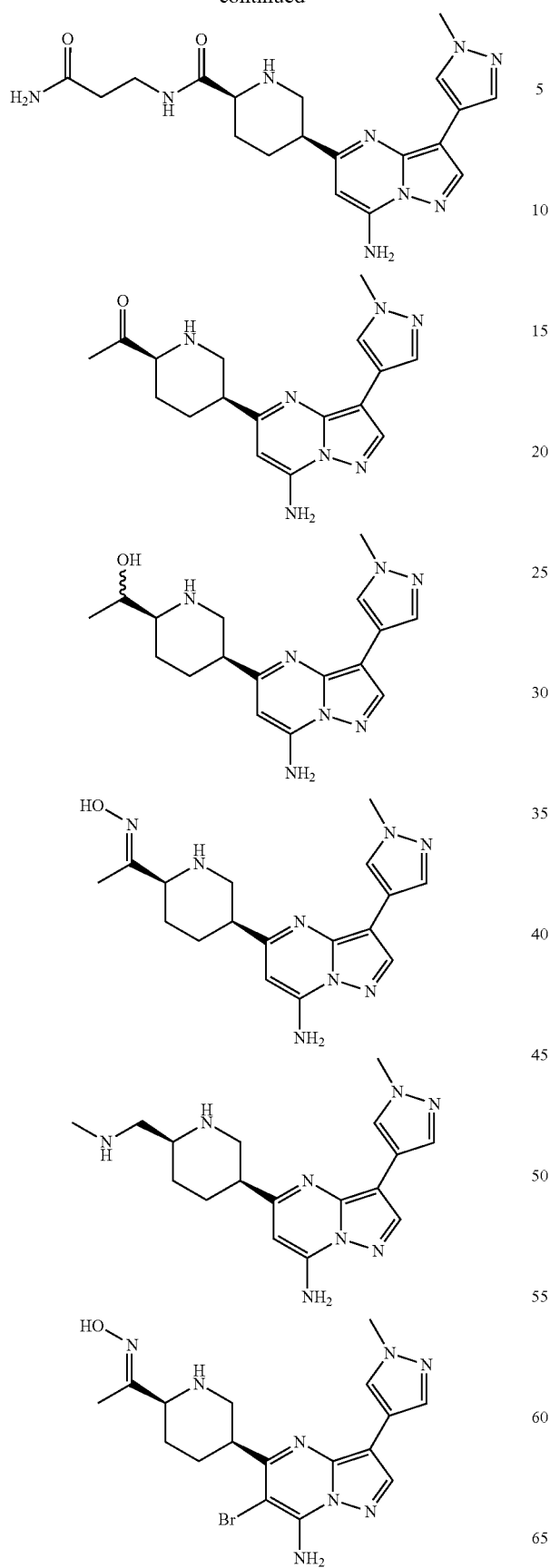
72
-continued
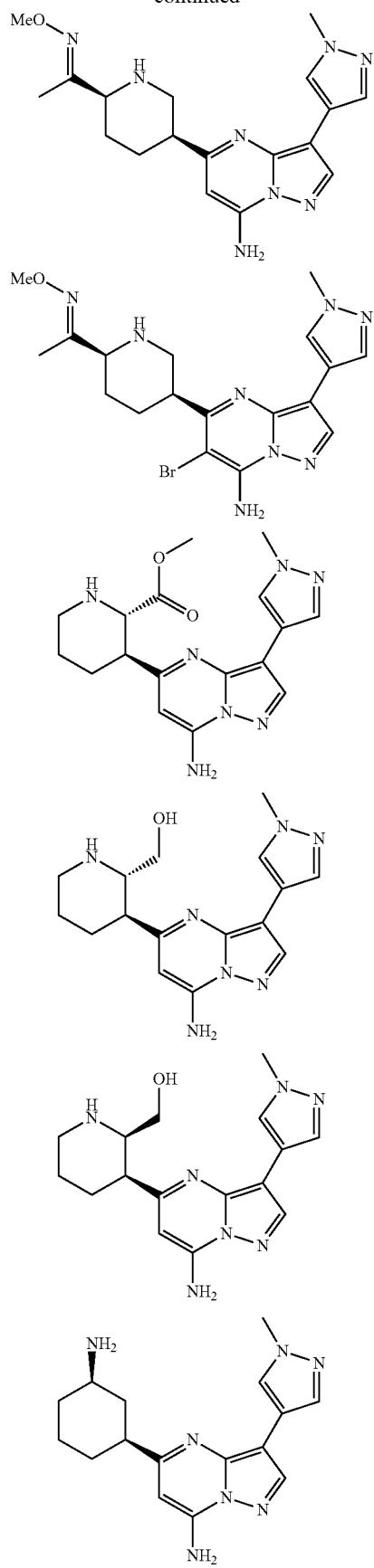

73
-continued
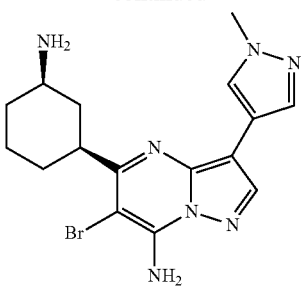
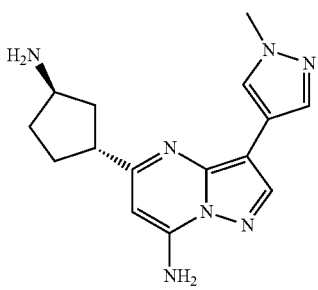
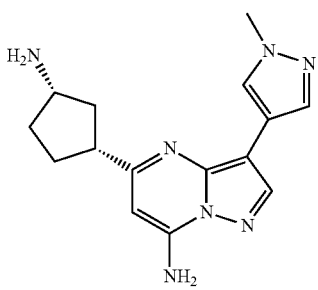
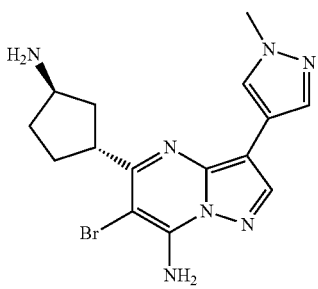
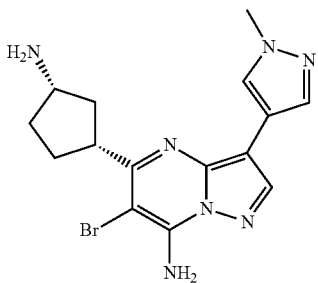
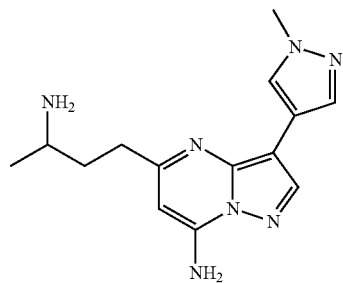
74
-continued
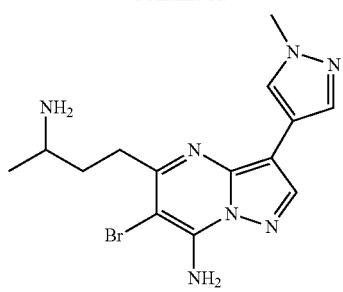
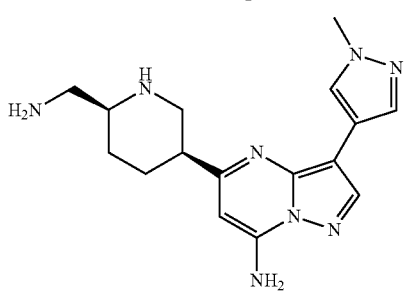
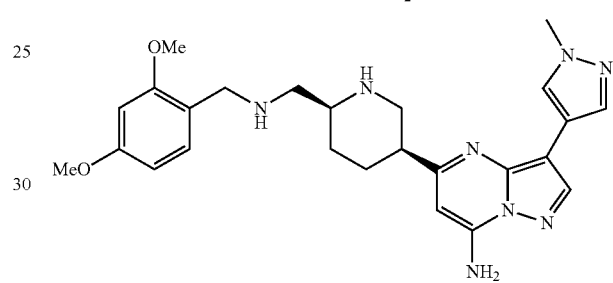
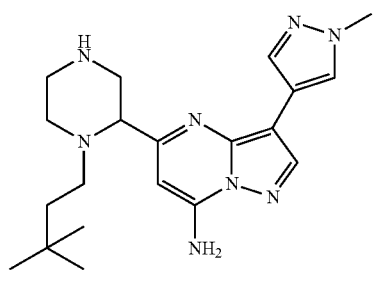
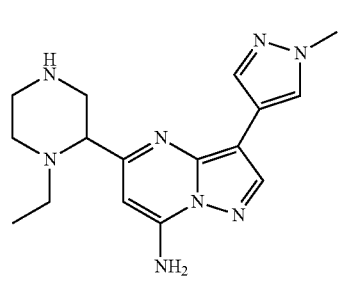
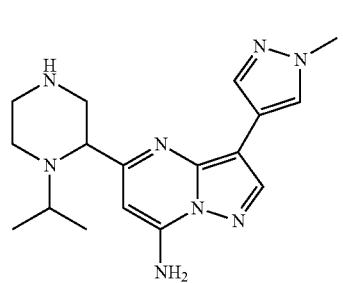

75
-continued
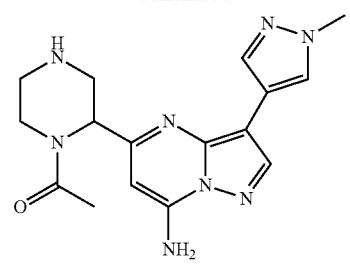
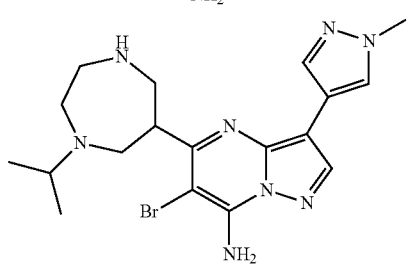
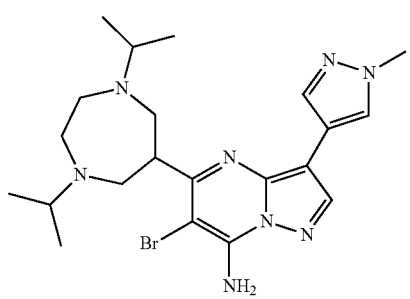
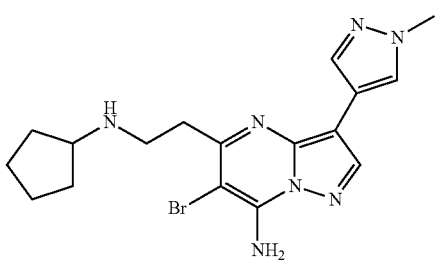
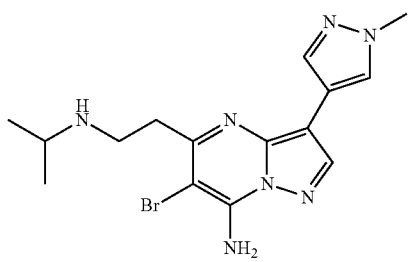
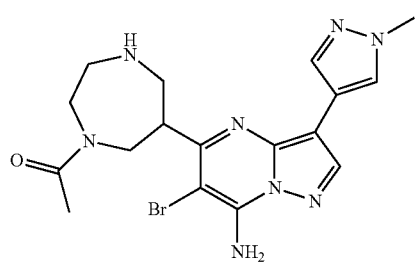
76
-continued
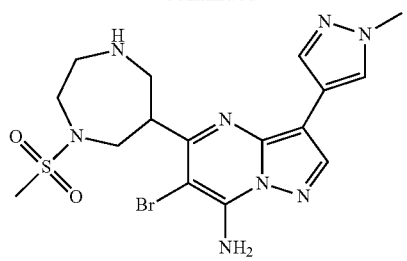
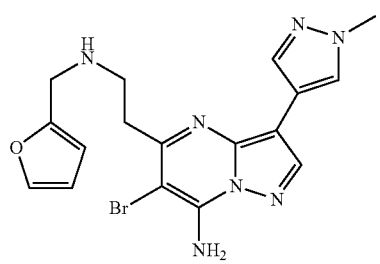
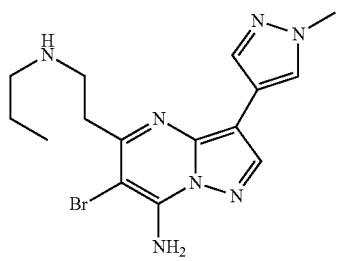
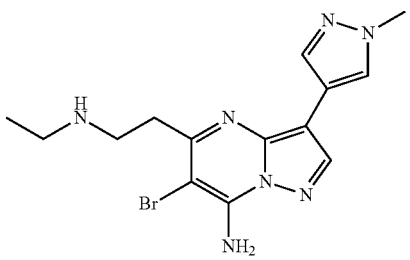
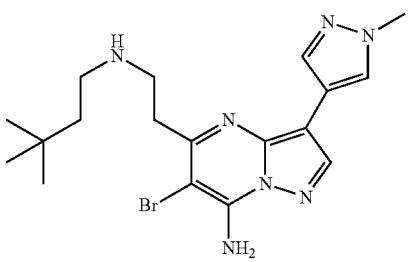
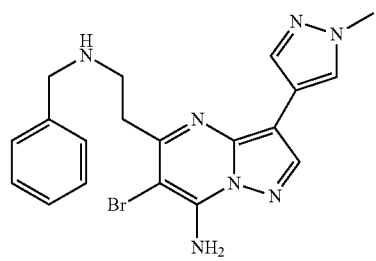

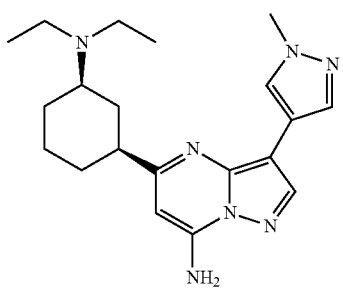
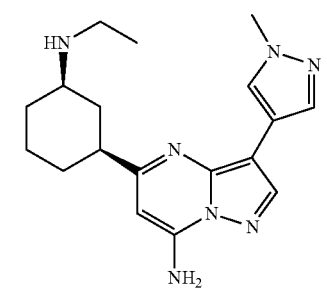
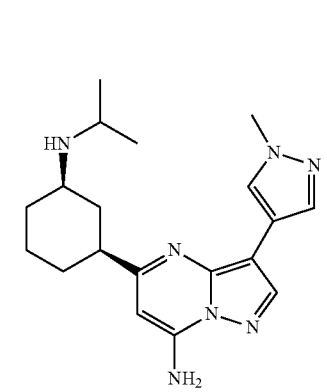
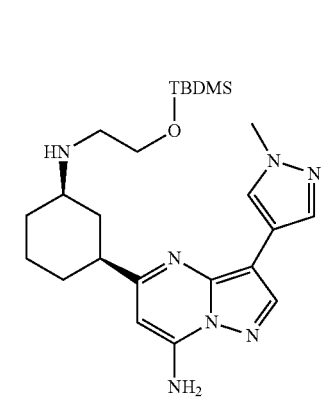
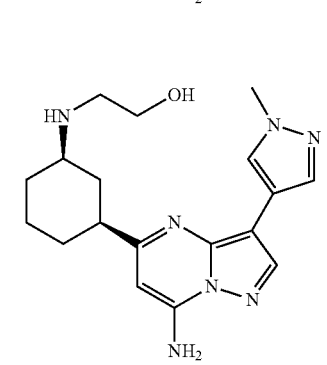
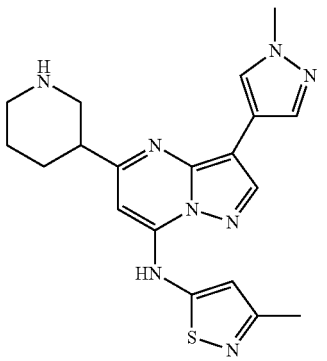
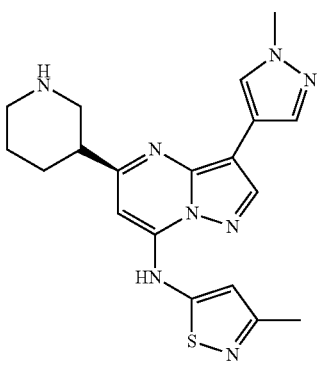
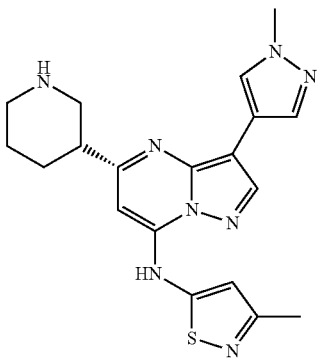
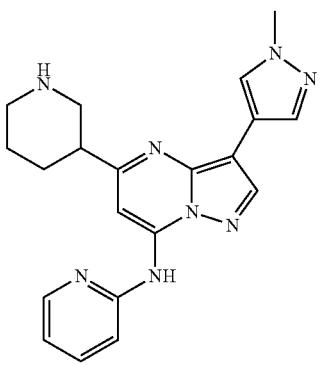

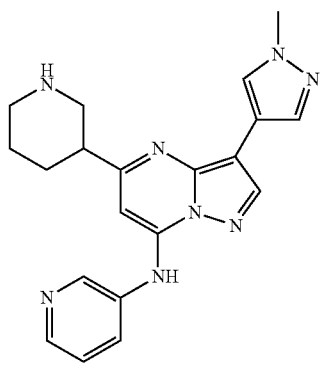
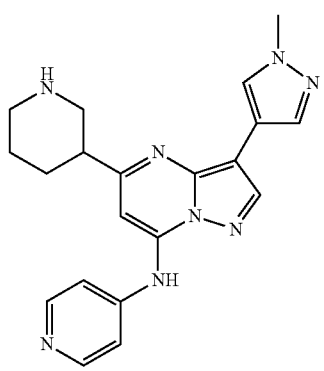
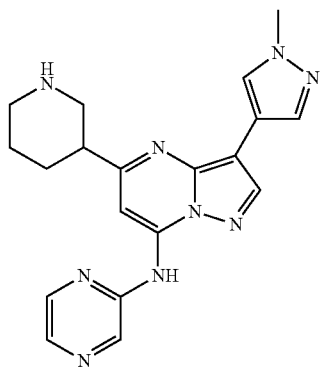
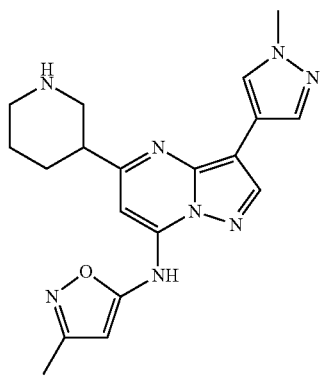
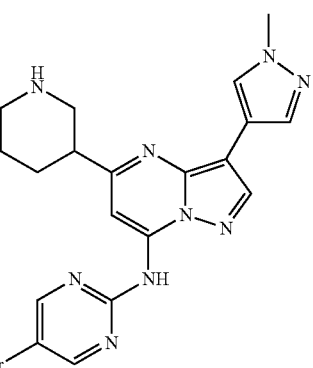
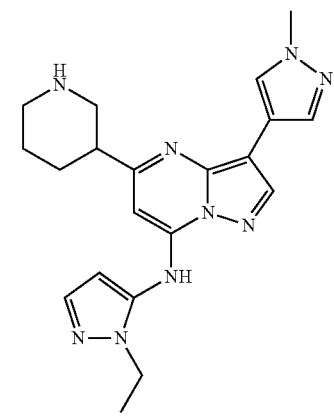
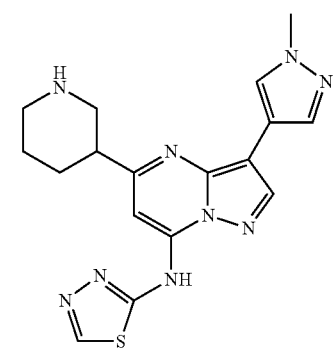
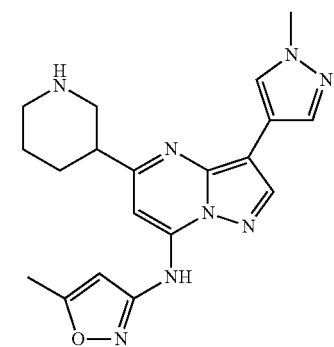

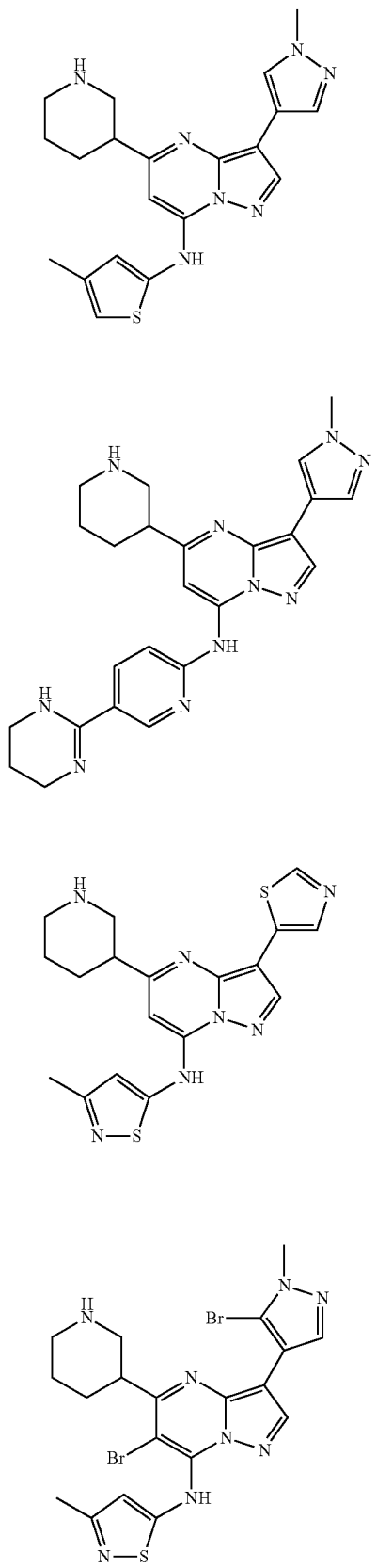
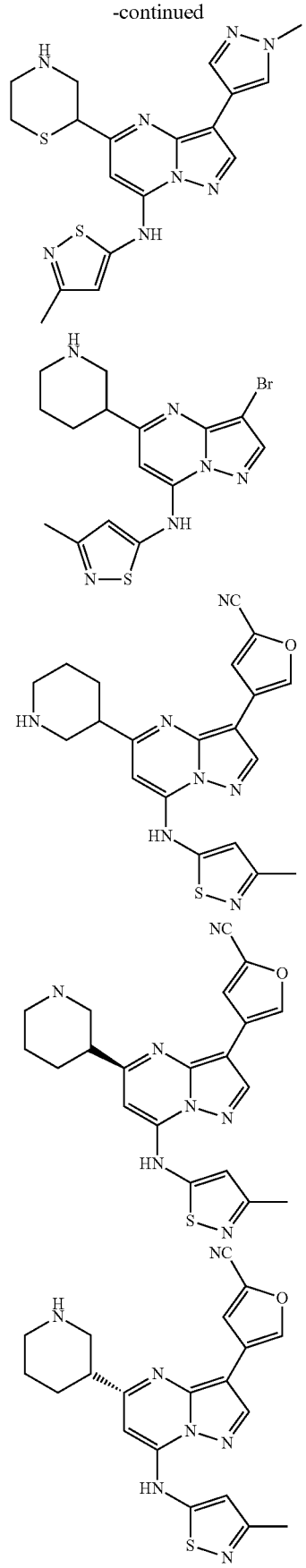

83
-continued
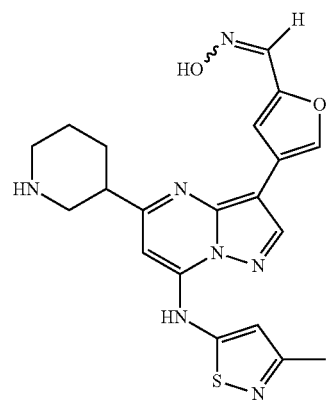
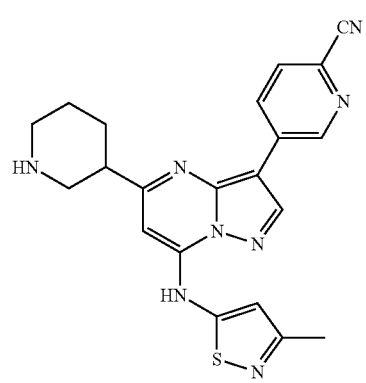
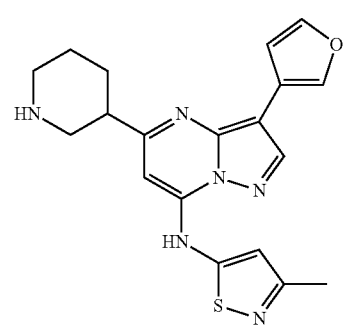
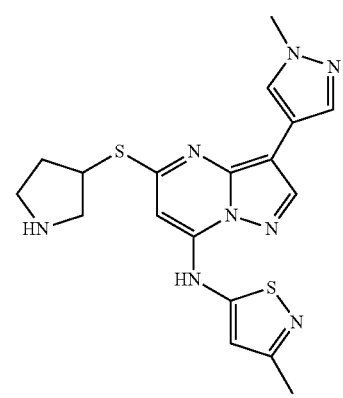
84
-continued
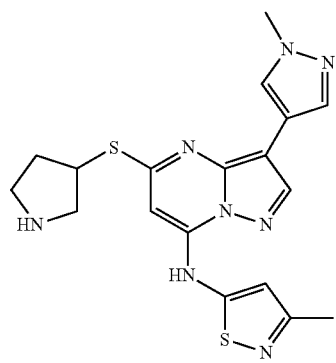
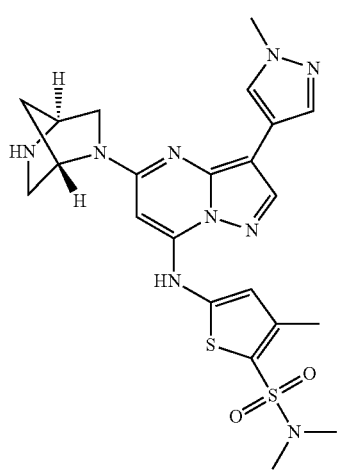
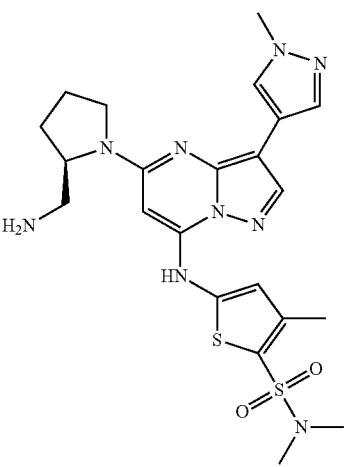

85
-continued
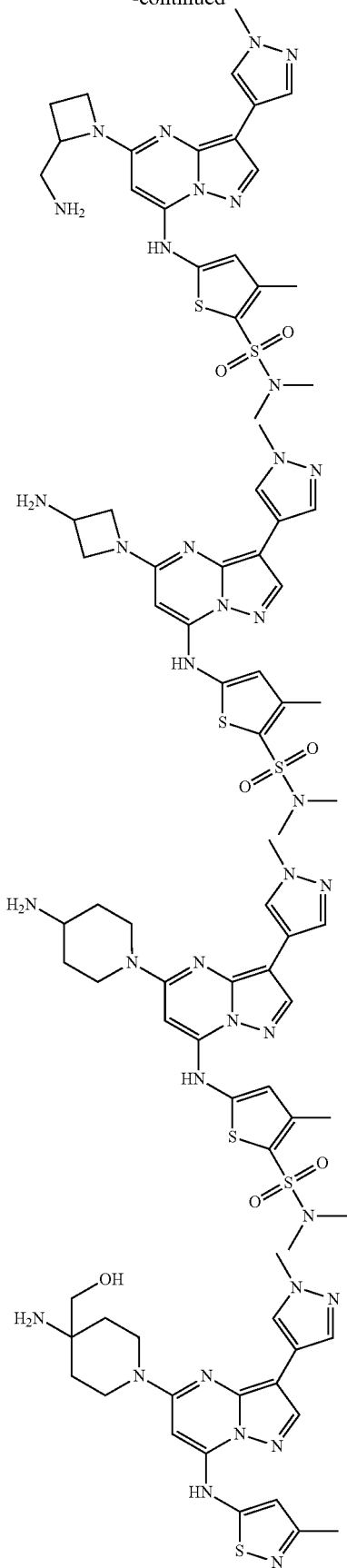
86
-continued
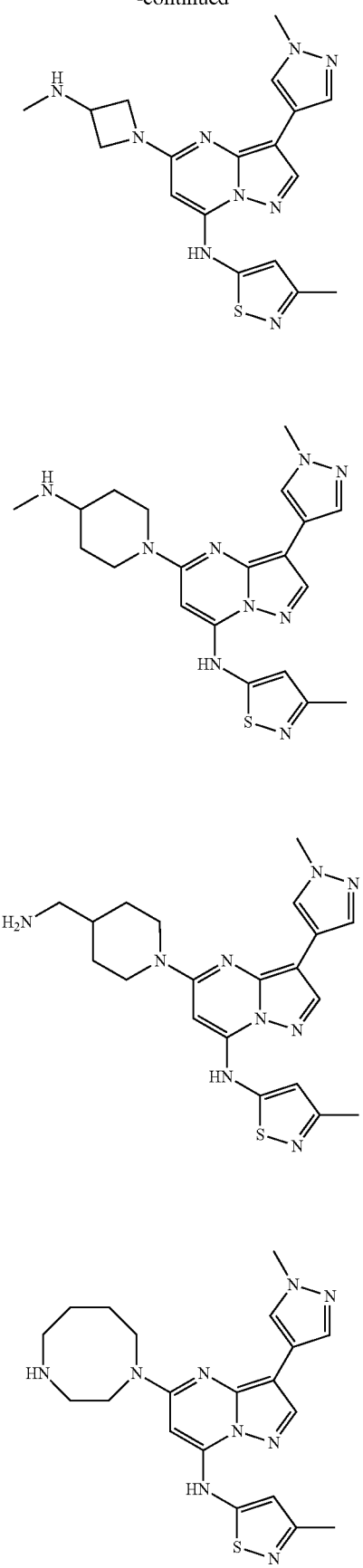

87
-continued
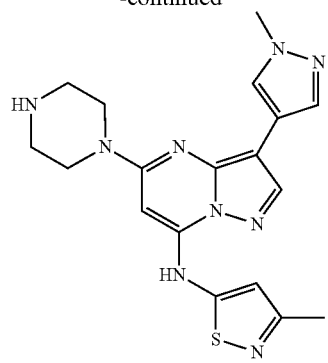
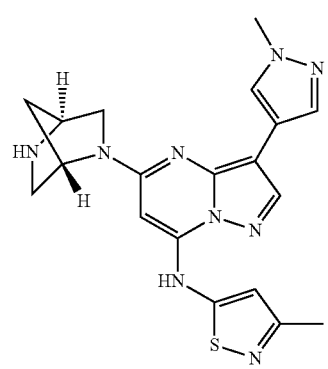
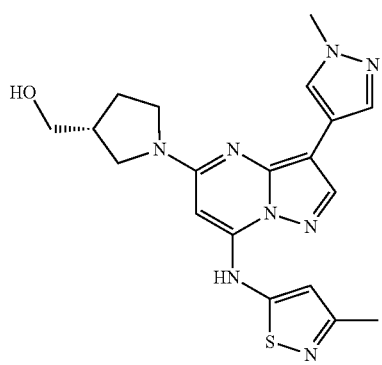
88
-continued
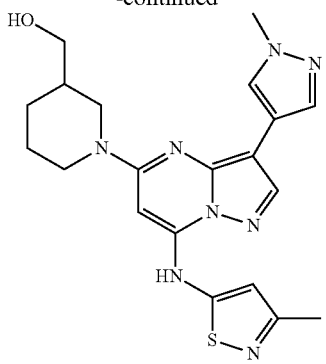
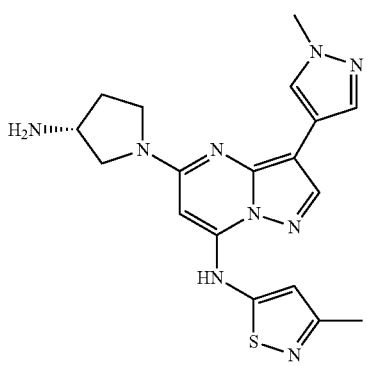
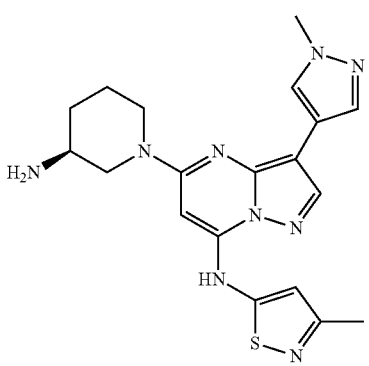

Non-limiting examples of preferred imidazopyrazine compounds, suitable as combination agents according to one aspect of this invention, are the following compounds:

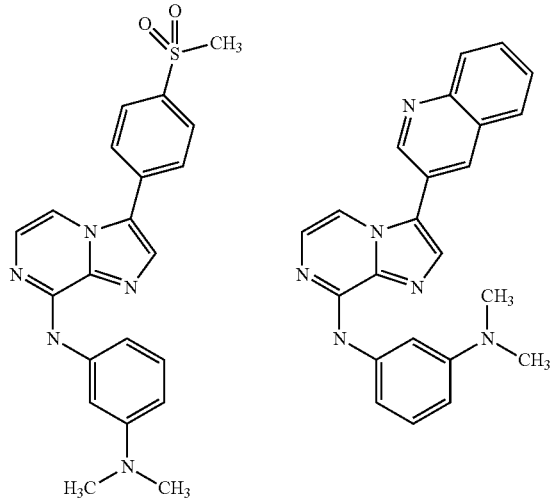
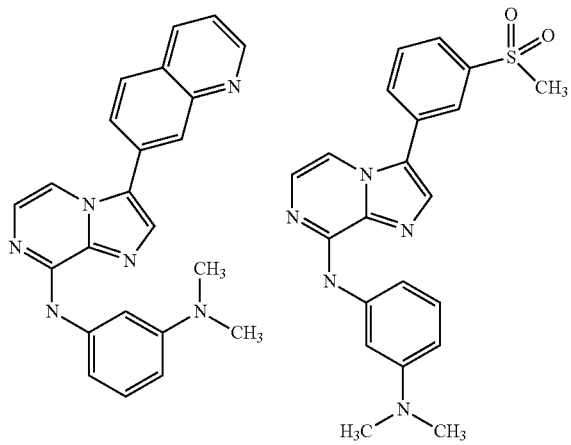
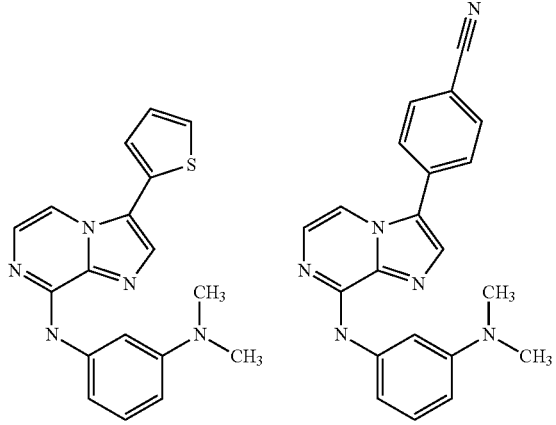
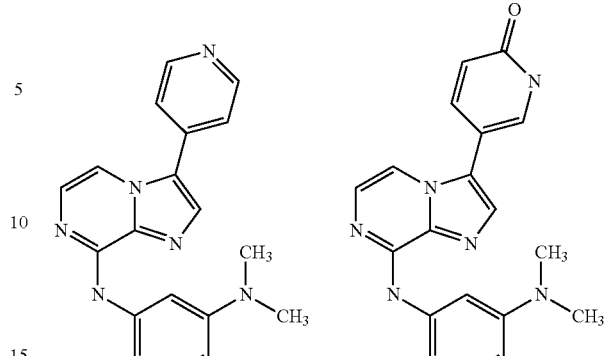
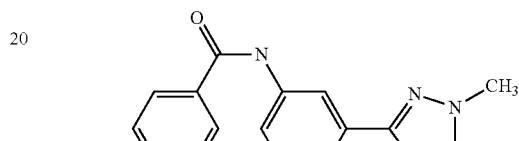
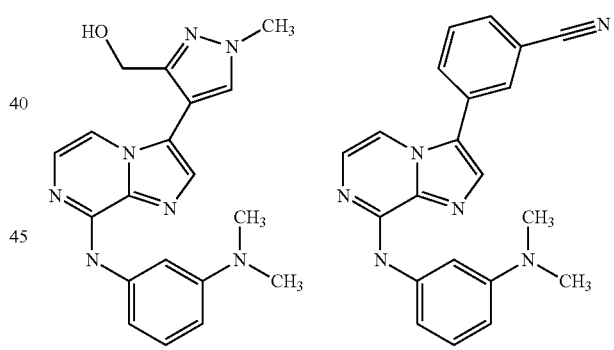
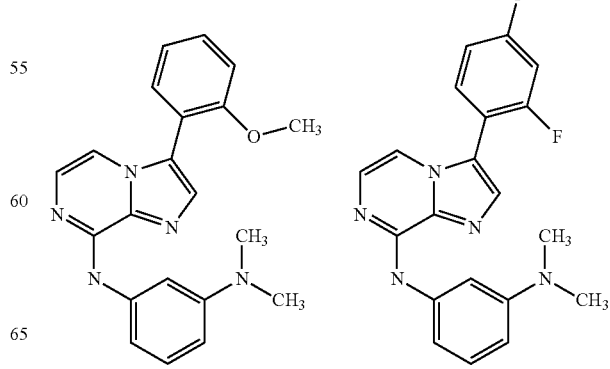

-continued
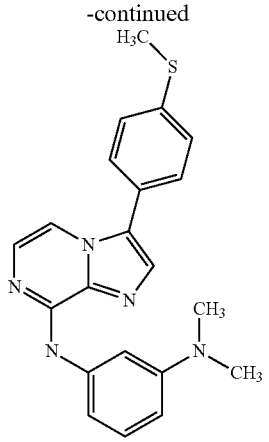
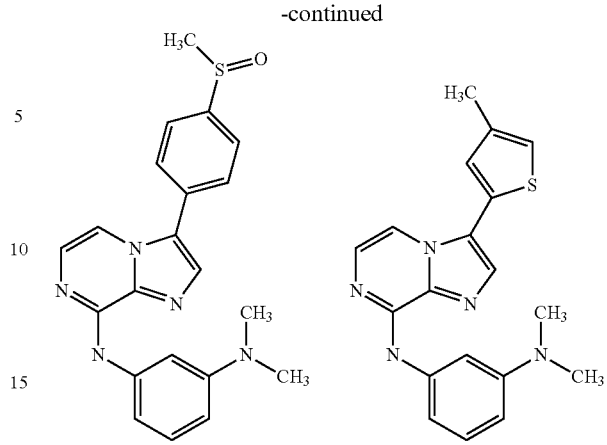
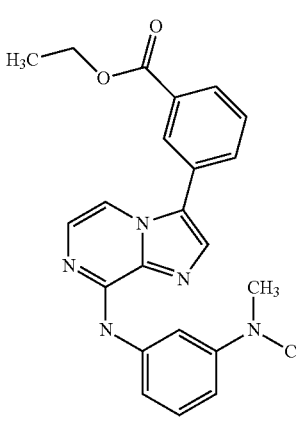
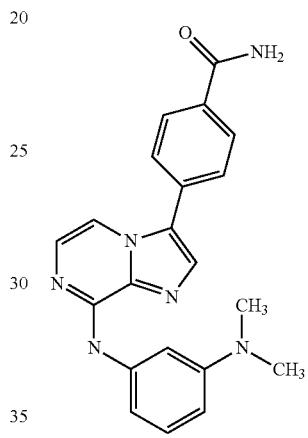
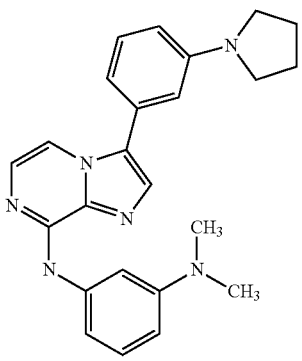
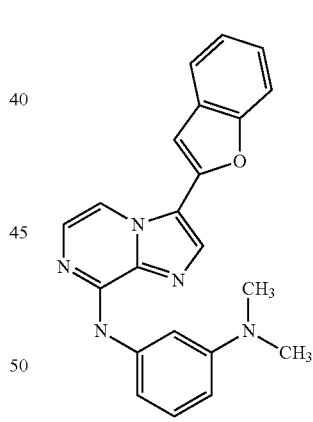
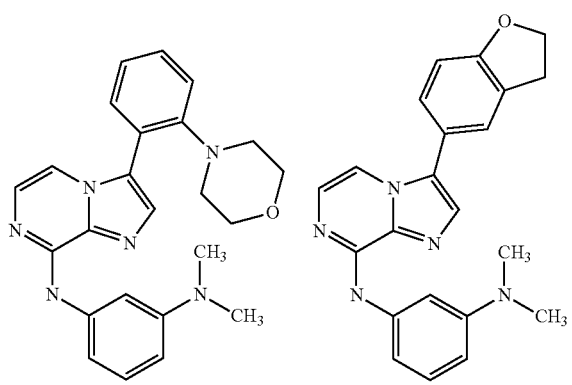
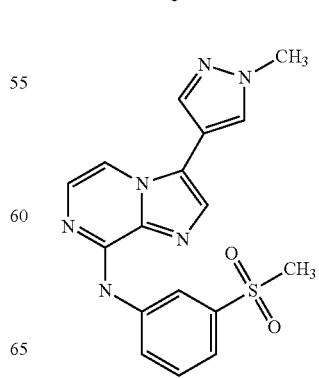
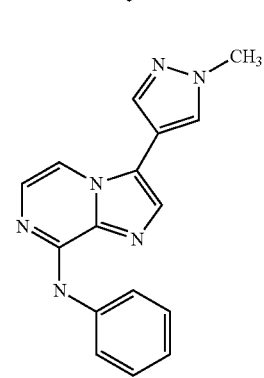

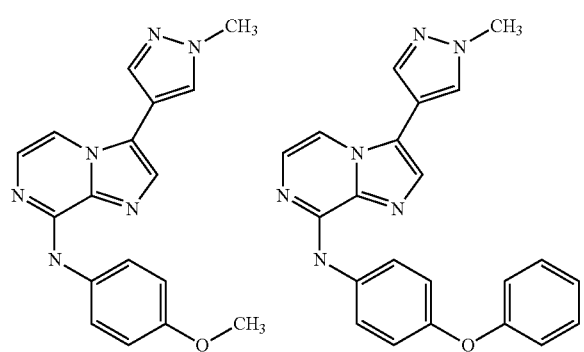
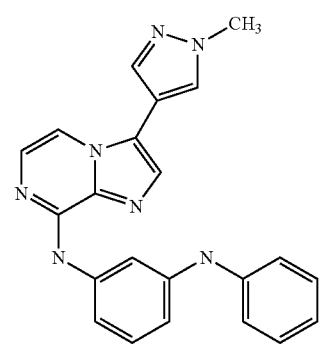
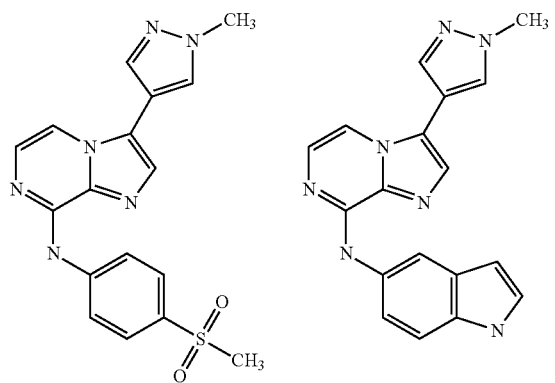
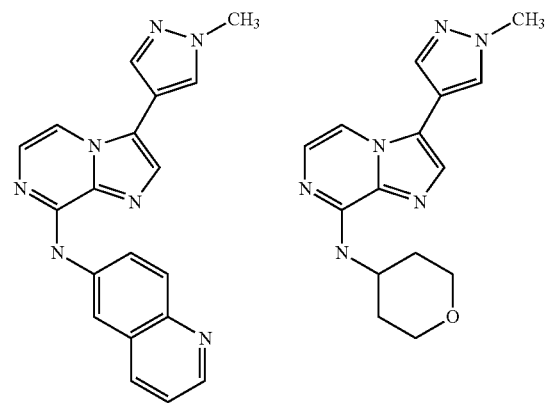
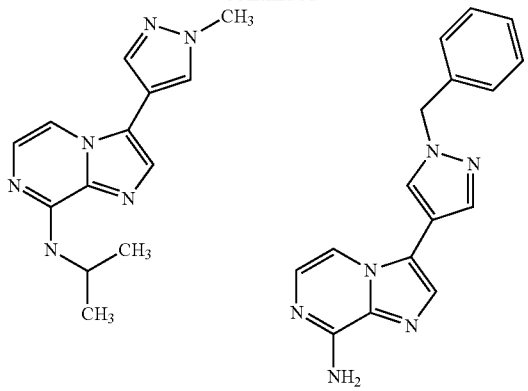
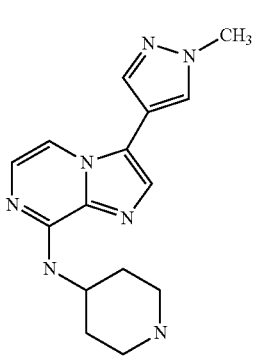
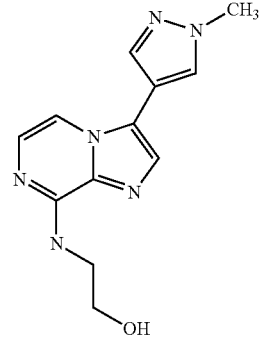
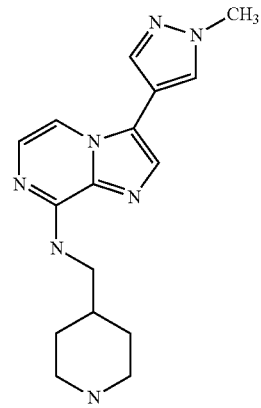

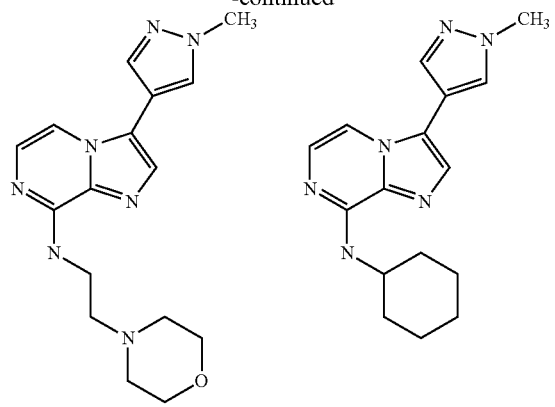
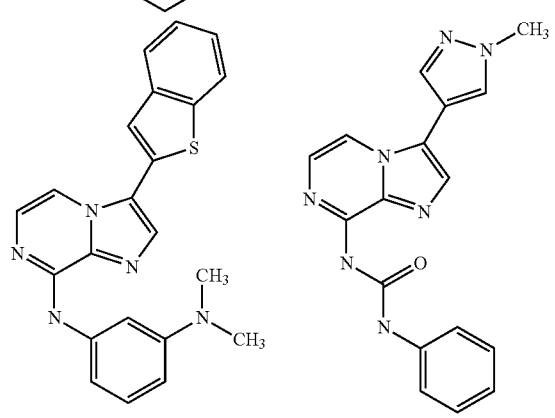
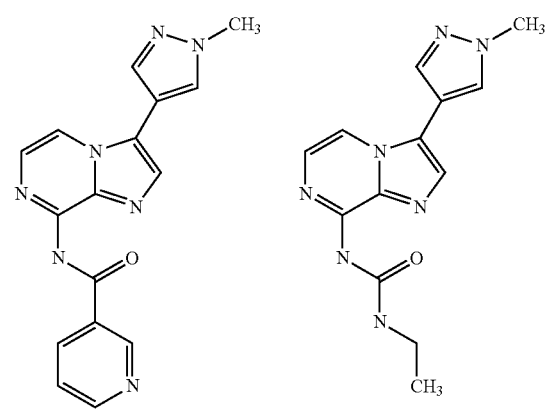
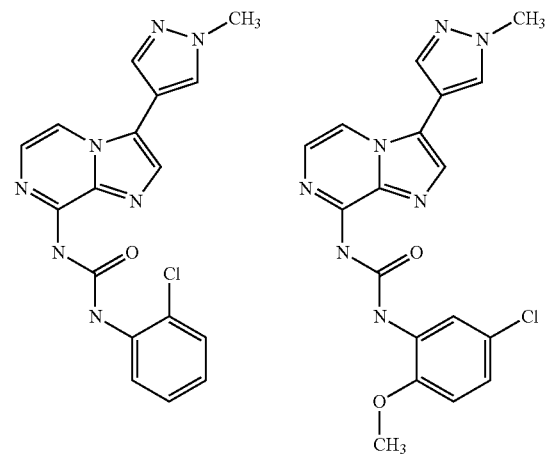
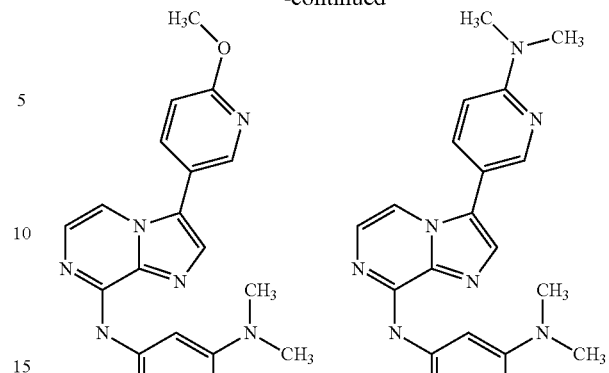
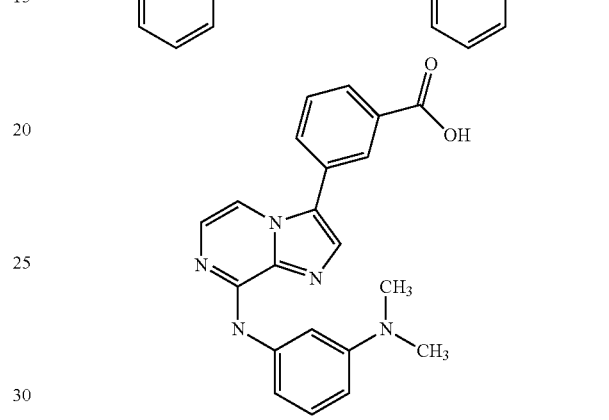
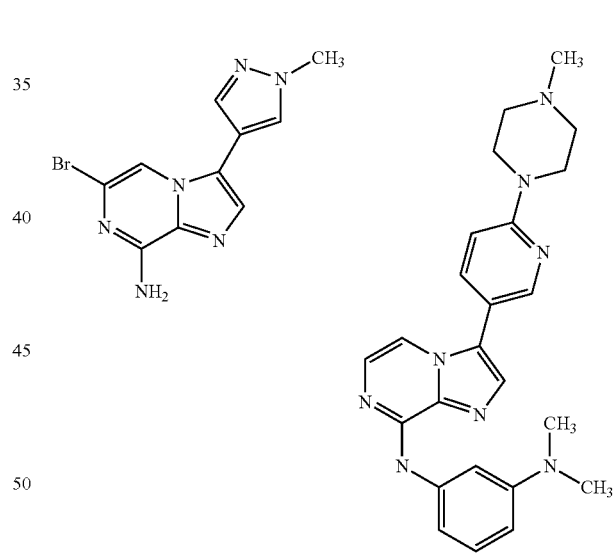
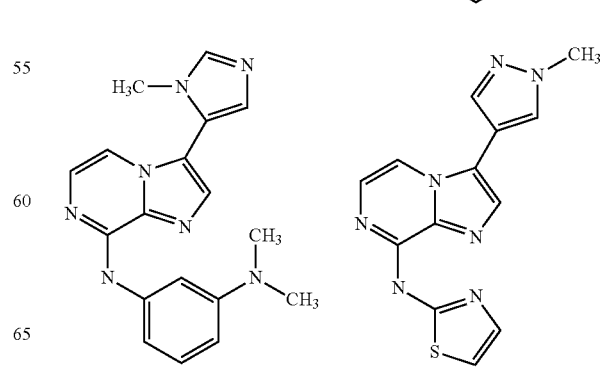

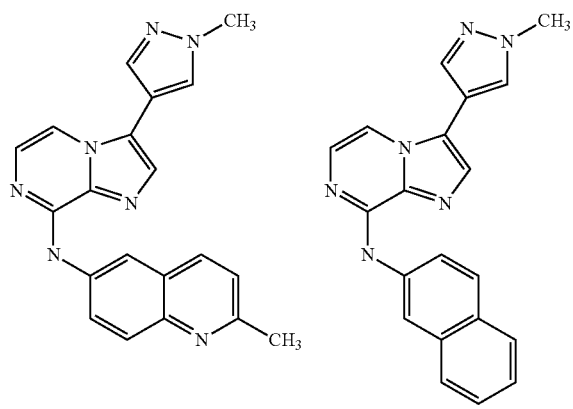
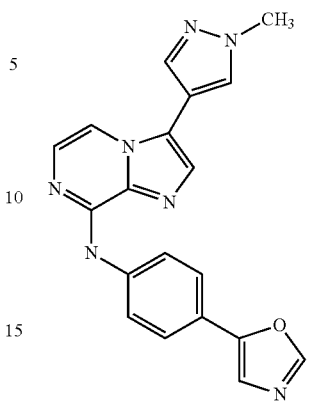
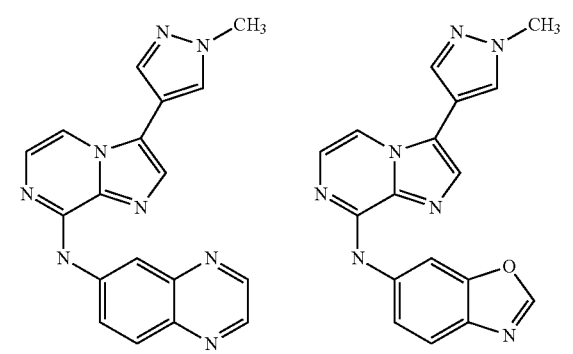
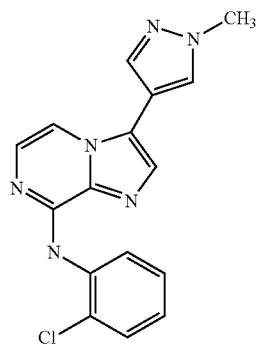
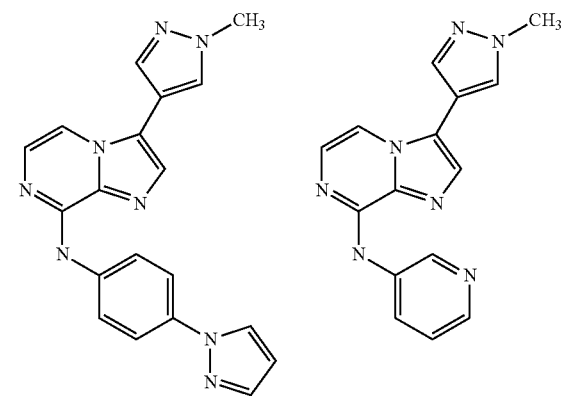
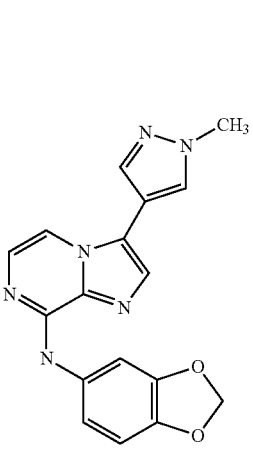
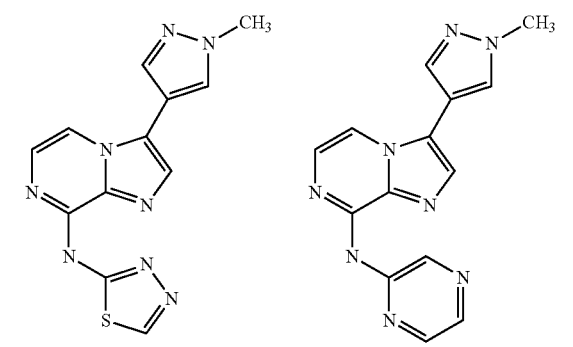
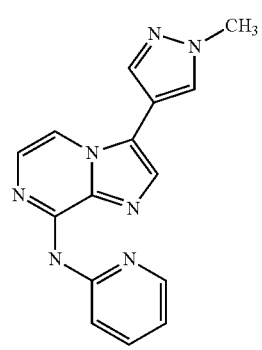

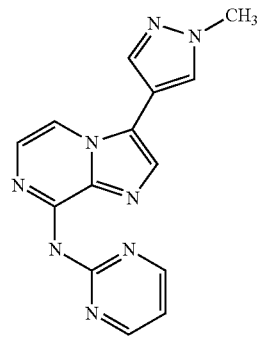
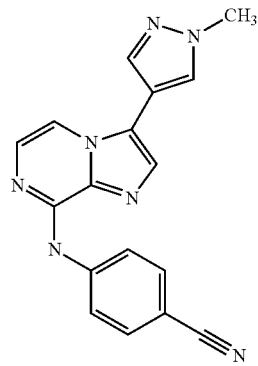
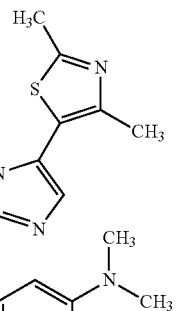
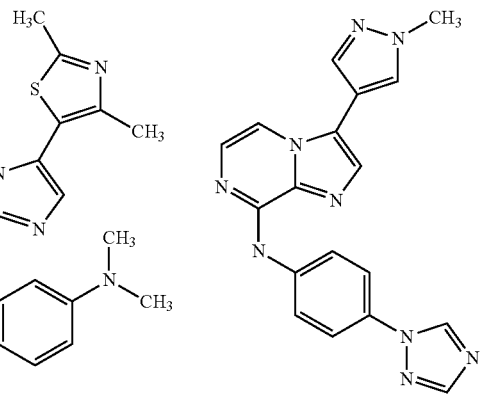
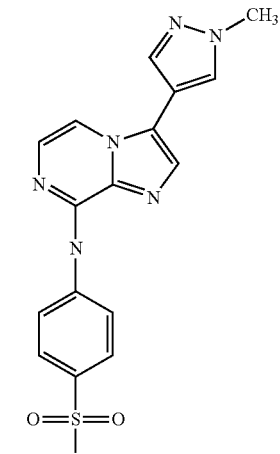
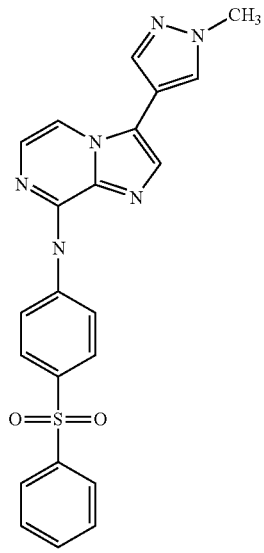
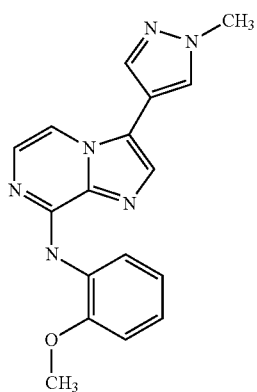
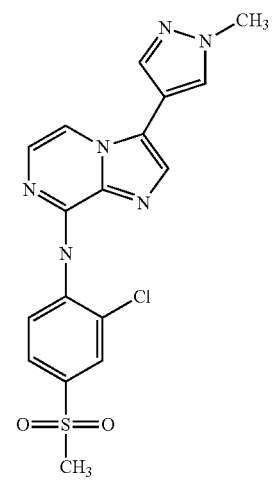
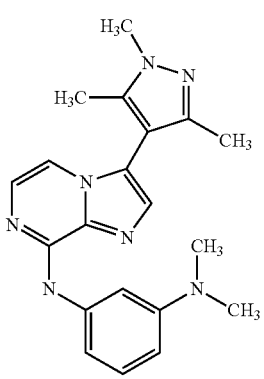
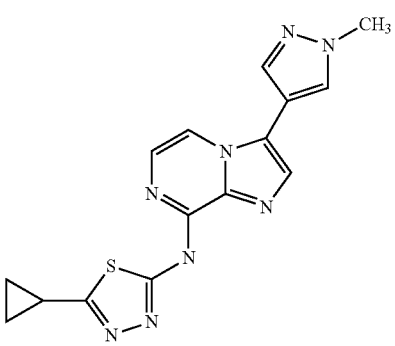
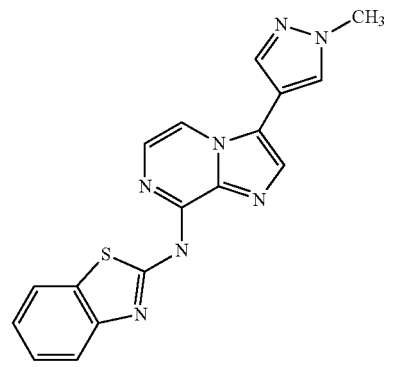

103
-continued
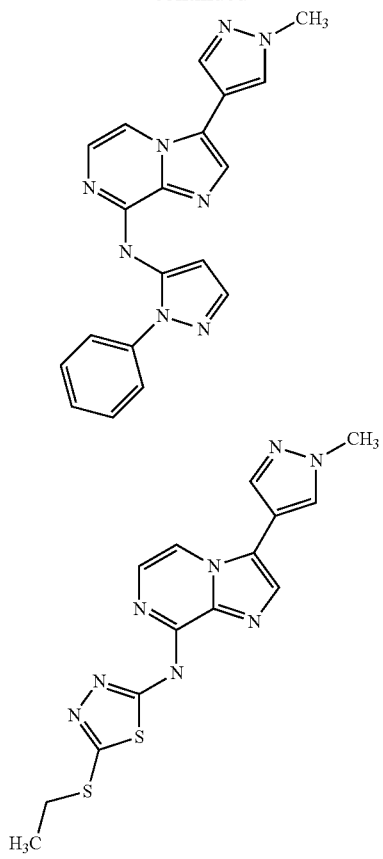
104
-continued
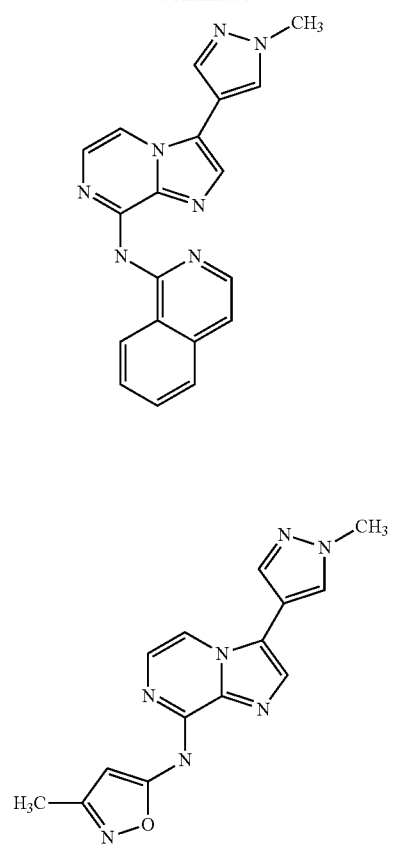
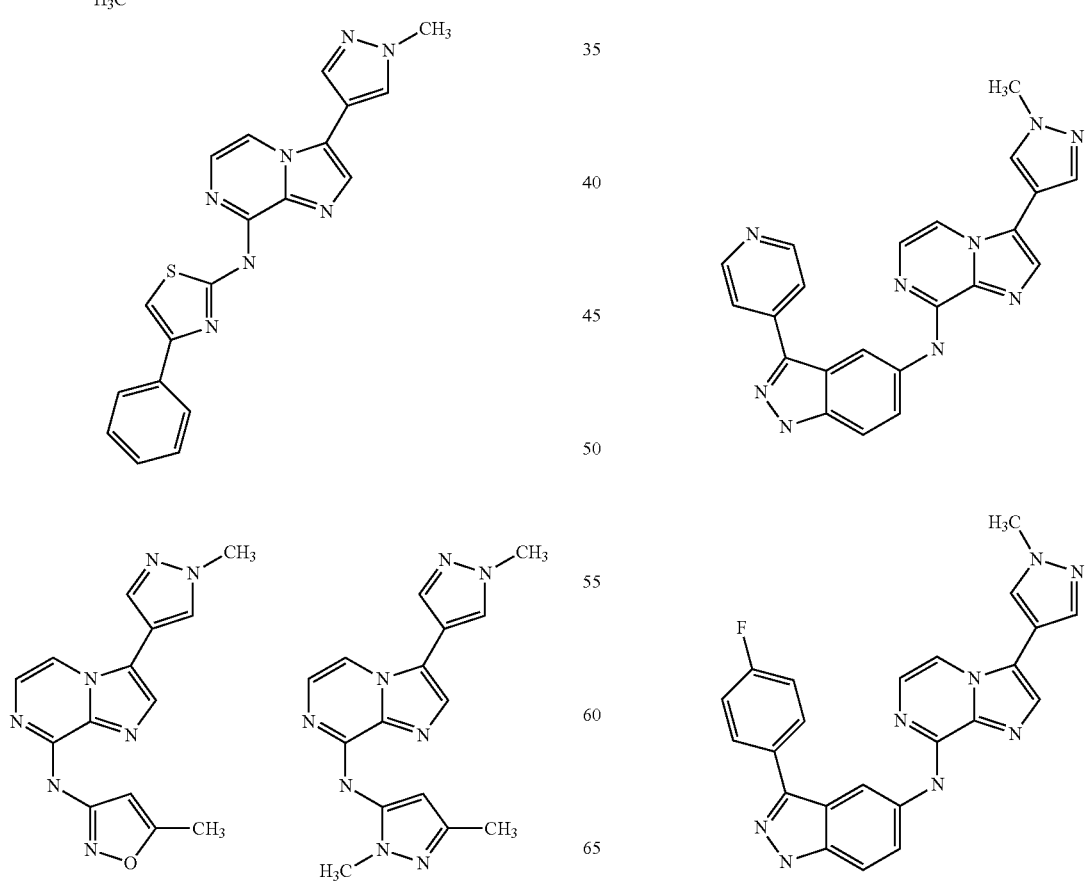

105
-continued
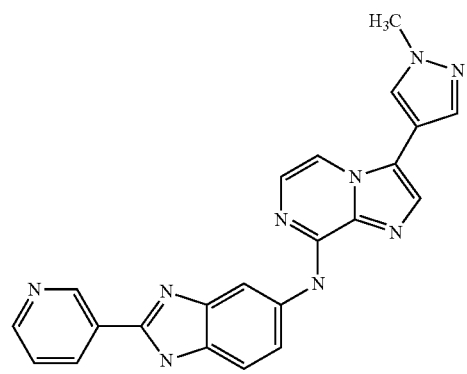
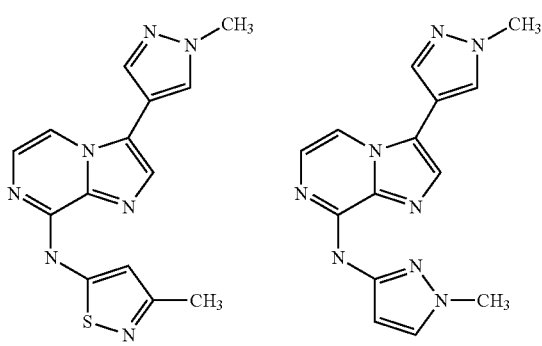
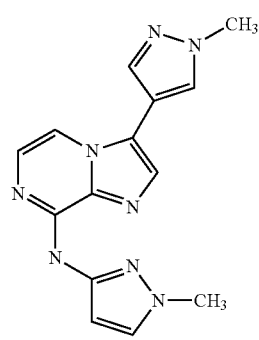
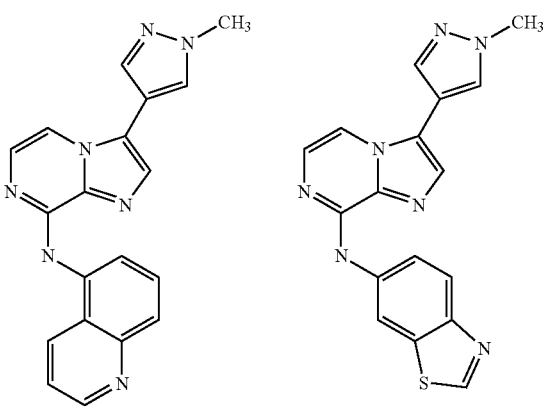
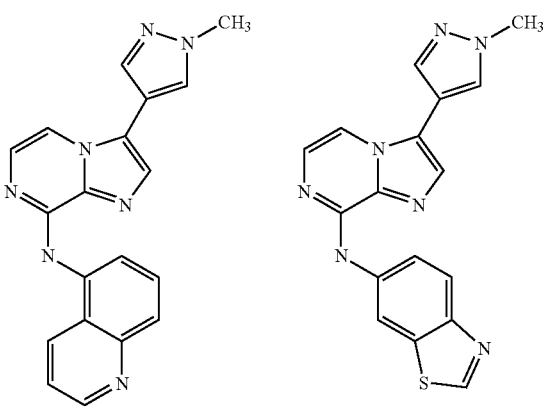
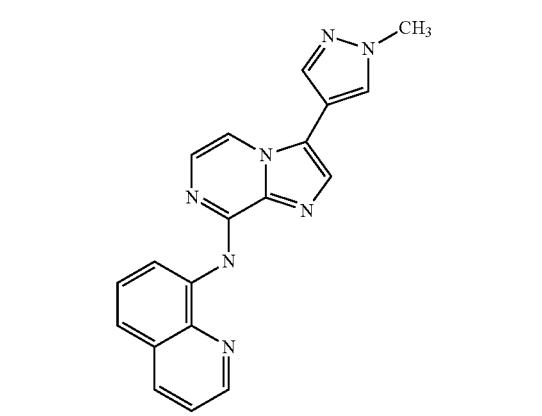
106
-continued
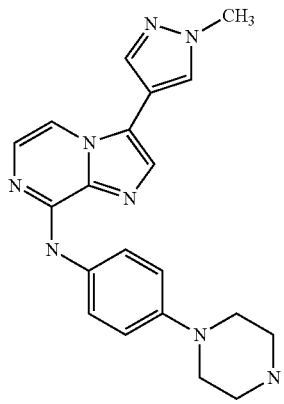
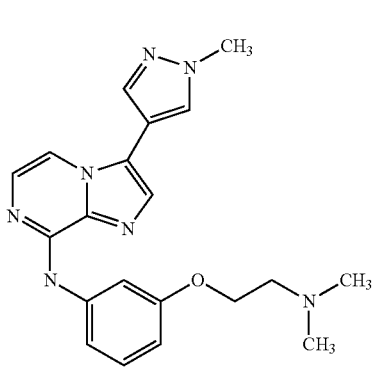
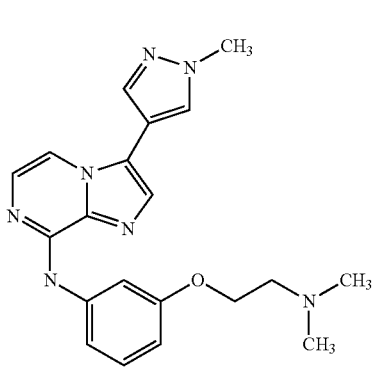
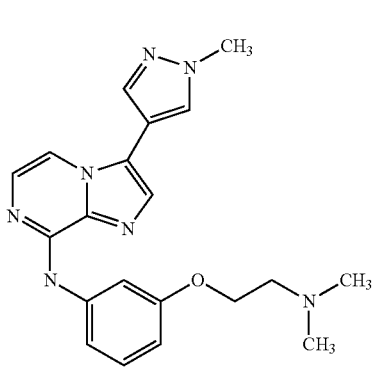
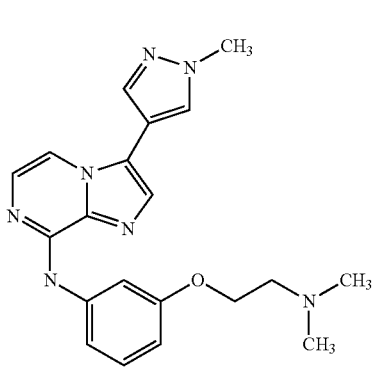

107
-continued
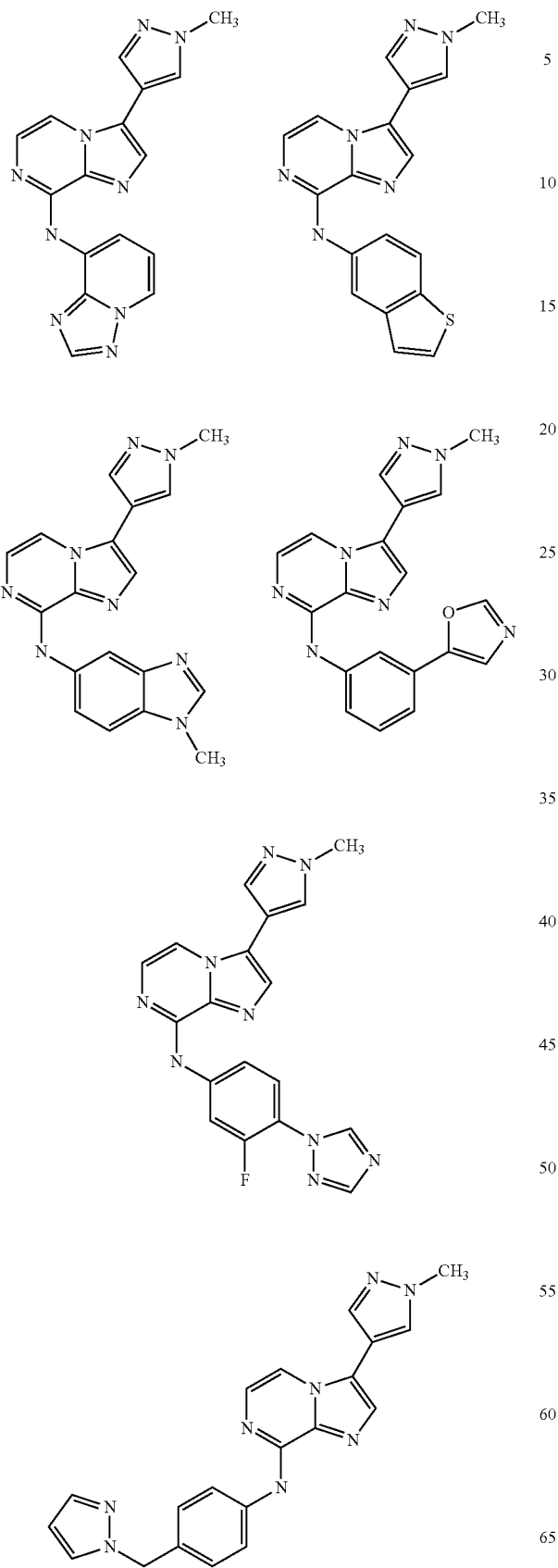
108
-continued
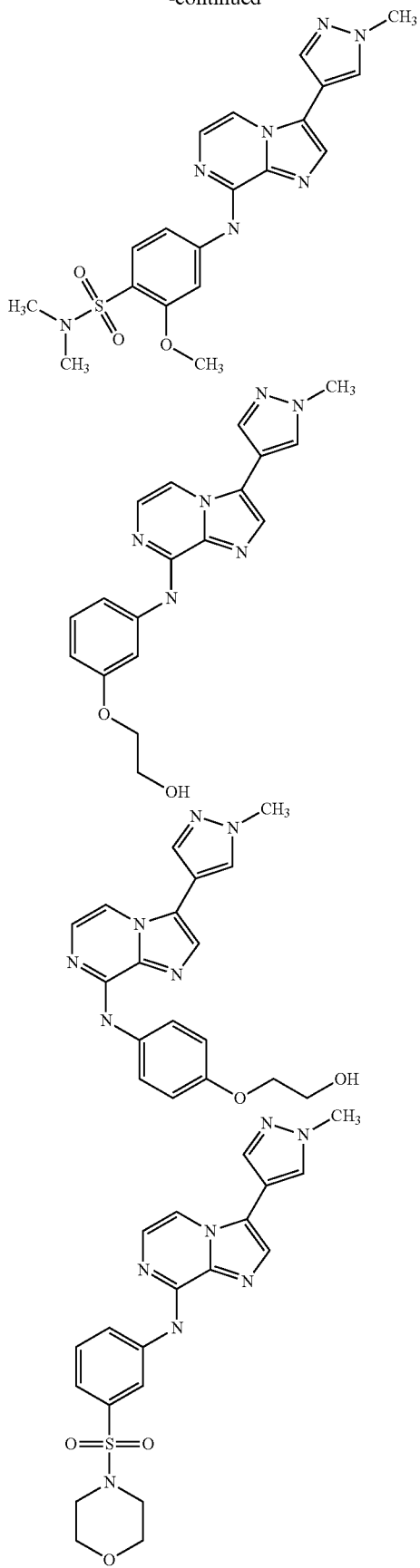

109
-continued
110
-continued
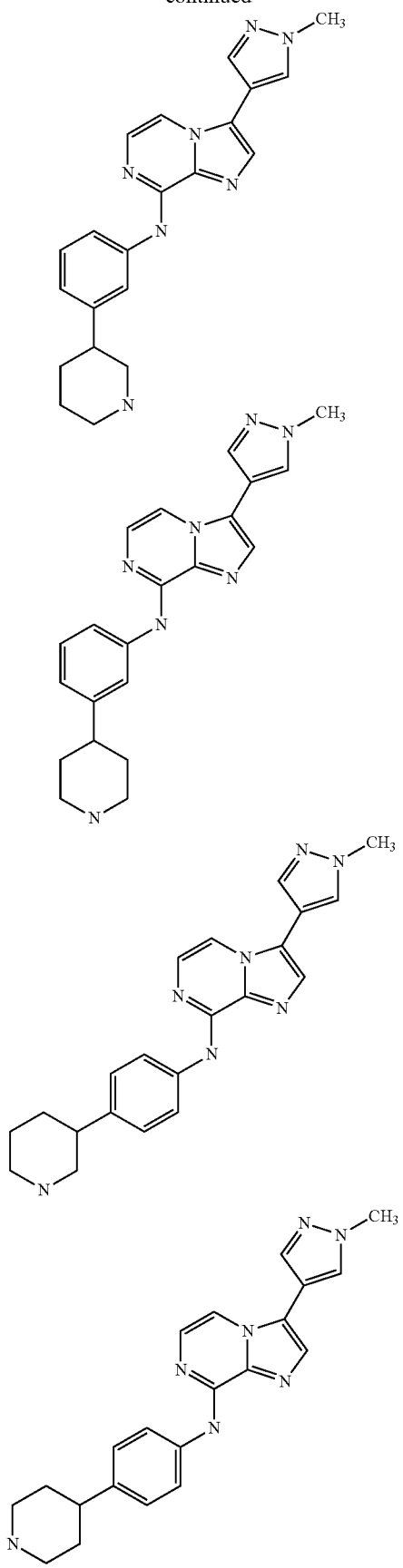
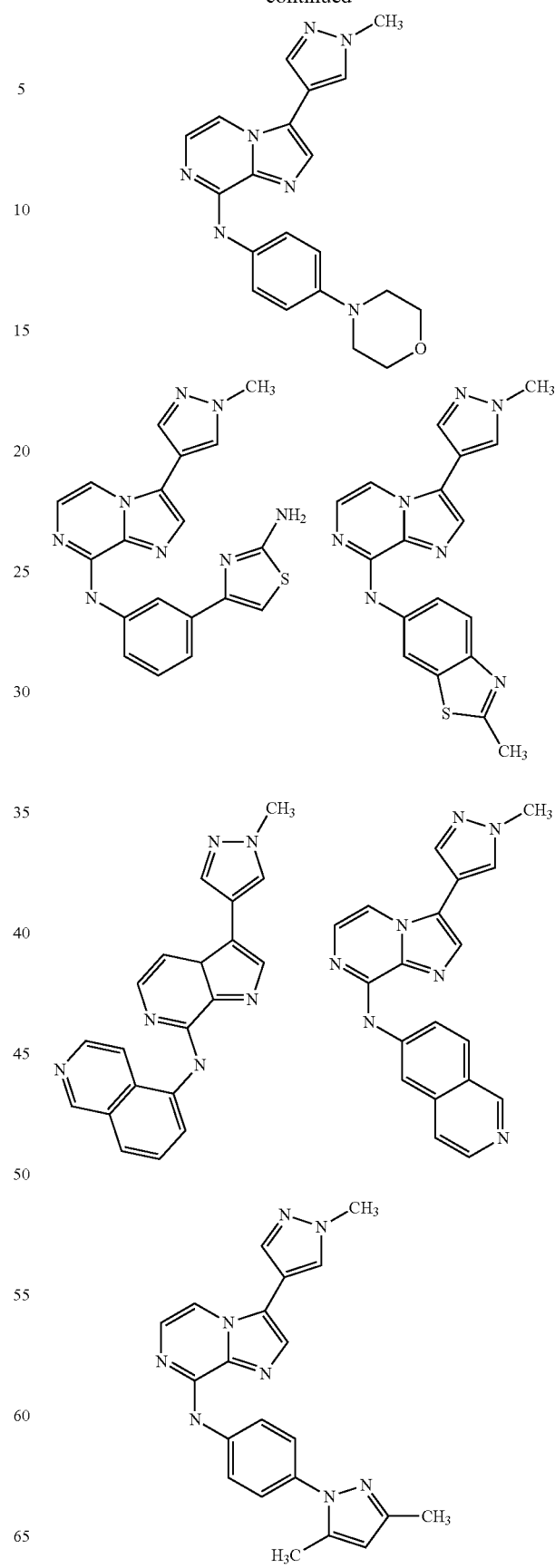

111
-continued
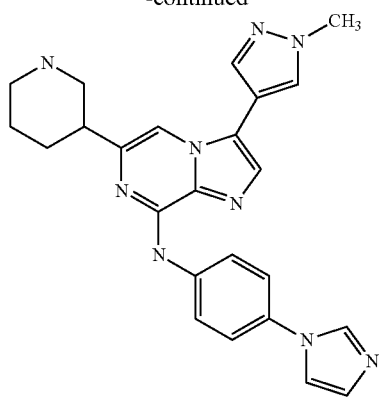
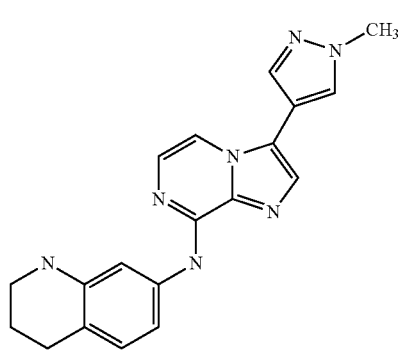
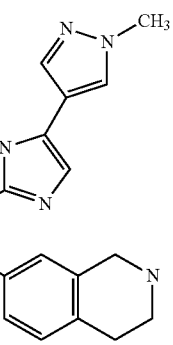 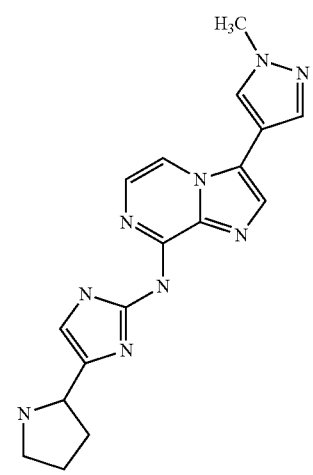
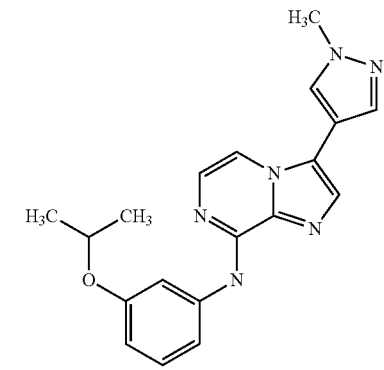
112
-continued
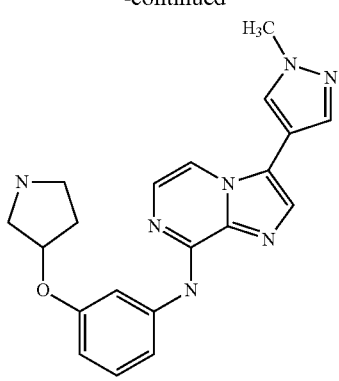
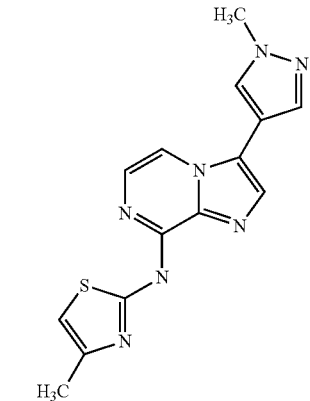
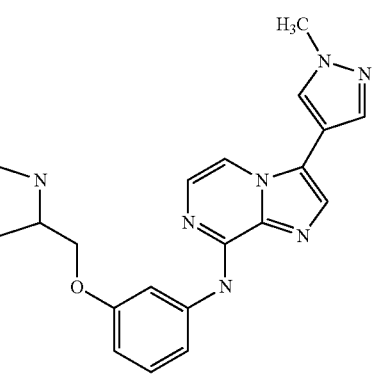
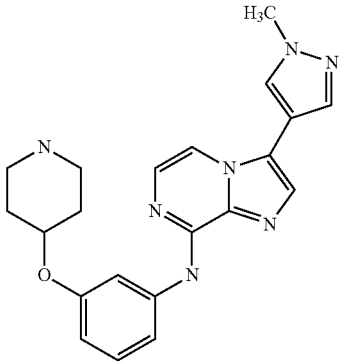

113
-continued
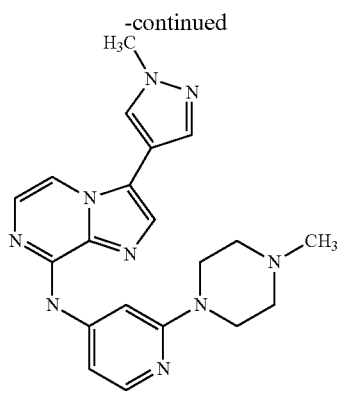
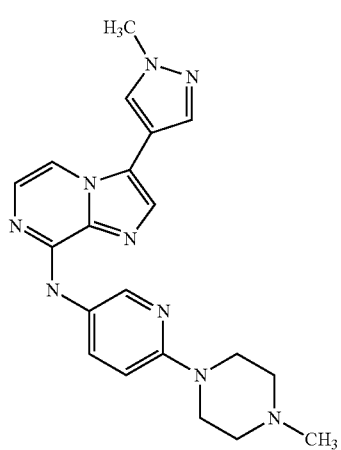
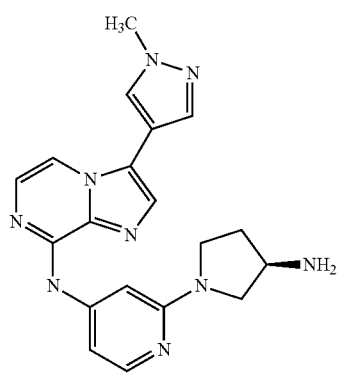
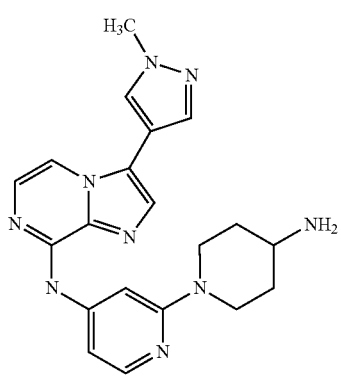
114
-continued
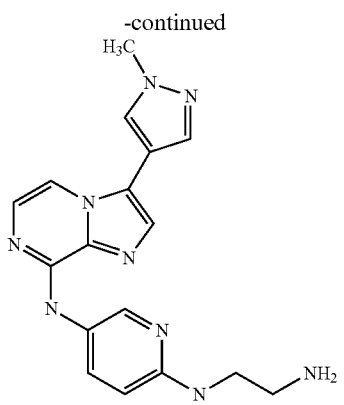
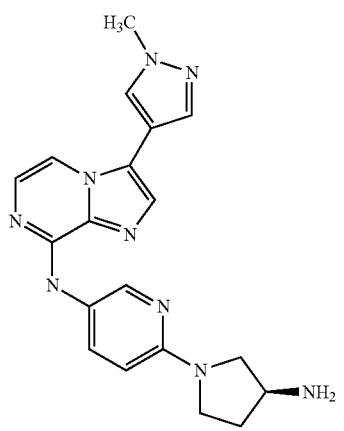
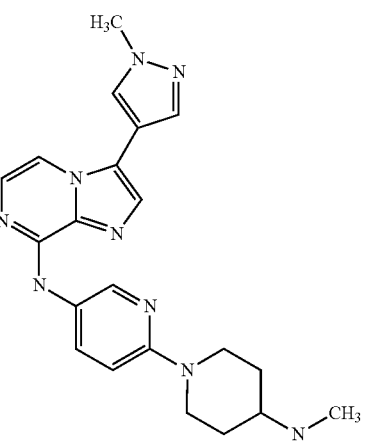
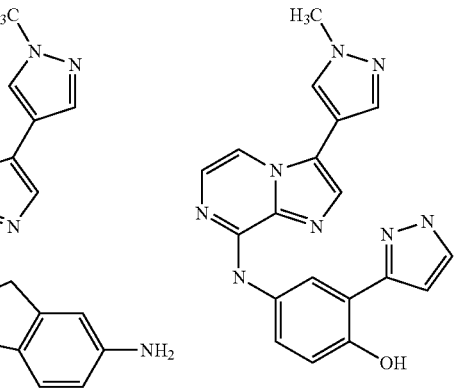

115
-continued
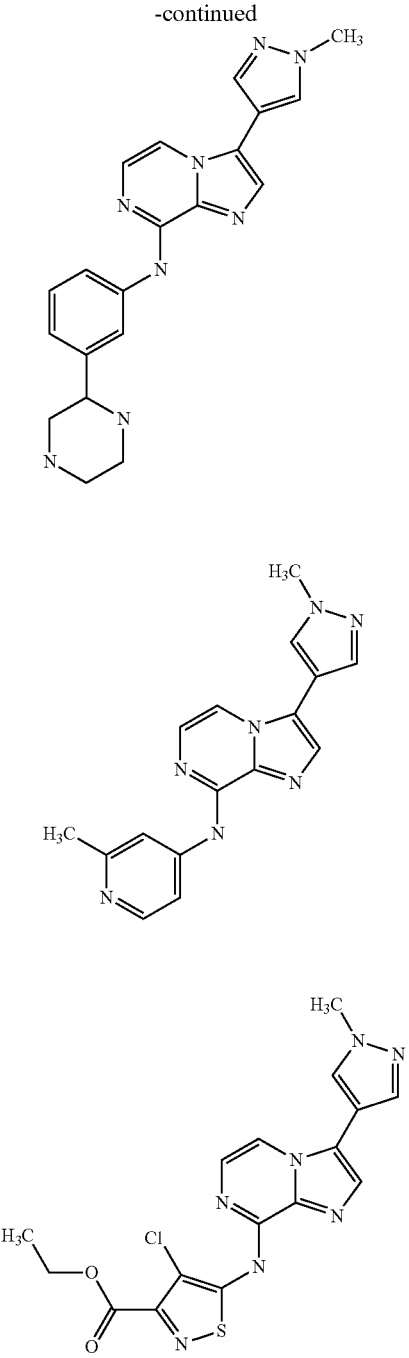
116
-continued
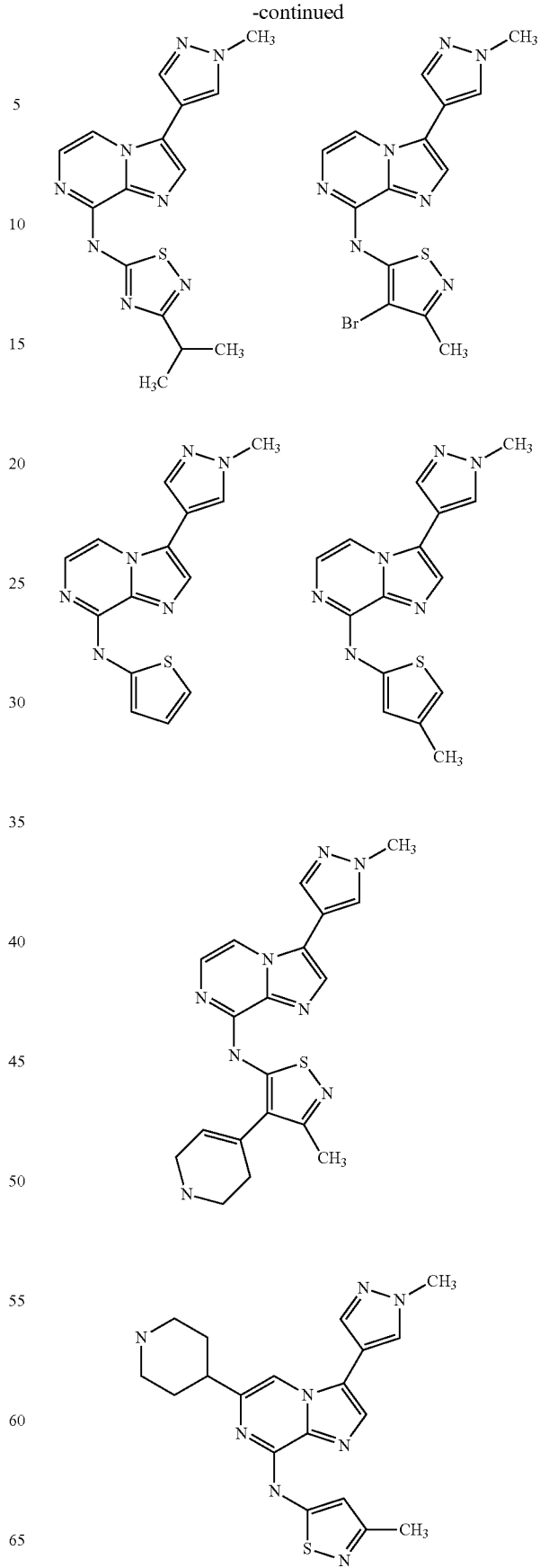

117
-continued
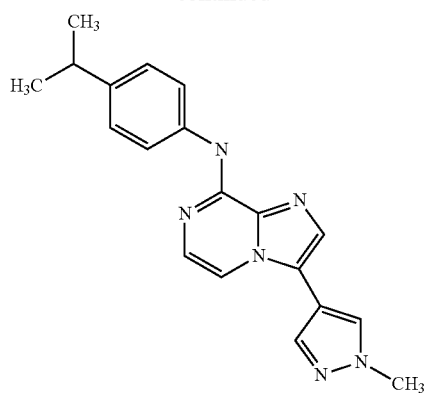
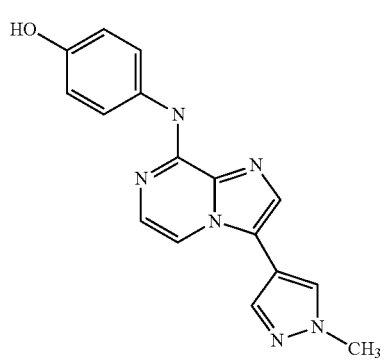
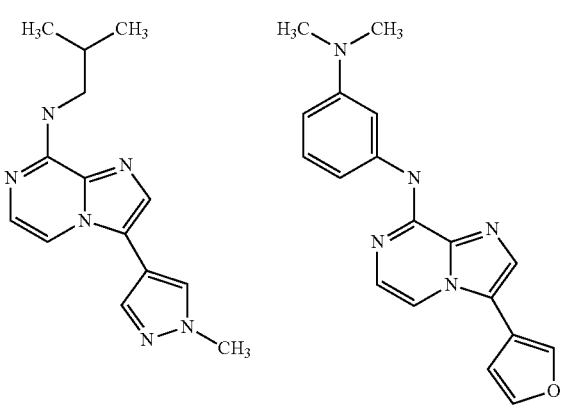
118
-continued
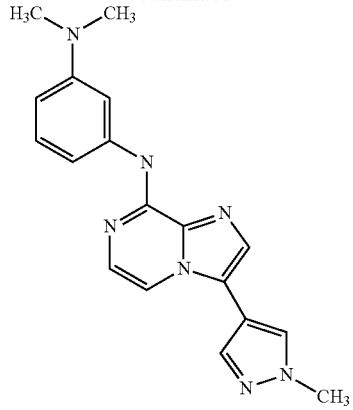
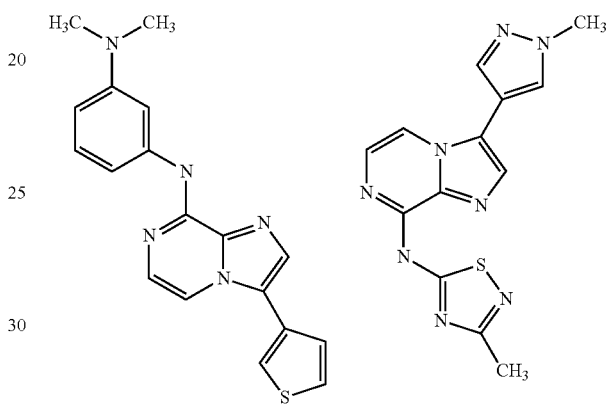
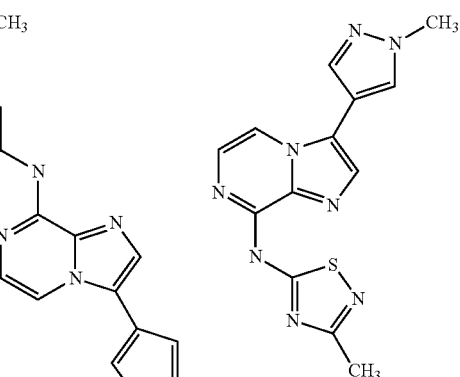
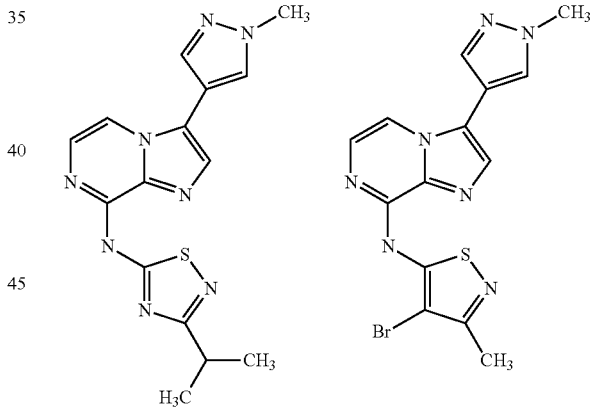
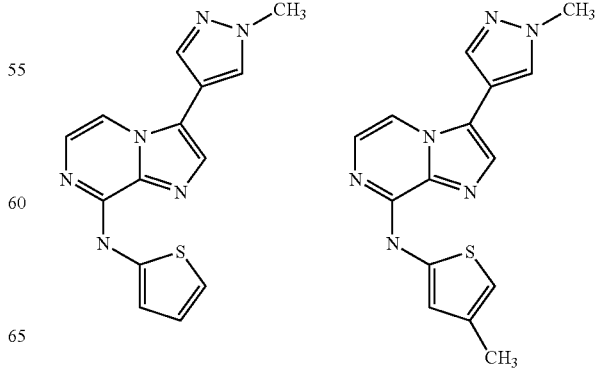

-continued
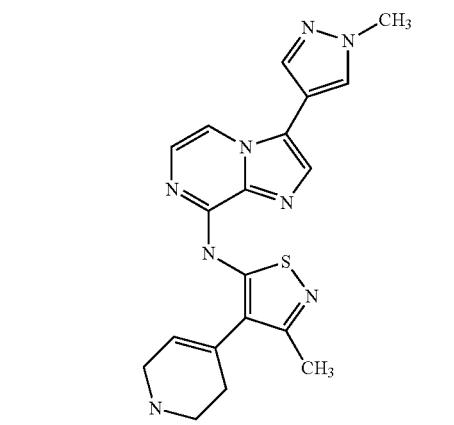
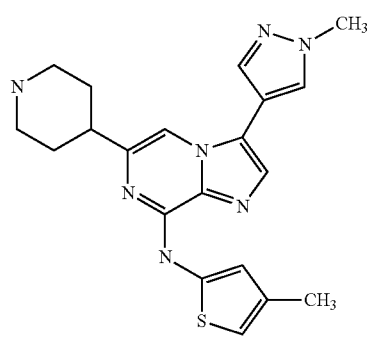
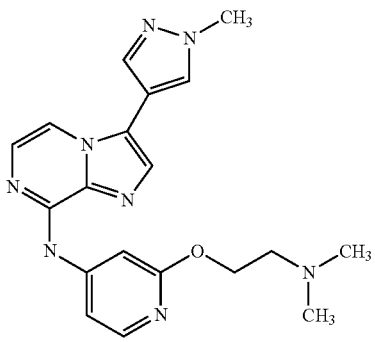
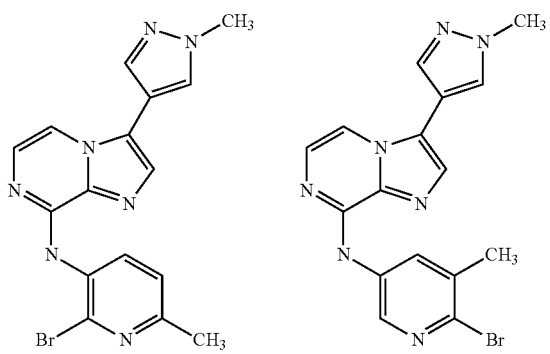 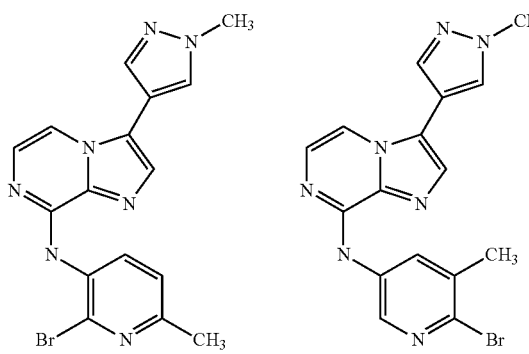
-continued
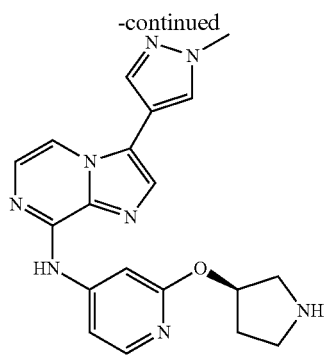
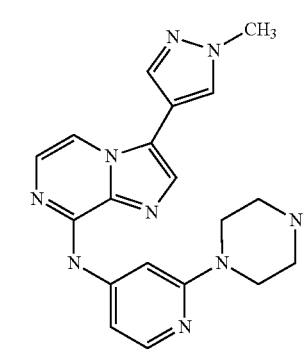
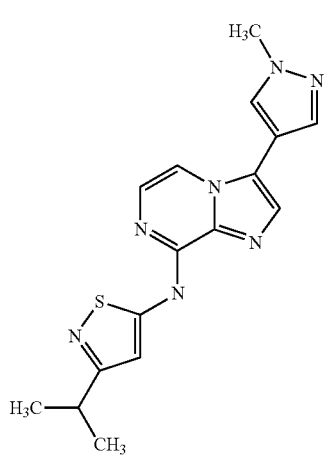
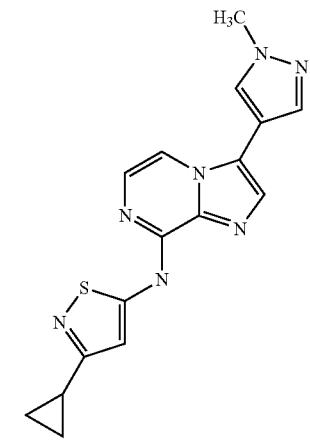

121
-continued
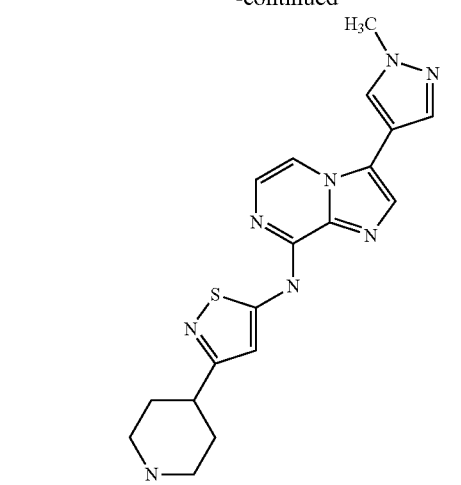
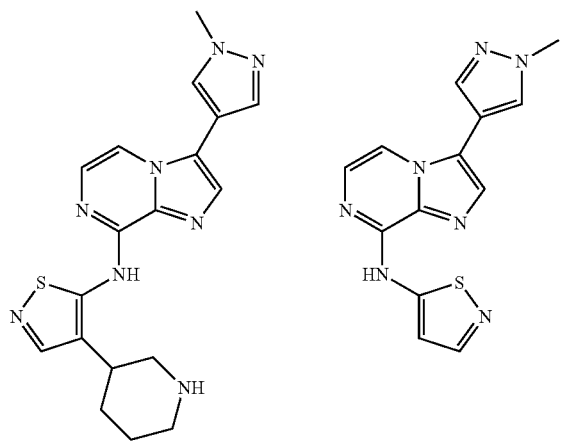
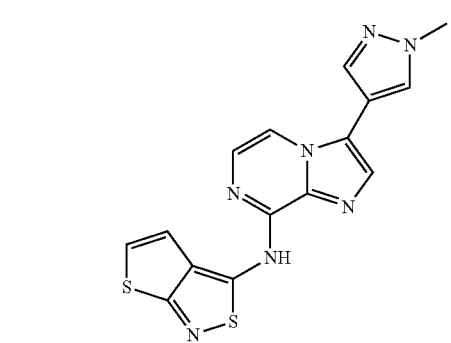
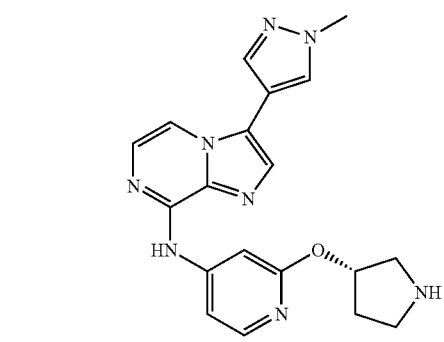
122
-continued
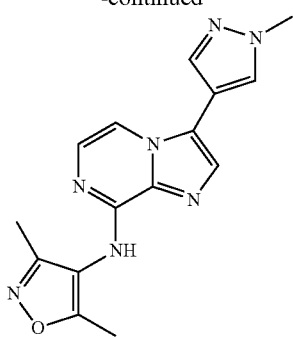
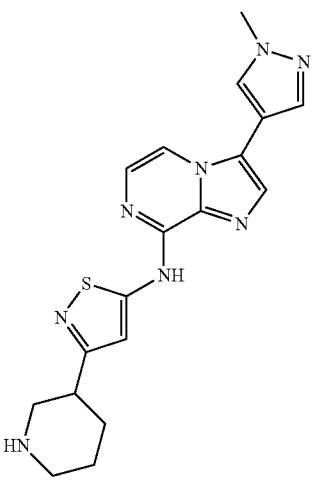
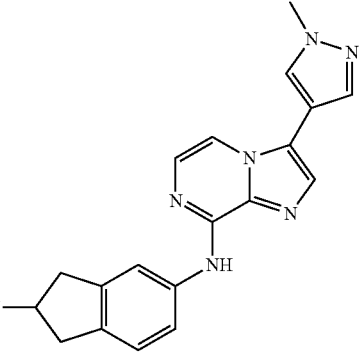
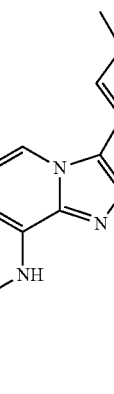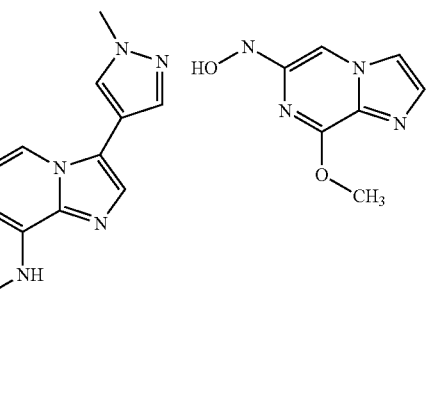

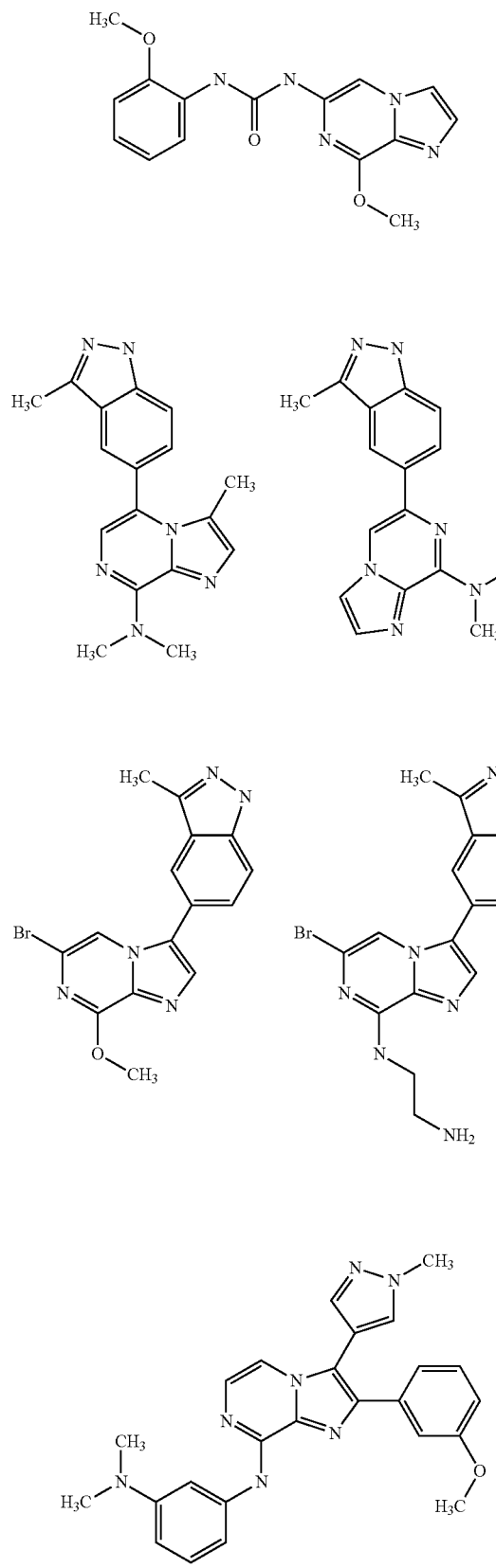
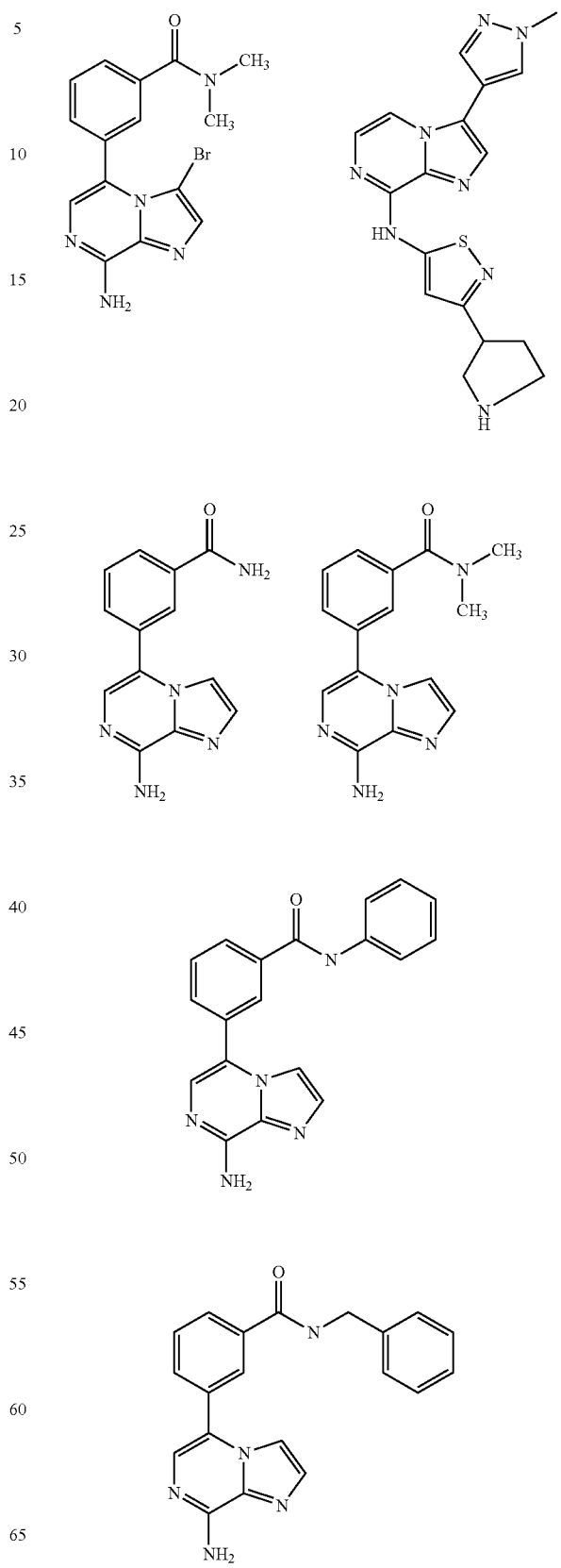

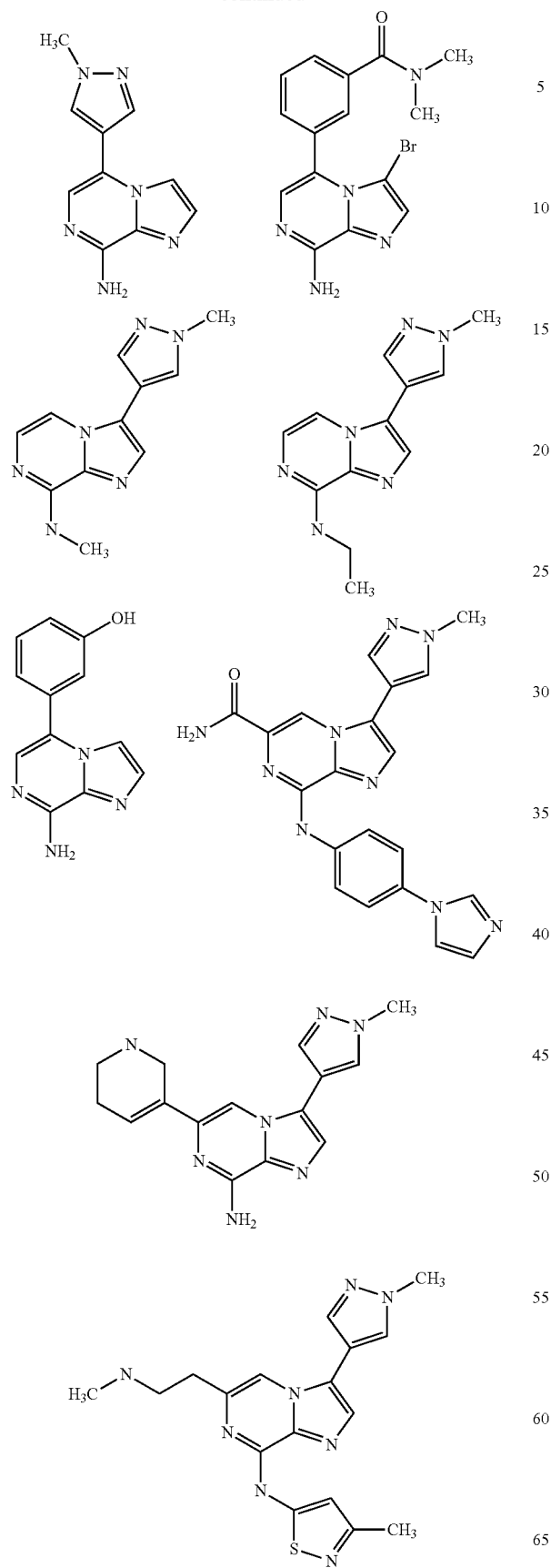
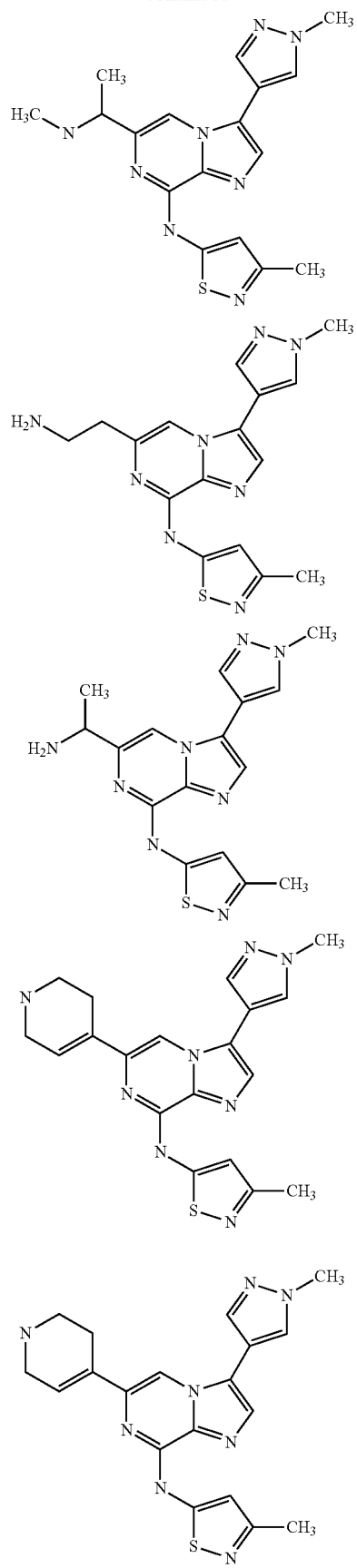

127
-continued
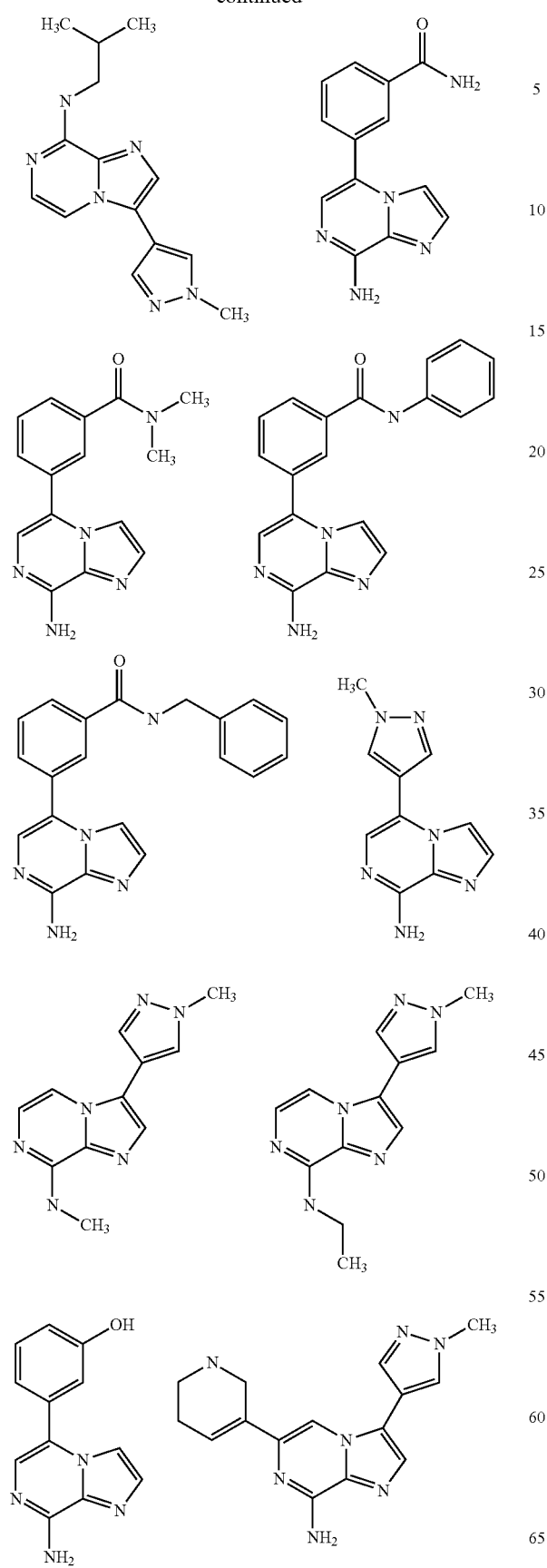
128
-continued
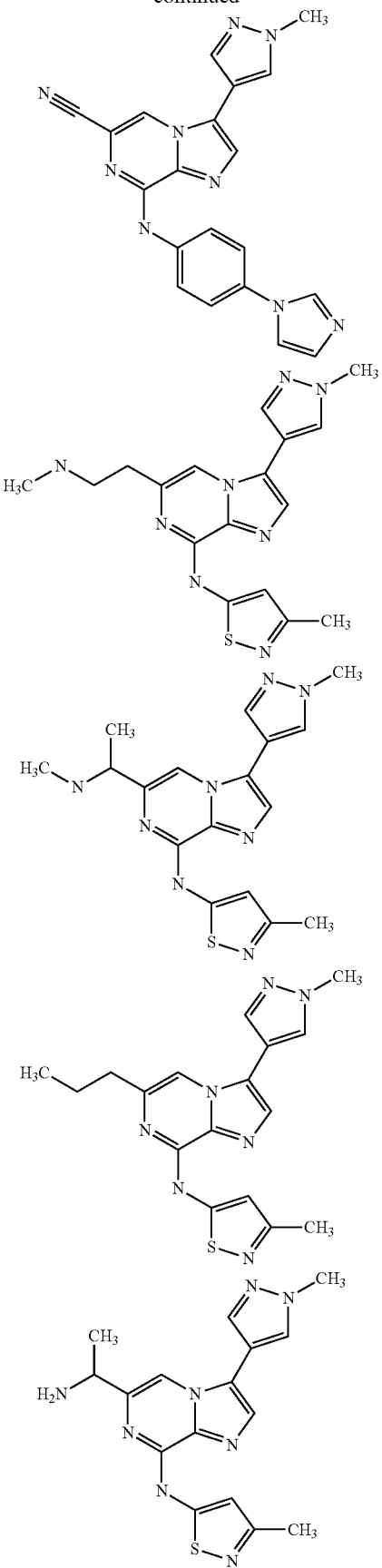

129
-continued
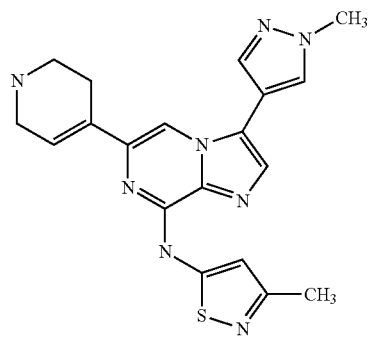
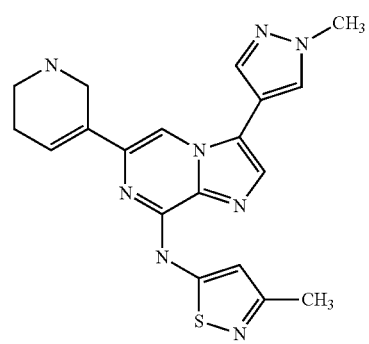
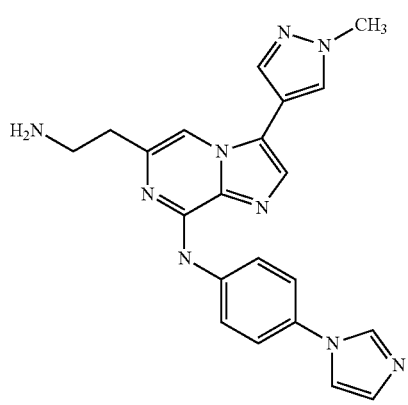
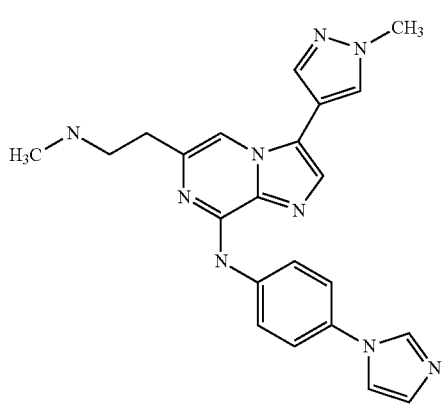
130
-continued
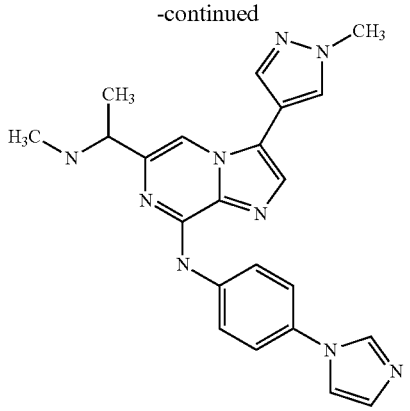
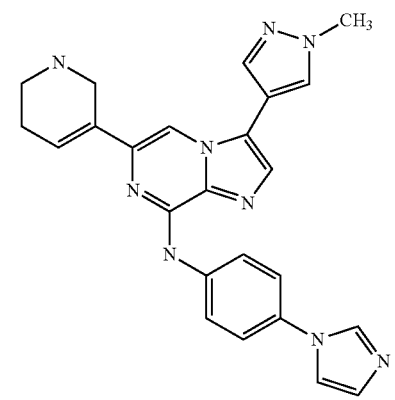
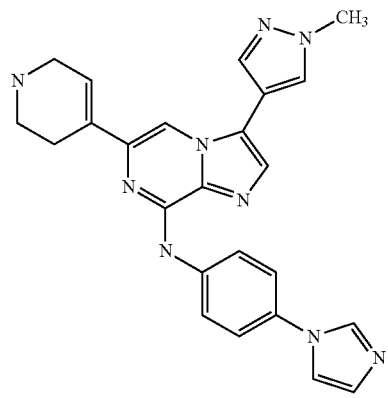
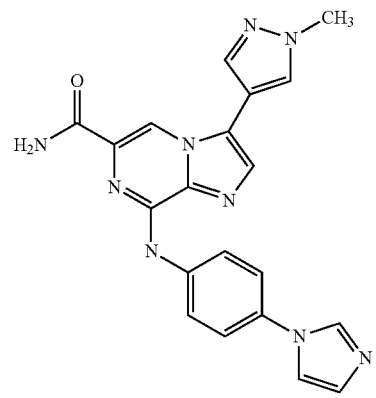

131
-continued
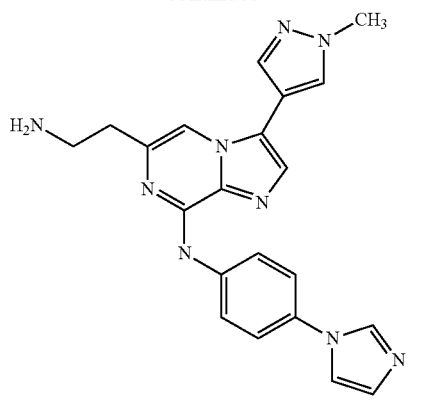
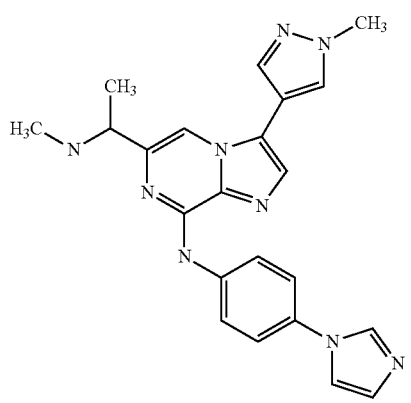
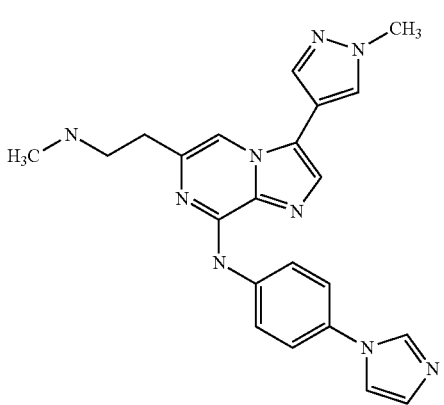
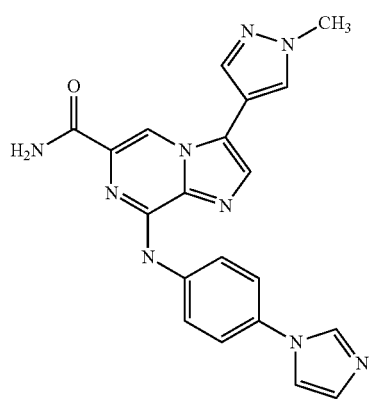
132
-continued
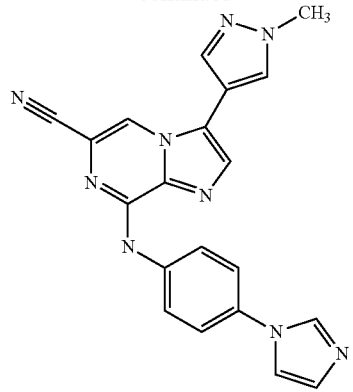
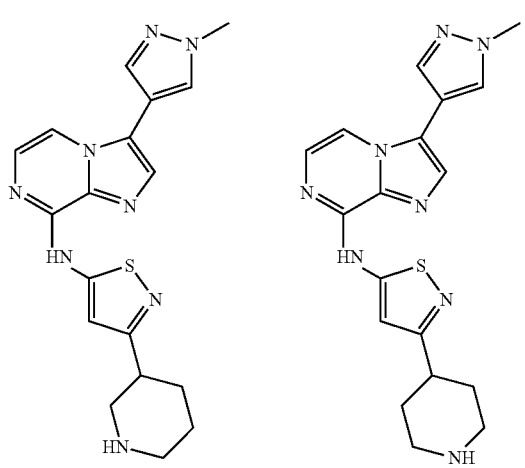
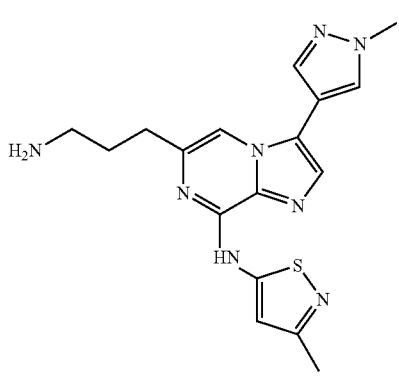
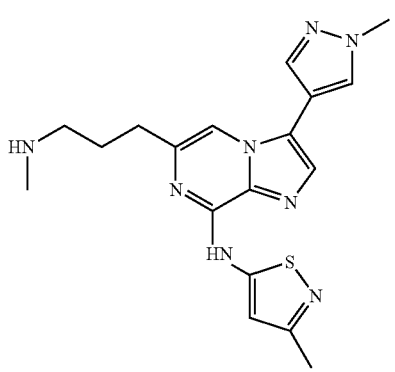

133
-continued
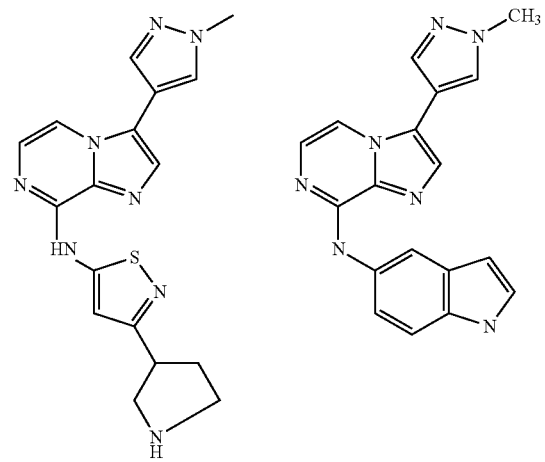
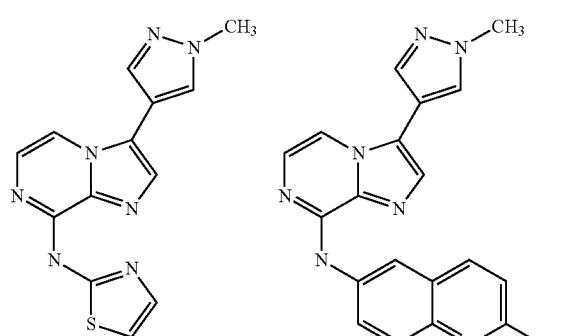
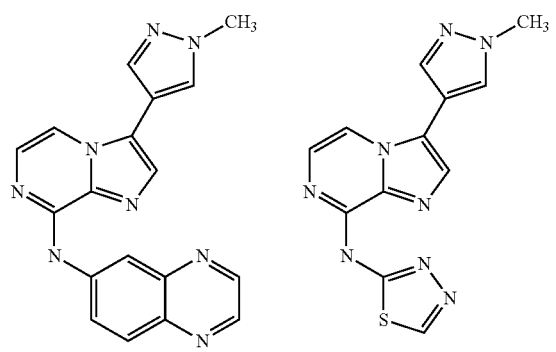
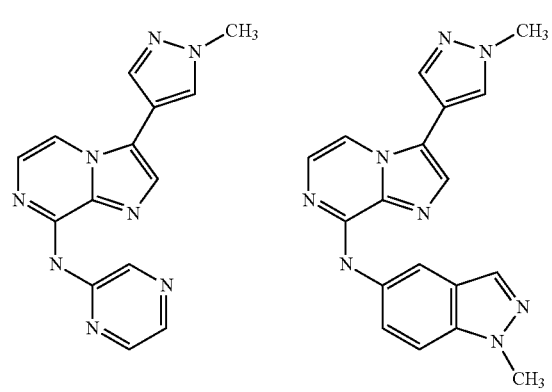
134
-continued
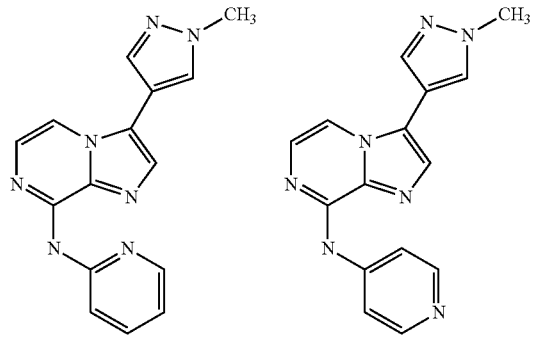
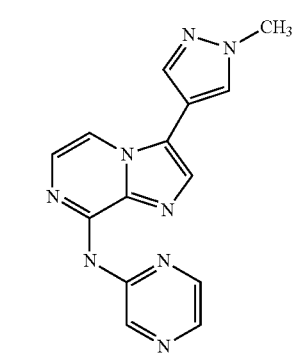
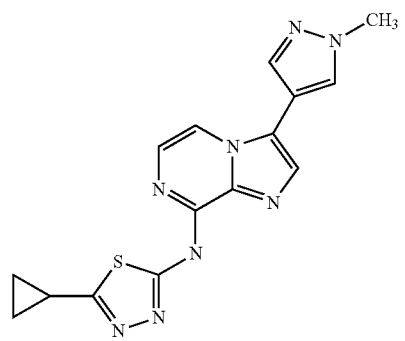
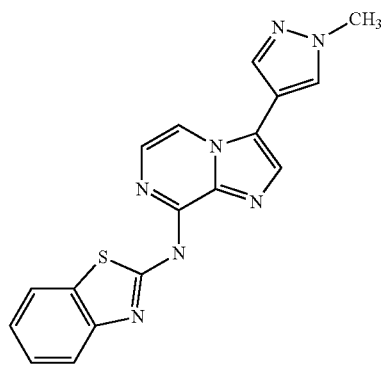

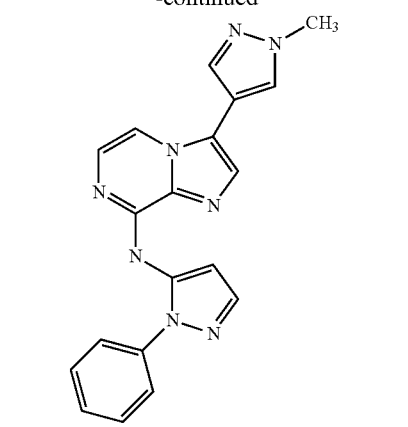
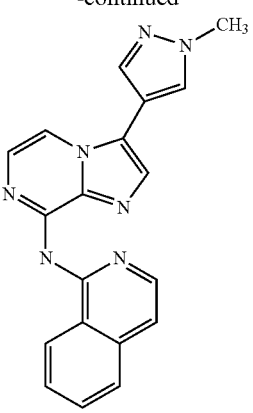
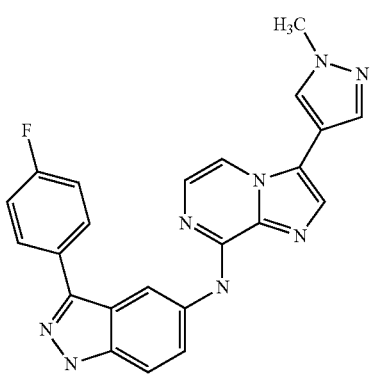

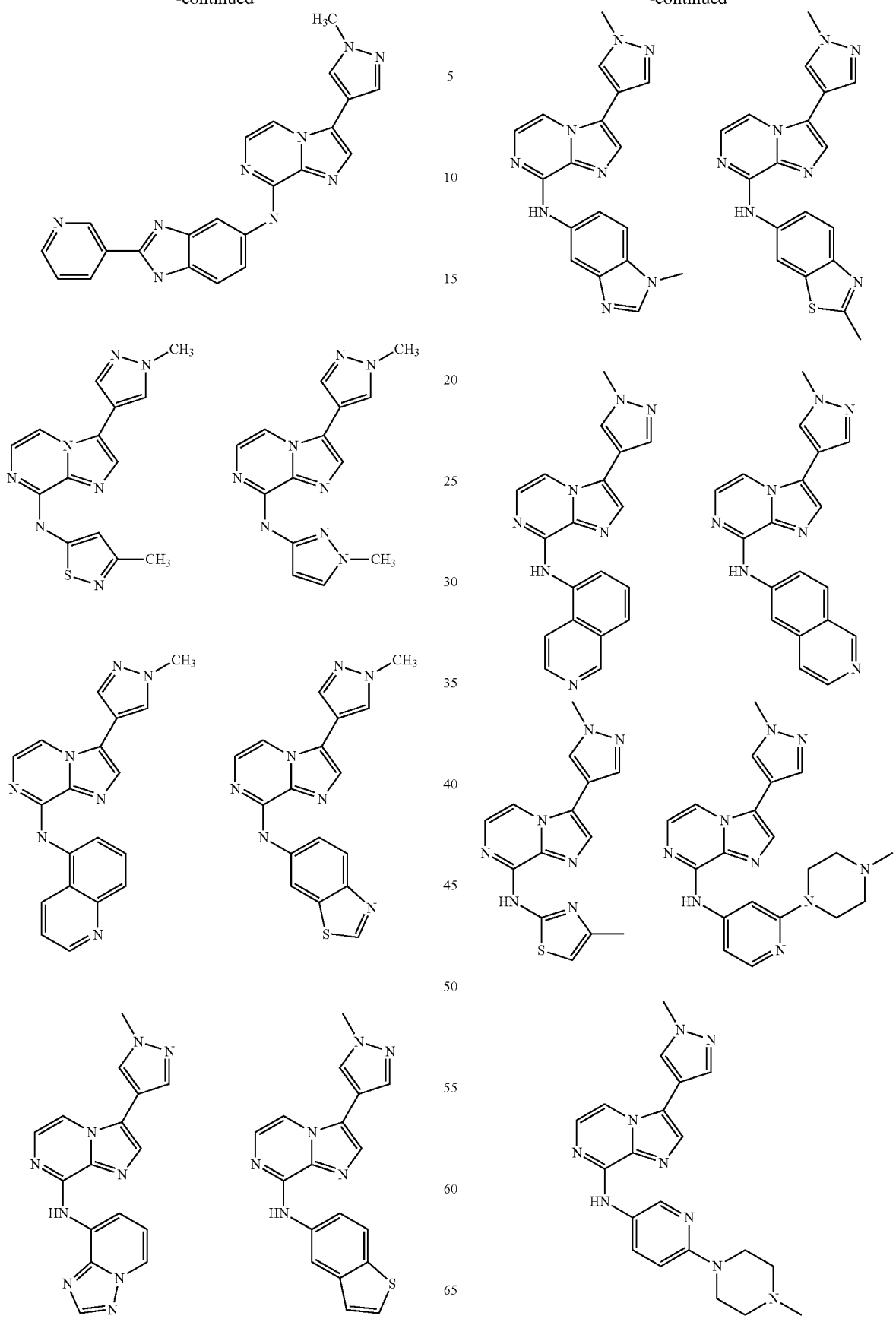

139
-continued
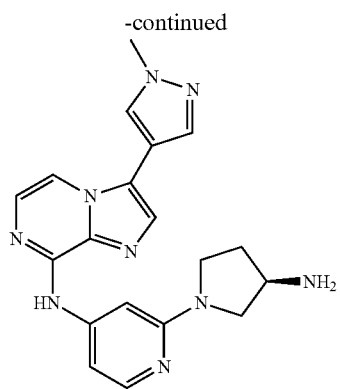
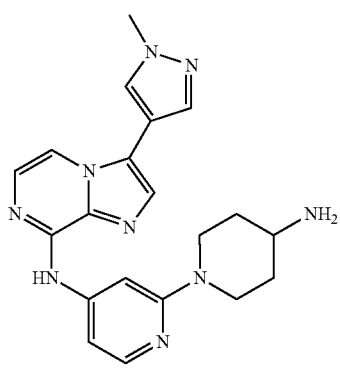
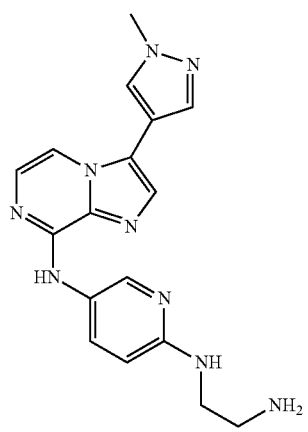
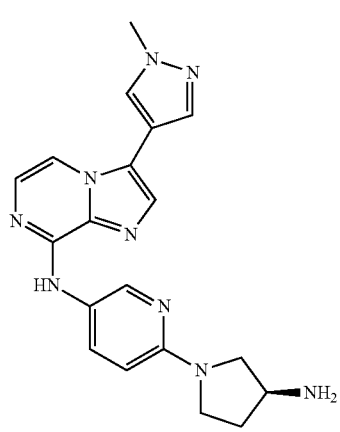
140
-continued
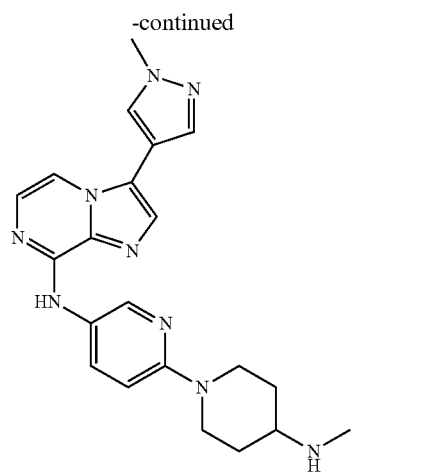
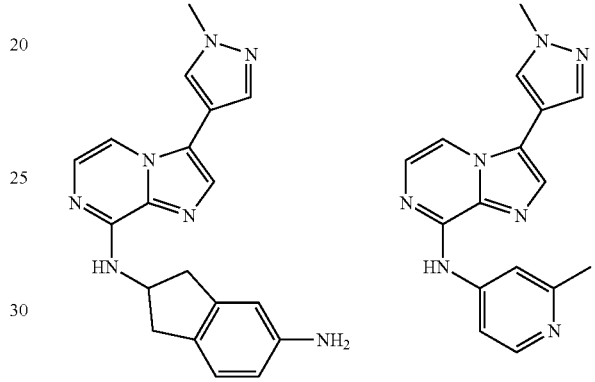
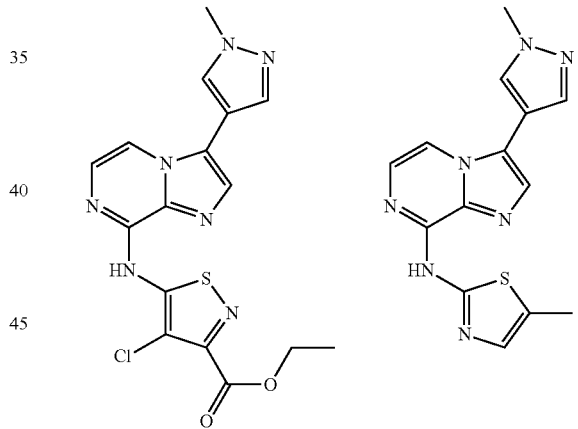
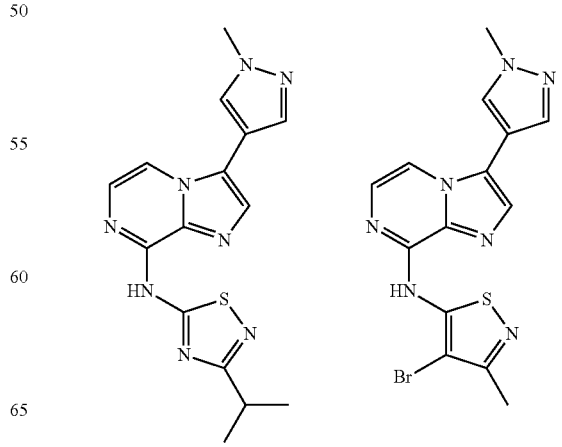

141
-continued
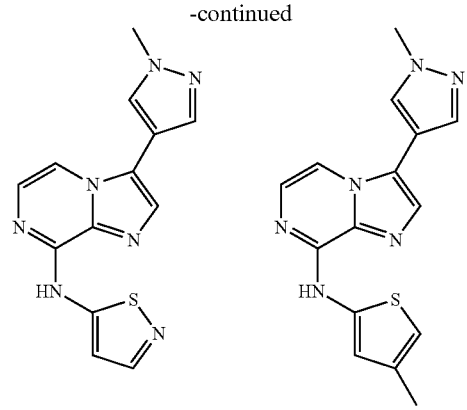
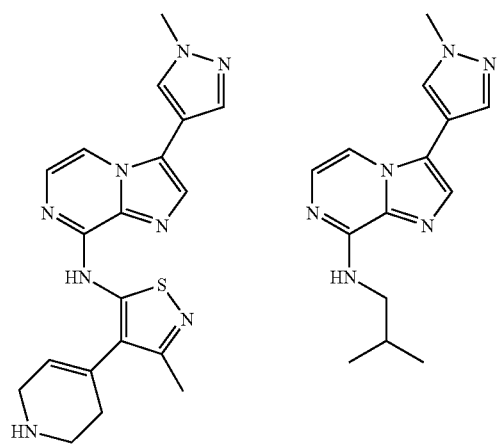
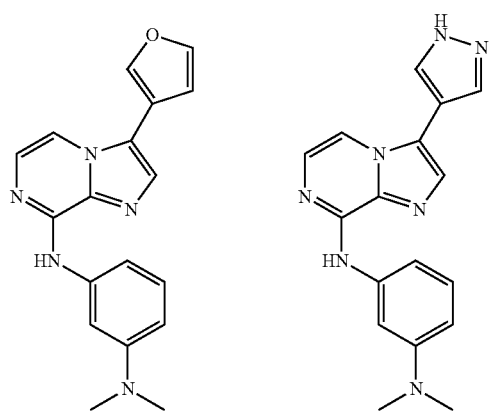
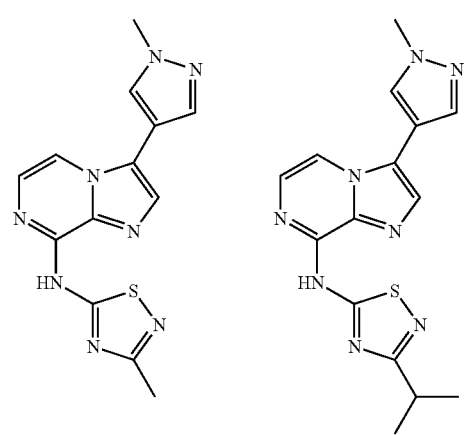
142
-continued
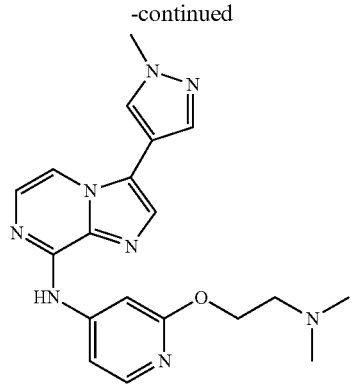
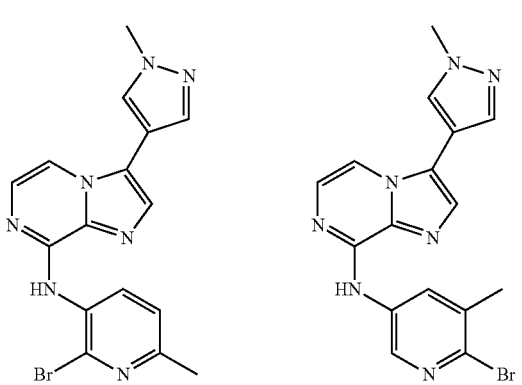
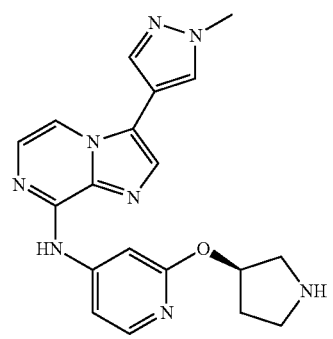
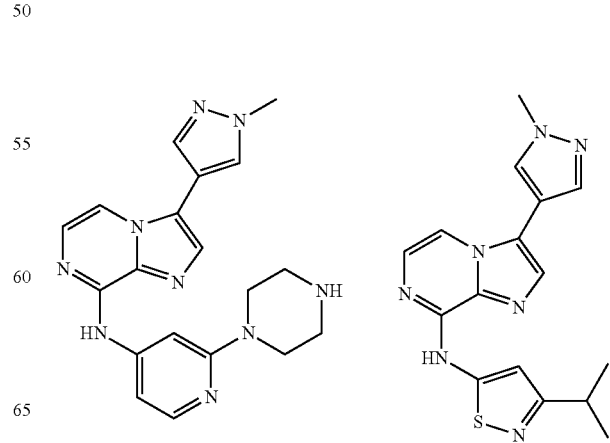

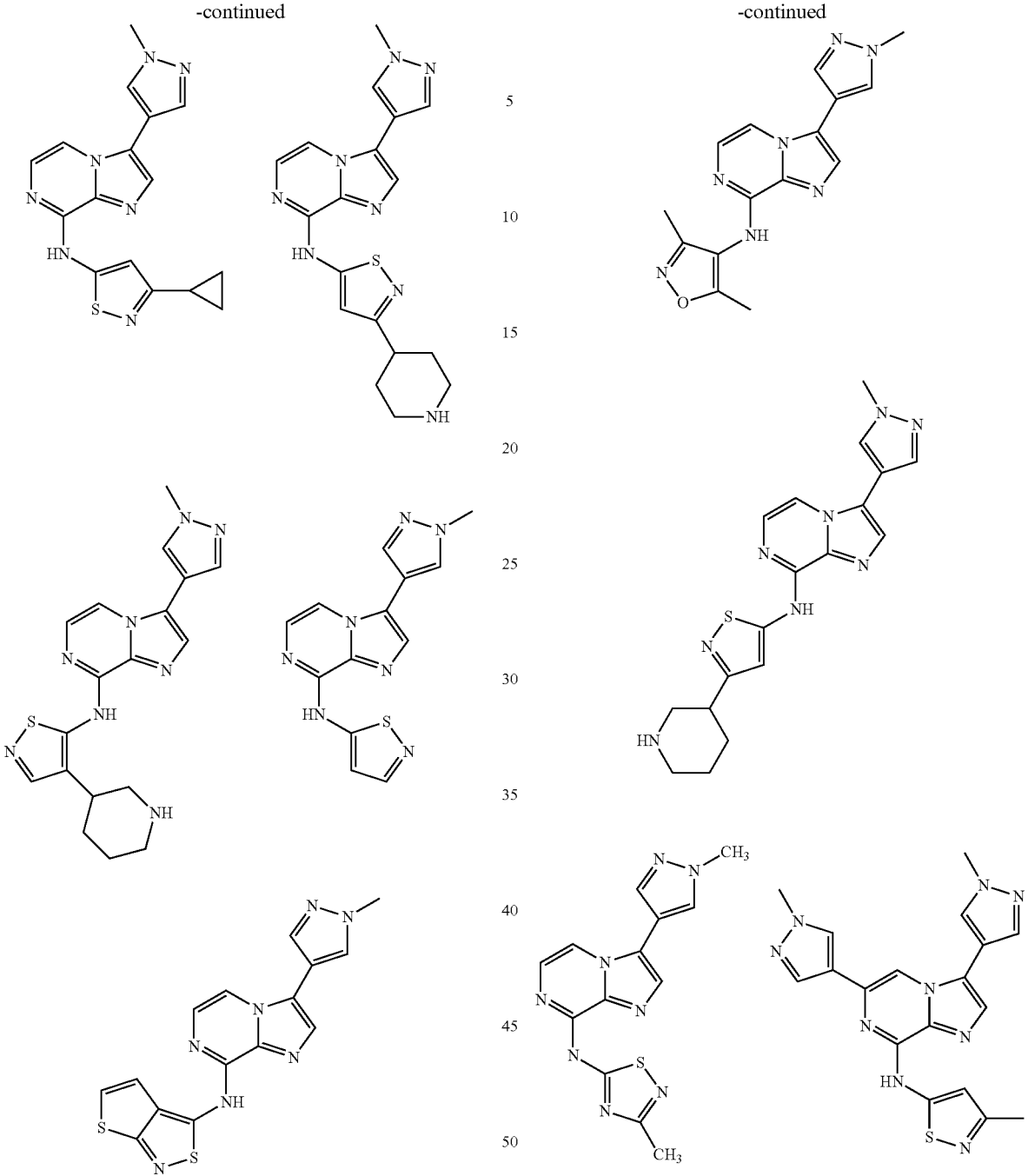

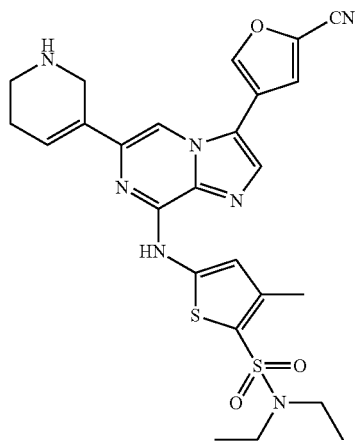
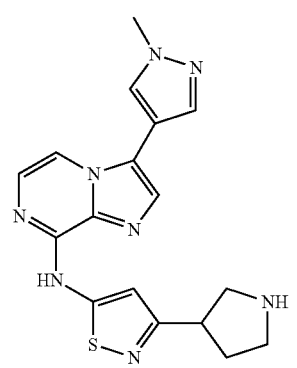
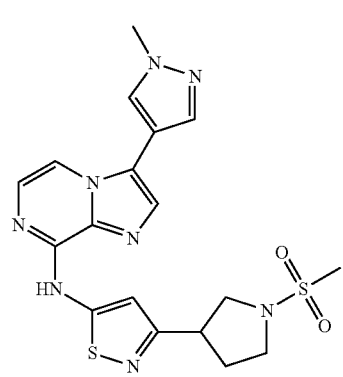
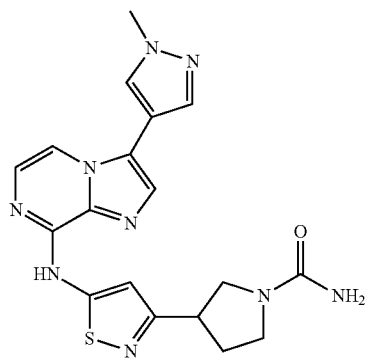
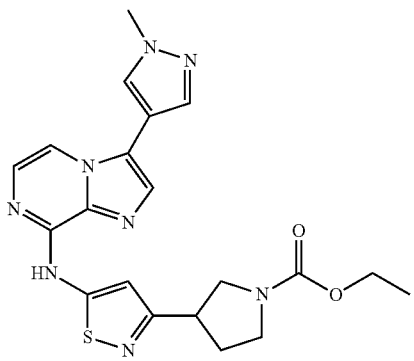
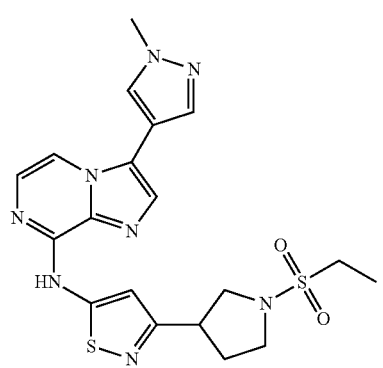
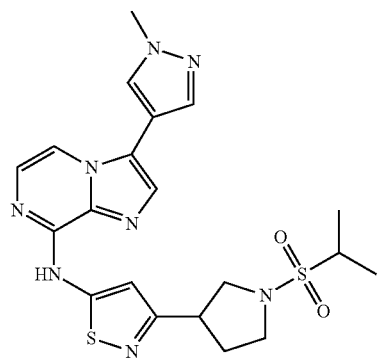
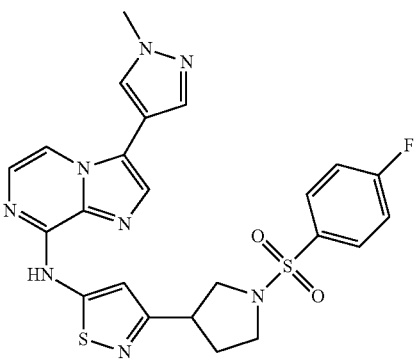

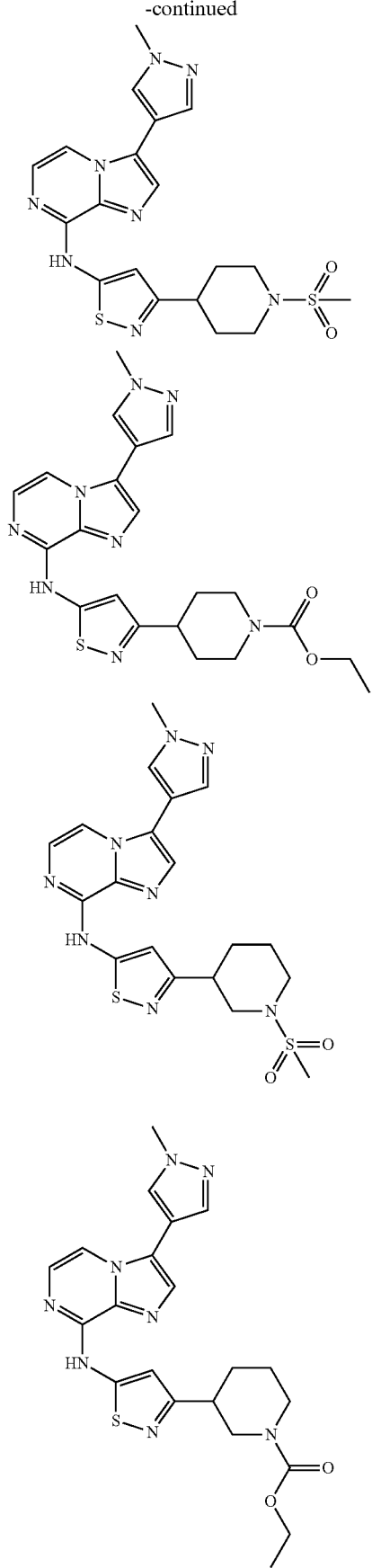
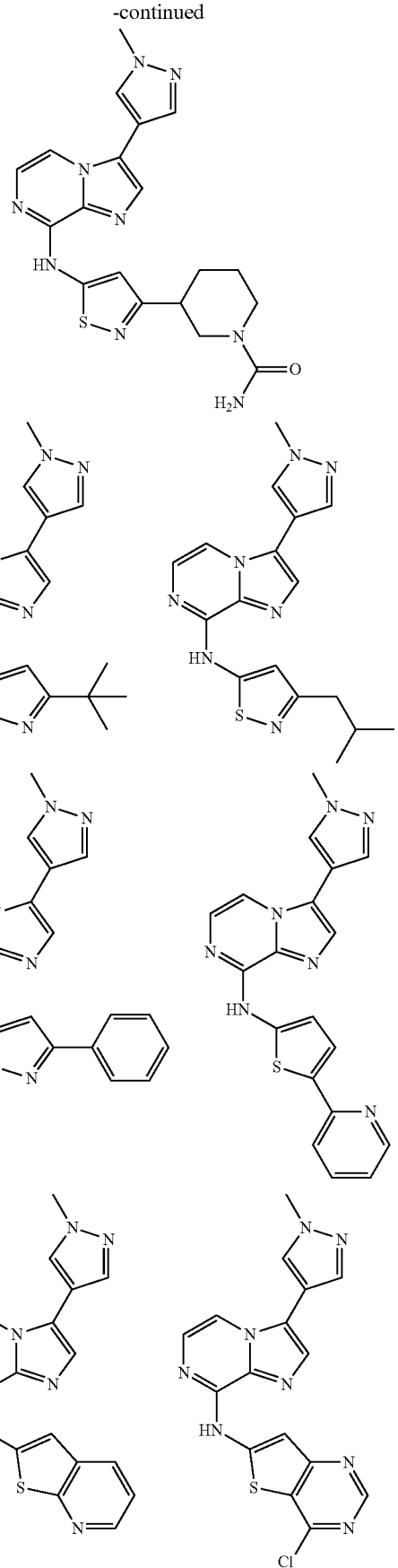

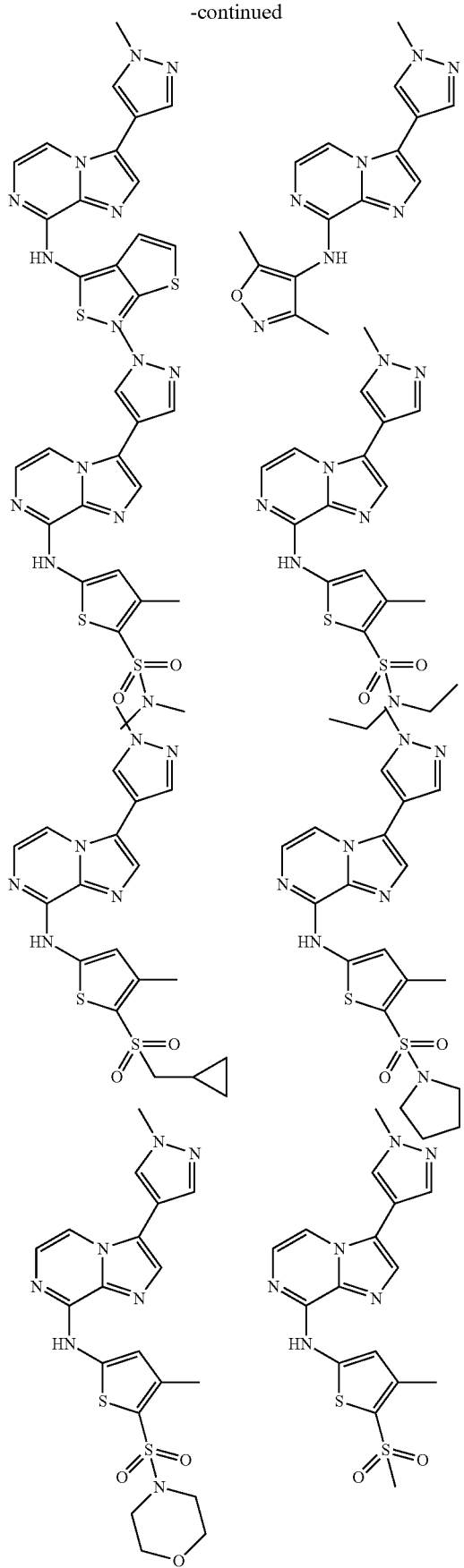
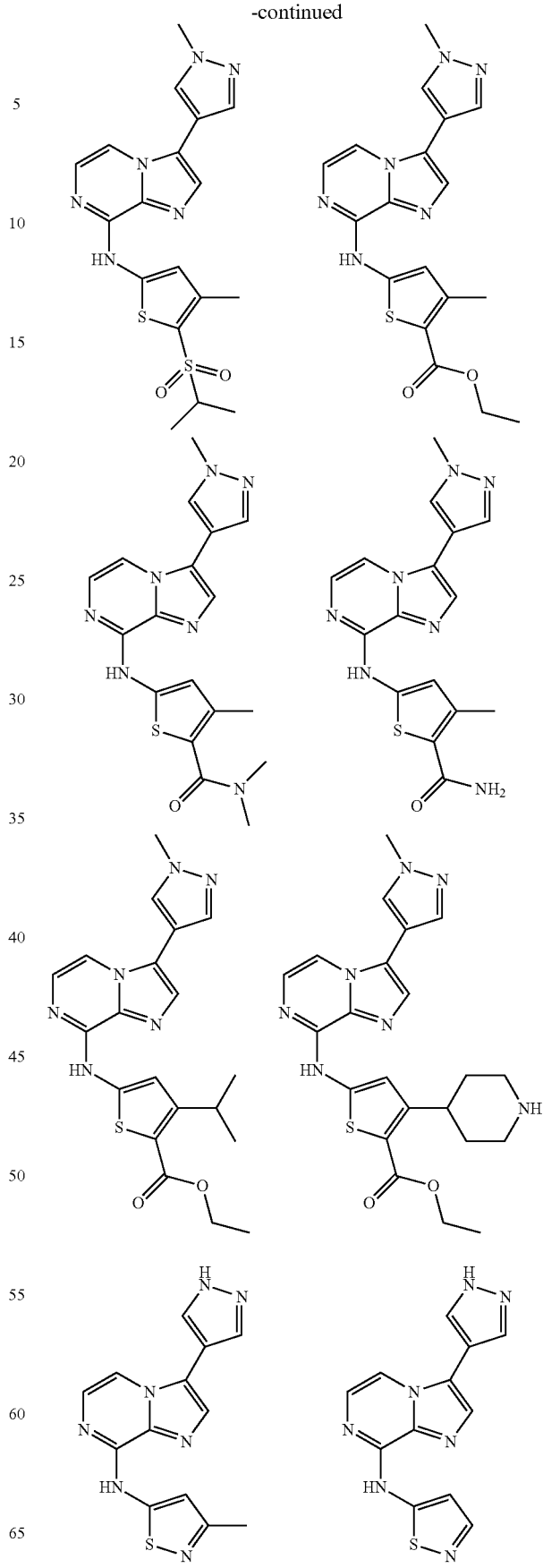

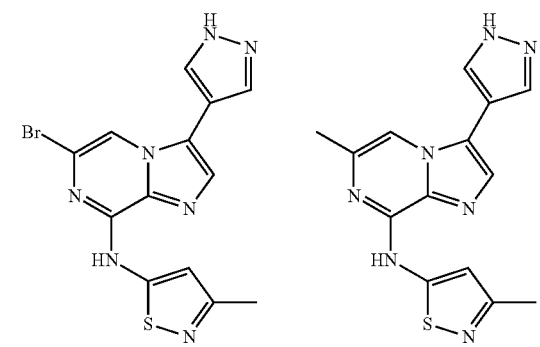
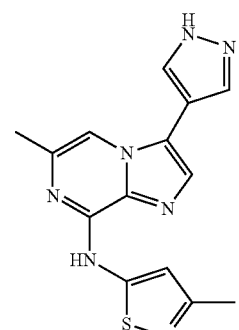
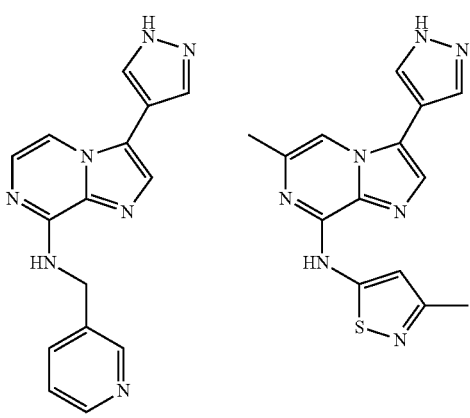
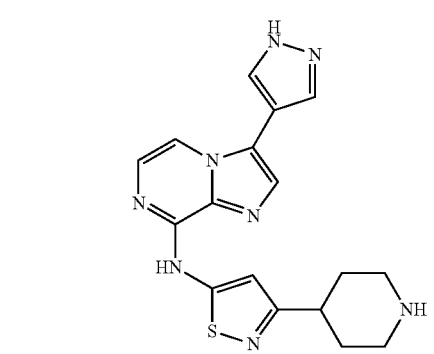
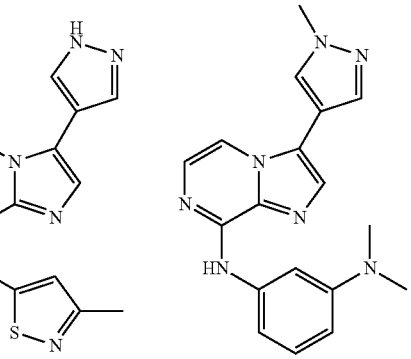
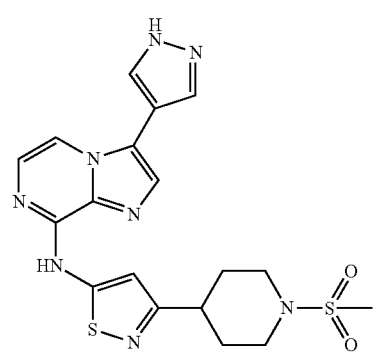
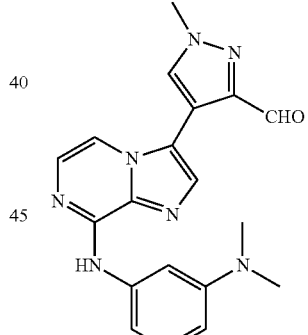
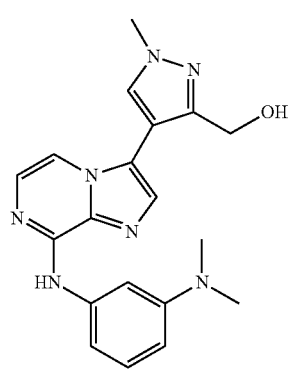
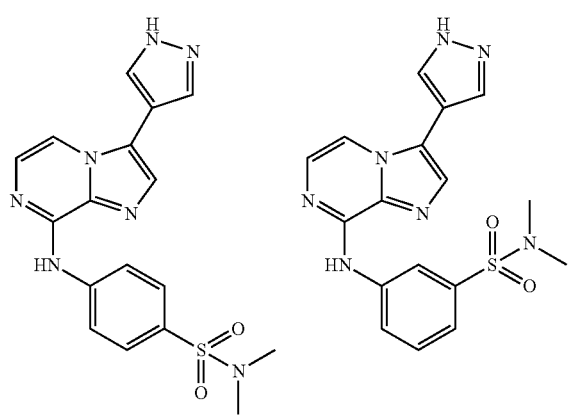
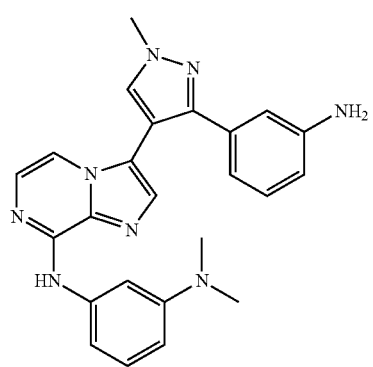

153
-continued
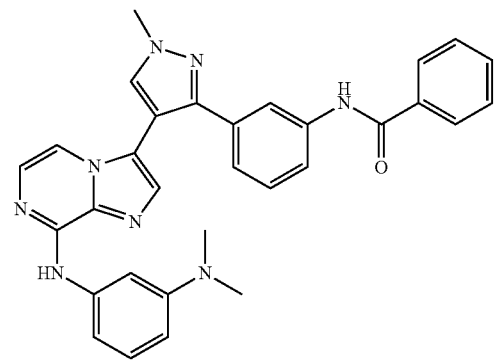
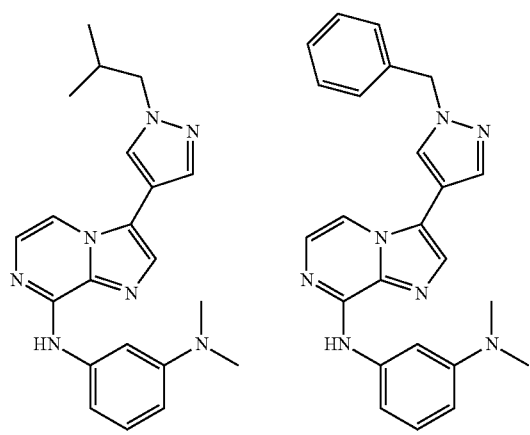
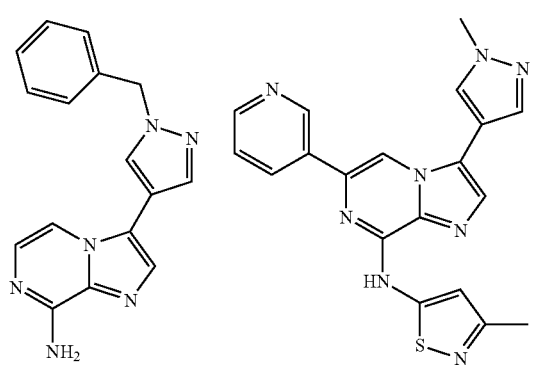
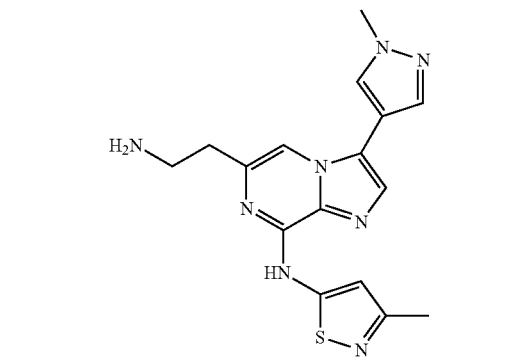
154
-continued
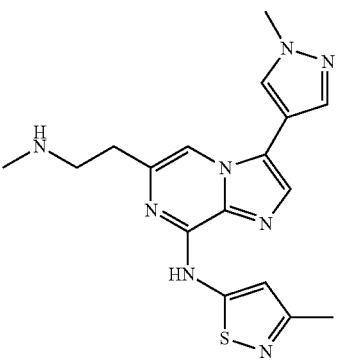
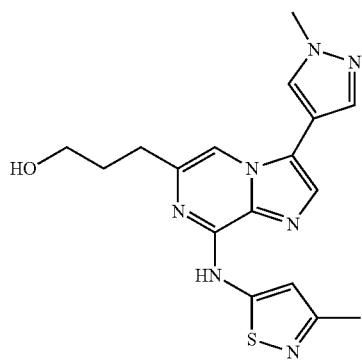
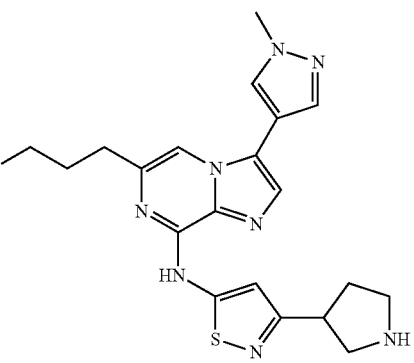
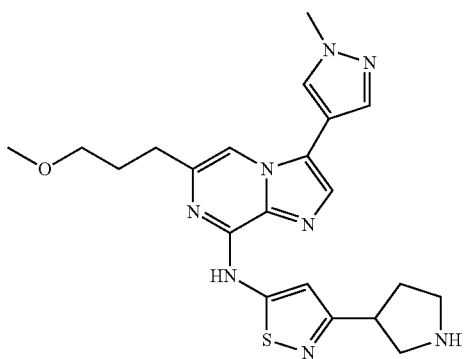

155
-continued
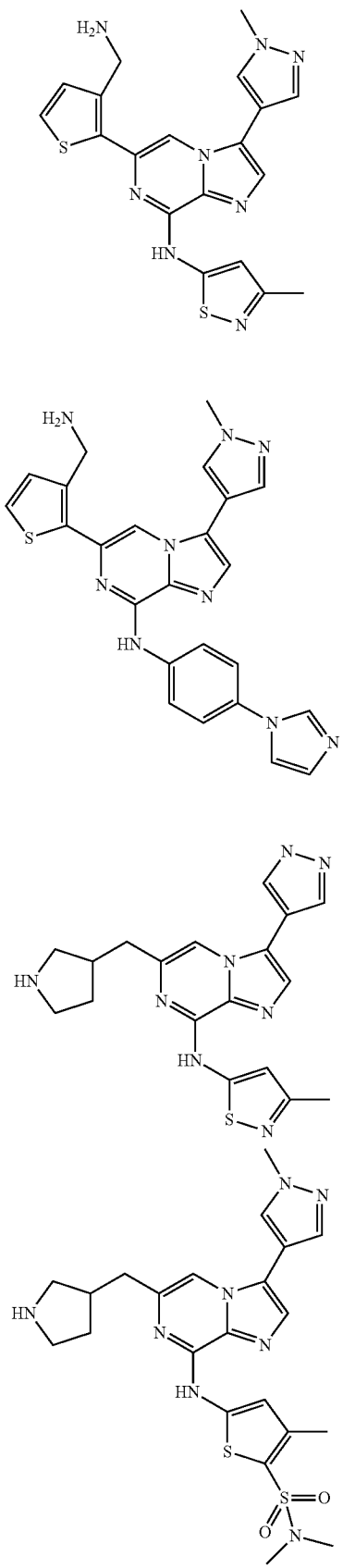
156
-continued
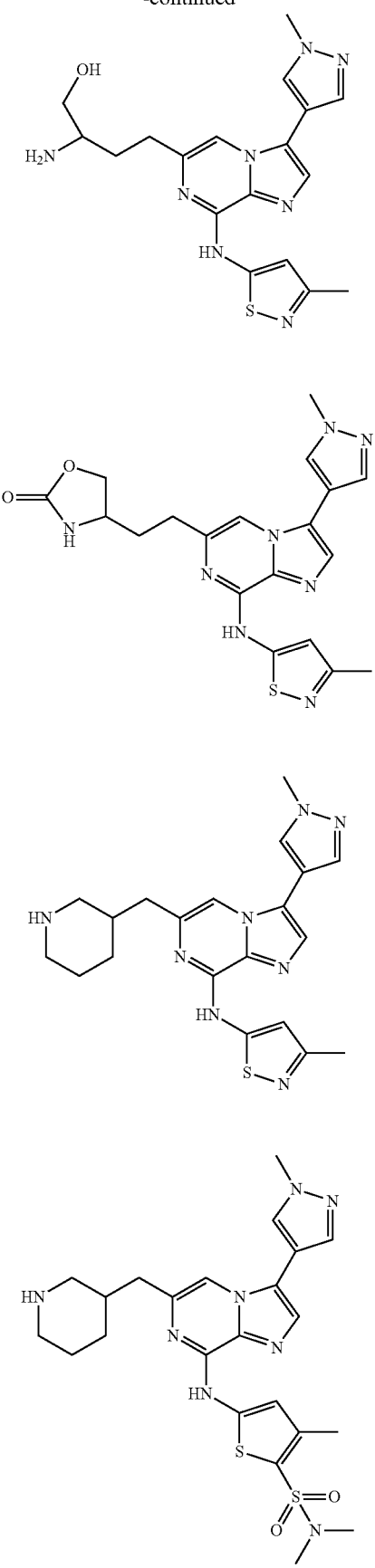

157
-continued
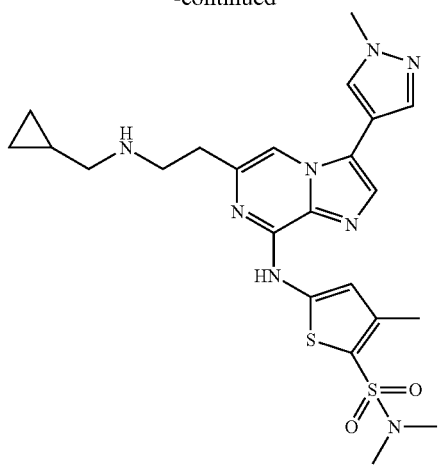
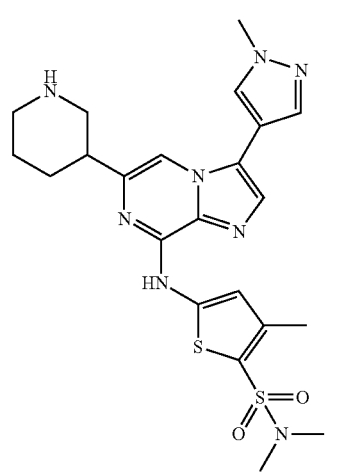
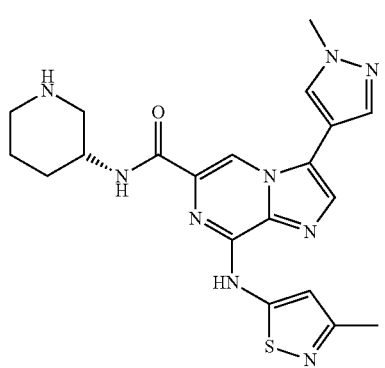
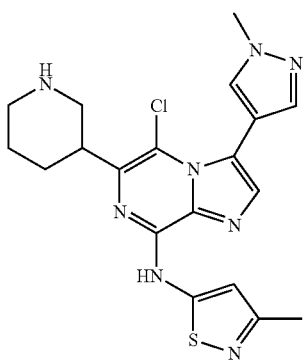
158
-continued
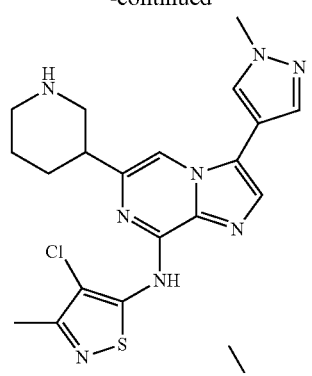

159
-continued
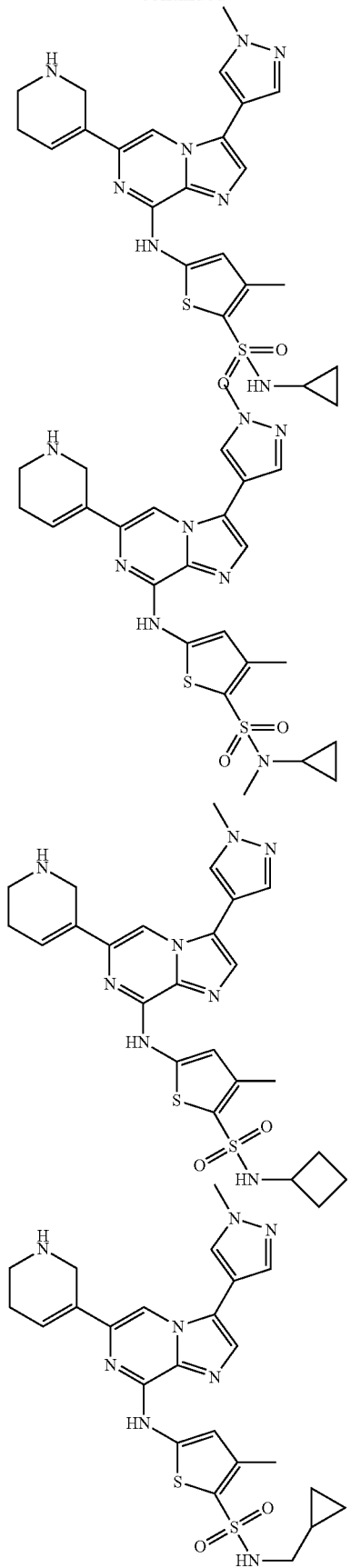
160
-continued
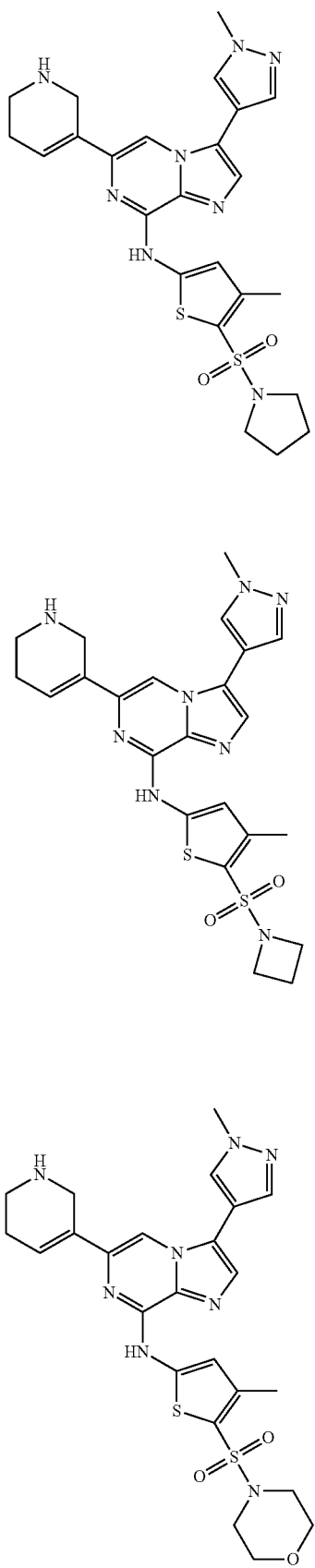

161
-continued
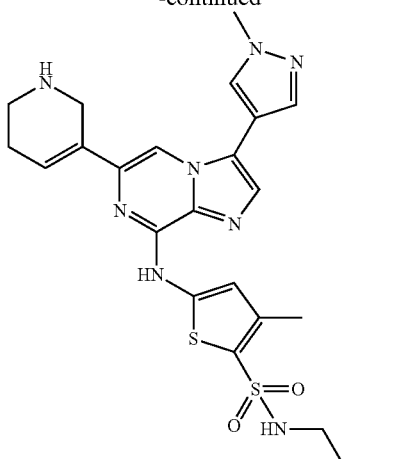
162
-continued
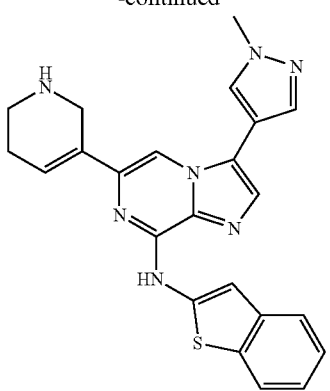
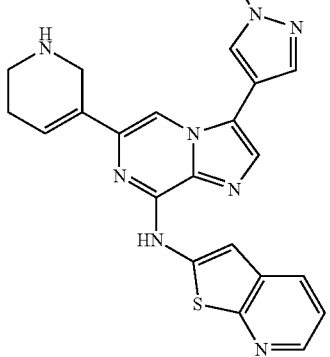
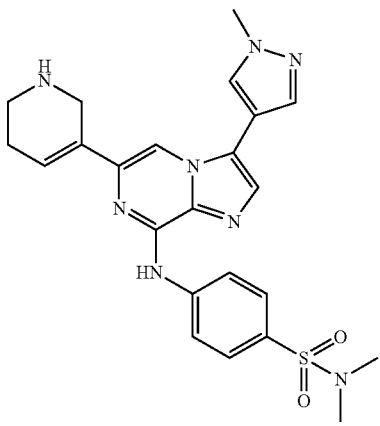
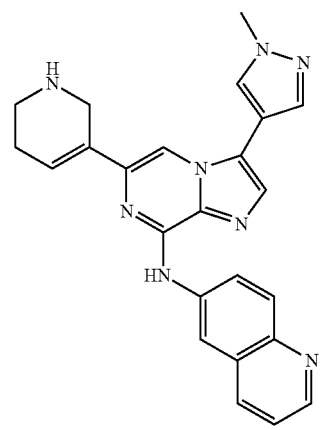

163
-continued
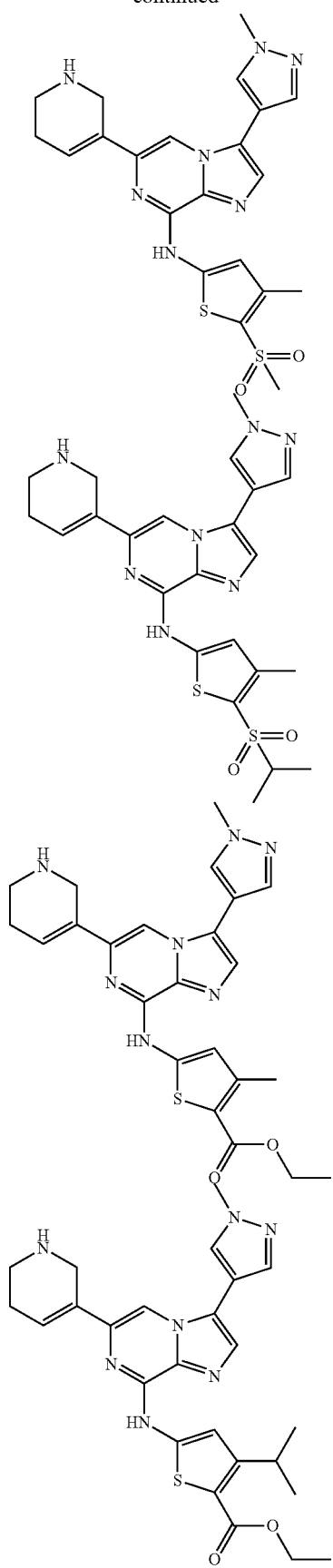
164
-continued
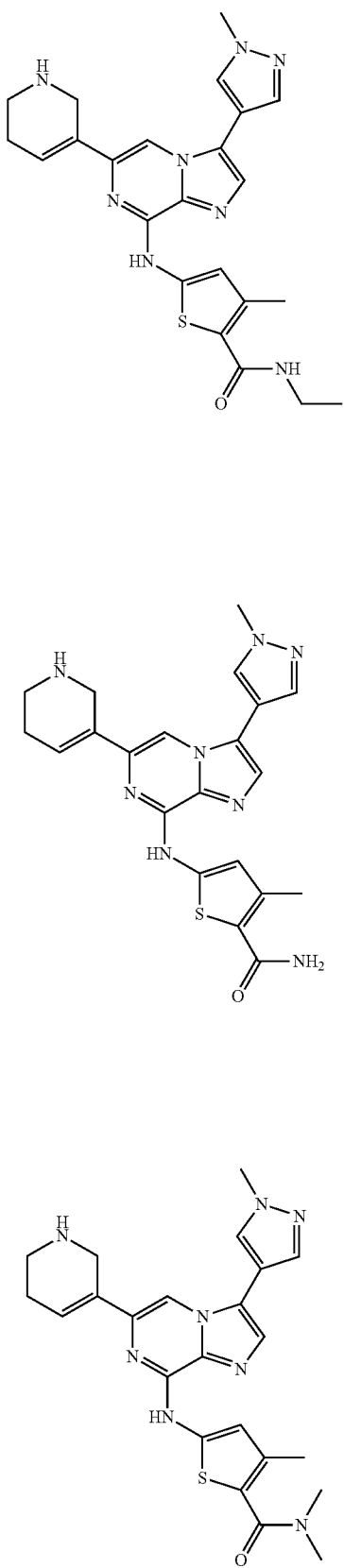

165
-continued
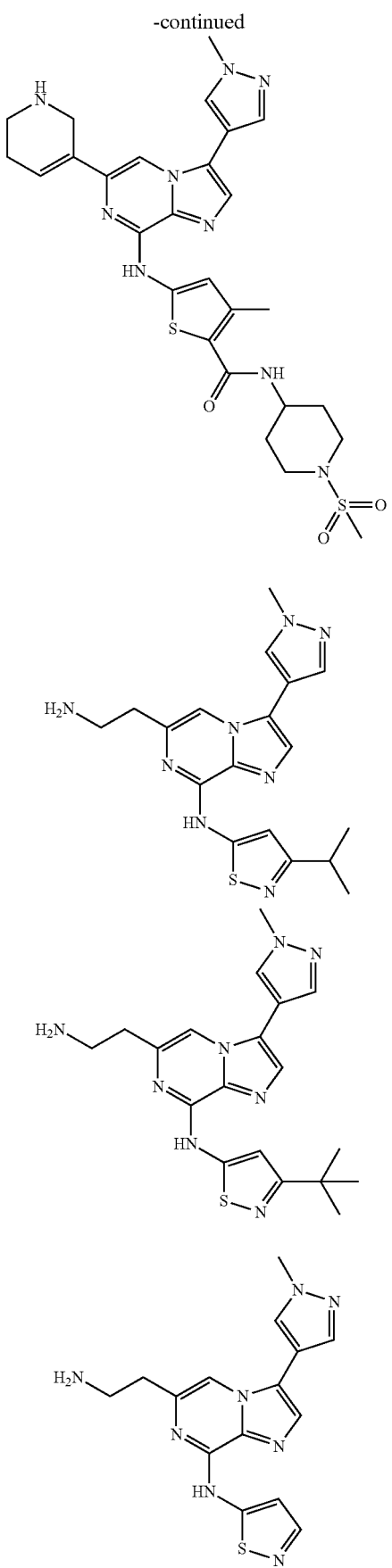
166
-continued
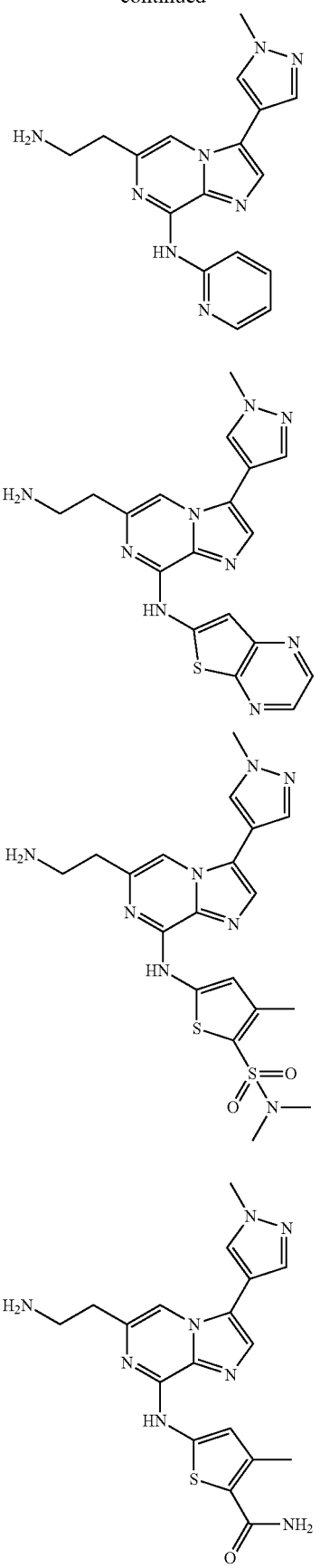

167
-continued
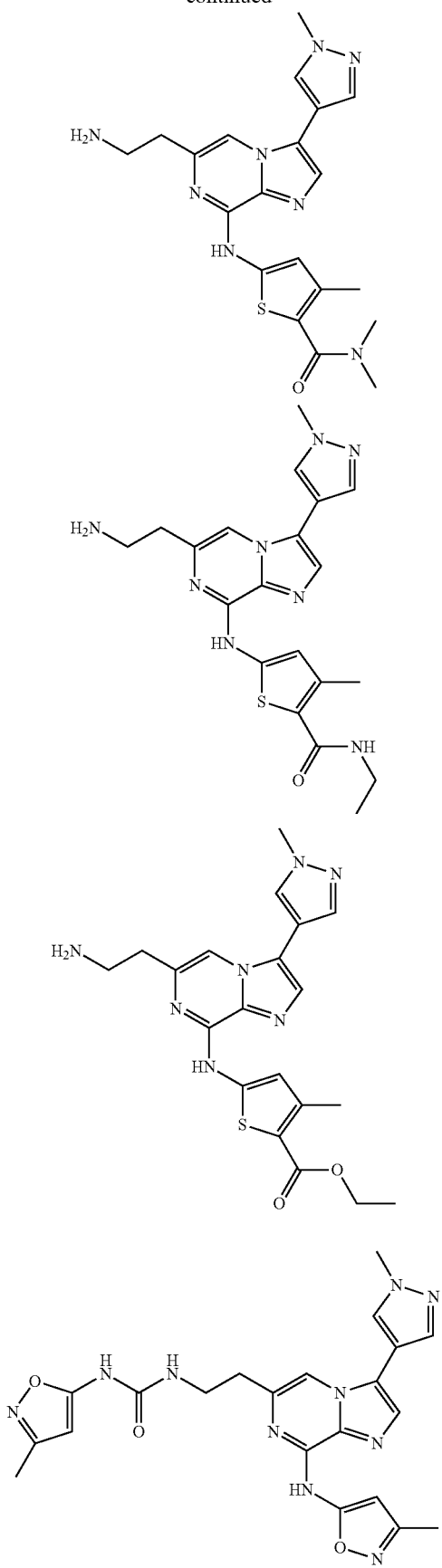
168
-continued
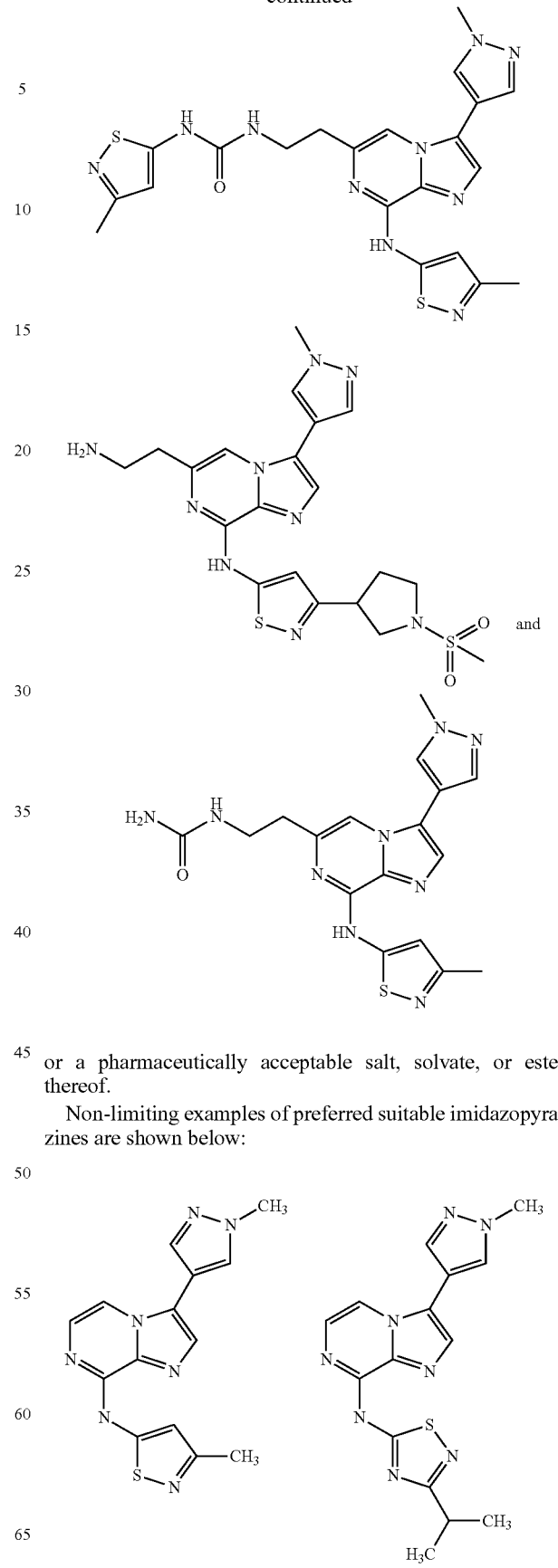
or a pharmaceutically acceptable salt, solvate, or ester thereof.
Non-limiting examples of preferred suitable imidazopyrazines are shown below:
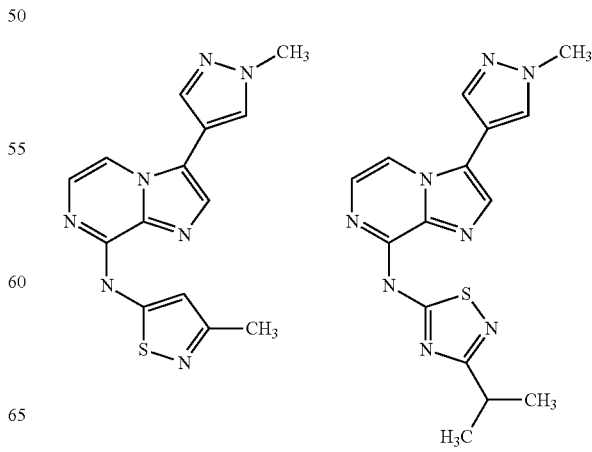

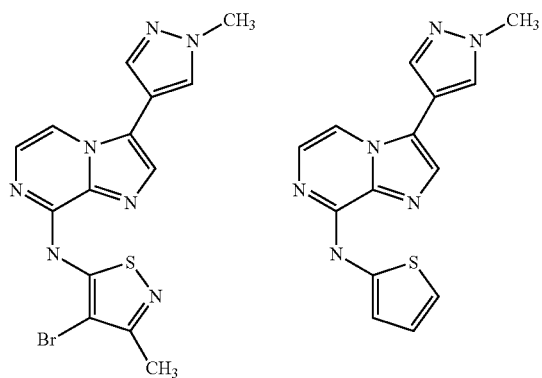
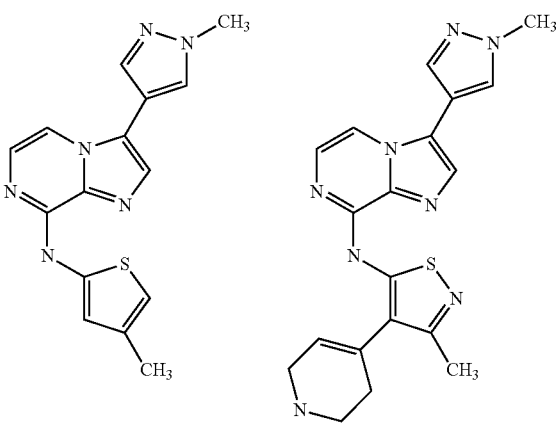
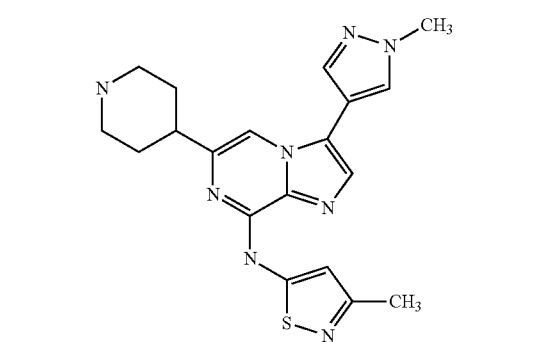
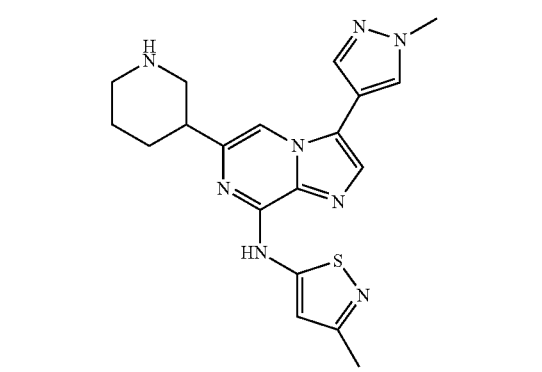
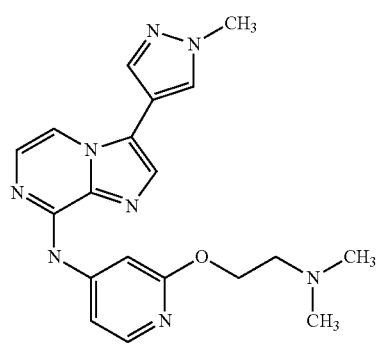
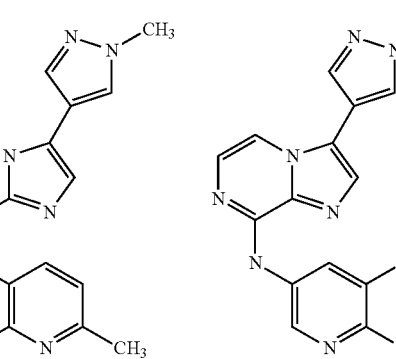
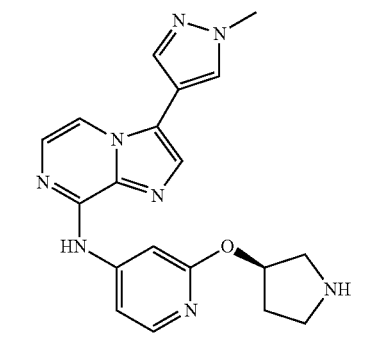
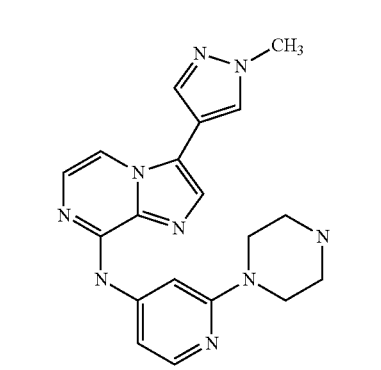

171
-continued
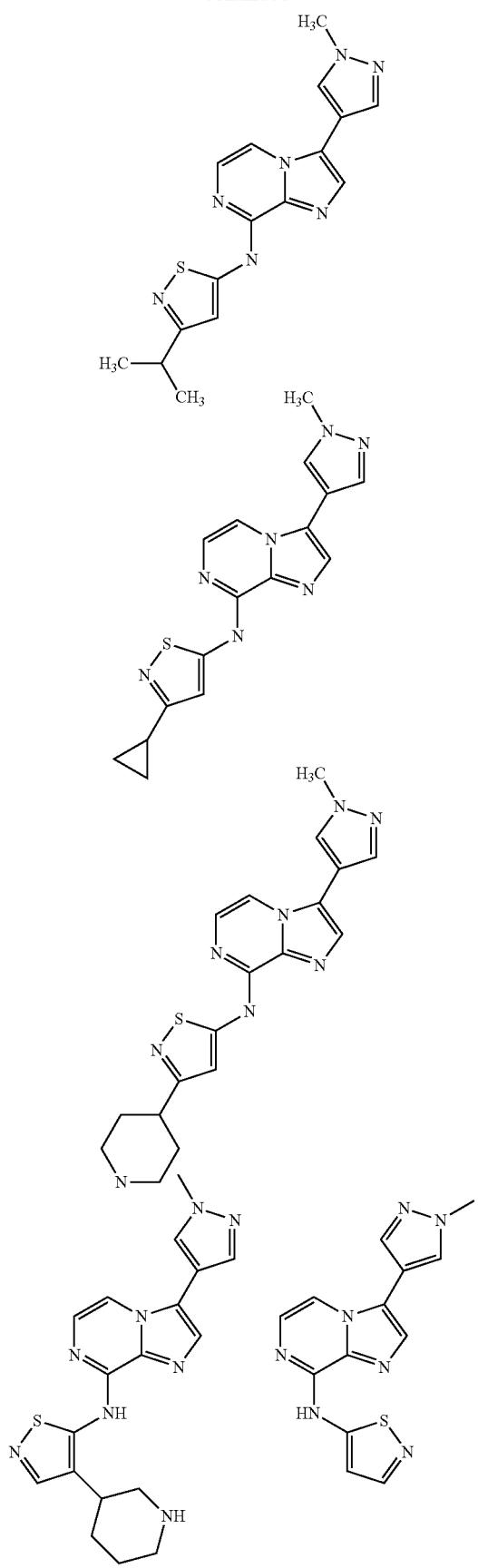
172
-continued
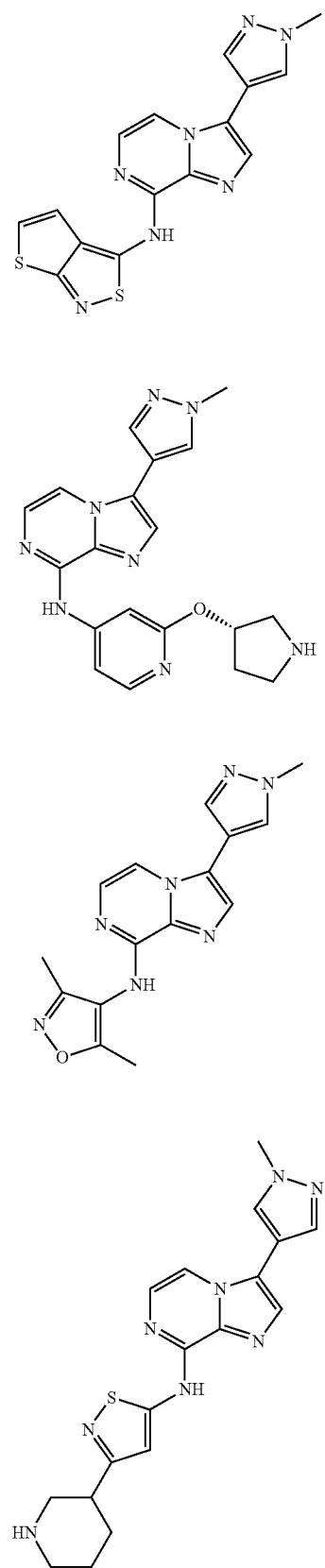

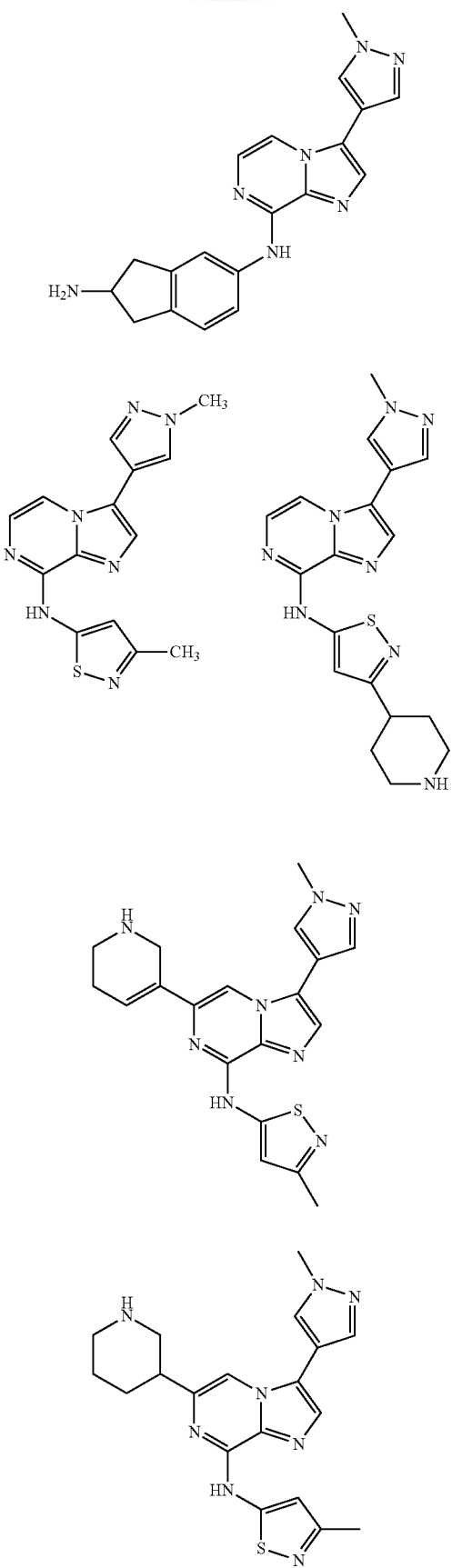
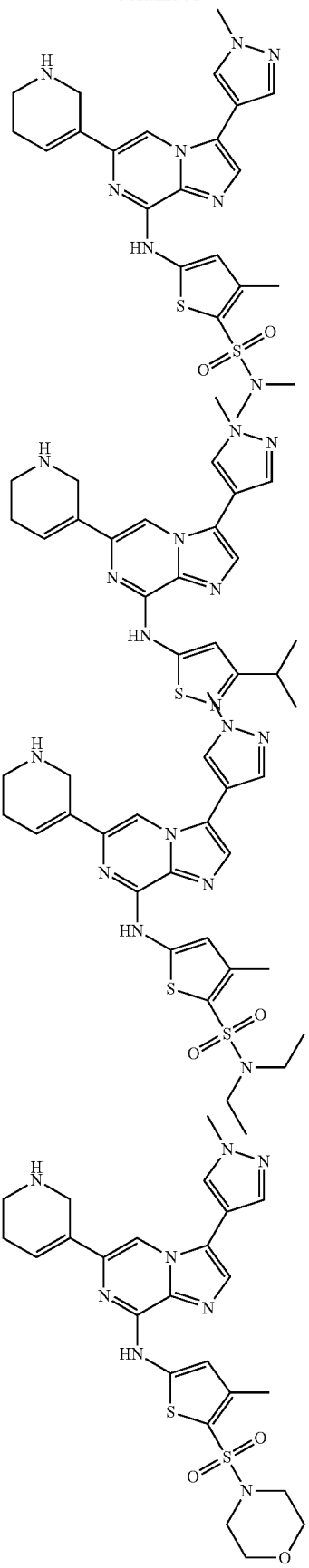

-continued

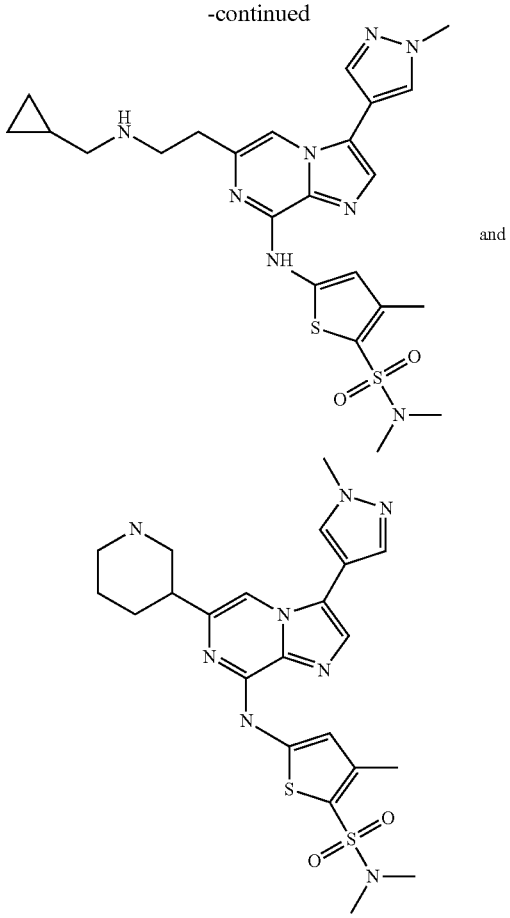

or a pharmaceutically acceptable salt, solvate, ester or prodrug thereof.

The aforementioned US 2007/0072881, U.S. Pat. No. 7,161,003, U.S. Pat. No. 7,119,200, U.S. Pat. No. 7,196,078, U.S. Pat. No. 7,067,661, U.S. Pat. No. 7,205,308, US 2007/0072880, U.S. Pat. No. 7,078,525, U.S. Pat. No. 7,196,092, US 2007/0072882, U.S. Pat. No. 7,084,271, and U.S. Pat. No. 7,074,924, U.S. Pat. No. 6,919,341, US 2006/0106023, US 2007/0083044, US 2007/0082900, US 2007/0105864, US 2007/0117804, U.S. Pat. No. 7,186,740, U.S. application Ser. No. 11/758,243 (filed Jun. 5, 2007), U.S. provisional Patent application Ser. No, 60/858,244 (filed Nov. 8, 2006) and U.S. provisional patent application Ser. No. 60/943,999 (filed Jun. 14, 2007), describe various additional therapeutic agents ("anticancer agents") that could be used as combination agents for such CHK-1 inhibitors in the treatment of various diseases. Such disclosures are to be considered as being incorporated in this invention in their entirety and, therefore, such combination agents therein should be considered as being useful as additional combination agents in the treatments envisaged in the use of the present inventive compounds too.

In another embodiment, the present invention relates to a method for treating inflammation, arthritis, viral diseases, neurodegenerative diseases such as Alzheimer's disease, cardiovascular diseases, and fungal diseases in a subject by administering to the subject at least one cell cycle checkpoint modulator of Formula V, or a pharmaceutically acceptable salt, solvate, ester or prodrug thereof.

In another embodiment, the present invention relates to a method for treating inflammation, arthritis, viral diseases, neurodegenerative diseases such as Alzheimer's disease, cardiovascular diseases, and fungal diseases in a subject by administering to the subject at least one cell cycle checkpoint modulator of Formula V, or a pharmaceutically acceptable salt, solvate, ester or prodrug thereof, in combination with a suitable second agent such as an anti-inflammatory agent, anti-infective, antifungal, antimicrobial, cardiovascular or central nervous system agent.

In another embodiment, the present invention relates to a method for treating cancer in a subject by administering to the subject at least one cell cycle checkpoint modulator of Formula V, or a pharmaceutically acceptable salt, solvate, ester or prodrug thereof, together with a Checkpoint kinase inhibitor, e.g., Chk1 inhibitor, Chk2 inhibitor and the like, or a pharmaceutically acceptable salt, solvate, ester or prodrug thereof, in a therapeutically effective amount, under conditions such that the cancer is treated. In one embodiment, the Checkpoint kinase inhibitor is Chk1 inhibitor. In another embodiment, cancer is selected from the group consisting of multiple myeloma, chronic myelogenous leukemia, pancreatic cancer, non-small cell lung cancer, lung cancer, breast cancer, colon cancer, ovarian cancer, prostate cancer, malignant melanoma, non-melanoma skin cancers, hematologic tumors, hematologic tumors, hematologic malignancies, childhood leukemia, childhood lymphomas, multiple myeloma, Hodgkin's disease, lymphomas of lymphocytic origin, lymphomas of cutaneous origin, acute leukemia, chronic leukemia, acute lymphoblastic leukemia, acute myelocytic leukemia, chronic myelocytic leukemia, plasma cell neoplasm, lymphoid neoplasm and cancers associated with AIDS. Non-limiting examples of the cancer include: tumor of the bladder, breast (including BRCA-mutated breast cancer, colorectal, colon, kidney, liver, lung, small cell lung cancer, non-small cell lung cancer, head and neck, esophagus, bladder, gall bladder, ovary, pancreas, stomach, cervix, thyroid, prostate, and skin, including squamous cell carcinoma;

leukemia, acute lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma and Burkett's lymphoma;

chronic lymphocytic leukemia ("CLL"), acute and chronic myelogenous leukemia, myelodysplastic syndrome and promyelocytic leukemia;

fibrosarcoma, rhabdomyosarcoma; head and neck, mantle cell lymphoma, myeloma;

astrocytoma, neuroblastoma, glioma, glioblastoma, malignant glial tumors, astrocytoma, hepatocellular carcinoma, gastrointestinal stromal tumors ("GIST") and schwannomas;

melanoma, multiple myeloma, seminoma, teratocarcinoma, osteosarcoma, xenoderoma pigmentosum, keratoctanthoma, thyroid follicular cancer and Kaposi's sarcoma.

The above description sets forth rather broadly the more important features of the present invention in order that the detailed description thereof that follows may be understood, and in order that the present contributions to the art may be better appreciated. Other objects and features of the present invention will become apparent from the following examples considered in conjunction with the accompanying drawings. It is to be understood, however, that the drawings are designed solely for the purposes of illustration and not as a definition of the limits of the invention, for which reference should be made to the appended claims.

The pharmacological properties of the compounds of this invention may be confirmed by a number of pharmacological assays. The exemplified pharmacological assays which are described herein below have been carried out with compounds according to the invention and their salts, solvates, esters or prodrugs.

The invention disclosed herein is exemplified by the following preparations and examples which should not be construed to limit the scope of the disclosure. Alternative mechanistic pathways and analogous structures will be apparent to those skilled in the art.

The following abbreviations are used in the procedures and schemes:

| | |
|---|---|
| ACN | Acetonitrile |
| AcOH | Acetic acid |
| Aq | Aqueous |
| BINAP | 2,2'-bis(diphenylphosphino)-1,1'-binaphthalene |
| BOC | tert-Butoxycarbonyl |
| BOC-ON | [2-(tert-butoxycarbonyloxyimino)-2-phenylacetonitril] |
| BOC$_2$O | BOC Anhydride |
| Bz | Benzoyl |
| C. | degrees Celsius |
| Calcd | Calculated |
| CBZCl | Benzyl chloroformate |
| CDI | Carbonyldiimidazole |
| dba | Dibenzylidineacetone |
| DBU | 1,8-Diazabicyclo[5.4.0]undec-7-ene |
| DCE | 1,2-Dichloroethane |
| DCM | Dichloromethane |
| DEAD | Diethyl azodicarboxylate |
| (DHQ)2PHAL | Hydroquinine 1,4-phthalazinediyl diether |
| DIAD | Diisopropylazodicarboxylate |
| DIPEA | Diisopropylethylamine |
| DMA | N,N-Dimethylacetamide |
| DMAP | 4-Dimethylaminopyridine |
| DME | Dimethoxyethane |
| DMF | Dimethylformamide |
| DMFDMA | N,N-Dimethylformamide dimethylacetal |
| DMPU | 1,3-Dimethyl-3,4,5,6-tetrahydro-2(1h)-pyrimidinone |
| DMSO | Dimethyl sulfoxide |
| dppf | 1,1'-Bis(diphenylphosphino)ferrocene |
| EDCl | 1-(3-Dimethylaminopropyl)-3-ethylcarbodiimide hydrochloride |
| EI | Electron ionization |
| Eq | Equivalents |
| EtOAc | Ethyl acetate |
| EtOH | Ethanol |
| F-TEDA | 1-chloromethyl-4-fluoro-1,4-diazoniabicyclo[2,2,2]octane bis(tetrafluoroborate) |
| g | grams |
| h. | hours |
| $^1$H | proton |
| HATU | N,N,N',N'-Tetramethy1-O-(7-Azabenzotriazol-1-yl)uronium hexafluorophosphate |
| HCl | Hydrogen chloride |
| Hex | hexanes |
| HOBT | 1-Hydroxybenzotriazole |
| HPLC | High pressure liquid chromatography |
| LAH | Lithium aluminum hydride |
| LCMS | Liquid Chromatography Mass Spectroscopy |
| LDA | Lithium diisopropylamide |
| LHMDS | Lithium hexamethyldisilazide |
| M | Molar |
| mmol | milimolar |
| mCPBA | meta-Chloroperoxybenzoic acid |
| Me | Methyl |
| MeCN | Acetonitrile |
| MeOH | Methanol |
| min | Minutes |
| mg | Milligrams |
| MHZ | Megahertz |
| mL | Milliliter |
| MPLC | Medium Pressure Liquid Chromatography |
| MsO | Mesylate (methanesulfonate) |
| Ms | methanesulfonyl |
| MS | Mass Spectroscopy |
| N | Normal |
| NaHCO$_3$ | Sodium bicarbonate |
| Na$_2$SO$_4$ | Sodium sulfate |
| NMR | Nuclear Magnetic Resonance |
| NBS | N-Bromosuccinimide |
| NCS | N-Chlorosuccinimide |
| NIS | N-Iodosuccinimide |
| nm | nanometers |
| NMM | N-Methylmorpholine |
| NsO | Nosylate (p-nitrobenzenesulfonate) |
| Obsd | Observed |
| ON | Overnight |
| PCC | Pyridinium Chlorochromate |
| Ph | Phenyl |
| PTLC | Preparative thin layer chromatography |
| PyBop | (Benzotriazol-1-yloxy)tripyrrolidinophosphonium hexafluorophosphate |
| PyBrOP | Bromo-tris-pyrrolidino-phosphonium hexafluorophosphate |
| Pyr | Pyridine |
| RT | Room temperature |
| Satd | saturated |
| SEM | 2-(Trimethylsilyl)ethoxymethyl |
| sgc | Silica gel 60 chromatography |
| soln | Solution |
| tBOC | tert-Butoxycarbonyl |
| TBAF | tetrabutylammonium fluoride |
| TBDMS | tert-butyldimethylsilyl |
| TEA | Triethylamine |
| TFA | Trifluoroacetic acid |
| THF | Tetrahydrofuran |
| TIPS | Triisopropylsilyl |
| TLC | Thin layer chromatography |
| TMS | Trimethylsilyl |
| Ts | p-toluenesulfonyl |
| TsO | Tosylate (p-toluenesulfonate) |
| $t_R$ | Retention time |
| UV$_{254\,nm}$ | ultraviolet light 254 nm |

NMR spectra were acquired on the following instruments: 400 MHZ NMR (Bruker), 500 MHZ NMR (Bruker), 400 MHz NMR (Varian), 300 MHZ NMR (Varian) using CD$_3$OD, CDCl$_3$ or DMSO-d$_6$ as solvents. LC-MS data were obtained using a PESciex API 150EX quadropole mass spectrometer using electroscopy ionization. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop. The retention time and observed parent ion are given.

Purification via reverse phase chromatography (Gilson) was accomplished using a C18 reverse phase column with a gradient of (0.1% formic acid) 5:95 to 90:10 acetonitrile: water, at a flow rate of 14 ml/min. Samples were collected using UV detection. Alternatively an ISCO Companion with (0.1% formic acid) 5:95 to 95:5 acetonitrile:water, at a flow rate=10-55 ml/min.

Normal phase silica gel chromatography was either accomplished on a Biotage instrument using a 60 Å 12/M, 25/M, or 40/M flash cartridges, or on a Jones Flash Master Personal instrument using Isolute flash SI 5 g, 10 g, 20 g, 50 g, or 70 g cartridges, or on ISCO CombiFlash Rf system using RediSep Rf silica gel, basic alumina or amine columns.

EXAMPLES

Preparative Example 10

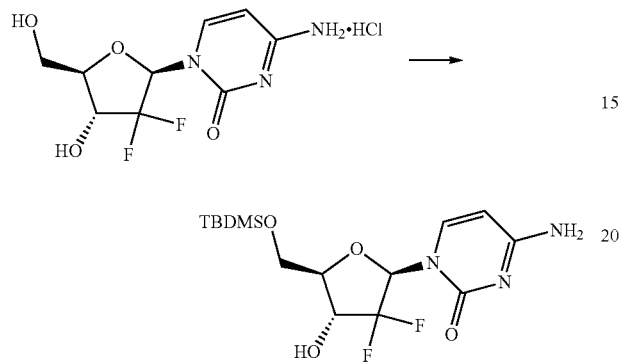

A solution of Gemcitibine-hydrochloride (3.00 g, 10.01 mmol) in DMF (20.1 mL) at 25° C. was treated successively with imidazole (2.04 g, 3.00 equiv.) and tert-butyldimethylsilyl chloride (1.66 g, 1.10 equiv). The solution was stirred at 25° C. for 15 h. The solvent was evaporated and the residue was purified using silica gel chromatography with a gradient of 10-40% MeOH in $CH_2Cl_2$. $MH^+$=378.

Preparative Example 20

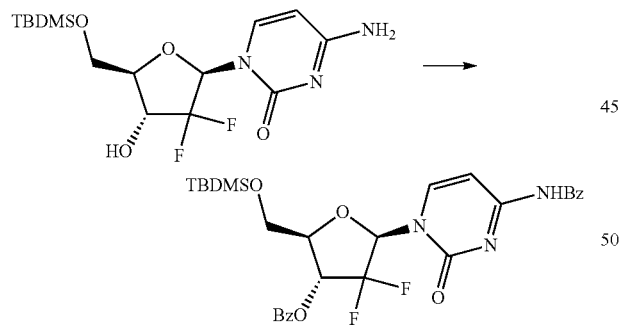

A solution of silyl ether from Preparative Example 10 (3.52 g, 9.32 mmol) in pyridine (47 mL) at 25° C. was treated successively with 4-dimethylaminopyridine (1.71 g, 1.50 equiv.) and benzoyl chloride (2.71 mL, 2.50 equiv.). The solution was stirred at 25° C. for 15 h. The solution was concentrated and the residue was dissolved in $CH_2Cl_2$ (100 ml). The organic layer was washed with saturated aqueous $NaHCO_3$ solution (50 mL), saturated aqueous NaCl solution (50 mL), and water (100 mL). The organic layer was dried ($Na_2SO_4$), filtered and concentrated. The residue was purified using silica gel chromatography with a gradient of 10-50% acetone in $CH_2Cl_2$. $MH^+$=586.

Preparative Example 30

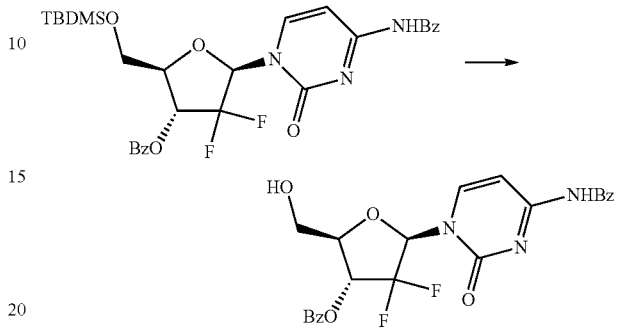

A solution of silyl ether from Preparative Example 20 (4.64 g, 7.92 mmol) in a 1.0M solution of tetrabutylammonium fluoride in THF (30.6 mL, 3.86 equiv.) at 25° C. was treated with acetic acid (3.06 mL, 6.74 equiv.). The solution was stirred at 25° C. for 3 h. The solution was concentrated and the residue was partitioned between water (100 mL) and $CH_2Cl_2$ (50 mL). The aqueous layer was further extracted with $CH_2Cl_2$ (2×50 mL). The combined organic layer was washed with saturated aqueous NaCl solution (50 mL), dried ($Na_2SO_4$), filtered and concentrated. The residue was purified using silica gel chromatography with a gradient of 25-50% acetone in $CH_2Cl_2$. $MH^+$=472.

Preparative Example 40

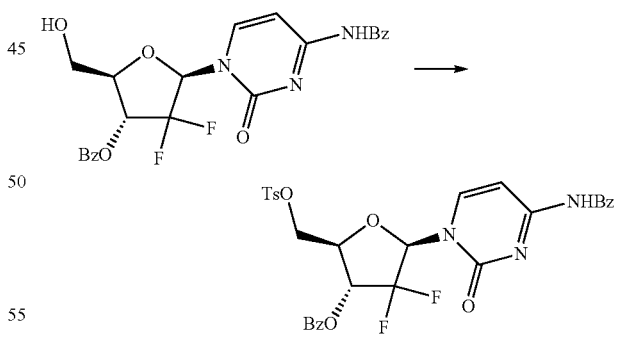

A solution of alcohol from Preparative Example 30 (3.73 g, 7.91 mmol) in pyridine (79 mL) at 0° C. was treated successively with p-toluenesulfonyl chloride (6.03 g, 400 equiv.) and triethylamine (2.20 mL, 2.00 equiv.). The solution was stirred at 0° C. for 3 h and the ice bath was removed and stirring was continued at 25° C. for 15 h. The solution was concentrated and the residue was purified using silica gel chromatography with a gradient of 0-25% acetone in $CH_2Cl_2$.

Example 50

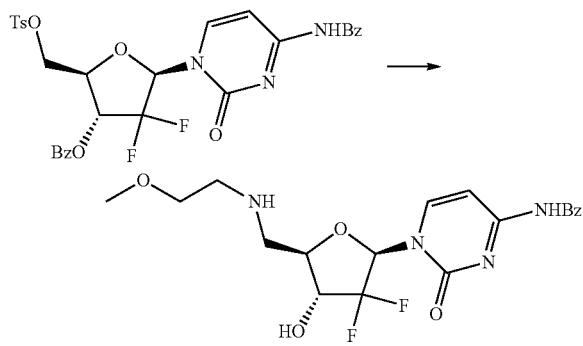

A solution of tosylate from Preparative Example 40 (0.15 g, 0.17 mmol) and 2-methoxyethanamine (0.073 mL, 5 equiv.) in DMF (0.67 mL), in a sealed tube, was heated at 100° C. for 3 h. The solution was cooled to room temperature and concentrated under reduced pressure. The residue was purified using silica gel chromatography with a gradient of 0-40% MeOH in $CH_2Cl_2$. A white solid (0.011 g, 20%) was obtained. $^1$H NMR ($CD_3OD$) δ 7.67 (d, J=7.3 Hz, 1H), 6.19 (t, J=8.8 Hz, 1H), 5.91 (d, J=7.3 Hz, 1H), 4.06-4.14 (m, 1H), 3.92-3.97 (m, 1H), 3.50 (t, J=5.1 Hz, 2H), 3.35 (s, 3H), 3.05 (dd, J=2.9 Hz, J=13.0 Hz, 1H), 2.97 (dd, J=2.9 Hz, J=13.0 Hz, 1H), 2.82-2.85 (m, 2H); $MH^+$=321.

Examples 60-170

Following the procedure set forth in Example 50, either with or without DMF as a solvent, only using the nucleophiles given in Column 1 of Table 10, compounds given in Column 2 of Table 10 were prepared.

TABLE 10

| Example | Column 1 | Column 2 | Data<br>1. $^1$H NMR or mp (° C.)<br>2. $MH^+$ |
|---|---|---|---|
| 60 | (morpholine) | (morpholine-substituted nucleoside) | 1. $^1$H NMR ($CD_3OD$) δ 7.68 (d, J = 8.0 Hz, 1H), 6.19 (t, J = 8.0 Hz, 1H), 5.93 (d, J = 7.3 Hz, 1H), 3.99-4.11 (m, 2H), 3.67-3.71 (m, 4H), 2.73-2.84 (m, 2H), 2.57-2.62 (m, 4H)<br>2. $MH^+$ = 333. |
| 70 | (furfurylamine) | (furfurylamino-substituted nucleoside) | 1. $^1$H NMR ($CD_3OD$) δ 7.67 (d, J = 8.0 Hz, 1H), 7.44 (d, J = 2.2 Hz, 1H), 6.25-6.36 (m, 1H), 6.27 (d, J = 3.6 Hz, 1H), 6.18 (t, J = 8.0 Hz, 1H), 5.90 (d, J = 7.3 Hz, 1H), 4.07-4.14 (m, 1H), 3.91-3.96 (m, 1H), 3.83 (s, 2H), 3.03 (dd, J = 2.9 Hz, J = 13.9 Hz, 1H), 2.94 (dd, J = 6.6 Hz, J = 13.2 Hz, 1H)<br>2. $MH^+$ = 343. |
| 80 | (3-methoxypropylamine) | (3-methoxypropylamino-substituted nucleoside) | 1. $^1$H NMR ($CD_3OD$) δ 7.66 (d, J = 7.3 Hz, 1H), 6.18 (t, J = 8.0 Hz, 1H), 5.92 (d, J = 7.3 Hz, 1H), 4.05-4.13 (m, 1H), 3.92-3.98 (m, 1H), 3.46 (t, J = 5.8 Hz, 2H), 3.30 (s, 3H), 3.01 (dd, J = 2.9 Hz, J = 10.2 Hz, 1H), 2.93 (dd, J = 7.3 Hz, J = 13.2 Hz, 1H), 2.70-2.76 (m, 2H), 1.74-1.80 (m, 2H)<br>2. $MH^+$ = 335. |

TABLE 10-continued

| Example | Column 1 | Column 2 | Data<br>1. ¹H NMR or mp (° C.)<br>2. MH⁺ |
|---|---|---|---|
| 90 | 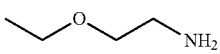 | 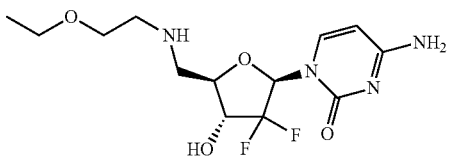 [SMILES: CCOCCNC[C@H]1O[C@@H](n2ccc(N)nc2=O)C(F)(F)[C@@H]1O] | 1. ¹H NMR (CD$_3$OD) δ 7.66 (d, J = 8.0 Hz, 1H), 6.18 (t, J = 8.8 Hz, 1H), 5.92 (d, J = 7.3 Hz, 1H), 4.08-4.17 (m, 1H), 3.94-3.99 (m, 1H), 3.49-3.57 (m, 4H), 2.99-3.11 (m, 2H), 2.85-2.88 (m, 2H), 1.18 (t, J = 7.3 Hz, 3H)<br>2. MH⁺ = 335. |
| 100 | 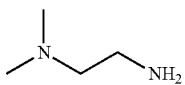 | 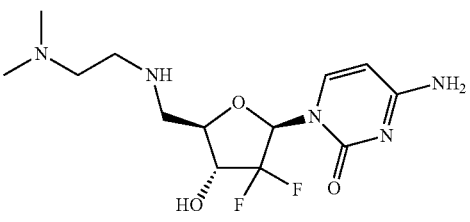 [SMILES: CN(C)CCNC[C@H]1O[C@@H](n2ccc(N)nc2=O)C(F)(F)[C@@H]1O] | 1. ¹H NMR (CD$_3$OD) δ 7.66 (d, J = 7.3 Hz, 1H), 6.18 (t, J = 8.8 Hz, 1H), 5.92 (d, J = 8.0. Hz, 1H), 4.09-4.16 (m, 1H), 3.92-3.97 (m, 1H), 3.05 (dd, J = 3.7 Hz, J = 13.2 Hz, 1H), 2.97 (dd, J = 7.3 Hz, J = 13.2 Hz, 1H), 2.79-2.83 (m, 2H), 2.58 (t, J = 6.6 Hz, 2H), 2.34 (s, 6H)<br>2. MH⁺ = 334. |
| 110 | 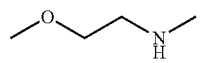 | 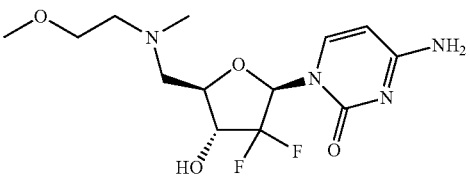 | 1. ¹H NMR (CD$_3$OD) δ 7.76 (d, J = 7.3 Hz, 1H), 6.18 (t, J = 8.0 Hz, 1H), 5.91 (d, J = 8.0. Hz, 1H), 4.07-4.15 (m, 1H), 3.95-3.99 (m, 1H), 3.50-3.53 (m, 2H), 3.33 (s, 3H), 2.85-2.95 (m, 2H), 2.72-2.75 (m, 2H), 2.40 (s, 3H)<br>2. MH⁺ = 335. |
| 120 | 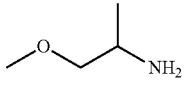 | 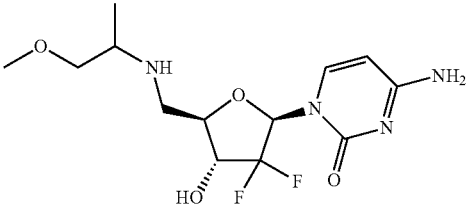 [SMILES: COCC(C)NC[C@H]1O[C@@H](n2ccc(N)nc2=O)C(F)(F)[C@@H]1O] | 1. ¹H NMR (CD$_3$OD) δ 7.68 (d, J = 8.0 Hz, 1H), 6.18 (t, J = 8.0 Hz, 1H), 5.91 (d, J = 8.0. Hz, 1H), 4.08-4.17 (m, 1H), 3.92-3.96 (m, 1H), 3.34-3.39 (m, 4H), 3.23-3.28 (m, 1H), 2.89-3.16 (m, 3H), 1.05 (d, J = 6.6 Hz, 3H)<br>2. MH⁺ = 335. |
| 130 | 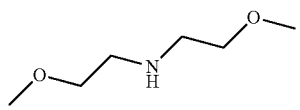 | 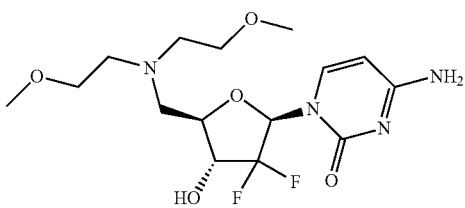 [SMILES: COCCN(CCOC)C[C@H]1O[C@@H](n2ccc(N)nc2=O)C(F)(F)[C@@H]1O] | 1. ¹H NMR (CD$_3$OD) δ 7.88 (d, J = 8.0 Hz, 1H), 6.19 (t, J = 8.0 Hz, 1H), 5.91 (d, J = 7.3. Hz, 1H), 4.21-4.29 (m, 1H), 3.86-3.91 (m, 1H), 3.44-3.54 (m, 4H), 3.31 (s, 6H), 3.05 (dd, J = 2.9 Hz, J = 15.4 Hz, 1H), 2.92 (dd, J = 5.1 Hz, J = 15.4 Hz, 1H), 2.80-2.83 (m, 4H)<br>2. MH⁺ = 379. |

TABLE 10-continued

| Example | Column 1 | Column 2 | Data<br>1. $^1$H NMR or mp (° C.)<br>2. MH$^+$ |
|---|---|---|---|
| 140 | (structure) | (structure) | 1. $^1$H NMR (CD$_3$OD) δ 7.67 (d, J = 7.3 Hz, 1H), 6.19 (t, J = 8.0 Hz, 1H), 5.92 (d, J = 8.0 Hz, 1H), 4.06-4.14 (m, 1H), 3.93-3.98 (m, 1H), 3.65 (t, J = 4.4 Hz 2H), 3.59 (t, J = 5.1 Hz 2H), 3.53 (t, J = 4.4 Hz 2H), 3.05 (dd, J = 2.2 Hz, J = 13.2 Hz, 1H), 2.97 (dd, J = 7.3 Hz, J = 13.2 Hz, 1H), 2.84 (t, J = 5.1 Hz, 2H)<br>2. MH$^+$ = 351. |
| 150 | (structure) | (structure) | 1. $^1$H NMR (CD$_3$OD) δ 7.67 (d, J = 7.3 Hz, 1H), 6.20 (t, J = 8.8 Hz, 1H), 5.92 (d, J = 7.3 Hz, 1H), 4.07-4.15 (m, 1H), 3.93-3.98 (m, 1H), 3.65 (t, J = 5.1 Hz, 4H, 3.05 (dd, J = 3.7 Hz, J = 13.2 Hz, 1H), 2.97 (dd, J = 6.6 Hz, J = 13.2 Hz, 1H), 2.76-2.80 (m, 2H)<br>2. MH$^+$ = 307. |
| 160 | (structure) | (structure) | 1. 200° C.<br>2. 347.2 |
| 170 | (structure) | (structure) | 1. 183-187° C.<br>2. 320.2 |

Preparative Example 180

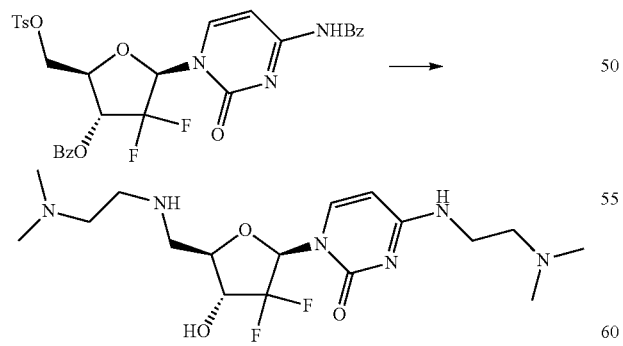

A solution of tosylate from Preparative Example 40 (0.11 g, 0.17 mmol) and N,N-dimethylethylenediamine (0.38 mL, 20 equiv.), in a sealed tube, was heated at 100° C. for 12 h. The solution was cooled to room temperature and concentrated under reduced pressure. The residue was purified using silica gel chromatography in 10% 7N NH$_3$ in MeOH solution in CH$_2$Cl$_2$. A white solid (0.010 g, 14.2%) was obtained. $^1$H NMR (CD$_3$OD) δ 7.58 (d, J=7.3 Hz, 1H), 6.18 (t, J=8.7 Hz, 1H), 5.88 (d, J=8.0 Hz, 1H), 4.07-4.15 (m, 1H), 3.92-3.98 (m, 1H), 3.50-3.55 (m, 2H), 3.31 (s, 6H), 3.04 (dd, J=3.7 Hz, J=13.2 Hz, 1H), 2.95 (dd, J=7.3 Hz, J=13.2 Hz, 1H), 2.77-2.81 (m, 2H), 2.50-2.58 (m, 4H), 2.29-2.30 (m, 12H); MH$^+$=405. Further elution provided Example 100 in Table XX.

Preparative Example 190

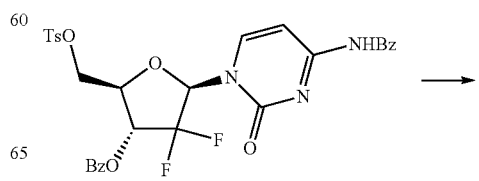

187

-continued

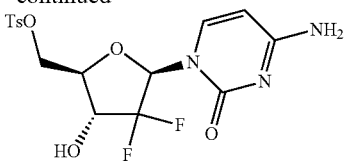

A solution of tosylate from Preparative Example 40 (2.06 g, 3.29 mmol) in 7N NH$_3$ in MeOH solution (100 mL) was stirred at 25° C. for 2 h. The solution was concentrated and the residue was purified using silica gel chromatography with a gradient 10-30% MeOH in CH$_2$Cl$_2$. A white solid (0.80 g, 58%) was obtained. Further elution with a 30-80% gradient of MeOH in CH$_2$Cl$_2$ provided Gemcitabine.

Example 200

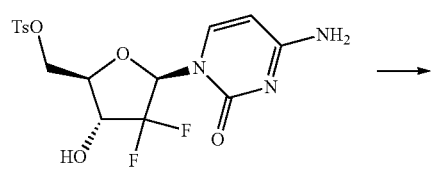

188

-continued

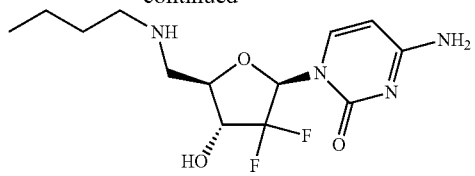

A solution of tosylate from Preparative Example 190 (0.250 g, 0.599 mmol), n-butylamine (1.78 mL, 30 equiv.) was heated at 40° C. in a sealed 1-dram vial for 20 h. The solution was cooled to 25° C. and concentrated. The residue was purified by preparative chromatography using 20% 7N NH$_3$ in MeOH/CH$_2$Cl$_2$ as eluent. A white solid (0.160 g, 83.9%) was obtained. $^1$H NMR (CD$_3$OD) δ 7.66 (d, J=7.3 Hz, 1H), 6.16 (t, J=8.0 Hz, 1H), 5.91 (d, J=7.3 Hz, 1H), 4.07-4.15 (m, 1H), 3.94-3.98 (m, 1H), 2.95-3.07 (m, 2H), 2.68 (t, J=7.3 Hz, 2H), 1.48-1.55 (m, 2H), 1.32-1.41 (m, 2H), 0.94 (t, J=7.3 Hz, 3H); MH$^+$=319.

Examples 210-350

Following the procedure set forth in Example 200, either with or without DMF as solvent, only using different nucleophiles given in Column 1 of Table 20, compounds given in Column 2 of Table 20 were prepared.

TABLE 20

| Example | Column 1 | Column 2 | Data<br>1. $^1$H NMR or mp (° C.)<br>2. MH$^+$ |
|---|---|---|---|
| 210 | ![neopentylamine] | ![product 210] | 1. $^1$H NMR (CD$_3$OD) δ 7.65 (d, J = 7.3 Hz, 1H), 6.15 (t, J = 8.0 Hz, 1H), 5.92 (d, J = 7.3 Hz, 1H), 4.12-4.20 (m, 1H), 3.96-4.00 (m, 1H), 3.03-3.12 (m, 2H), 2.72-2.76 (m, 2H), 1.45-1.49 (m, 2H), 0.93 (s, 9H)<br>2. MH$^+$ = 347. |
| 220 | ![propylamine] | ![product 220] | 1. $^1$H NMR (CD$_3$OD) δ 7.69 (d, J = 7.3 Hz, 1H), 6.19 (t, J = 8.8 Hz, 1H), 5.94 (d, J = 7.3 Hz, 1H), 4.11-4.19 (m, 1H), 3.97-4.02 (m, 1H), 2.99-3.10 (m, 2H), 2.68 (t, J = 7.3 Hz, 2H), 1.54-1.63 (m, 2H), 0.97 (t, J = 7.3 Hz, 3H)<br>2. MH$^+$ = 305. |
| 230 | ![isoamylamine] | ![product 230] | 1. $^1$H NMR (CD$_3$OD) δ 7.68 (d, J = 7.3 Hz, 1H), 6.16 (t, J = 8.8 Hz, 1H), 5.92-5.99 (m, 1H), 4.18-4.26 (m, 1H), 4.00-4.05 (m, 1H), 3.09-3.18 (m, 2H), 3.09-3.18 (m, 2H), 2.78-2.83 (m, 2H), 1.62-1.72 (m, 1H), 1.46-1.52 (m, 2H), 0.96 (d, J = 6.6 Hz, 6H)<br>2. MH$^+$ = 333. |

TABLE 20-continued
| Example | Column 1 | Column 2 | Data<br>1. $^1$H NMR or mp (° C.)<br>2. MH$^+$ |
|---|---|---|---|
| 240 | 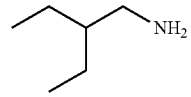 | 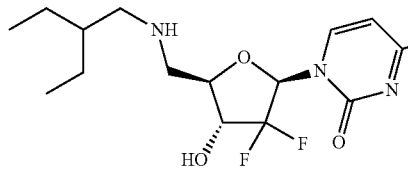 | 1. $^1$H NMR (CD$_3$OD) δ 7.73 (d, J= 7.3 Hz, 1H), 6.20 (t, J = 8.8 Hz, 1H), 5.94 (d, J = 7.3 Hz, 1H), 4.12-4.20 (m, 1H), 3.97-4.02 (m, 1H), 3.08 (dd, J = 2.9 Hz, J = 13.0 Hz, 1H), 2.99 (dd, J = 6.6 Hz, J = 13.2 Hz, 1H), 2.58-2.67 (m, 2H), 1.34-1.48 (m, 5H), 0.92 (t, J = 7.3 Hz, 6H)<br>2. MH$^+$ = 347. |
| 250 | 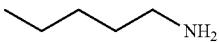 | 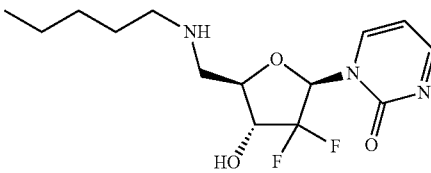 | 1. $^1$H NMR (CD$_3$OD) δ 7.68 (d, J = 7.3 Hz, 1H), 6.17 (t, J = 8.0 Hz, 1H), 5.94 (d, J = 7.3 Hz, 1H), 4.15-4.23 (m, 1H), 3.99-4.04 (m, 1H), 3.05-3.15 (m, 2H), 2.74-2.77 (m, 2H), 1.55-1.63 (m, 2H), 1.31-1.42 (m, 4H), 0.95 (t, J = 6.6 Hz, 3H)<br>2. MH$^+$ = 333. |
| 260 | 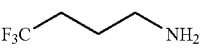 | 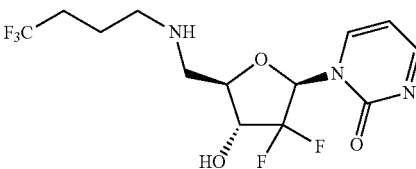 | 1. $^1$H NMR (CD$_3$OD) δ 7.69 (d, J = 8.0 Hz, 1H), 6.19 (t, J = 8.0 Hz, 1H), 5.94 (d, J = 8.0 Hz, 1H), 4.14-4.22 (m, 1H), 3.96-4.01 (m, 1H), 3.00-3.13 (m, 2H), 2.77-2.81 (m, 2H), 2.19-2.32 (m, 2H), 1.76-1.84 (m, 2H)<br>2. MH$^+$ = 373. |
| 270 | 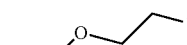 | 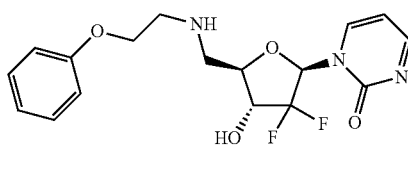 | 1. 140-142° C.<br>2. 383.3 |
| 280 |  | 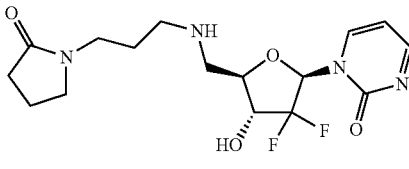 | 1. 53-57° C.<br>2. 388.2 |
| 290 |  | 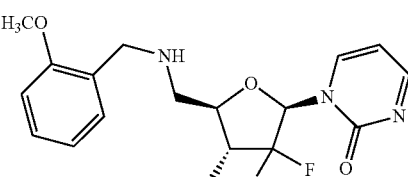 | 1. 98-100° C.<br>2. 383.2 |
| 300 | 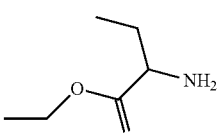 | 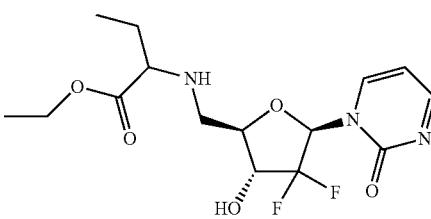 | 1. 64-66° C.<br>2. 377.2 |

TABLE 20-continued

| Example | Column 1 | Column 2 | Data<br>1. ¹H NMR or mp (° C.)<br>2. MH⁺ |
|---|---|---|---|
| 310 | | | 1. 124-126° C.<br>2. 347.2 |
| 320 | | | 1. 84-86° C.<br>2. 374.2 |
| 330 | | | 1. 149-150° C.<br>2. 317.2 |
| 340 | | | 1. 111-114° C.<br>2. 359.2 |
| 350 | | | 1. 96-98° C.<br>2. 303.1 |

Example 360

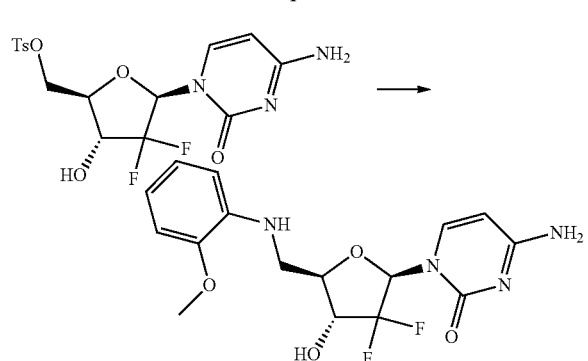

A solution of tosylate from Preparative Example 190 (0.050 g, 0.120 mmol), 2-methoxyaniline (0.27 mL, 20 equiv.) was heated at 90° C. in a sealed 1-dram vial for 10 h. The solution was cooled to 25°. The residue was purified by preparative chromatography using 10% MeOH in CH₂Cl₂ as eluent. A solid (0.006 g, 13.4%) was obtained. ¹H NMR (CD₃OD) δ 7.59 (d, J=8.0 Hz, 1H), 6.75-6.84 (m, 4H), 6.64-6.67 (m, 1H), 6.17 (t, J=8.0 Hz, 1H), 5.81 (d, J=7.3 Hz, 1H), 4.13-4.21 (m, 1H), 4.04-4.19 (m, 1H), 3.86 (s, 3H), 3.68 (dd, J=2.9 Hz, J=14.6 Hz, 1H), 3.52 (dd, J=4.4 Hz, J=15.4 Hz, 1H); MH⁺=369.

Examples 370

Following the procedure set forth in Example 360, only using the nucleophile given in Column 1 of Table 30, compounds given in Column 2 of Table 30 were prepared.

TABLE 30

| Example | Column 1 | Column 2 | Data |
|---------|----------|----------|------|
| 370 | 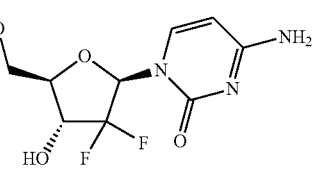 | | $^1$H NMR (CD$_3$OD) δ 7.99 (d, J = 8.0 Hz, 1H), 6.23 (t, J = 7.3 Hz, 1H), 5.93 (d, J = 8.0 Hz, 1H), 4.29-4.37 (m, 1H), 3.99-4.01 (m, 1H), 3.89-3.92 (m, 1H), 3.68-3.80 (m, 3H), 3.57-3.64 (m, 2H), 3.42 (s, 3H); MH$^+$ = 322. |

Preparative Example 380

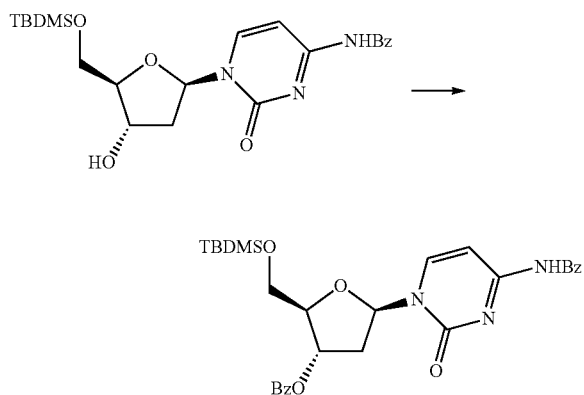

A solution of the starting material (2.00 g, 4.50 mmol) in anhydrous pyridine (15 mL) at 25° C. was treated successively with benzoyl chloride (1.90 g, 13.5 mmol) and DMAP (0.41 g, 3.37 mmol). The mixture was stirred at 25° C. for 20 h, poured into saturated aqueous NaHCO$_3$ (100 mL), and extracted with CH$_2$Cl$_2$ (3×30 mL). The combined extracts were dried over Na$_2$SO$_4$, filtered and the solvent was evaporated. The residue was purified by chromatography on silica gel with 3:1 CH$_2$Cl$_2$/EtOAc as eluent. 1.64 g (67%) of the product was obtained as white solid. MH$^+$=550.

Preparative Example 390

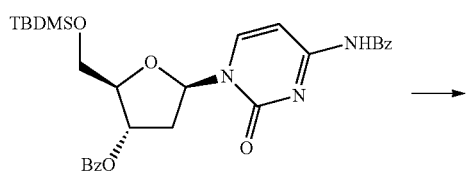

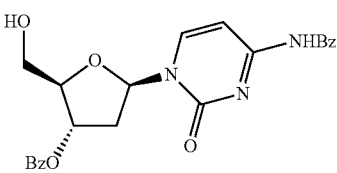

Acetic acid (1.20 g, 20.0 mmol) was added to a stirred mixture of the product from Preparative Example 1000 (1.60 g, 2.91 mmol) and tetrabutylammonium fluoride (1.0 M in THF, 11.4 mL). The mixture was stirred at 25° C. for 1.5 hr, the solvents were evaporated and the residue was purified by chromatography on silica gel with 25:1 CH$_2$Cl$_2$/MeOH as eluent. 120 g (95%) of the product was obtained as white solid. MH$^+$=436.

Preparative Example 400

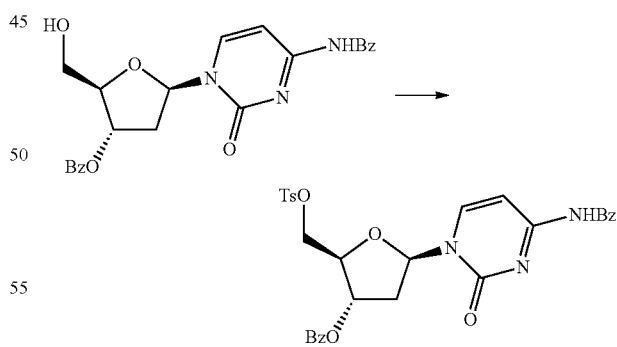

Triethylamine (255 mg, 2.53 mmol) was added to a solution of the product from Preparative Example 1010 (500 mg, 1.15 mmol) and TsCl (877 mg, 4.60 mmol) in anhydrous pyridine (10 mL) at 25° C. The mixture was stirred at 25° C. for 24 h, poured into saturated aqueous NaHCO$_3$ (150 mL), and extracted with CH$_2$Cl$_2$ (2×30 mL). The combined extracts were dried over Na$_2$SO$_4$, filtered and the solvent was evaporated. The residue was purified by chromatography on

Preparative Example 410

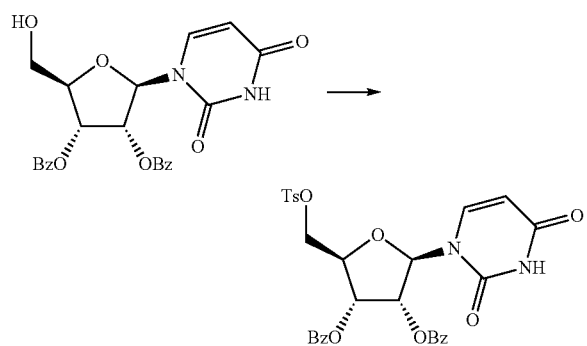

A solution of the starting material (452 mg, 1.00 mmol) and TsCl (200 mg, 1.05 mmol) in anhydrous pyridine (6 mL) was stirred at 25° C. for 24 h. The mixture was poured into saturated aqueous NaHCO$_3$ (100 mL) and extracted with CH$_2$Cl$_2$ (3×20 mL). The combined extracts were dried over Na$_2$SO$_4$, filtered and the solvent was evaporated. The residue was purified by chromatography on silica gel with 3:1 CH$_2$Cl$_2$/EtOAc as eluent. 350 mg (58%) of the product was obtained as slightly orange solid. MH$^+$=607.

Preparative Example 420A and 420B

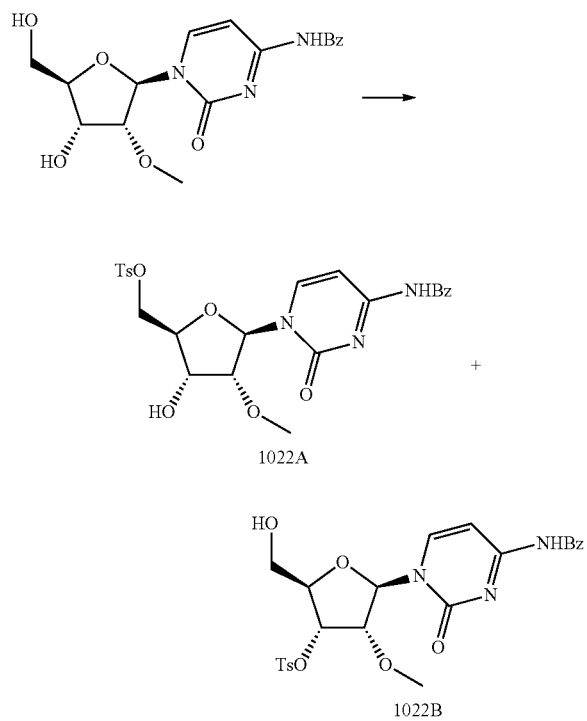

By essentially same procedure set forth in Preparative Example 1021 the title compounds were prepared and separated by chromatography on silica gel with 20:1 CH$_2$Cl$_2$/MeOH as eluent. The desired more polar product 1022A was isolated as colorless solid. MH$^+$=516.

Preparative Example 430

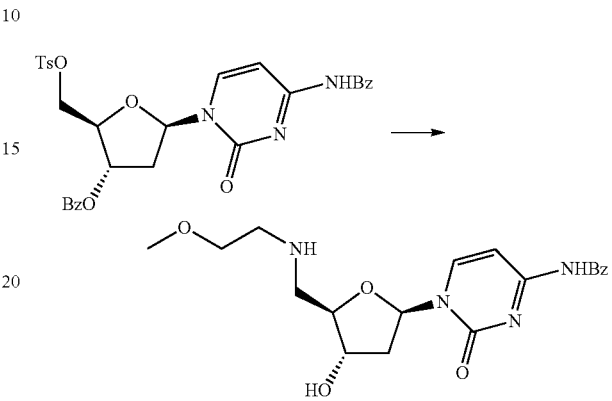

A solution of the product from Preparative Example 1020 (160 mg, 0.27 mmol) and 2-methoxyethylamine (0.20 mL, 2.24 mmol) in anhydrous DMF (1.0 mL) was stirred in a closed flask at 25° C. for 72 hr. The solvent was evaporated and the residue was purified by chromatography on silica gel with 4:1 CH$_2$Cl$_2$/MeOH as eluent. 62 mg (59%) of the product was obtained as white solid. MH$^+$=389.

Preparative Example 440

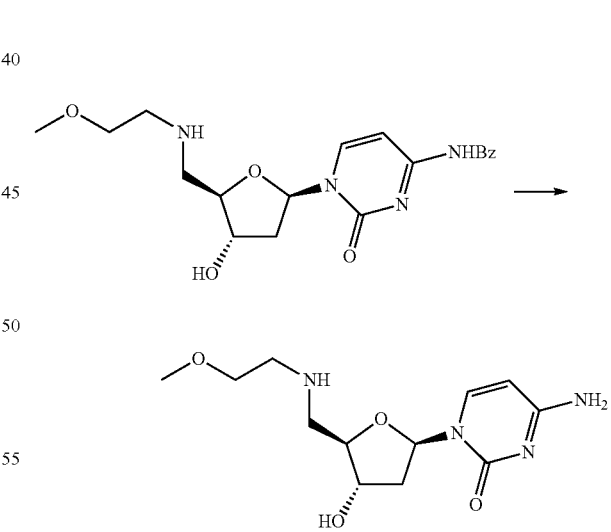

A solution of the product from Preparative Example 1030 (30 mg, 0.077 mmol), 7N NH$_3$ in MeOH (1.0 mL) and dioxane (0.3 mL) was stirred an a closed pressure vessel at 25° C. for 20 hr. The solvents were evaporated and the residue was purified by chromatography on silica gel with 3:1 CH$_2$Cl$_2$/MeOH as eluent. 6 mg (27%) of the product was obtained as colorless solid. MH$^+$=285.

Preparative Example 450

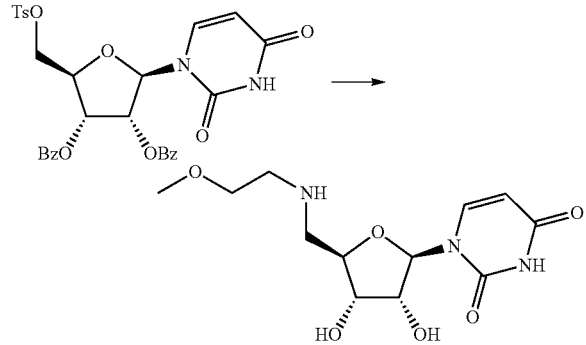

A solution of the product from Preparative Example 1021 (100 mg, 0.165 mmol) and 2-methoxyethylamine (0.20 mL, 2.24 mmol) in anhydrous DMF (0.6 mL) was stirred in a closed flask at 25° C. for 24 hr. The solvent was evaporated and the residue was purified by chromatography on silica gel with 4:1 $CH_2Cl_2$/MeOH as eluent. 8 mg (16%) of the product was obtained as colorless solid. $MH^+$=302.

Preparative Example 460

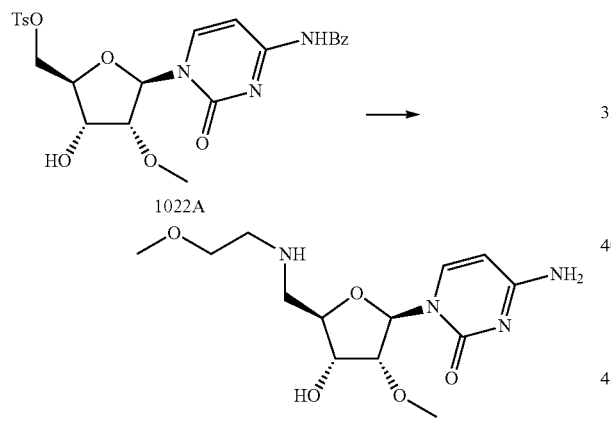

A solution of the product from Preparative Example 1022A (27 mg, 0.066 mmol) and 2-methoxyethylamine (0.10 mL, 1.12 mmol) in anhydrous DMF (0.5 mL) was stirred in a closed flask at 25° C. for 72 hr. The solvent was evaporated and the residue was purified by chromatography on silica gel with 8:1 $CH_2Cl_2$/7N $NH_3$ in MeOH as eluent. 11 mg (53%) of the product was obtained as colorless solid. $MH^+$=315.

Preparative Example 470

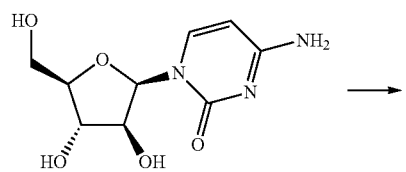

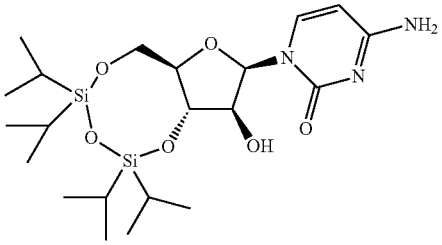

1,3-dichloro-1,1,3,3-tetraisopropyl-disiloxane (1.70 mL, 5.50 mmol) was added to a solution of the starting material (1.22 g, 5.00 mmol) in anhydrous pyridine (20 mL) at 25° C. The mixture was stirred at 25° C. for 2 h, evaporated and the residue was partitioned between $H_2O$ (100 mL) and $CH_2Cl_2$ (50 mL). The aqueous part was extracted with $CH_2Cl_2$ (2×50 mL) and the combined extracts were dried over $MgSO_4$, filtered, the solvent was evaporated and then $PhCH_3$ (2×100 mL) was added to the residue and it was evaporated. The residue was purified by chromatography on silica gel with 15:1 $CH_2Cl_2$/MeOH as eluent. 1.70 g (70%) of the product was obtained as white solid. $MH^+$=486.

Preparative Example 480

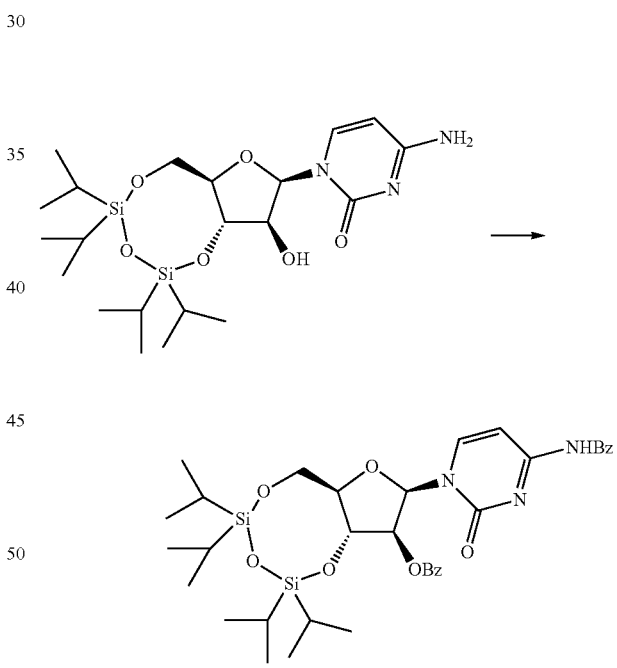

A solution of the product from Preparative Example 1050 (1.60 g, 3.30 mmol) in anhydrous pyridine (10 mL) at 25° C. was treated with benzoyl chloride (1.16 g, 8.25 mmol). The mixture was stirred at 25° C. for 20 h, poured into saturated aqueous $NaHCO_3$ (100 mL), and extracted with $CH_2Cl_2$ (3×30 mL). The combined extracts were dried over $MgSO_4$, filtered and the solvent was evaporated. The residue was purified by chromatography on silica gel with 2:1 $CH_2Cl_2$/EtOAc as eluent. 2.08 g (91%) of the product was obtained as white solid. $MH^+$=694.

Preparative Example 490

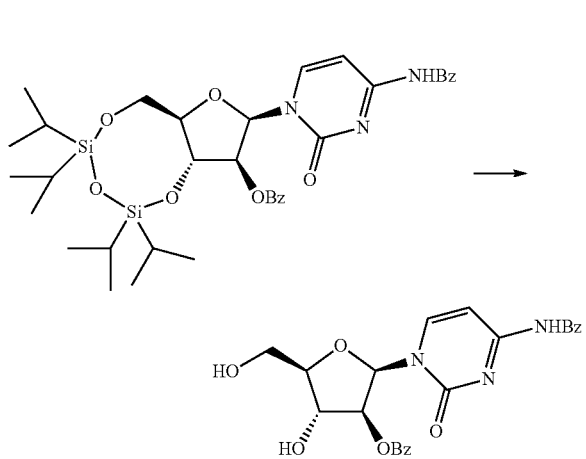

A mixture of the product from Preparative Example 1051 (0.50 g, 0.72 mmol) and tetrabutylammonium fluoride (1.0 M in THF, 3.0 mL) was stirred at 25° C. for 1.5 hr, the solvents were evaporated and the residue was purified by chromatography on silica gel with 20:1 $CH_2Cl_2$/MeOH as eluent. Quantitative yield of the product (white solid) was obtained. $MH^+=452$.

Preparative Example 500

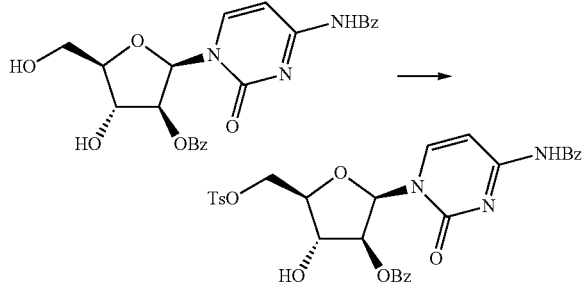

A solution of the product from Preparative Example 1052 (350 mg, 0.77 mmol) and TsCl (152 mg, 0.80 mmol) in anhydrous pyridine (5 mL) was stirred at 25° C. for 48 h. The solvent was evaporated and the residue was purified by chromatography on silica gel with 40:1 $CH_2Cl_2$/MeOH as eluent. 190 mg (41%) of the product was obtained as white solid. $MH^+=606$.

Preparative Example 510

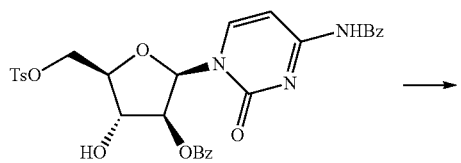

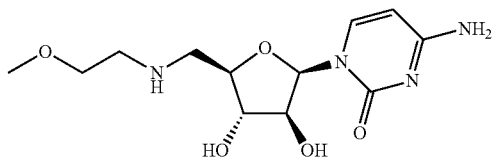

A solution of the product from Preparative Example 1053 (100 mg, 0.17 mmol) and 2-methoxyethylamine (0.15 mL, 1.68 mmol) in anhydrous DMF (0.5 mL) was stirred in a closed flask at 25° C. for 72 hr. The solvent was evaporated and the residue was purified by chromatography on silica gel with 4:1 $CH_2Cl_2$/7N $NH_3$ in MeOH as eluent. 12 mg (24%) of the product was obtained as white solid. $MH^+=301$.

Preparative Example 520

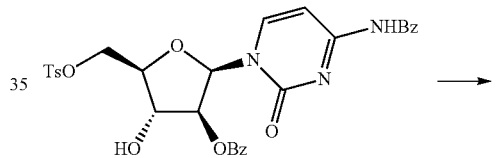

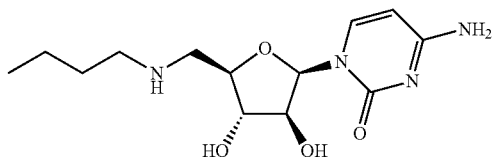

A solution of the product from Preparative Example 1053 (40 mg, 0.066 mmol) and n-butylamine (0.10 mL) in anhydrous DMF (0.2 mL) was stirred in a closed flask at 25° C. for 72 hr, then additional n-butylamine (0.10 mL) was added and the mixture was stirred in a closed flask at 25° C. for additional 24 hr. The solvent was evaporated and the residue was purified by chromatography on silica gel with 4:1 $CH_2Cl_2$/7N $NH_3$ in MeOH as eluent. 11 mg (56° A)) of the product was obtained as white solid. $MH^+=299$.

The following compounds were prepared as described below or in a similar manner thereto:

| Compound No. | Structure | NMR Data<br>¹H NMR (400 MHz, CD₃OD) δ (ppm) |
|---|---|---|
| 600 | 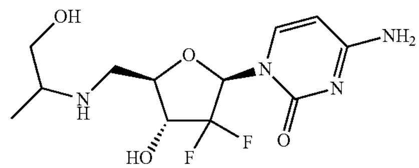 [SMILES: CC(CO)NC[C@H]1O[C@@H](n2ccc(N)nc2=O)C(F)(F)[C@@H]1O] | 7.70 (dd, J = 2.4 Hz, 1.6 Hz, 1H), 6.21 (t, J = 8.4 Hz, 1H), 5.93 (d, J = 7.6 Hz, 1H), 4.12 (m, 1H), 3.96 (m, 1H) 3.53 (m, 1H), 3.38 (m, 1H), 3.07 (m, 1H), 2.85 (m, 1H), 1.05 (d, J = 5.2 Hz, 3H). |
| 601 | 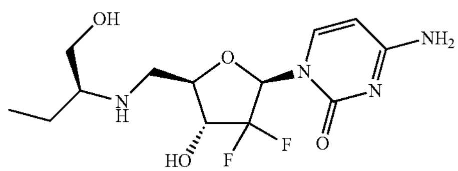 [SMILES: CC[C@@H](CO)NC[C@H]1O[C@@H](n2ccc(N)nc2=O)C(F)(F)[C@@H]1O] | 7.72 (t, J = 7.2 Hz, 1H), 6.21 (t, J = 8.4 Hz, 1H), 5.93 (d, J = 8.0 Hz, 1H), 4.15 (m, 1H), 3.96 (m, 1H), 3.95 (m, 1H), 3.63 (m, 1H), 3.42 (m, 1H), 3.09 (m, 1H), 2.96 (m, 1H), 2.57 (m, 1H), 1.52 (m, 1H), 1.44 (m, 1H), 0.94 (td, J = 7.2 Hz, 2.0 Hz, 3H). |
| 602 | 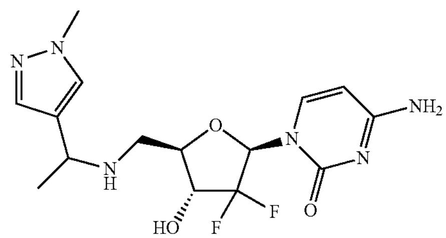 [SMILES: CC(NC[C@H]1O[C@@H](n2ccc(N)nc2=O)C(F)(F)[C@@H]1O)c1cnn(C)c1] | 7.63 (dd, J = 7.6 Hz, 24.8 Hz, 1H), 7.50 (dd, J = 6.8 Hz, 34.8 Hz, 1H), 6.17 (m, 1H), 5.91 (d, J = 6.0 Hz, 1H), 4.10 (m, 1H), 3.93 (m, 1H), 3.86 (s, 3H), 3.95 (m, 1H), 1.41 (dd, J = 1.2 Hz, 6.8 Hz 3H). |
| 603 | 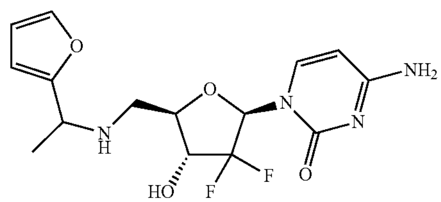 [SMILES: CC(NC[C@H]1O[C@@H](n2ccc(N)nc2=O)C(F)(F)[C@@H]1O)c1ccco1] | 7.84 (dd, J = 7.6 Hz, 16.0 Hz, 1H), 7.65 (s, 1H), 6.66 (dd, J = 3.2 Hz, 8.4 Hz, 1H), 6.52 (m, 1H), 6.11 (t, J = 7.6 Hz, 1H), 4.68 (m, 1H), 4.33 (m, 1H), 3.42 (m, 1H), 4.13 (m, 1H), 3.36 (m, 1H), 1.71 dd, J = 2.0 Hz, 6.8 Hz, 3H). |
| 604 | 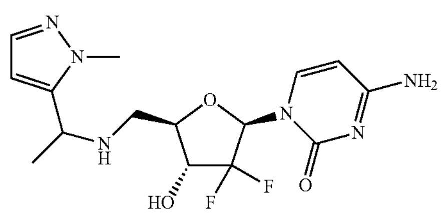 [SMILES: CC(NC[C@H]1O[C@@H](n2ccc(N)nc2=O)C(F)(F)[C@@H]1O)c1ccnn1C] | 7.62 (dd, J = 7.2 Hz, 18.0 Hz, 1H), 7.39 (t, J = 1.6 Hz, 1H), 6.26 (d, J = 2.0 Hz, 1H), 6.18 (td, J = 3.2 Hz, 8.0 Hz, 1H), 5.88 (dd, J = 7.2 Hz, 15.6 Hz, 1H), 4.10 (m, 2H), 3.91 (m, 1H), 3.85 (d, J = 16.4 Hz, 3H), 2.97 (m, 1H), 2.85 (m, 1H), 1.42 (t, J = 5.6 Hz, 3H). |
| 605 | 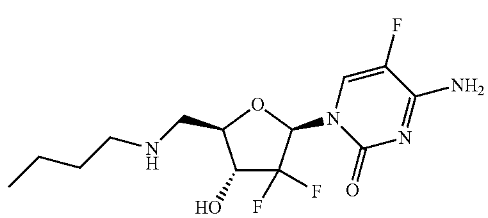 [SMILES: CCCCNC[C@H]1O[C@@H](n2cc(F)c(N)nc2=O)C(F)(F)[C@@H]1O] | 7.85 (d, J = 6.4 Hz, 1H), 6.07 (m, 1H), 4.37 (m, 1H), 4.14 (m, 1H), 3.49 (m, 2H), 3.13 (m, 1H), 3.08 (t, J = 7.6 Hz, 1H), 1.69 (m, 2H), 1.44 (m, 2H), 1.00 (t, J = 7.2 Hz, 3H). |
| 606 | 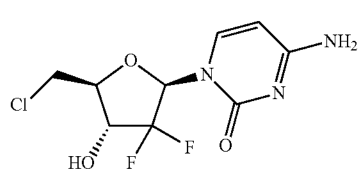 [SMILES: Nc1ccn([C@@H]2O[C@H](CCl)[C@@H](O)C2(F)F)c(=O)n1] | 7.51 (d, J = 7.2 Hz, 1H), 7.44 (d, J = 9.6 Hz, 2H), 6.48 (d, J = 6.4 Hz, 1H), 6.19 (t, J = 2 Hz, 1H), 5.81 (d, J = 7.2 Hz, 1H), 4.05 (m, 1H), 4.03-3.92 (m, 3H). |

| Compound No. | Structure | NMR Data $^1$H NMR (400 MHz, CD$_3$OD) δ (ppm) |
|---|---|---|
| 713 | 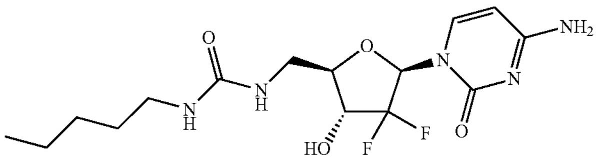 [SMILES: CCCCCNC(=O)NC[C@H]1O[C@@H](n2ccc(N)nc2=O)C(F)(F)[C@@H]1O] | 7.60 (d, J = 7.4 Hz, 1H), 6.17 (t, J = 9.0 Hz, 1H), 5.92 (d, J = 7.4 Hz, 1H), 4.08 (m, 1H), 3.90 (m, 1H), 3.57 (dd, J = 14.2, 4.1 Hz, 1H), 3.52 (dd, J = 14.2, 6.1 Hz, 1H), 3.11 (t, J = 6.9 Hz, 2H), 1.47 (m, 2H), 1.32 (m, 4H), 0.91 (t, J = 7.0 Hz, 3H). |
| 714 | 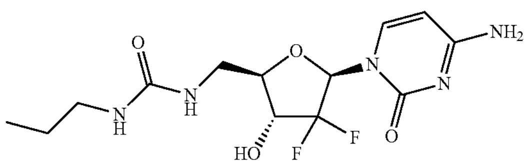 [SMILES: CCCNC(=O)NC[C@H]1O[C@@H](n2ccc(N)nc2=O)C(F)(F)[C@@H]1O] | 7.60 (d, J = 7.4 Hz, 1H), 6.17 (t, J = 9.0 Hz, 1H), 5.92 (d, J = 7.4 Hz, 1H), 4.07 (m, 1H), 3.89 (m, 1H), 3.58 (dd, J = 14.5, 3.6 Hz, 1H), 3.51 (dd, J = 14.5, 5.7 Hz, 1H), 3.08 (t, J = 6.7 Hz, 2H), 1.48 (m, 2H), 0.91 (t, J = 7.3 Hz, 3H). |
| 715 | 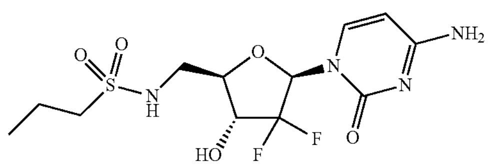 [SMILES: CCCS(=O)(=O)NC[C@H]1O[C@@H](n2ccc(N)nc2=O)C(F)(F)[C@@H]1O] | 7.70 (d, J = 7.7 Hz, 1H), 6.22 (t, J = 8.5 Hz, 1H), 5.92 (d, J = 7.7 Hz, 1H), 4.19 (m, 1H), 3.91 (m, 1H), 3.51 (dd, J = 14.7, 3.6 Hz, 1H), 3.42 (dd, J = 14.7, 5.1 Hz, 1H), 3.06 (m, 2H), 1.81 (m, 2H), 1.05 (t, J = 7.3 Hz, 3H). |

Example 600

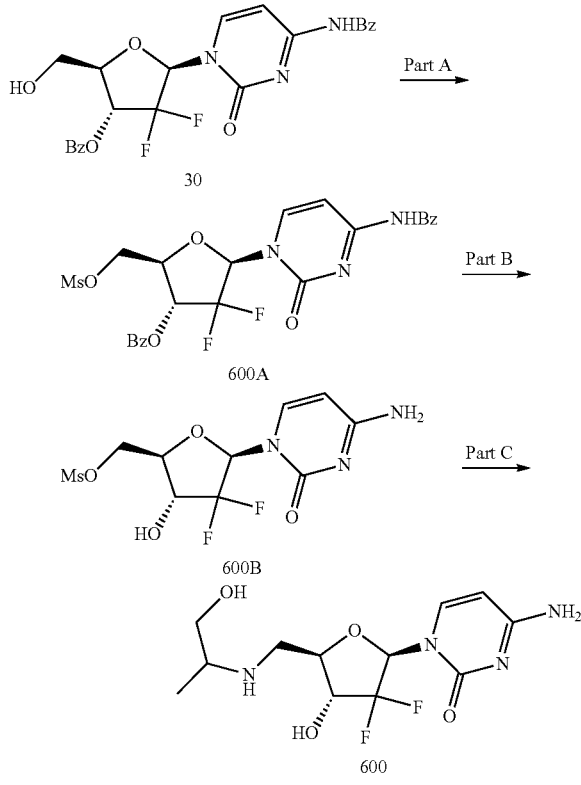

Part A:

Into a round-bottom flask was added compound 30 (0.78 g, 1.65 mmol), pyridine (30 mL) and triethylamine (1.2 mL, 8.25 mmol) followed by addition of methanesulfonyl chloride (0.26 mL, 3.3 mmol) under argon atmosphere. The reaction mixture was stirred at rt for 2 h and concentrated. The residue was diluted with dichloromethane (3×30 mL) and 1 N HCl (10 mL), and the separated aqueous layer was extracted with DCM (3×30 mL). The combined organic layers were washed with satd. aqueous NaHCO$_3$ solution (2×20 mL), brine (2×30 mL), dried over Na$_2$SO$_4$, filtered and concentrated. The residue was purified by column chromatography (SO$_2$, 10% methanol/DCM) to afford 600A (0.86 g; 95%) as a white solid. HPLC-MS $t_R$=2.12 min (UV$_{254\,nm}$); mass calculated for formula C$_{24}$H$_{21}$F$_2$N$_3$O$_8$S 549.10, observed LCMS m/z 550.0 (M+H).

Part B:

Into a sealed pressure bottle was added compound 600A (0.86 g, 1.57 mmol) and 7 M ammonia in methanol (54 mL). The heterogeneous mixture became clear 30 min later, and was kept stirring at rt for 2 h. The solution was concentrated and purified by column chromatography (SO$_2$, 25% methanol/DCM) to afford 600B (0.52 g; 96%) as a white solid; HPLC-MS $t_R$=0.22 min (UV$_{254\,nm}$); mass calculated for formula C$_{10}$H$_{13}$F$_2$N$_3$O$_6$S 341.05, observed LCMS m/z 342.1 (M+H).

Part C;

Compound 600B (0.1 g, 0.29 mmol) in DMF (0.2 mL) was treated with 2-amino-propanol (0.57 mL, 7.32 mmol) in a 4 ml vial, and was heated to 60° C. overnight. The mixture was concentrated and purified by column chromatography (RediSep amine column, 15% methanol/DCM), followed by lyophilization to afford 600 (53.5 mg; 57%) as a white solid; HPLC-MS $t_R$=0.71 min (UV$_{254\,nm}$, 10 min); mass calculated for formula C$_{12}$H$_{18}$F$_2$N$_4$O$_4$ 320.13, observed LCMS m/z 321.1 (M+H). Compound 600: $^1$H NMR (400 MHz, CD$_3$OD) δ 7.70 (dd, J=2.4 Hz, 1.6 Hz, 1H), 6.21 (t, J=8.4 Hz, 1H), 5.93

(d, J=7.6 Hz, 1H), 4.12 (m, 1H), 3.96 (m, 1H), 3.53 (m, 1H), 3.38 (m, 1H), 3.07 (m, 1H), 2.85 (m, 1H), 1.05 (d, J=5.2 Hz, 3H).

Example 605

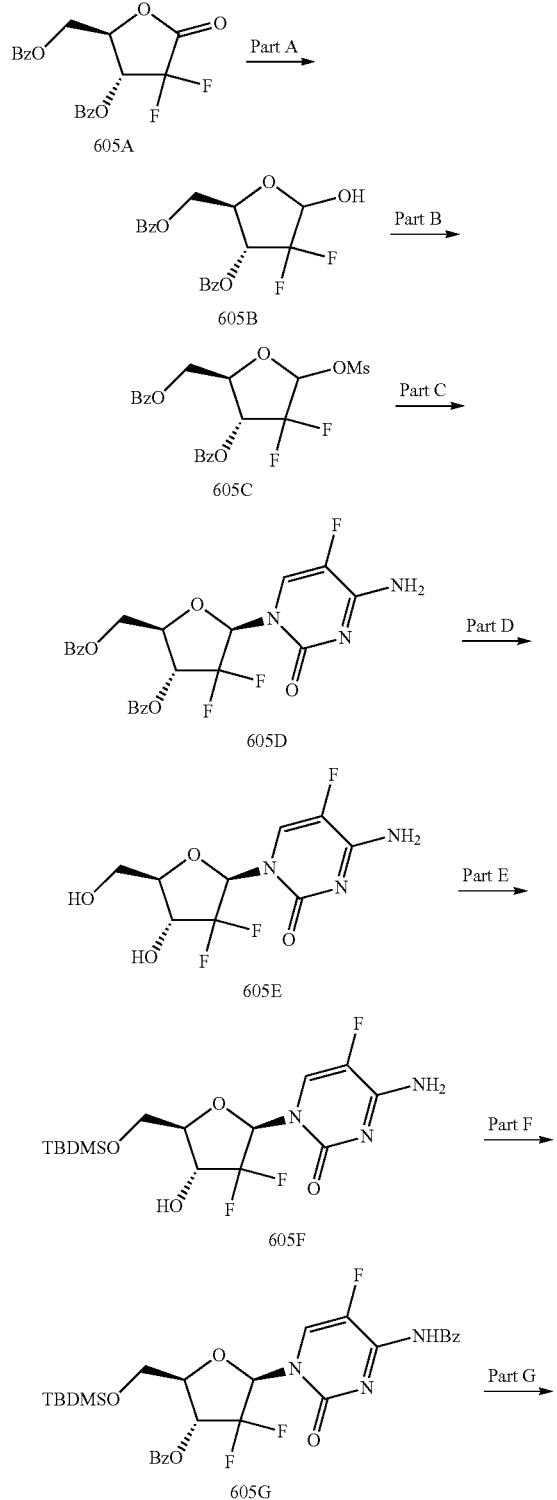

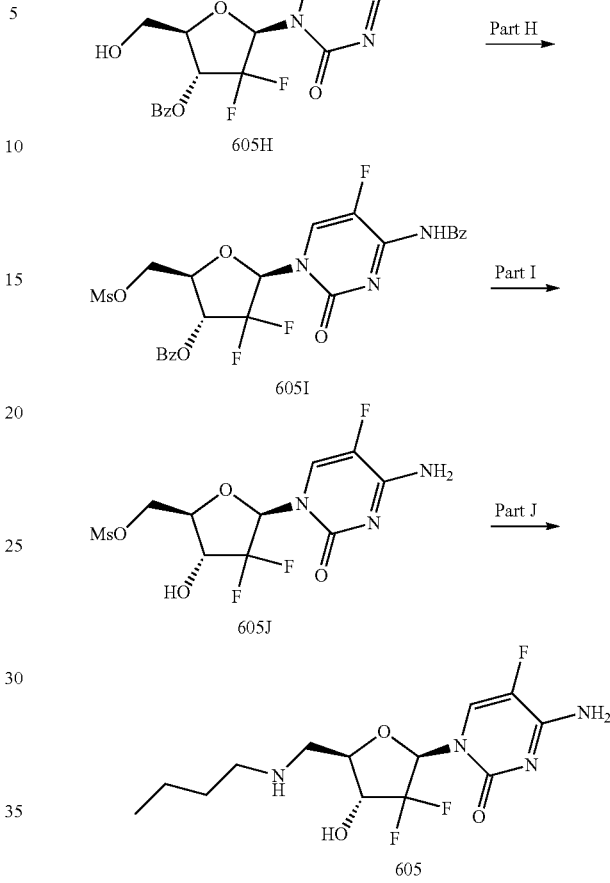

Part A:

According to a modification of a literature procedure (Chou. T. S, et al. *Synthesis* 1992, 565) a solution of lactone 605A (10.0 g, 26.6 mmol) in dry diethylether (80 mL) and dry THF (30 under argon atmosphere, was stirred at rt for 10 min. Then lithium tri-tert-butoxy aluminum hydride (8.25 g, 32.4 mmol) was added in 3 portions. The mixture was stirred at rt for 1 h and then quenched with methanol (20 mL) slowly, followed by 1N HCl solution (100 mL). The aqueous layer was separated, extracted with DCM (3×50 mL), and the combined organic layers were washed with satd. NaHCO$_3$ solution (50 mL) and brine (2×50 mL), dried over Na$_2$SO$_4$, filtered and concentrated. The residue was purified by column chromatography (SiO$_2$, 30% ethyl acetate/hexanes) to afford 605B (7.64 g; 76%) as an oil. HPLC-MS $t_R$=1.92 min (UV$_{254\,nm}$); mass calculated for formula C$_{19}$H$_{16}$F$_2$O$_6$ 378.09, observed LCMS m/z 401.0 (M+Na) and 361.0 (M−OH, oxonium ion).

Part B:

Into a round-bottom flask was added lactol 605B (5.10 g, 13.5 mmol), anhydrous DCM (30 mL) and triethylamine (2.63 mL, 18.9 mmol) followed by methanesulfonyl chloride (1.25 mL, 16.2 mmol) under argon atmosphere. After stirring at rt for 2 h, the reaction mixture was washed with 1 N HCl solution (20 mL), satd. NaHCO$_3$ solution (20 mL) and brine (2×30 mL). The solution was dried over Na$_2$SO$_4$, filtered and concentrated to afford 605C (5.84 g; 95%) as a yellow oil, which was used without further purification; HPLC-MS $t_R$=2.12 min (UV$_{254\ nm}$); mass calculated for formula C$_{20}$H$_{18}$F$_2$O$_8$S 456.07, observed LCMS m/z 479.0 (M+Na).

Part C:

According to a modification of a literature procedure (Kotra, L. P, et al. *J. Med. Chem.*, 1997, 40, 3635) 5-fluorocytosine (1.42 g, 10.9 mmol) was treated with excess hexamethyldisilazane (35 mL, 167.8 mmol) in the presence of ammonium sulfate (50 mg) under argon and refluxed at 125° C. for 4 h. The reaction mixture was concentrated to remove excess solvent, and the resulting residue was dissolved in dry DCE (20 mL). A solution of compound 605C (2.50 g, 5.48 mmol) in DCE (20 mL) was added, and the reaction mixture was stirred for 10 min under argon. Then trimethylsilyl trifluoromethanesulfonate (1.98 mL, 10.9 mmol) was added to the mixture slowly, and the reaction was heated at 90-100° C. under argon overnight. The reaction mixture was cooled to rt and washed with satd. NaHCO$_3$ solution (2×40 mL) and brine (2×40 mL), dried over Na$_2$SO$_4$, filtered and concentrated. The residue was purified by chromatography (chiralpak AD, 5 cm, 20 micron, 3/7 hexane/ethanol; 50 mL/min) to afford 605O (0.82 g; 32%) as a white solid. HPLC-MS $t_R$=1.90 min (UV$_{254\ nm}$); mass calculated for formula C$_{23}$H$_{18}$F$_3$N$_3$O$_6$ 489.11, observed LCMS m/z 490.1 (M+H).

Part D:

According to a modification of a literature procedure (Kotra, L. P, et a). *J. Med. Chem.*, 1997, 40, 3635) compound 605D (0.68 g, 1.4 mmol) was treated with methylamine (40% solution in water, 1.1 ml, 14 mmol) in methanol (20 ml) at rt for 2.5 h. The reaction mixture was concentrated and purified by column chromatography (SiO$_2$, 20-25% methanol/DCM) to afford 600E (0.37 g; 94%) as a white solid. HPLC-MS $t_R$=0.35 min (UV$_{254\ am}$); mass calculated for formula C$_9$H$_{10}$F$_3$N$_3$O$_4$ 281.06, observed LCMS m/z 282.1 (M+H).

Part E:

Compound 605F was prepared from 605E using a previously described procedure; HPLC-MS $t_R$=1.75 min (UV$_{254\ nm}$); mass calculated for formula C$_{15}$H$_{24}$F$_3$N$_3$O$_4$Si 395.15, observed LCMS m/z 396.1 (M+H).

Part F:

Compound 605G was prepared from 605F using a previously described procedure; HPLC-MS $t_R$=2.52 min (UV$_{254\ nm}$); mass calculated for formula C$_{29}$H$_{32}$F$_3$N$_3$O$_6$Si 603.20, observed LCMS m/z 604.2 (M+H).

Part G:

Compound 605H was prepared from 605G using a previously described procedure; HPLC-MS $t_R$=1.90 min (UV$_{254\ nm}$); mass calculated for formula C$_{23}$H$_{18}$F$_3$N$_3$O$_6$ 489.11, observed LCMS m/z 490.1 (M+H).

Part H:

Compound 605I was prepared from 605H using a previously described procedure; HPLC-MS $t_R$=2.12 min (UV$_{254\ nm}$); mass calculated for formula C$_{24}$H$_{20}$F$_3$N$_3$O$_8$S 567.09, observed LCMS m/z 568.1 (M+H).

Part I:

Compound 605J was prepared from 605I using a previously described procedure; HPLC-MS $t_R$=0.78 min (UV$_{254\ nm}$); mass calculated for formula C$_{10}$H$_{12}$F$_3$N$_3$O$_6$S 359.04, observed LCMS m/z 360.0 (M+H).

Part J:

Compound 605 was prepared from 605J using a previously described procedure; HPLC-MS $t_R$=0.28 min (UV$_{254\ nm}$, 10 min); mass calculated for formula C$_{13}$H$_{19}$F$_3$N$_4$O$_3$ 336.14, observed LCMS m/z 337.1 (M+H).

Example 606

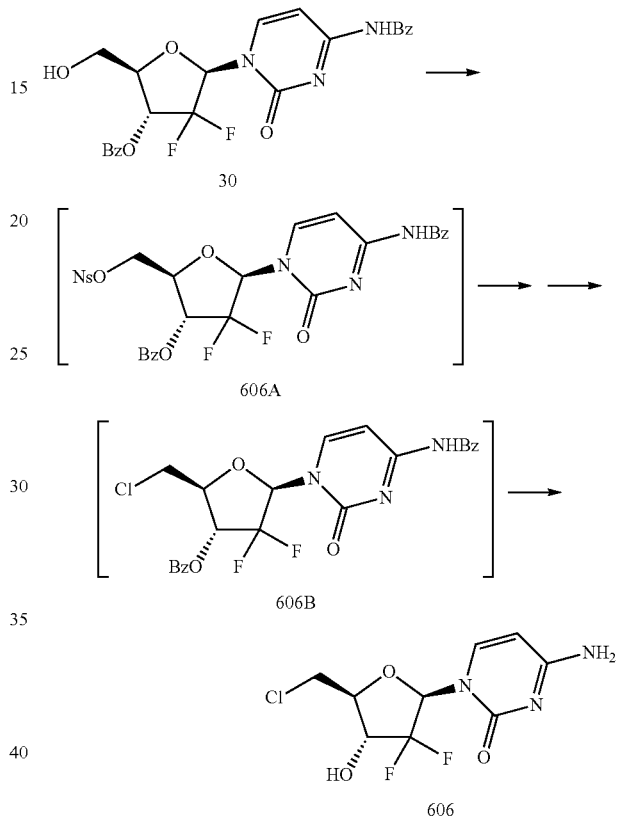

In a round-bottom flask was added Compound 30 (0.5 g; 1.06 mmol), pyridine (8 mL) and p-nitrobenzenesulfonyl chloride (0.47 g, 2.12 mmol) in two portions and the mixture was stirred at rt overnight, when LC-MS indicated intermediate 606B as the major component of the mixture, and only a small amount of intermediate 606A. Then p-nitrobenzenesulfonyl chloride (0.12 g, 0.5 eq.) was added and the reaction mixture was stirred at rt for 1 h and concentrated. The resulting crude material was treated with 7 M ammonia in methanol (30 mL) for 4 h at rt and then concentrated. The residue was triturated with MeOH, and the undissolved solid was filtered off (pyridine hydrochloride). The filtrate was concentrated and purified by column chromatography (SiO$_2$, 10-15% methanol/DCM) to give a 1.66:1 mixture of 606:p-nitrobenzenesulfonic acid (115 mg), which was subsequently purified by column chromatography (RediSep amine column, 10% methanol/DCM) to afford 606 as a white solid (68 mg; 23%); HPLC-MS $t_R$=0.71 min (UV$_{254\ nm}$, 10 min); mass calculated for formula C$_9$H$_{10}$ClF$_2$N$_3$O$_3$ 281.04, observed LCMS m/z 282.1 (M+H).

Example 701

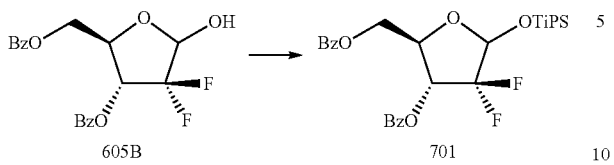

Compound 605B (8.0 g, 21.2 mmol) was dissolved in anhydrous DCM (100 mL). To the solution at 0° C. was added 2,6-ludine (2.7 mL, 23.3 mmol), followed by dropwise addition of triisopropylsilyl trifluoromethanesulfonate (6.0 mL, 23.3 mmol). The solution was stirred at 0° C. for 1 h. The solvent was removed in vacuo and the residue was purified using silica gel chromatography with a gradient of 0-20% EtOAc in hexane to afford 701 (9.6 g, 85%). $^1$H NMR (CDCl$_3$) δ 8.07 (d, J=8.0 Hz, 2H), 7.98 (d, J=8.0 Hz, 2H), 7.60 (dd, J=7.5, 7.5 Hz, 1H), 7.51 (dd, J=7.5, 7.5 Hz, 1H), 7.46 (dd, J=8.0, 7.5 Hz, 2H), 7.33 (dd, J=8.0, 7.5 Hz, 2H), 5.79 (m, 1H), 5.33 (d, J=6.9 Hz, 1H), 4.68 (m, 1H), 4.51 (2H, m), 1.07 (m, 21H).

Example 702

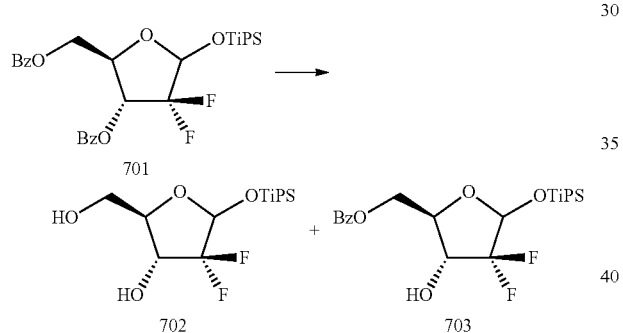

Compound 701 (9.6 g, 18.0 mmol) was dissolved in methanol (100 mL). Water (20 mL) and triethylamine (20 mL) was added. The solution was stirred at 23° C. for 17 h. The solvent was removed in vacuo and the residue was purified using silica gel chromatography with a gradient of 0-40% EtOAc in hexane to afford 702 (3.3 g, 56%) and 703 (2.5 g, 32%).

702: $^1$H NMR (CDCl$_3$) δ 5.22 (m, 1H), 4.54 (m, 0.5H), 4.17 (m, 0.5H), 3.97 (m, 1H), 3.87-3.68 (m, 2H), 1.08 (m, 21H);

703: $^1$H NMR (CDCl$_3$) δ 8.05 (d, J=8.0 Hz, 2H), 7.57 (dd, J=7.5, 7.5 Hz, 1H), 7.43 (dd, J=8.0, 7.5 Hz, 2H), 5.24 (d, 7.2 Hz, 1H), 4.60 (m, 1H), 4.48 (m, 1H), 4.40 (m, 1H), 4.13 (m, 1H), 1.08 (m, 21H).

Example 704

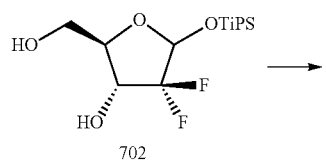

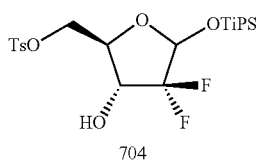

Compound 702 (16.2 g, 49.8 mmol) was dissolved in anhydrous pyridine (230 mL). To the solution at 0° C. was added a solution of p-TsCl (12.3 g, 64.7 mmol) in anhydrous DCM (110 mL) dropwise via an addition funnel over 45 min. The resulting solution was slowly warmed up to 23° C., and stirred for 16 h. The solution was quenched with ice-cold water, extracted with DCM. The organic layers were combined, dried with MgSO$_4$, filtered, and concentrated in vacuo. Purification of the residue using silica gel chromatography with a gradient of 0-40% EtOAc in hexane afforded 704 (14.2 g, 59%). HPLC-MS t$_R$=2.69 min (UV$_{254\ nm}$); mass calculated for formula C$_{21}$H$_{34}$F$_2$O$_6$SSi 480.18, observed LCMS m/z 481.1 (M+H).

Example 705

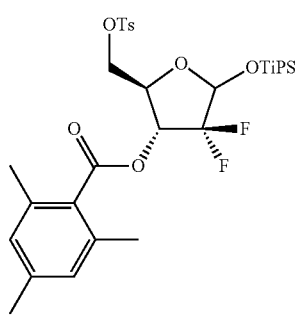

Compound 704 (7.0 g, 14.6 mmol) was dissolved in anhydrous THF (60 mL). To the solution at 23° C. was added 2,4,6-trimethylbenzoyl chloride (4.3 mL, 25.5 mmol), which was followed by dropwise addition of a solution of Lithium bis(trimethylsilyl)amide in THF (1.0 M, 25.5 mL). The solution was stirred at 23° C. for 3 h, quenched with water, extracted with Et$_2$O. The organic layers were combined, dried with MgSO$_4$, filtered, and concentrated in vacuo. Purification of the residue using silica gel chromatography with a gradient of 0-20% EtOAc in hexane afforded 705 (7.0 g, 69%). HPLC- MS $t_R$=2.93 min (UV$_{254\ nm}$); mass calculated for formula C$_{31}$H$_{44}$F$_2$O$_7$SSi 626.25, observed LCMS m/z 649.2 (M+Na).

Example 706

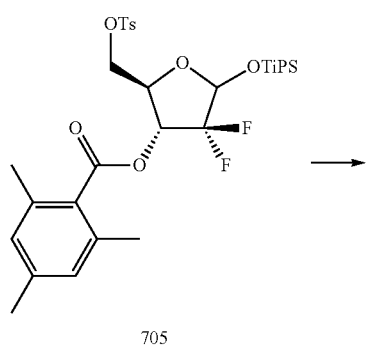
705

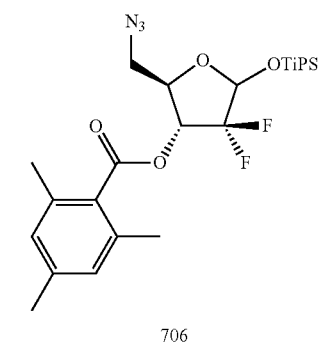
706

Compound 705 (3.1 g, 5.0 mmol) was dissolved in anhydrous DMF (20 mL). Sodium azide (4.4 g, 67.2 mmol) was added. The mixture was stirred at 70° C. for 3 h, quenched with water, extracted with dichloromethane. The organic layers were combined, dried with MgSO$_4$, filtered, and concentrated in vacuo. Purification of the residue using silica gel chromatography with a gradient of 0-10% EtOAc in hexane afforded 706 (1.85 g, 75%). $^1$H NMR (CDCl$_3$) δ 6.88 (s, 2H), 5.61 (m, 1H), 5.28 (m, 1H), 4.16 (m, 1H), 3.62 (m, 2H), 2.32 (s, 6H), 2.29 (s, 3H), 1.11 (m, 21H).

Example 707

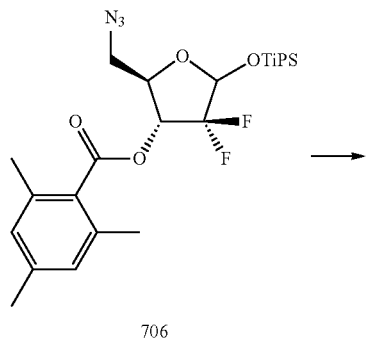
706

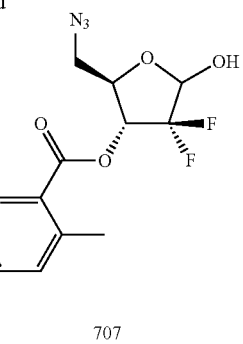
707

Compound 706 (671 mg, 1.35 mmol) was dissolved in anhydrous THF (7.0 mL). A solution of TBAF in THF (1.0 M, 1.4 mL) was added dropwise. The solution was stirred at 23° C. for 30 min, quenched with water, and extracted with EtOAc. The organic layers were combined, dried with MgSO$_4$, filtered, and concentrated in vacuo. Purification of the residue using silica gel chromatography with a gradient of 0-30% EtOAc in hexane afforded 707 (417 mg, 91%). $^1$H NMR (CDCl$_3$) δ 6.87 (s, 2H), 5.44 (t, J=5.8 Hz, 1H), 5.32 (dd, J=16.4, 5.3 Hz, 1H), 4.53 (m, 1H), 3.68 (1H, m), 3.57 (1H, m), 2.99 (1H, J=5.3 Hz, 1H), 2.31 (s, 6H), 2.28 (3H, s).

Example 708

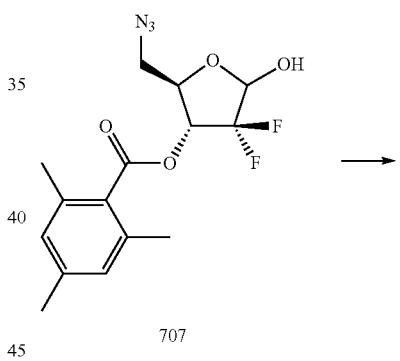
707

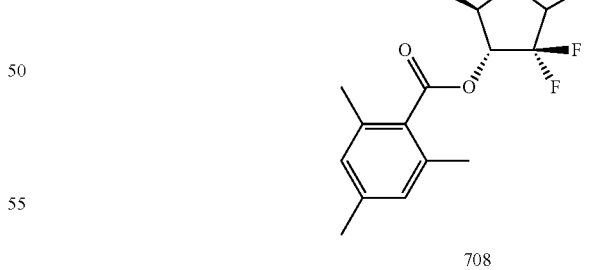
708

Compound 707 (420 mg, 1.23 mmol) was dissolved in anhydrous DCM (10 mL). Et$_3$N (186 mg, 1.85 mmol) and MSCl (149 mg, 1.29 mmol) was added. The solution was stirred at 23° C. for 1 h and concentrated in vacuo. Purification of the residue using silica gel chromatography with 100% DCM afforded 708 (525 mg, 100%). $^1$H NMR (CDCl$_3$) δ 6.89 (s, 2H), 6.08 (d, J=5.7 Hz, 0.5H), 5.97 (d, J=6.2 Hz, 0.5H), 5.75 (m, 0.5H), 5.37 (dd, J=17.4, 4.6 Hz, 0.5H), 4.58

(m, 0.5H), 4.35 (m, 0.5H), 3.75 (m, 1H), 3.65 (m, 1H), 3.19 (s, 1.5H), 3.12 (s, 1.5H), 2.30 (m, 9H).

Example 709

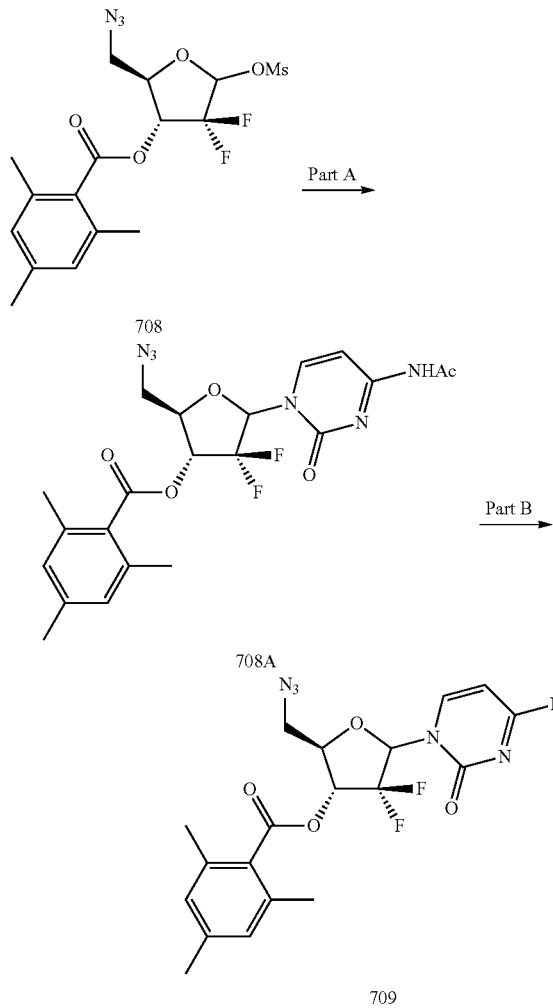

Part A:

N⁴-Acetylcytosine (1.5 g, 9.6 mmol), (NH₄)₂SO₄ (6.3 mg, 0.05 mmol) and hexamethyldisilazane (15 mL) were heated at 130° C. for 3 h and concentrated in vacuo. To the residue was added a solution of compound 708 (1.3 g, 3.1 mmol) in DCE (16 mL) followed by trimethylsilyl trifluoromethanesulfonate (2.1 g, 9.6 mmol). The solution was heated at 95° C. for 15 h. The reaction mixture was cooled down, quenched with water, and extracted with EtOAc. The organic layers were combined, dried over Na₂SO₄, and concentrated in vacuo to provide crude 708A. HPLC-MS $t_R$=1.85 min (UV$_{254\ nm}$); mass calculated for formula $C_{21}H_{22}F_2N_6O_5$ 476.16, observed LCMS m/z 477.1 (M+H).

Part B:

The crude product 708A was dissolved in MeOH (5 mL) and a solution of ammonia in MeOH (7 N, 10 mL) was added. The solution was stirred at 23° C. for 3 h, filtered, and concentrated in vacuo Purification of the residue using silica gel chromatography with 0-30% MeOH in DCM afforded 709 (1.3 g, 97%). HPLC-MS $t_R$=1.75 min (UV$_{254\ nm}$); mass calculated for formula $C_{19}H_{20}F_2N_6O_4$ 434.15, observed LCMS m/z 435.1 (M+H).

Example 710

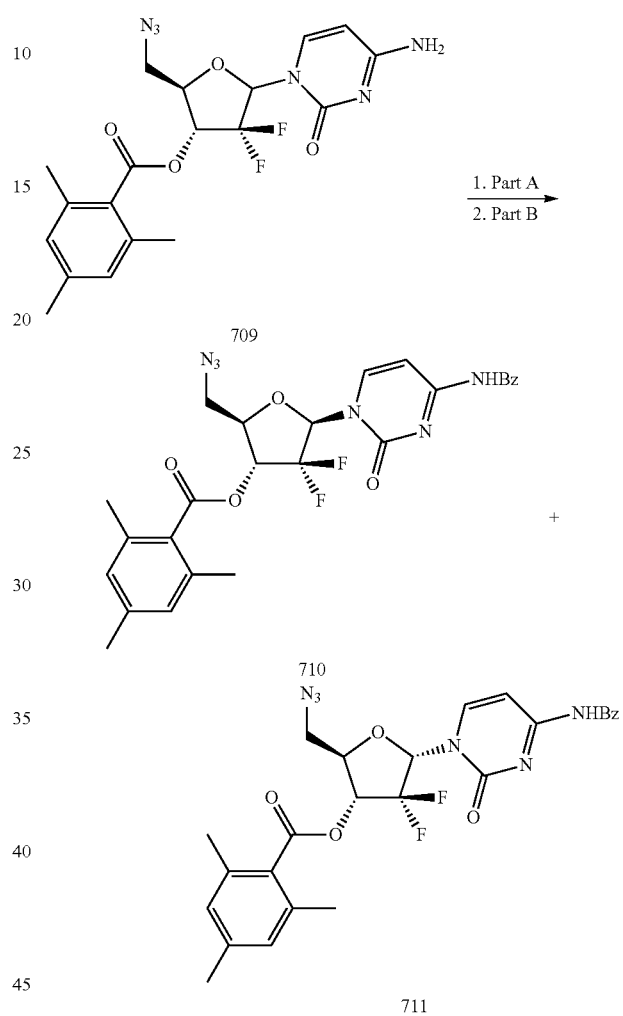

Part A:

Compound 709 (1.35 g, 3.11 mmol) was dissolved in anhydrous pyridine (15 mL). To the solution was added DMAP (3.6 mg, 0.03 mmol) and BzCl (1.0 mL, 8.4 mmol) dropwise. The solution was stirred at 23° C. for 2 h, quenched with 5% NaHCO₃, extracted with EtOAc, dried over Na₂SO₄, and concentrated in vacuo. Purification of the residue using silica gel chromatography with 0-50% EtOAc in hexane afforded a mixture of 710 and 711 (989 mg, 59%). HPLC-MS $t_R$=2.26 min (UV$_{254\ nm}$); mass calculated for formula $C_{26}H_{24}F_2N_6O_5$ 538.18, observed LCMS m/z 539.2 (M+H).

Part B:

Separation of the mixture obtained from Part A using Chiralcel OD column (5 cm×50 cm) with 100% MeOH (50 mL/min, UV$_{254\ nm}$) afforded compound 710 ($t_R$=43 min, 206 mg) and 711 ($t_R$=36 min, 600 mg).

710: ¹H NMR (CDCl₃) δ 8.97 (br s, 1H), 7.93 (br s, 3H), 7.72 (br s, 1H), 7.64 (dd, J=7.5, 7.5 Hz, 1H), 7.54 (dd, J=8.0, 7.5 Hz, 2H), 6.90 (s, 2H), 6.46 (t, J=8.2 Hz, 1H), 5.56 (m, 1H), 4.34 (m, 1H), 3.92 (dd, J=13.8, 3.2 Hz, 1H), 3.72 (dd, J=13.8, 3.8 Hz, 1H), 2.32 (s, 2.30 (s, 3H);

711: $^1$H NMR (CDCl$_3$) δ 8.87 (br s, 1H), 7.90 (br d, J=6.5 Hz, 2H), 7.70 (d, J=7.4 Hz, 1H), 7.63 (dd, J=7.5, 7.5 Hz, 1H), 7.58 (br s, 1H), 7.52 (dd, J=8.0, 7.5 Hz, 2H), 6.88 (s, 2H), 6.66 (dd, J=8.0, 6.9 Hz, 1H), 5.76 (m, 1H), 4.60 (m, 1H), 3.73 (m, 2H), 2.29 (s, 3H), 2.28 (s, 6H).

Example 712

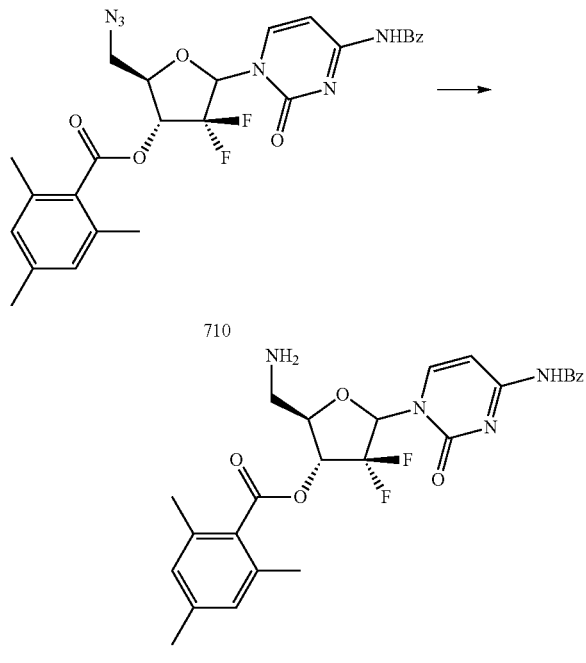

Compound 710 (45 mg, 0.084 mmol) was dissolved in 0.8 mL of THF/H$_2$O (6/1). To the mixture was added a solution of Me$_3$P in THF (0.66 M, 0.19 mL) dropwise. The solution was stirred at 23° C. for 30 min and concentrated in vacuo Purification of the residue using silica gel chromatography with 5-10% MeOH in DCM afforded 712 (29 mg, 67%). HPLC-MS t$_R$=1.52 min (UV$_2$ mass calculated for formula C$_{26}$H$_{26}$F$_2$N$_4$O$_5$ 512.19, observed LCMS m/z 513.2 (M+H).

Example 713

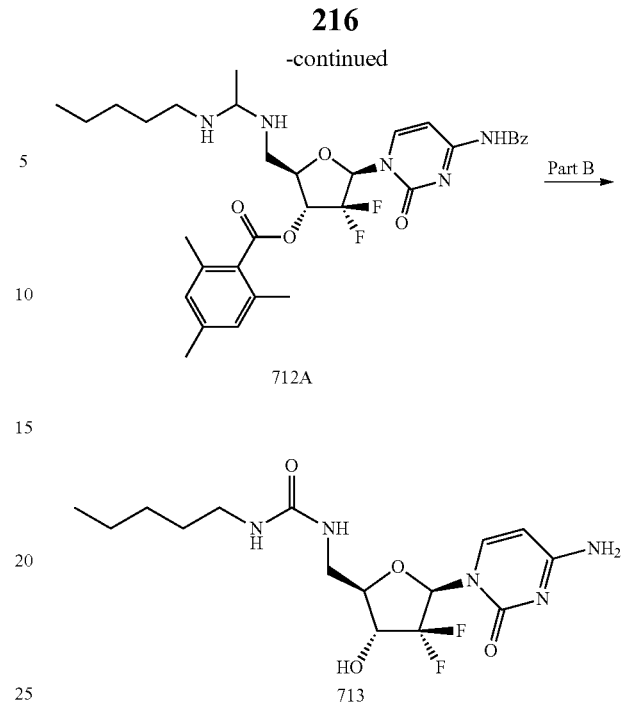

Part A:

Compound 712 (10 mg, 0.02 mmol) was dissolved in anhydrous THF (0.5 mL). To the solution was added 1-pentyl isocyanate (6.8 mg, 0.06 mmol). The solution was stirred at 23° C. for 2 h. Concentration in vacuo provided crude 712A, HPLC-MS t$_R$=2.16 min (UV$_{254\ nm}$); mass calculated for formula C$_{32}$H$_{37}$F$_2$N$_5$O$_6$ 625.27, observed LCMS m/z 626.2 (M+H).

Part B:

The crude product 712A was dissolved in MeOH (0.4 mL). An aqueous KOH solution (5 M, 0.08 mL) was added. The solution was stirred at 23° C. for 19 h and concentrated in vacua. Purification of the residue using silica gel chromatography with 20% MeOH in DCM afforded 713 (3.8 mg, 51%). HPLC-MS t$_R$=1.01 min (UV$_{254}$ man); mass calculated for formula C$_{15}$H$_{23}$F$_2$N$_5$O$_4$ 375.17, observed LCMS m/z 376.1 (M+H).

Example 714

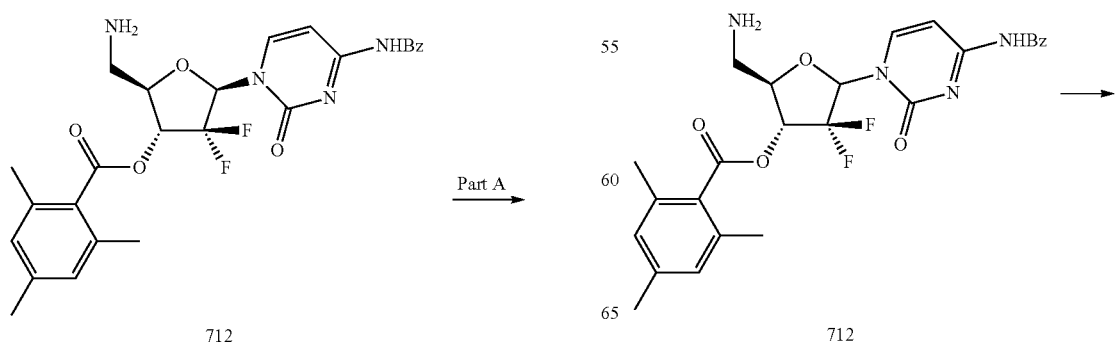

217

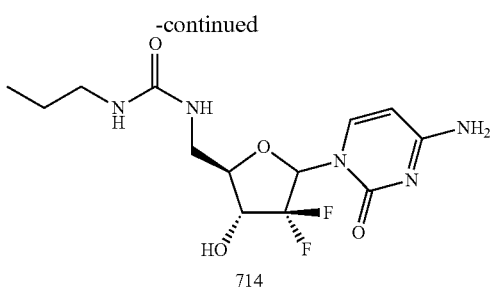

714

Compound 714 was prepared using the procedure described in example 713. HPLC-MS $t_R$=1.14 min (UV$_{254\ nm}$); mass calculated for formula C$_{13}$H$_{19}$F$_2$N$_5$O$_4$ 347.14, observed LCMS m/z 348.1 (M+H).

Example 715

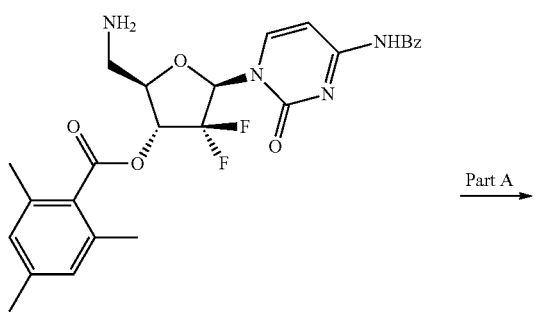

712

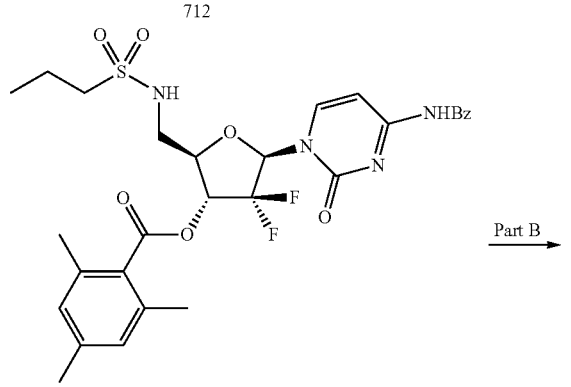

712B

715

Part A:

Compound 712 (17 mg, 0.033 mmol) was dissolved in anhydrous THF (0.5 mL). To the solution was added TEA (5.0 mg, 0.05 mmol) and 1-propanesulfonyl chloride (4.7 mg, 0.033 mmol). The solution was stirred at 23° C. for 40 min, diluted with EtOAc and filtered through a silica gel plug. The filtrate was concentrated in vacuo to afford crude 712B.

218

HPLC-MS $t_R$=1.99 min (UV$_{254\ nm}$); mass calculated for formula C$_{29}$H$_{32}$F$_2$N$_4$O$_7$S 618.20, observed LCMS m/z 619.2 (M+H).

Part B:

The crude product 712B was dissolved in MeOH (0.5 mL). An aqueous KOH solution (5 M, 0.14 mL) was added. The solution was stirred at 23° C. for 17 h and concentrated in vacuo. Purification of the residue using silica gel chromatography with 10-15% MeOH n DCM afforded 715 (4.5 mg, 37%). HPLC-MS $t_R$=0.72 min (UV$_{254\ nm}$); mass calculated for formula C$_{12}$H$_{18}$F$_2$N$_4$O$_5$S 368.10, observed LCMS m/z 369.1 (M+H).

Example 720

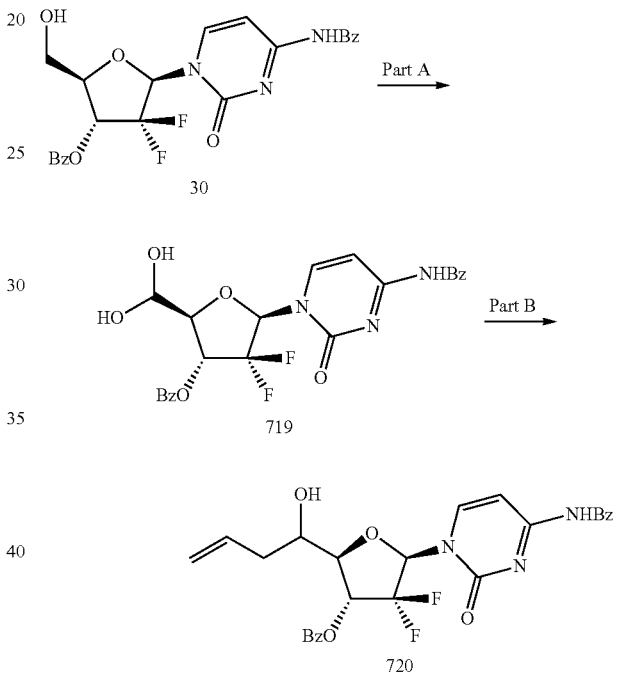

30

719

720

Part A:

Compound 30 (305 mg, 0.65 mmol) was dissolved in anhydrous DCM (5.4 mL). To the solution was added Dess-Martin Periodinane solution in DCM (0.3 M, 2.4 mL). The solution was stirred at 23° C. for 1 h and loaded on a 12 G silica gel column. Purification with 0-100% EtOAc in DCM afforded 346 mg of product 719. HPLC-MS $t_R$=1.48 min (UV$_{254\ nm}$); mass calculated for formula C$_{23}$H$_{19}$F$_2$N$_3$O$_7$ 487.12, observed LCMS m/z 488.0 (M+H).

Part B:

The product 719 was dissolved in anhydrous DCM (5.0 mL). To the solution at 0° C. was added allyltrimethylsilane (0.52 mL, 3.25 mmol) and boron trifluoride diethyl etherate (0.41 mL, 3.25 mmol). The solution was stirred at 0° C. for 3 h, quenched with 5% NaHCO$_3$, extracted with DCM (1×) and EtOAc (2×). The organic layers were combined, dried over Na$_2$SO$_4$, and concentrated in vacuo. Purification of the residue using silica gel chromatography with a gradient of 0-100% EtOAc in DCM afforded 720 (221 mg, 67%). HPLC- MS $t_R$=2.08 min (UV$_{254 nm}$); mass calculated for formula C$_{26}$H$_{23}$F$_2$N$_3$O$_6$ 511.16, observed LCMS m/z 512.0 (M+H).

Example 721

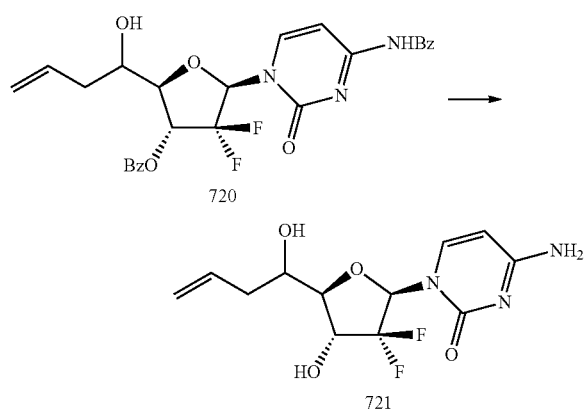

To compound 720 (26 mg, 0.051 mmol) was added a solution of ammonia in MeOH (7 N, 1.0 mL). The solution was stirred at 23° C. for 4 h and concentrated in vacuo. Purification of the residue using silica gel chromatography with a gradient of 0-20% MeOH in DCM afforded 721 (15 mg, 97%). HPLC-MS $t_R$=0.73 min (UV$_{254 nm}$); mass calculated for formula C$_{12}$H$_{15}$F$_2$N$_3$O$_4$ 303.10, observed LCMS m/z 304.1 (M+H).

Example 722

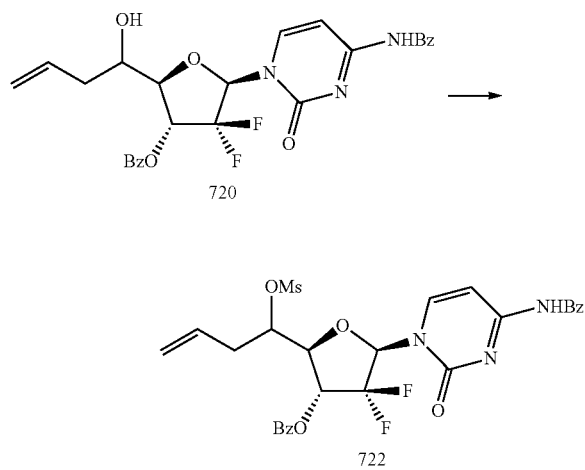

Compound 720 (221 mg, 0.43 mmol) was dissolved in anhydrous DCM (5.4 mL). To the solution was added TEA (0.12 mL, 0.86 mmol) and MsCl (60 mg, 0.52 mmol). The solution was stirred at 23° C. for 1.5 h and loaded on a 12 G silica gel column. Purification with a gradient of 0-50% EtOAc in hexane afforded 722 (232 mg, 92%). HPLC-MS $t_R$=2.15 min (UV$_{254 nm}$); mass calculated for formula C$_{27}$H$_{25}$F$_2$N$_3$O$_8$S 589.13, observed LCMS m/z 590.0 (M+H).

Example 723

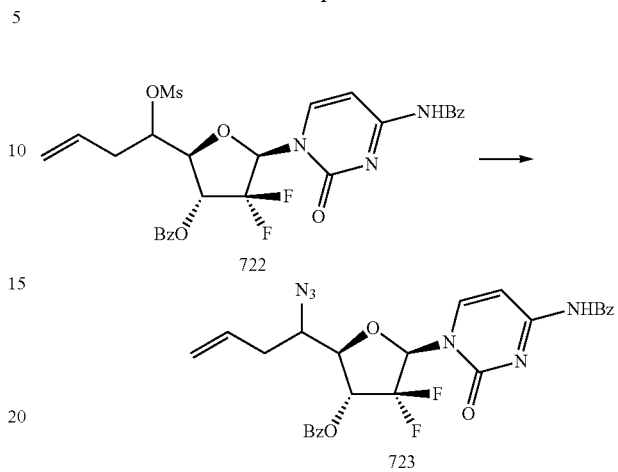

Compound 722 (232 mg, 0.39 mmol) was dissolved in anhydrous DMF (4 mL). To the solution was added NaN$_3$ (520 mg, 8.0 mmol) and the mixture was heated at 75° C. for 3 h. The reaction was cooled to RT, diluted with EtOAc and filtered. The filtrate was concentrated and the residue was purified using silica gel chromatography with a gradient of 0-50% EtOAc in hexane afforded 723 (133 mg, 64%). HPLC-MS $t_R$=2.17 min (UV$_{254 nm}$); mass calculated for formula C$_{26}$H$_{22}$F$_2$N$_6$O$_5$ 536.16, observed LCMS m/z 537.1 (M+H).

Example 724

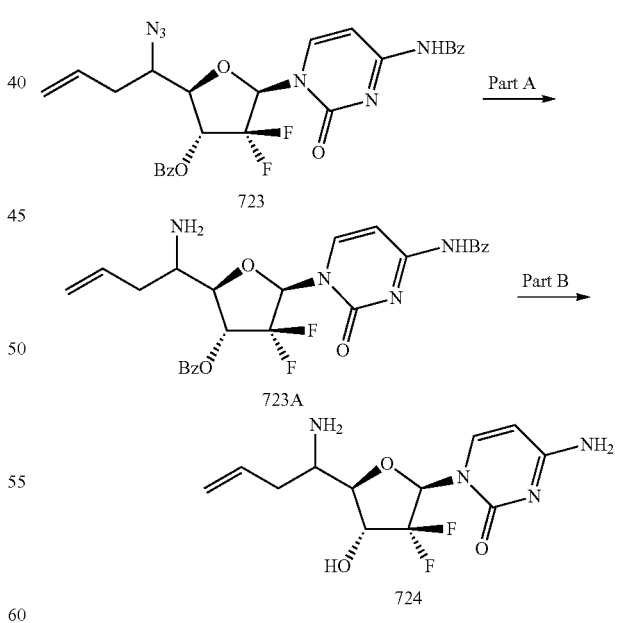

Part A:
Compound 723 (133 mg, 0.25 mmol) was dissolved in 5 mL of THF/H$_2$O (6/1). To the mixture was added a solution of Me$_3$P in THF (0.66 M, 0.57 mL) dropwise. The solution was stirred at 23° C. for 45 min and concentrated in vacuo. Purification of the residue using silica gel chromatography with 0-10% MeOH in DCM afforded amine product 723A (81 mg, 64%). HPLC-MS $t_R$=1.49 min (UV$_{254\ nm}$); mass calculated for formula $C_{26}H_{24}F_2N_4O_5$ 510.17, observed LCMS m/z 511.1 (M+H).

Part B:

Compound 724 was prepared using a previously described procedure of example 721. HPLC-MS $t_R$=0.42 min (UV$_{254\ nm}$); mass calculated for formula $C_{12}H_{16}F_2N_4O_3$ 302.12, observed LCMS m/z 303.1 (M+H).

Example 725

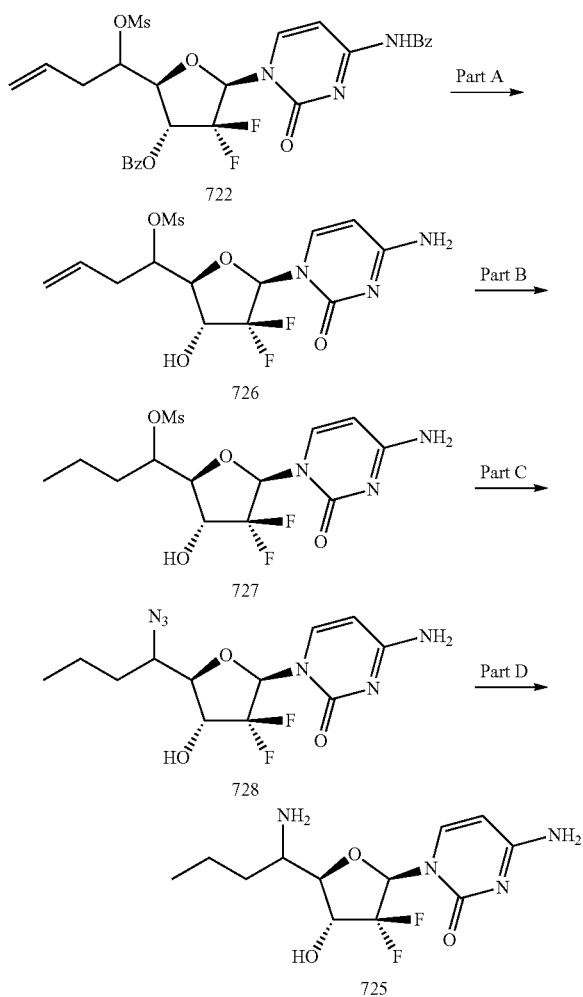

Part A:

Compound 726 was prepared using the procedure described in example 721, HPLC-MS $t_R$=1.02 min (UV$_{254\ nm}$); mass calculated for formula $C_{13}H_{17}F_2N_3O_6S$ 381.08, observed LCMS m/z 382.1 (M+H).

Part B:

Compound 726 (15 mg, 0.039 mmol) was dissolved in MeOH (15 mL). The solution was treated with Pd/C and hydrogen (30 bar) at 40° C. for 30 min in a H-Cube hydrogenator. Evaporation of the solvent afforded product 727 (12 mg, 80%). HPLC-MS $t_R$=0.90 mm (UV$_{254\ nm}$); mass calculated for formula $C_{13}H_{17}F_2N_3O_6S$ 383.10, observed LCMS m/z 384.1 (M+H).

Part C:

Compound 728 was prepared using the procedure described in example 723. HPLC-MS $t_R$=1.10 min (UV$_{254\ nm}$); mass calculated for formula $C_{12}H_{16}F_2N_6O_3$ 330.13, observed LCMS m/z 331.1 (M+H).

Part C:

Compound 725 was prepared using the procedure described in example 723A. HPLC-MS $t_R$=0.55 min (UV$_{254\ nm}$); mass calculated for formula $C_{12}H_{18}F_2N_4O_3$ 304.13, observed LCMS m/z 305.2 (M+H).

ASSAYS:

Phospho-H2A.X (ser139) Cell-Based Assay

The purpose of the assay was to determine the levels of phospho-H2AX in U20S cells that have been co-exposed with a compound of the instant invention and a Chk1 inhibitor. The compounds of the present invention that were used in this assay are shown below in Table 2.

The Chk1 inhibitor that was used in the assay is a pyrazol pyrimidine compound shown below:

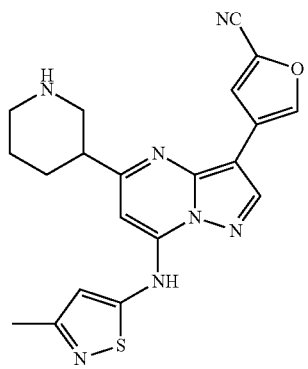 [SMILES: Cc1cc(Nc2cc(C3CCCNC3)nc3c(-c4coc(C#N)c4)cnn23)sn1]

Materials

U20S cells (split twice a week 1:6)

Dulbecco's Modification of Eagle's Medium (DMEM) with 4.5 g/L Glucose and L-Glutamine, Cellgro, Cat#10-013-CV Fetal Bovine Serum (FBS), HyClone, Cat# SH30071.03

Hepes buffer solution (1M). Gibco, Cat#15630-080

MEM Nonessential Amino Acids (NEAA) mixture (100×), BioWhittaker, Cat#13-114E

Penicillin/Streptomycin L-Glutamine mixture, 25,000U Pen/mL, 25,000 μg Strep/mL (4.5 mL/vial) BioWhittaker, Cat#17-718R 96 well Black TC plates, Perkin Elmer, Cat #6005182

Fluorescein isothiocyanate (FITC) conjugated anti phospho-histone H2A.X (ser139), Upstate cat#16-202-A Propidium Iodide, Biocarta, Part #638

20×TBST (800 mL Tris-HCl pH 7.4, 1200 mL 5M NaCl, 40 mL Tween 20)

70% ethanol (ETOH)

Blocking buffer-3% BSA in DPBS

DABCO Mounting Medium (2.33% 1,4-Diazabicyclo [2.2.2]octane (DABCO) Sigma, Cat # D2522, 90% glycerol, 20 mM Tris-HCl, pH 8)

Assay 1. plate 1×10⁴ cells/well on 96 well Black TC plate, incubate 24 hrs
2. Expose cells to compounds of instant invention titration over night. The next day add 1 μM Chk1 inhibitor (500 nM final) to rows A-D and media to rows E-H.

Dilution of Compounds
  Dilution of the Compounds of Instant Invention
    a. 500 μM start: add 10 μl of 100 mM compound to 2000 μl DMEM
      +1% NEAA+1% hepes buffer+1% pen/strep+10% FBS (complete DMEM)
      *** keep DMSO constant
      and make 9 1:2 serial dilutions in complete DMEM+DMSO
    b. add 100 μl of the compounds diluted in complete DMEM per well (8 wells/conc)
  Dilution of the Chk1 Inhibitor
    a. 500 nM Chk1 inhibitor=make 2×3 μl 5 mM Chk1 inhibitor+15 mL complete DMEM
    b. add 100 μl of the Chk1 inhibitor diluted in media per well (4 wells/conc) and add 100 μL of complete DMEM+DMSO
3. Fixation and staining of cells for immunofluorescence
    a. Aspirate off media
    b. Fix with 100 μL/well ice cold 70% ETOH at 4° C. for 30 minutes to 1 hr
    c. Aspirate off 70% ETOH
    d. add 100 μL/well blocking buffer incubate 1 hr on orbital shaker at room temperature
    e. Aspirate off blocking buffer
    f. add 2004/well of 0.34 μg/mL FITC-conjugated anti phospho-histone H2A.X (ser 139) diluted in blocking buffer, incubate overnight at 4° C. on orbital shaker. No antibody control is blocking buffer only.
    g. wash 2 times with 1×TBST 5 min each at room temperature on orbital shaker
    h. add 100 μL of propidium iodide (PI) stain (0.5 μl of 250 μg/ml PI+100 μL 1×TBST per well) incubate 5 minute on an orbital shaker
    i. wash 1 time with 1×TBST 5 minute at room temperature on orbital shaker
    j. add 50 μL of DABCO mounting media
    k. View slides on immunofluorescence-equipped microscope and quantify FITC positive nuclei as a percentage of the PI-positive total population of nuclei.

Some illustrative compounds of the present invention with $IC_{50}$ values determined according to the above method and $IC_{50}$ in the range 0.001-10 μM are shown below in Table 2:

TABLE 2

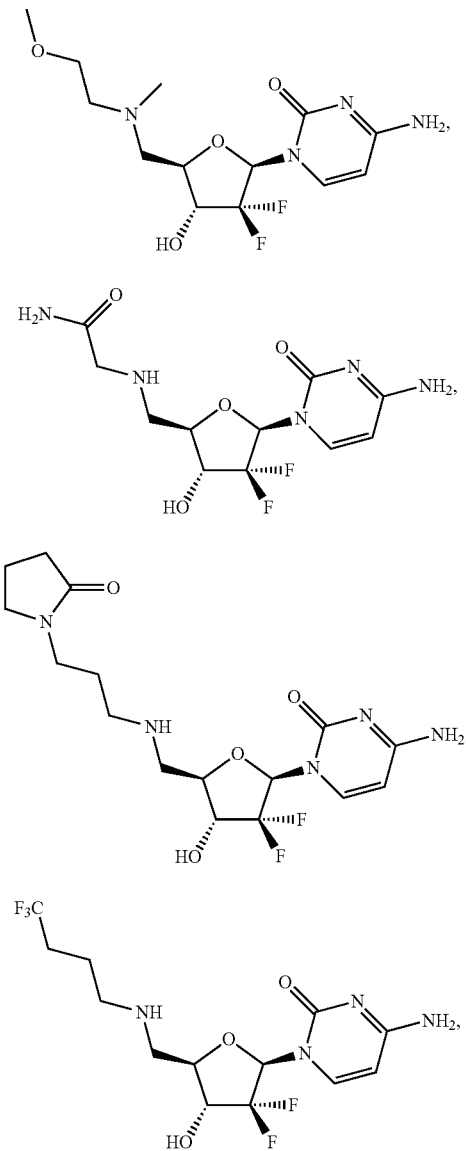

| | Plate Map | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | 500 uM + CHK1 inhibitor | 250 uM + CHK1 inhibitor | 125 uM + CHK1 inhibitor | 62.5 uM + CHK1 inhibitor | 31.2 uM + CHK1 inhibitor | 15.6 uM + CHK1 inhibitor | 7.8 uM + CHK1 inhibitor | 3.9 uM + CHK1 inhibitor | 1.95 uM + CHK1 inhibitor | 0.976 uM + CHK1 inhibitor | CHK1 inhibitor | No anti-H2A.X |
| B | | | | | | | | | | | | |
| C | | | | | | | | | | | | |
| D | | | | | | | | | | | | |
| E | 500 uM | 250 uM | 125 uM | 62.5 uM | 31.2 uM | 15.6 uM | 7.8 uM | 3.9 uM + CHK1 inhibitor | 1.95 uM | 0.976 uM + CHK1 inhibitor | DMSO control | No anti-H2A.X |
| F | | | | | | | | | | | | |
| G | | | | | | | | | | | | |
| H | | | | | | | | | | | | |

TABLE 2-continued
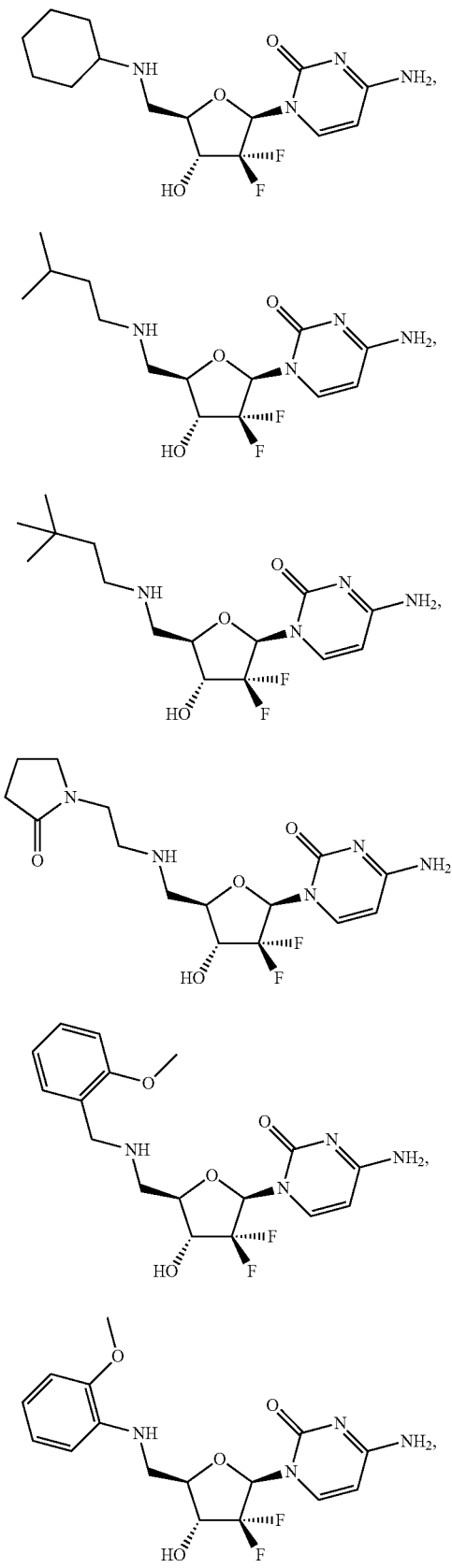
TABLE 2-continued
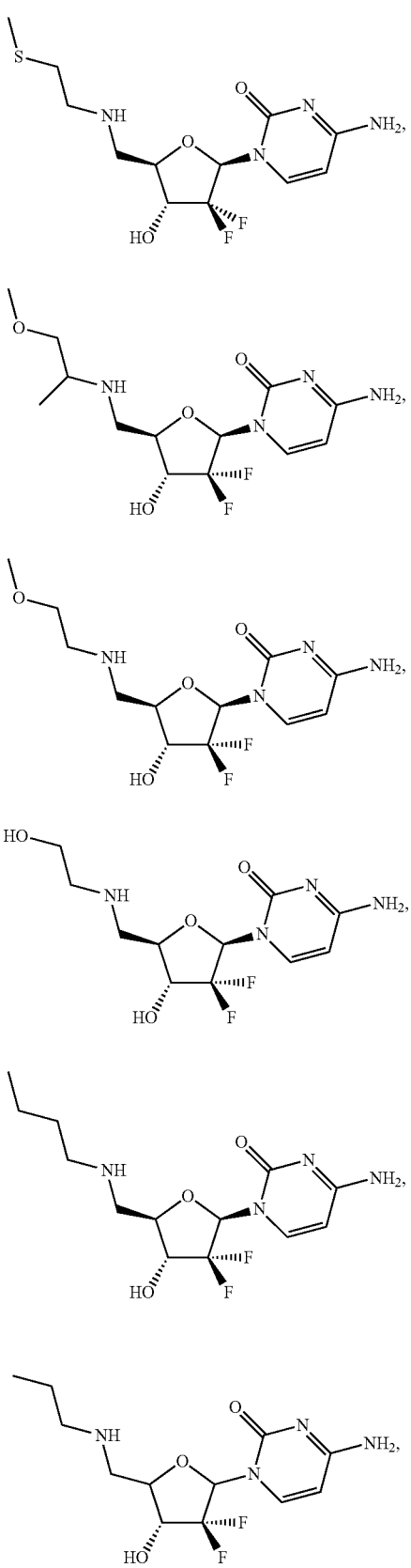

TABLE 2-continued

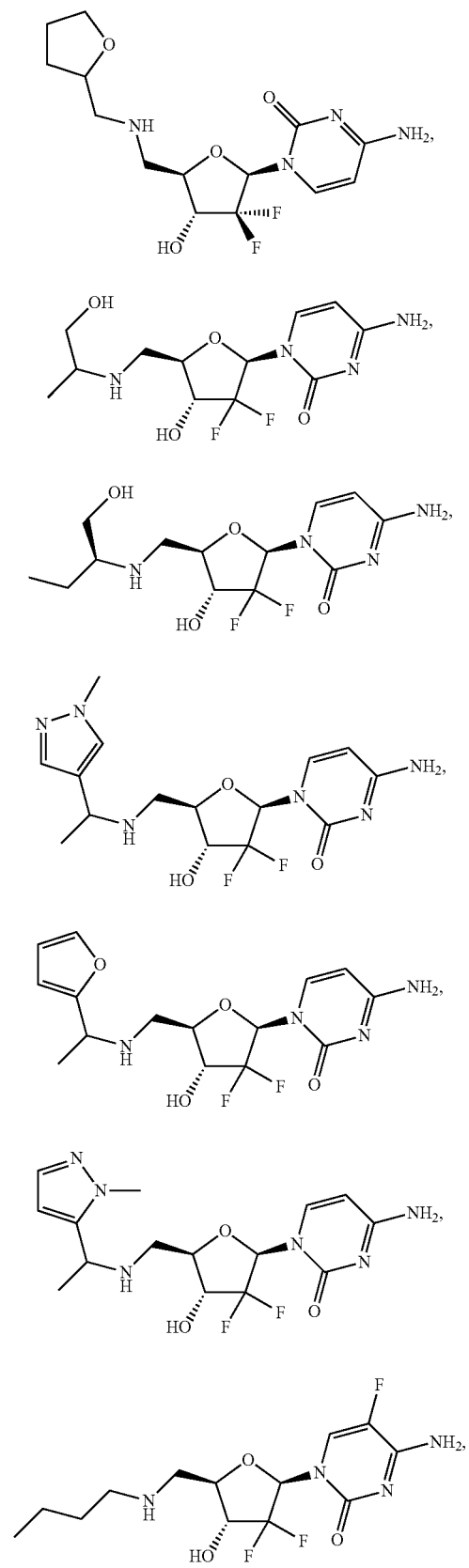

TABLE 2-continued

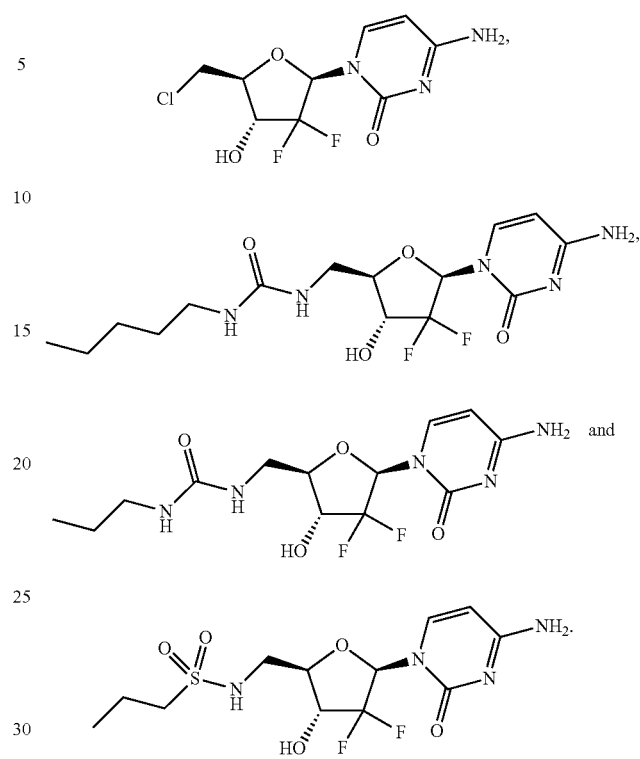

As demonstrated above by the assay values, the compounds of the present invention exhibit desirable properties.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound selected from the group consisting of:

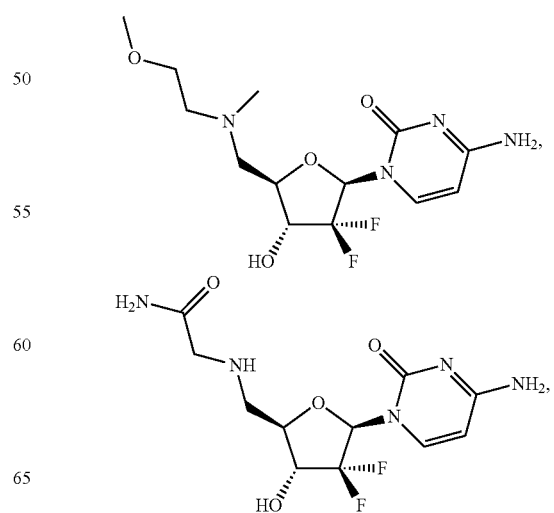

229
-continued
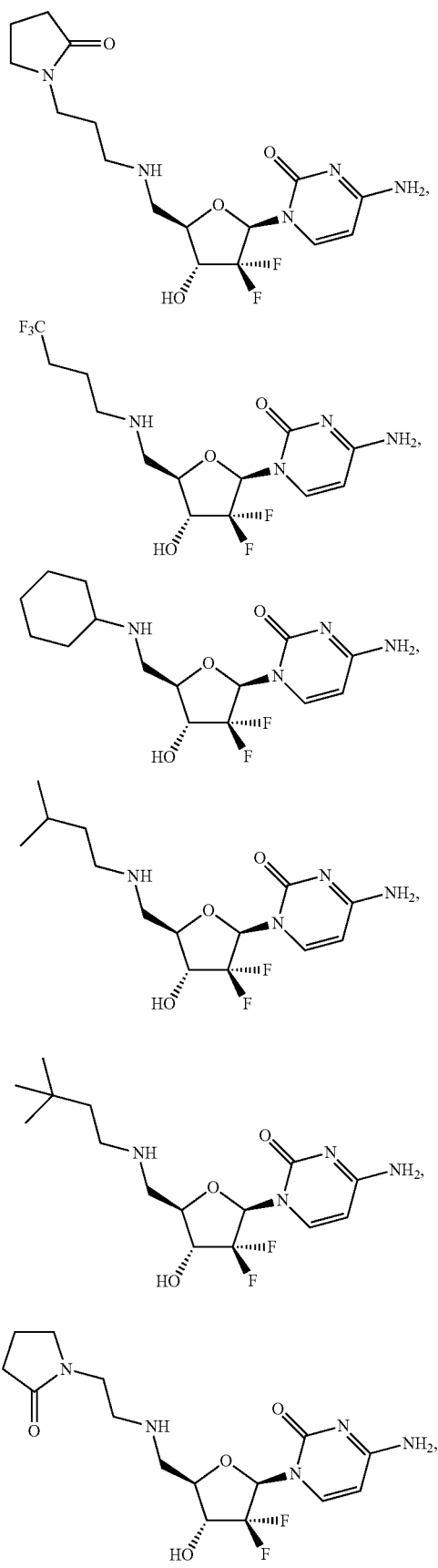
230
-continued
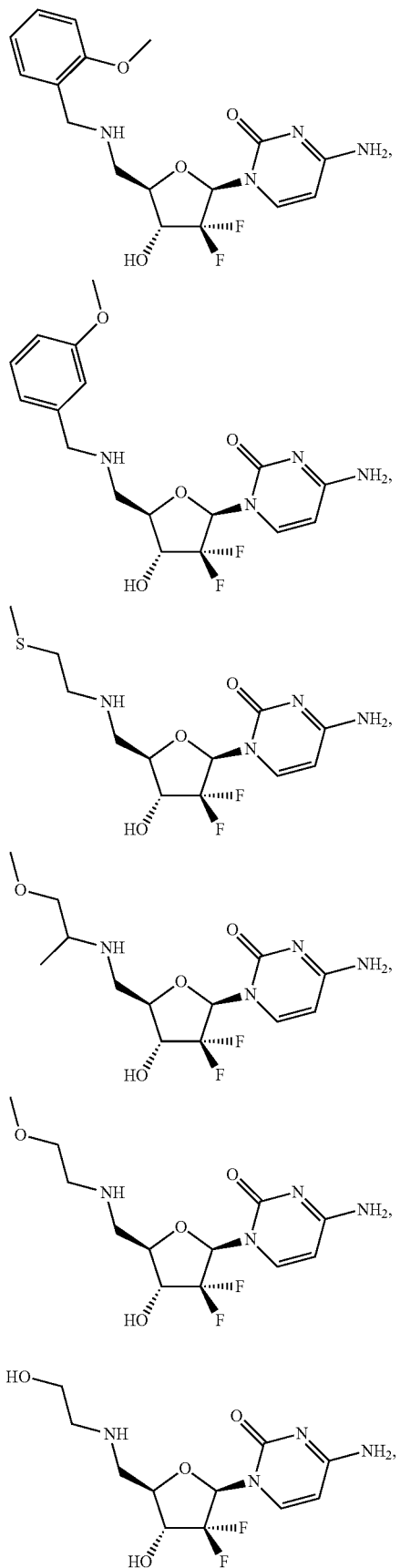

231
-continued

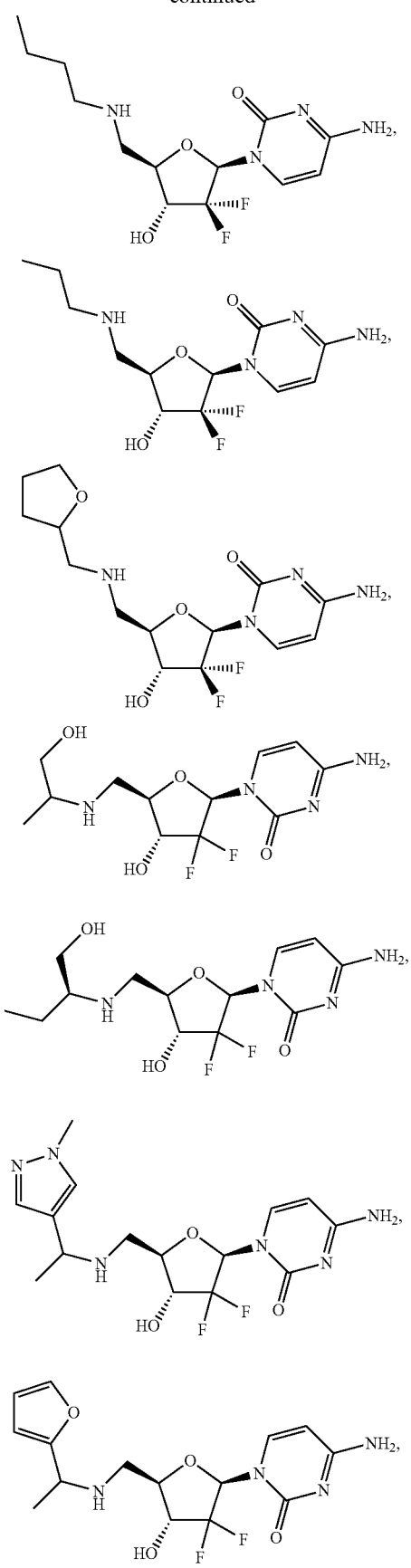

232
-continued

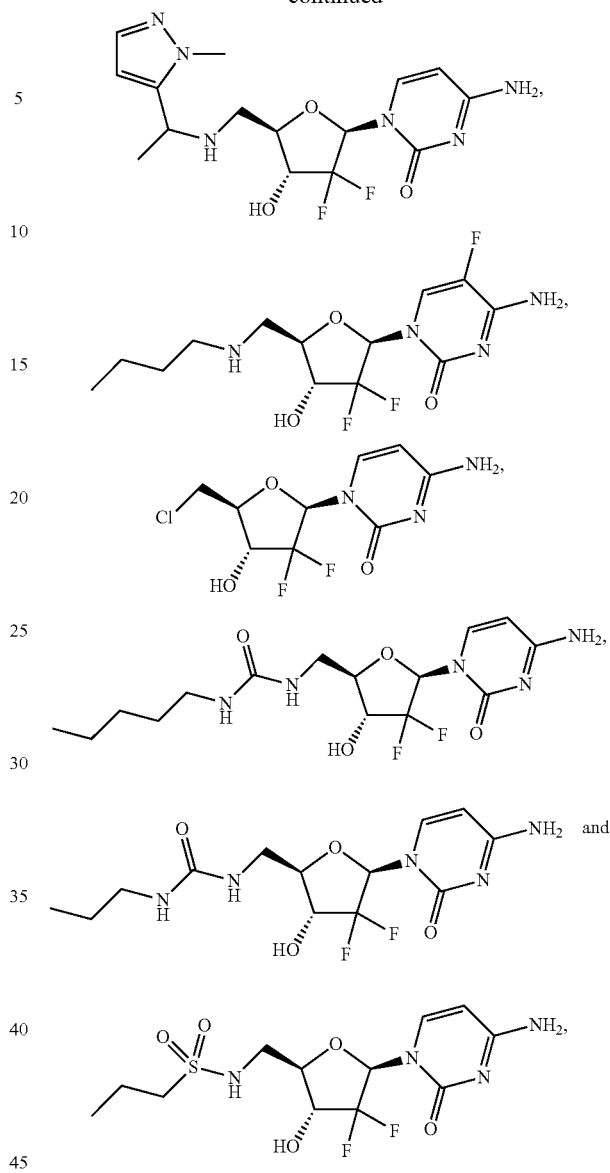

or a pharmaceutically acceptable salt thereof.

2. A pharmaceutical composition comprising a therapeutically effective amount of at least one compound of claim 1, or a pharmaceutically acceptable salt thereof, in combination with at least one pharmaceutically acceptable carrier.

3. The pharmaceutical composition according to claim 2, further comprising one or more inhibitor of Checkpoint kinase.

4. The composition of claim 3, wherein said Chk1 inhibitor is an imidazopyrazine, or a pharmaceutically acceptable salt thereof.

5. The composition of claim 3, wherein said checkpoint kinase is checkpoint kinase 1 (Chk1).

6. The composition of claim 5, wherein said Chk1 inhibitor is a pyrazolopyrimidine, or a pharmaceutically acceptable salt thereof.

7. The composition of claim 6, wherein said pyrazolopyrimidine is selected from the group consisting of:

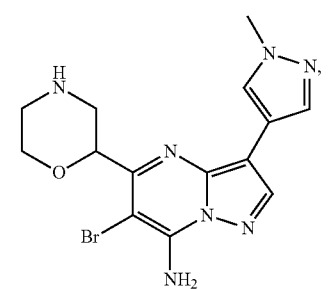
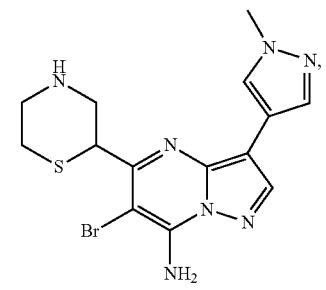
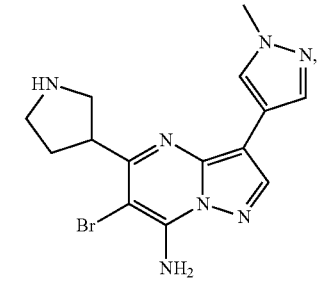
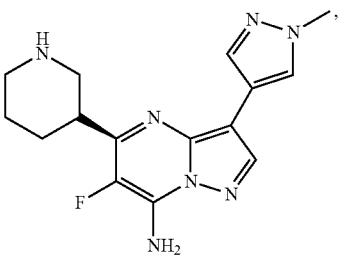
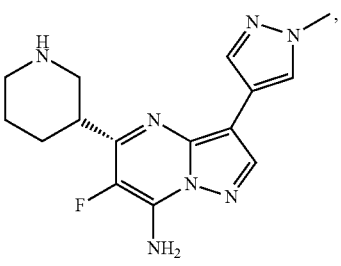
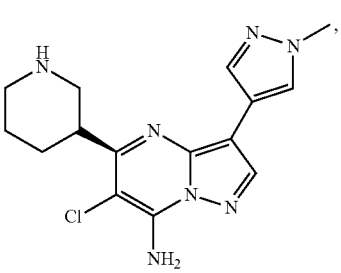
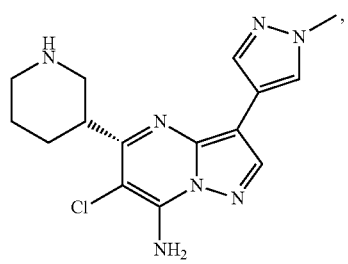
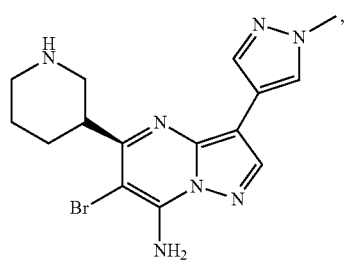
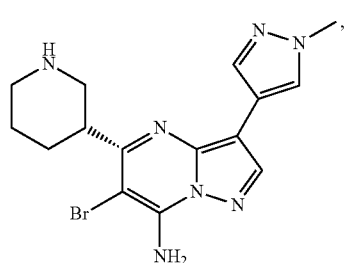
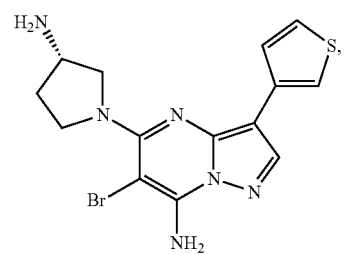
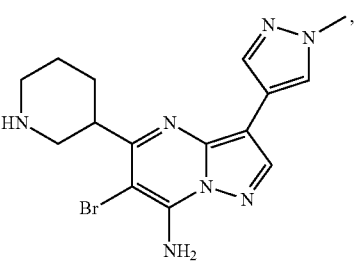
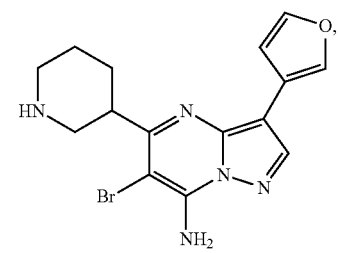

235
-continued
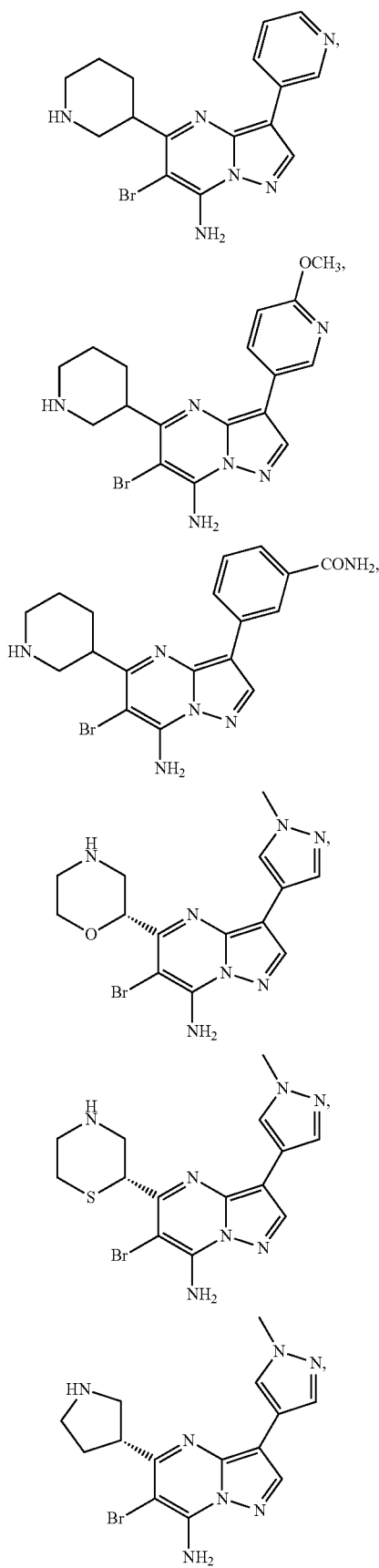
236
-continued
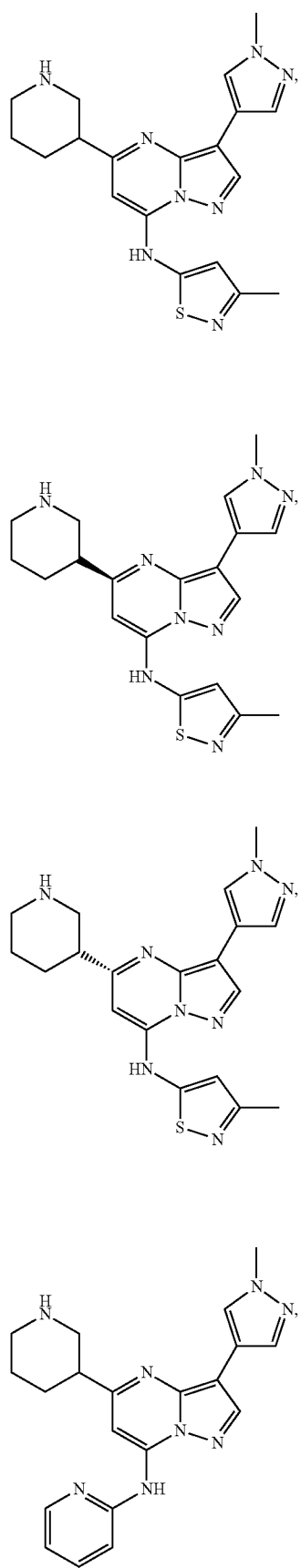

237
-continued
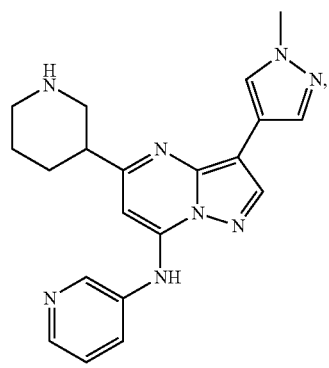
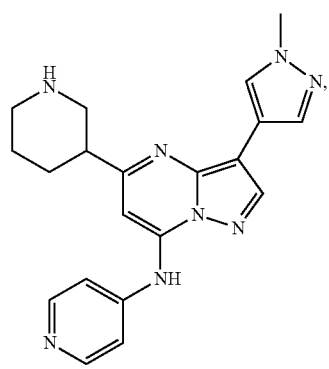
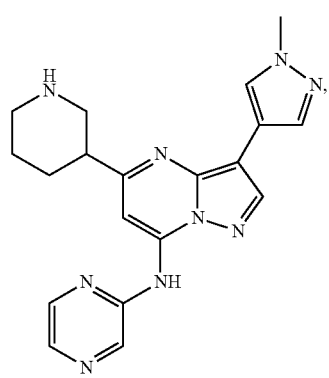
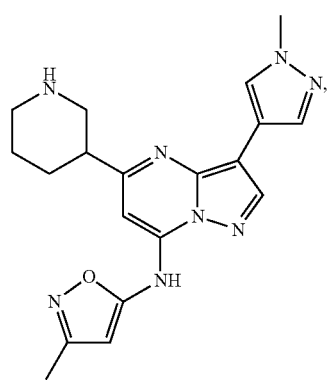
238
-continued
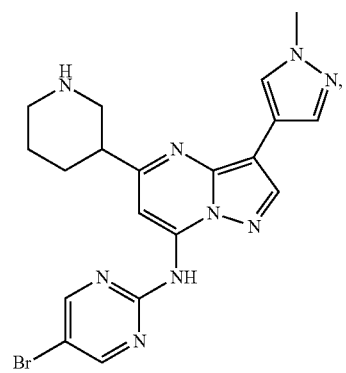
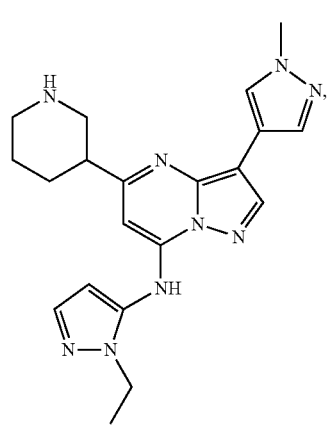
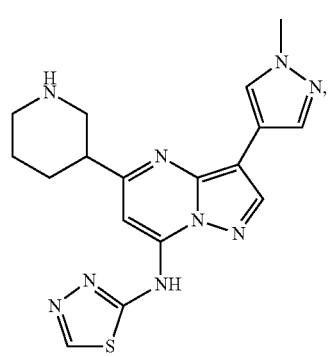
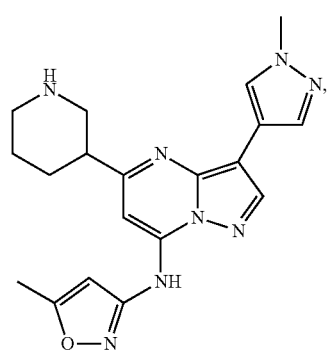

-continued
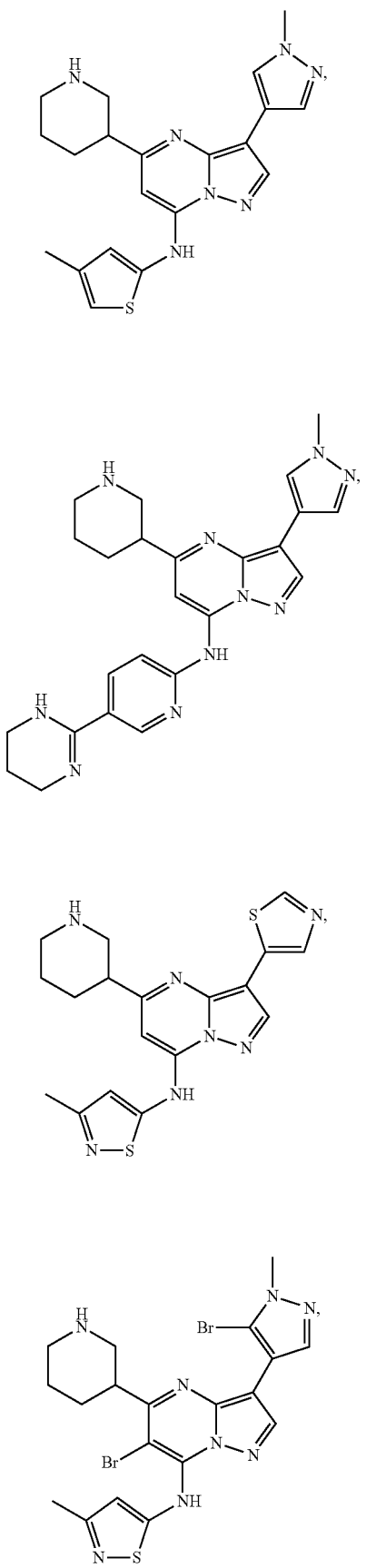
-continued
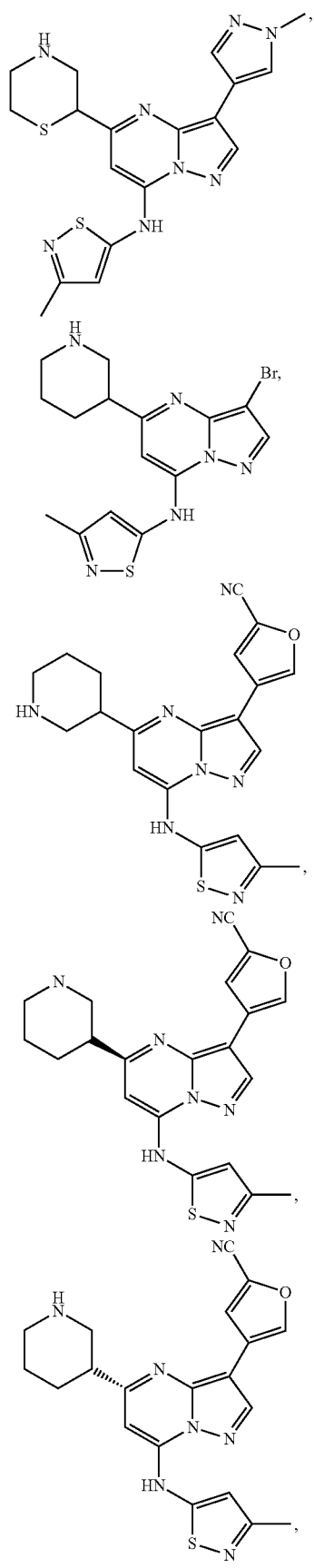

241
-continued
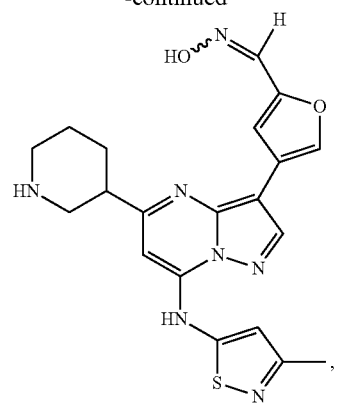
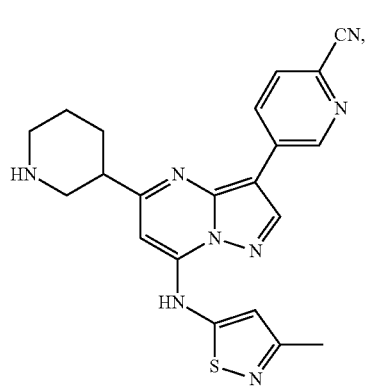
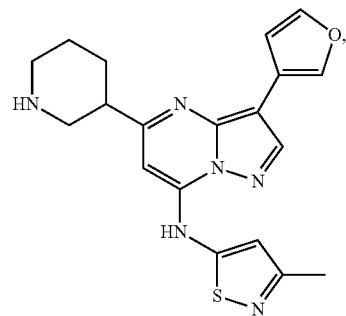
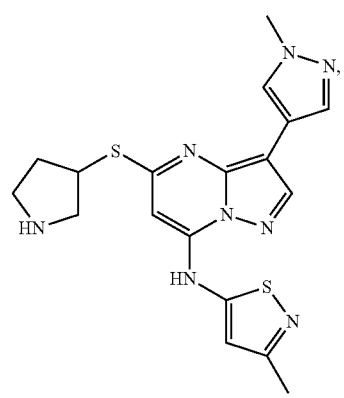
242
-continued
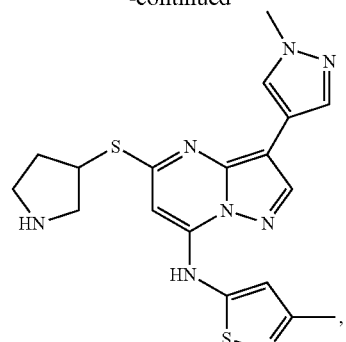
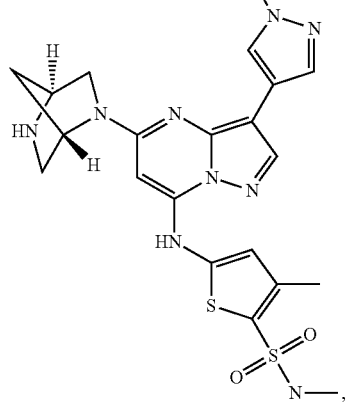
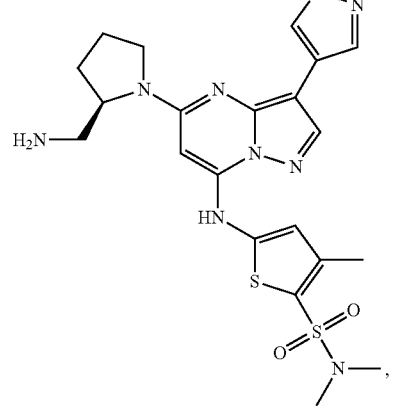
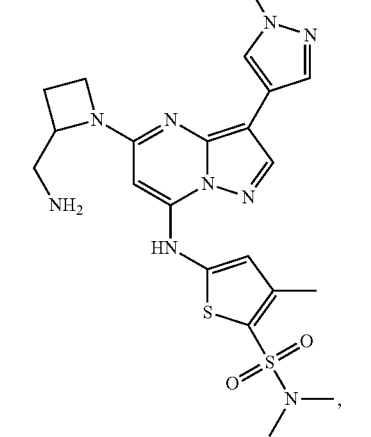

243
-continued
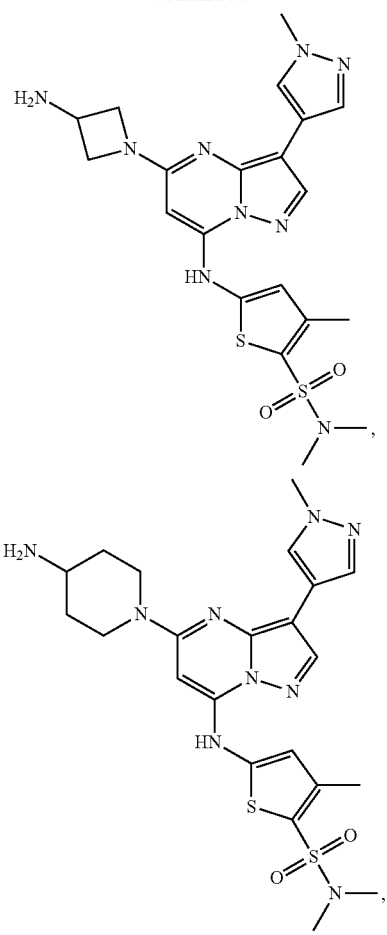
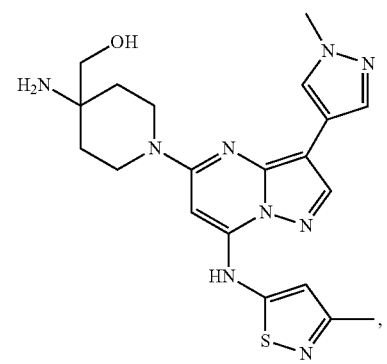
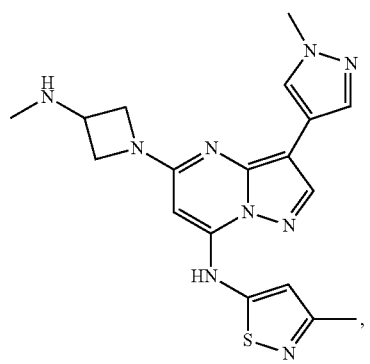
244
-continued
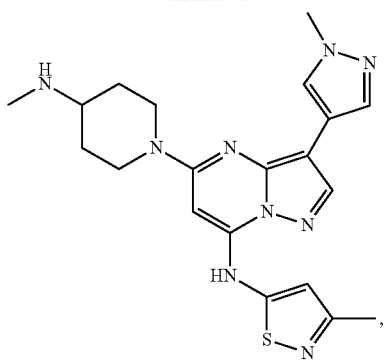
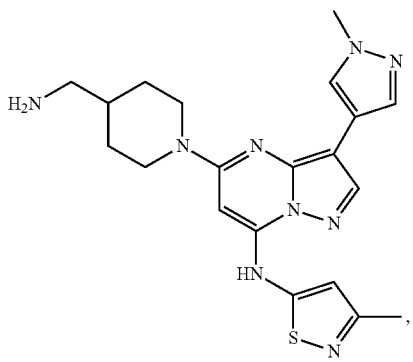
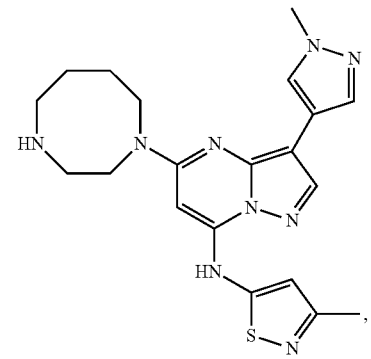
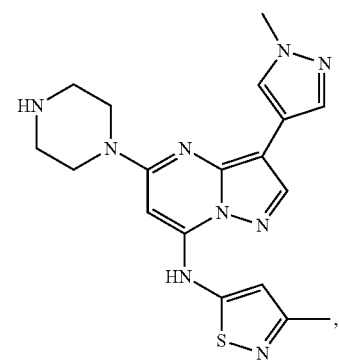

245
-continued
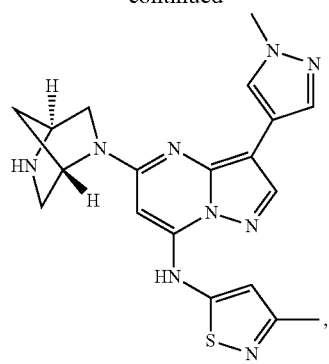
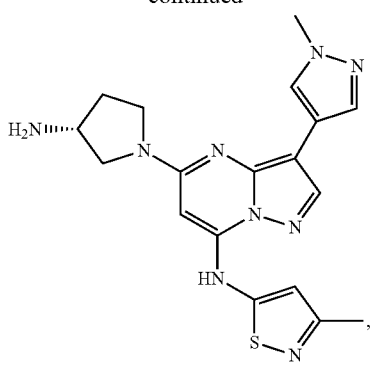
246
-continued
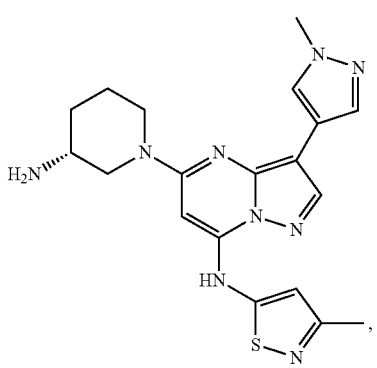
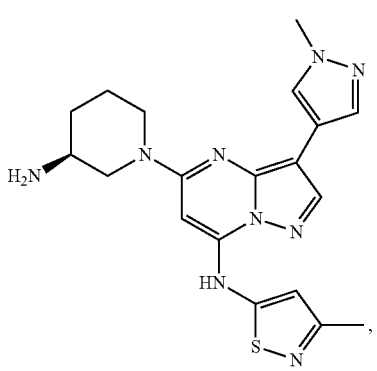
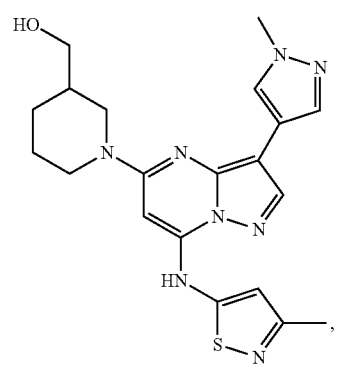

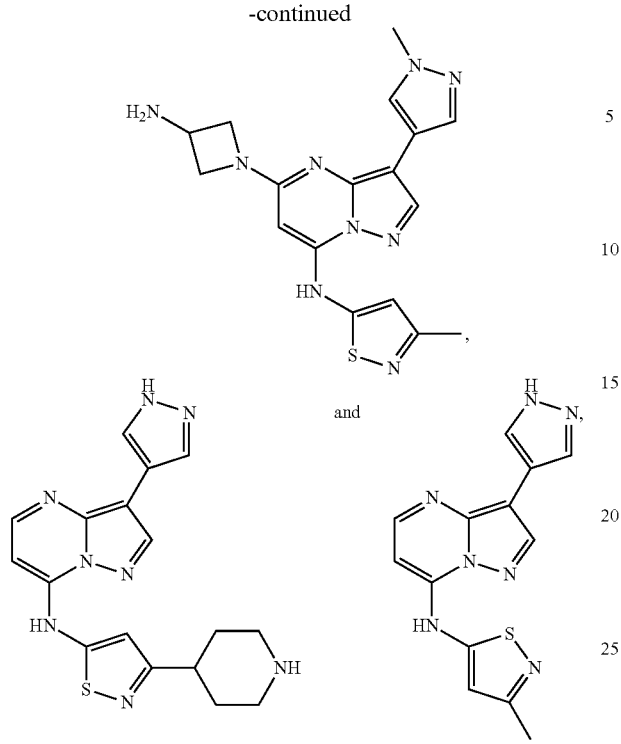
or a pharmaceutically acceptable salt thereof.
* * * * *

UNITED STATES PATENT AND TRADEMARK OFFICE
CERTIFICATE OF CORRECTION

PATENT NO. : 8,603,998 B2  Page 1 of 1
APPLICATION NO. : 12/744021
DATED : December 10, 2013
INVENTOR(S) : Guzi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 810 days.

Signed and Sealed this

Twenty-second Day of September, 2015

Michelle K. Lee
*Director of the United States Patent and Trademark Office*